US008716555B2

(12) United States Patent
Liu et al.

(10) Patent No.: US 8,716,555 B2
(45) Date of Patent: May 6, 2014

(54) COTTONSEED OIL AND USES

(75) Inventors: Qing Liu, Giralang (AU); Allan Graham Green, Red Hill (AU); Surinder Pal Singh, Downer (AU)

(73) Assignee: Commonwealth Scientific and Industrial Research Organisation, Campbell (AU)

( * ) Notice: Subject to any disclaimer, the term of this patent is extended or adjusted under 35 U.S.C. 154(b) by 243 days.

(21) Appl. No.: 13/011,773

(22) Filed: Jan. 21, 2011

(65) Prior Publication Data

US 2011/0223311 A1 Sep. 15, 2011

Related U.S. Application Data

(63) Continuation-in-part of application No. PCT/AU2009/000929, filed on Jul. 21, 2009.

(60) Provisional application No. 61/135,554, filed on Jul. 21, 2008.

(51) Int. Cl.
*C12N 15/82* (2006.01)
*A01H 5/10* (2006.01)
*C12N 15/05* (2006.01)
*C12N 15/87* (2006.01)
*C12N 5/14* (2006.01)
*C12N 5/04* (2006.01)
*C07H 21/04* (2006.01)

(52) U.S. Cl.
USPC ........ 800/281; 800/314; 800/298; 435/320.1; 435/419; 435/430; 435/468; 536/23.2; 536/24.1

(58) Field of Classification Search
None
See application file for complete search history.

(56) References Cited

U.S. PATENT DOCUMENTS

| | | | |
|---|---|---|---|
| 4,948,811 A | 8/1990 | Spinner et al. | |
| 5,500,361 A | 3/1996 | Kinney | |
| 6,100,077 A | 8/2000 | Sturley et al. | |
| 6,344,548 B1 | 2/2002 | Farese et al. | |
| 6,432,684 B1 | 8/2002 | Mukerji et al. | |
| 7,001,771 B1 | 2/2006 | Morell et al. | |
| 7,045,326 B2 | 5/2006 | Cases et al. | |
| 7,109,392 B1 | 9/2006 | Broglie et al. | |
| 7,135,617 B2 | 11/2006 | Lardizabal et al. | |
| 7,244,599 B2 | 7/2007 | Tanner et al. | |
| 7,417,176 B2 | 8/2008 | Lardizabal et al. | |
| 7,521,593 B2 | 4/2009 | Regina et al. | |
| 7,589,253 B2 | 9/2009 | Green et al. | |
| 7,619,105 B2 | 11/2009 | Green et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,741,532 B2 | 6/2010 | Lardizabal et al. | |
| 7,790,955 B2 | 9/2010 | Li et al. | |
| 7,807,849 B2 | 10/2010 | Singh et al. | |
| 7,812,221 B2 | 10/2010 | Morell et al. | |
| 7,834,248 B2 | 11/2010 | Green et al. | |
| 7,834,250 B2 | 11/2010 | Singh et al. | |
| 7,888,499 B2 | 2/2011 | Morell et al. | |
| 7,892,803 B2 | 2/2011 | Tanner et al. | |
| 7,919,132 B2 | 4/2011 | Regina et al. | |
| 7,932,438 B2 | 4/2011 | Singh et al. | |
| 7,932,440 B2 | 4/2011 | Reid et al. | |
| 7,993,686 B2 | 8/2011 | Bird et al. | |
| 8,049,069 B2 | 11/2011 | Wu et al. | |
| 8,071,341 B2 | 12/2011 | Singh et al. | |
| 8,106,226 B2 | 1/2012 | Singh et al. | |
| 8,115,087 B2 | 2/2012 | Regina et al. | |
| 8,158,392 B1 | 4/2012 | Singh et al. | |
| 8,178,759 B2 | 5/2012 | Morell et al. | |
| 8,188,336 B2 | 5/2012 | Li et al. | |
| 8,269,082 B2 | 9/2012 | Millar et al. | |
| 8,288,572 B2 | 10/2012 | Singh et al. | |
| 8,501,262 B2 | 8/2013 | Bird et al. | |
| 8,525,917 B2 | 9/2013 | Singh et al. | |
| 8,530,724 B2 | 9/2013 | Whitelaw et al. | |
| 2002/0104124 A1 | 8/2002 | Green et al. | |
| 2004/0221335 A1 | 11/2004 | Shewmaker et al. | |
| 2005/0106697 A1 | 5/2005 | Cases et al. | |
| 2005/0262588 A1 | 11/2005 | Dehesh et al. | |
| 2006/0053512 A1* | 3/2006 | Bao et al. | 800/281 |
| 2006/0094088 A1 | 5/2006 | Picataggio et al. | |

(Continued)

FOREIGN PATENT DOCUMENTS

EP 1806398 7/2007
EP 1837397 9/2007

(Continued)

OTHER PUBLICATIONS

Liu et al 1999 Australian Journal of Plant Physiology 26: p. 101-106.*
Pirtle et al 1999 Plant Cell Physiology 40:2 p. 155-163.*
O'Brien et al 2005 Cottonseed Oil, Baileys Industrial Oil and Fat Products, 6th Edition, edited by Fereidoon Shahidi.*
Lui et al 1997 EMBL Nucleotide Sequence Database as X97016.*
Klahre et al 2002 PNAS 99:18 p. 11981-11986.*
U.S. Appl. No. 13/093,252, filed Apr. 25, 2011, Singh et al.
U.S. Appl. No. 13/011,779, filed Jan. 21, 2011, Liu et al.
U.S. Appl. No. 12/989,405, filed May 16, 2011, Zhou et al.
U.S. Appl. No. 13/129,940, filed May 18, 2011, Petrie et al.
U.S. Appl. No. 13/171,032, filed Jun. 28, 2011, Petrie et al.
Liu et al., High-Stearic and High-Oleic Cottonseed Oils Produced by Hairpin RNA-Mediated Post-Transcriptional Gene Silencing. Plant Physiology, 2002, 129(4) 1732-1743.

(Continued)

*Primary Examiner* — Brent T Page
*Assistant Examiner* — Matthew Keogh
(74) *Attorney, Agent, or Firm* — John P. White; Gary J. Gershik; Cooper & Dunham LLP

(57) ABSTRACT

The present specification relates to the production of cotton plants and seeds and oil prepared therefrom having elevated levels of oleic and reduced levels of palmitic and linoleic acids. Furthermore, cottonseeds having low levels of cyclopropane and/or cyclopropene fatty acids and/or reduced levels of gossypol are described herein. The specification also describe FatB and CPA-FAS nucleotide and amino acid sequences derived from cotton facilitating, inter alia the direct modification of plant oil content and/or composition.

16 Claims, 27 Drawing Sheets

(56) References Cited

U.S. PATENT DOCUMENTS

| | | | |
|---|---|---|---|
| 2006/0206963 A1* | 9/2006 | Voelker et al. | 800/281 |
| 2008/0268539 A1 | 10/2008 | Singh et al. | |
| 2008/0311580 A1 | 12/2008 | Abrahams et al. | |
| 2009/0308041 A1 | 12/2009 | Whitelaw et al. | |
| 2010/0184130 A1 | 7/2010 | Koprowski et al. | |
| 2010/0221400 A1 | 9/2010 | Chapman et al. | |
| 2011/0015415 A1 | 1/2011 | Singh et al. | |
| 2011/0045127 A1 | 2/2011 | Ral et al. | |
| 2011/0054198 A1 | 3/2011 | Singh et al. | |
| 2011/0190521 A1 | 8/2011 | Damcevski et al. | |
| 2011/0218348 A1 | 9/2011 | Zhou et al. | |
| 2011/0223311 A1 | 9/2011 | Liu et al. | |
| 2011/0229623 A1 | 9/2011 | Liu et al. | |
| 2011/0281818 A1 | 11/2011 | Jenkins et al. | |
| 2011/0314725 A1 | 12/2011 | Petrie et al. | |
| 2012/0016144 A1 | 1/2012 | Petrie et al. | |
| 2012/0114770 A1 | 5/2012 | Regina et al. | |
| 2012/0129805 A1 | 5/2012 | Li et al. | |
| 2012/0208198 A1 | 8/2012 | Bogs et al. | |
| 2013/0115362 A1 | 5/2013 | Regina et al. | |
| 2013/0164798 A1 | 6/2013 | Vanhercke et al. | |

FOREIGN PATENT DOCUMENTS

| | | |
|---|---|---|
| EP | 1944375 | 7/2008 |
| WO | WO 98/55631 | 12/1998 |
| WO | WO 99/49050 | 9/1999 |
| WO | WO 99/67268 | 12/1999 |
| WO | WO 99/67403 | 12/1999 |
| WO | WO 00/01713 | 1/2000 |
| WO | WO 00/11176 | 3/2000 |
| WO | WO 00/32756 | 6/2000 |
| WO | WO 00/32793 | 6/2000 |
| WO | WO 00/36114 | 6/2000 |
| WO | WO 00/60095 | 10/2000 |
| WO | WO 00/66750 | 10/2000 |
| WO | WO 00/66749 | 11/2000 |
| WO | WO 03/078639 | 9/2003 |
| WO | WO 2004/011671 | 2/2004 |
| WO | WO 2005/003322 | 1/2005 |
| WO | WO 2005/063988 | 7/2005 |
| WO | WO 2005/103253 | 11/2005 |
| WO | WO 2007/107738 | 9/2007 |
| WO | WO 2008/025068 | 6/2008 |
| WO | WO 2008/130248 | 10/2008 |
| WO | WO 2008/157226 | 12/2008 |
| WO | WO 2008/157827 | 12/2008 |
| WO | WO 2009/027335 | 3/2009 |
| WO | WO 2009/129582 | 10/2009 |
| WO | WO 2009/143397 | 11/2009 |
| WO | WO 2010/009499 | 1/2010 |
| WO | WO 2010/009500 | 1/2010 |
| WO | WO 2010/057246 | 5/2010 |
| WO | WO 2012/0001326 | 1/2012 |

OTHER PUBLICATIONS

Liu et al., (2005) GenBank Accession No. AY574036.
Liu et al., (2005) GenBank Accession No. AY574037.
Liu et al., (2005) GenBank Accession No. AY574038.
File History of U.S. Patent No. 7,807,849, Singh et al., issued Oct. 5, 2010 (U.S. Appl. No. 11/112,882, filed Apr. 22, 2005).
File History of U.S. Patent No. 7,834,250, Singh et al., issued Nov. 16, 2010 (U.S. Appl. No. 11/587,092, filed Oct. 20, 2006).
File History of U.S. Patent No. 7,932,438, Singh et al., issued (U.S. Appl. No. 12/945,708, filed Nov. 12, 2010).
File History of U.S. Patent No. 7,589,253, Green et al., issued Sep. 15, 2009 (U.S. Appl. No. 09/981,124, filed Oct. 17, 2011).
File History of U.S. Patent No. 7,834,248, Green et al., issued Nov. 16, 2010 (U.S. Appl. No. 11/699,817, filed Jan. 30, 2007).
File History of U.S. Appl. No. 12/989,405, Zhou et al., filed May 16, 2011.
File History of U.S. Patent Application Publication No. 2011/0190521, Damcevski et al., published Aug. 4, 2011 (U.S. Appl. No. 12/310,645, filed Feb. 16, 2011).
File History of U.S. Patent Application Publication No. 2011/0015415, Singh, et al., published Jan. 20, 2011 (U.S. Appl. No. 12/661,978, filed Mar. 26, 2010).
File History of U.S. Patent Publication No. 2011-0229623, Liu et al., Sep. 22, 2011 (U.S. Appl. No. 13/011,779, filed Jan. 21, 2011).
Bäumlein, H., et al., (1991) "A Novel Seed Protein Gene From *Vicia faba* is Developmentally Regulated in Transgenic Tobacco and *Arabidopsis* Plants," Molecular and General Genetics, 225(3): 459-467.
Cherry, (1983) "Cottonseed Oil" J. Am. Oil Chem. Soc. 60: 360-367.
Domergue et al., (2005) "In vivo characterization of the first acyl-CoA Δ6-desaturase from a member of the plant kingdom, the microalga *Ostreococcus tauri*," Biochem J., 389, 483-490.
Dowd et al., (2004) "Gene Expression Profile Changes in Cotton Root and Hypocotyl Tissues in Response to Infection with *Fusarium oxysporum* f. sp. *vasinfectum*" Molecular Plant-Microbe Interactions. 17: 654-667.
Folch et al., (1957) "A Simple Method for the Isolation and Purification of total Lipides From Animal Tissues" J. Biol. Chem. 226: 497.
Fuller et al., (1966) "A Gas Chromatographic Method for Continuous Accelerated Study of $O_2$ Uptake in Fats" JAOCS. 43: 477-478.
Hutchins et al., (1968) "A New Process for the Selective Hydrogenation Cyclopropenoids in Cottonseed Oil" Journal of American Oil Chemists Society 45: 397-399.
Kargiotidou et al., (2008) "Low temperature and light regulate delta 12 fatty acid desaturases (FAD2) at a transcriptional level in cotton (*Gossypium hirsutum*)" Journal of Experimental Botany 2008 59(8): 2043-2056.
Lee, M., et al., (1998) "Identification of Non-Heme Diiron Proteins That Catalyze Triple Bond and Epoxy Group Formation," Science, 280(5365): 915-918.
Liu et al., (2002) "High-Stearic and High-Oleic Cottonseed Oils Produced by Hairpin RNA-Mediated Post-Transcriptional. Gene Silencing." Plant Physiology, 129(4):1732-1743.
Liu et al., (1999) "Cloning and Sequence Analysis of a Novel Member (Accession No. Y10112) of the Microsomal w-6 Fatty Acid Desaturase Family from Cotton" Plant Physiol. (PGR 99-063) 120: 339.
Liu et al., (1999) "Molecular cloning and expression of a cDNA encoding a microsomal w-6 fatty acid desaturase from cotton (*Gossypium hirsutum*)" Australian Journal of Plant Physiology 26: 101-106.
Mojovic et al., (1993) "*Rhizopus arrhizus* lipase-catalyzed interesterification of the midfraction of palm oil to a cocoa butter equivalent fat" Enzyme Microb Technol. 15: 438-443.
Mounts et al., (1998) "Effect of Altered Fatty Acid Composition on Soybean Oil Stability" J Am. Oil Chem. Soc. 65: 624-628.
Needleman, S. B., & Wunsch, C. D. (1970) "A general method applicable to the search for similarities in the amino acid sequence of two proteins," J. Mol. Biol., 48, 443-453.
Pirtle at al., (2001) "Molecular cloning and functional expression of the gene for a cotton v-12 fatty acid desaturase (FAD2)" Biochim. Biophys. Acta 1522: 122-129.
Shenstone and Vickery, (1961) "Occurrence of Cyclo-Propene Acids in Some Plants of the Order Malvales" Nature 190: 68-169.
Taira at al., (1988) "Fatty Acid Composition of Indica Sinica Javanica and Japonica Groups of Nonglutinous Brown Rice" Journal of Agricultural and Food Chemistry; vol. 36 No. 1, 45-47.
Trautwein, E.A., (2001) "n-3 Fatty Acids—Physiological and Technical Aspects for Their Use in Food," European Journal of Lipid Science and Technology, 103(1): 45-55.
Valvekens, D., et al., (1988) "*Agrobacterium tumefaciens*-Mediated Transformation of *Arabidopsis thaliana* Root Explants by Using Kanamycin Selection," Proceedings of the National Academy of Sciences of the United States of America, 85 (15) 5536-5540.
van de Loo, F. J., Braun, P., Turner, S., & Somerville, C. (1995) "An oleate 12-hydroxylase from *Ricinus communis* L. is a fatty acyl desaturase homolog," Proc. Natl. Acad. Sci. USA, 92, 6743-6747.
International Search Report issued on Sep. 8, 2009 in Connection with International Application No. PCT/AU2009/000929.
Written Opinion of the International Search Authority, issued on Sep. 8, 2009 in Connection with International Application No. PCT/AU2009/000929.

(56) References Cited

OTHER PUBLICATIONS

International Search Report issued by the International Searching Authority (ISA.AU) on Oct. 25, 2007 in connection with International Application No. PCT/AU2007/000977.

International Preliminary Report on Patentability issued on Jan. 14, 2009 in connection with PCT International Patent Application No. PCT/AU2007/000977.

English Translation of Jun. 26, 2013 Office Action, issued in connection with Chinese Patent Application No. 200980134226.8.

U.S. Appl. No. 14/021,173, filed Sep. 9, 2013 (Whitelaw et al.).

Aug. 8, 2013 Response, filed in connection with U.S. Appl. No. 13/011,773.

Andrianov et al. (2010) "Tobacco as a production platform for biofuel: overexpression of *Arabidopsis* DGAT and LEC2 genes increases accumulation and shifts the composition of lipids in green biomass" Plant Biotech. J. 8:277-287.

Alonso et al. (2010) "Catalytic conversion of biomass to biofuels" Green Chem. 12:1493-1513.

Awai et al., (2006) "A phosphatidic acid-binding protein of the chloroplast inner envelope membrane involved in lipid trafficking" PNAS 103(28) :10817-22.

Bouvier-Nave et al. (2000) "Expression in yeast and tobacco of plant cDNAs encoding acyl CoA:diacylglycerol acyltransferase" European Journal of Biochemistry/FEBS 267:85-96.

Broun et al. (1998) "A bifunctional oleate 12-hydroxylase: desaturase from *Lesquerella fenleri*." The Pant Journal, 13(2):201-210.

Burgal at al., (2008) "Metabolic engineering of hydroxy fatty acid production in plants: RcDGAT2 drives dramatic increases in ricinoleate levels in seed oil" Plant Biotechnology Journal 6(8):819-831.

Cernac and Benning (2004) "WRINKLED1 encodes an AP2/EREB domain protein involved in the control of storage compound biosynthesis in *Arabidopsis*" Plant J. 40:575-585.

Chappell et al (1998) "Vegetable Oil Production: Industry Profile" Preliminary Final Report, EPA contract 68-D4-0099, TRU Project # 7018-54, 1-1-5-26.

Durrett et al. (2008) "Plant triacylglycerols as feedstocks for the production of biofuels" Plant J. 54:593-607.

Eastmond, (2006) "SUGAR-DEPENDENT1 Encodes a Patatin Domain Triacylglycerol Lipase That Initiates Storage Oil Breakdown in 4 Germinating *Arabidopsis* Seeds" The Plant Cell, vol. 18, 665-675.

Endalew et al. (2011) "Inorganic heterogeneous catalysts for biodiesel production from vegetable oils" Biomass and Bioenergy 35:3787-3809.

Ghosal et al. (2007) "*Saccharomyces cerevisiae* phospholipid-:diacylglycerol acyl transferase (PDAT) devoid of its membrane anchor region is a soluble and active enzyme retaining its substrate specificities" Biochimica et Biophysica Acta 1771:1457-1463.

Gong and Jiang (2011) "Biodiesel production with microalgae as feedstock: from strains to biodiesel" Biotechnol. Lett. 33:1269-1284.

Greenwell et al. (2010) "Placing microalgae on the biofuels priority list: a review of the technological challenges" J. R. Soc. Interface 7:703-726.

Jain et al., (2000) "Enhancement of seed oil content by expression of glycerol-3-phosphate acyltransferase genes" Biochemical Society Transactions 29(6):958-961.

James et al (2010) "Disruption of the *Arabidopsis* CGI-58 homologue produces Chanarin-Dorfman-like lipid droplet accumulation in plants," 107(41):17833-17838 and supporting information pp. 1-3.

Karmakar et al. (2010) "Properties of various plants and animals feedstocks for biodiesel production" Bioresource Technology 101:7201-7210.

Kelly et al., (2011) "Seed Storage Oil Mobilization is Important But Not Essential for Geimination or Seedling Establishment in *Arabidopsis*" Plant Physiology, vol. 157, pp. 866-875.

Kinney (1996) Development of Genetically Engineered Soybean Oils for Food Applications. J. Food Lipids 3: 273-292.

Kodama et al. (1997) Structure, chromosomal location and expression of a rice gene encoding the microsome ω-3 fatty acid desaturase. Plant Molecular Biology 33: 493-502.

Kohno-Murase et al. (2006). Production of trans-10, cis-12 conjugated linoleic acid in rice. Transgenic Research 15:95-100.

Kozeil et al. (1996) "Optimizing expression of transgenes with an emphasis on post-transcriptional events." Plant Molecular Biology, 32:393-405.

Langridge et al., Trends in genetic and genome analysis in wheat: a review. Aust. J. Agric. Res., 2001, 52:1043-1077.

Lardizabal et al. (2001) "DGAT2 is a New Diacylglycerol Acyltransferase Gene Family" J. Biol. Chem. 276:38862-38869.

Lardizabal et al. (2008) "Expression of *Umbelopsis ramanniana* DGAT2A in Seed Increases Oil in Soybean" Plant Physiol. 148: 89-96.

Liu at al. (2010) "Producing biodiesel from high free fatty acids waste cooking oil assisted by radio frequency heating" Fuel 89:2735-2740.

Liu at al, (1997) EMBL Nucleotide Sequence Database as X97016.

Liu et al., Genetic modification of cotton seed oil using inverted-repeat gene-silencing techniques. Biochemical Society Transations, 2000, 28(6):927-929.

Liu et al., (1999) "Cloning and Sequence Analysis of a Novel Member (Accession No. Y10112) of the Microsomal w-6 Fatty Acid Desaturase Family from Cotton" Plant Physiol. (PGR 99-063) 120:339.

Lu at al., (2011) "New frontiers in oilseed biotechnology: meeting the global demand for vegetable oils for food, feed, biofuel, and industrial applications" Current Opinion in Biotechnology, 22:252-259.

Maher and Bressler (2007) "Pyrolysis of triglyceride materials for the production of renewable fuels and chemicals" Bioresource Technology 98:2351-2368.

O'Brien, (2002) Cottonseed Oil. In: F.D. Gunstone (Ed.) Vegetable Oils in Food Technology: Composition, Properties and Uses. Blackwell Publishing, Oxford, pp. 203-230.

Okuley et al. *Arabidopsis* FAD2 Gene Encodes the Enzyme that is Essential for Polyunsaturated Lipid Synthesis. Plant Cell, 1994, 6:147-158.

Parthibane et al. (2012) "Oleosin is a Bifunctional Enzyme That Has Both Monoacylglycerol Acyltransferase and Phospholipase Activities" J. Biol. Chem. 287:1946-1954.

Perez-Vich et al. (1998) "Determination of Seed Oil Content and Fatty Acid Composition in Sunflower Through the Analysis of Intact Seeds, Husked Seeds, Meal and Oil by Near-Infrared Reflectance Spectroscopy" JAOCS 75:547-555.

Petrie et al. (2012) "Recruiting a New Substrate for Triacylglycerol Synthesis in Plants: The Monoacylglycerol Acyltransferase Pathway" PLoS ONE 7:e35214.

Pokharkar et al., (2008) "Synthesis and Characterizationof Fatty Acid Methyl Ester by In-Situ Transesterification in *Capparis deciduas* Seed" Leonardo Electronic Journal of Practices and Technologies 13:12-18.

Rajasekharan et al., (2006) "Monoacylglycerol as an intermediate in triacylglycerol biosynthesis in plants" International Symposium on Plant Lipids, Abstract.

Roston et al., (2012) "TGD1, -2, and -3 Proteins Involved in Lipid Trafficking Form ATP-binding Cassette (ABC) Transporter with Multiple Substrate-binding Proteins" The Journal of Biological Chemistry vol. 287, No. 25, pp. 21406-21415.

Sanjaya et al, (2011) "Increasing the energy density of vegetative tissues by diverting carbon from starch to oil biosynthesis in transgenic *Arabidopsis*" Plant. Biotech, J. 9:874-883.

Sanjaya et al (2013) "Altered Lipid Composition and Enhanced Nutritional Value of *Arabidopsis* Leaves following Introduction of an Algal Diacylglycerol Acyltransferase 2" Plant Cell, 1-17.

Semwal et al. (2011) "Biodiesel production using heterogeneous catalysts" Bioresource Technology 102:2151-2161.

Sheikh et al (2002) "Fatty Acids Composition in Germinating Cotton Seedlings Affected by High Temperature Stress" Pakistan Journal of Applied Sciences 2:1 p. 97-99.

Shiina et al. (1997) "Identification of Promoter Elements Involved in Cytosolic Ca2+-Mediated Photoregulation of Maize cab-m1 Expression" Plant Physiol. 115:477-483.

(56) References Cited

OTHER PUBLICATIONS

Smith et al. (2000) "Total silencing by intron-spliced Nature 407:319-320 hairpin RNAs" Nature 407:319-320.
Slocombe et al (2009) "Oil accumulation in leaves directed by modification of fatty acid breakdown and lipid synthesis pathways" Plant Biotechnology Journal, 7, 694-703.
Srinivasan et al. (2007) "Heterologous expression of the Baby Boom AP2/ERF transcription factor enhances the regeneration capacity of tobacco (*Nicotiana tabacum* L.)" Planta 225:341-51.
Takeyama, H., et al., (1997) "Expression of The Eicosapentaenoic Acid Synthesis Gene Cluster From *Shewanella* sp. In a Transgenic Marine *Cyanobacterium, Synechococcus* sp.," Microbiology, 143(Pt 8): 2725-2731.
To et al., (2012) "WRINKLED Transcription Factors Orchestrate Tissue-Specific Regulation of Fatty Acid Biosynthesis in *Arabidopsis*" The Plant Cell, vol. 24: 5007-5023.
Vanhercke et al. (2012) "Maximizing lipid accumulation in vegetative plant tissues" 8th International Symposium on Biocatalysis and Agriculural Biotechnology.
Vanhercke et al. (2013) "Synergistic effect of WRI1and DGAT1 coexpression on triacylglycerol biosynthesis in plants" FEBS Letters 587:364-369.
Vanhercke et al (2013) "Metabolic engineering of biomass for high energy density: oilseed-like triacylglycerol yields from plant leaves" Plant Biotechnol. J., doi: 10.1111/pbi.12131.
Wood et al. (2009) "A leaf-based assay using interchangeable design principles to rapidly assemble multistep recombinant pathways" Plant Biotech. J. 7: 914-924.
Xu et al., (2008) "Cloning and characterization of an acyl-CoA-dependent diacylglycerol acyltransferase 1 (DGAT1) gene from *Tropaeolum majus*, and a study of the functional motifs of the DGAT protein using site-directed mutagenesis to modify enzyme activity and oil content" Plant Biotechnology Journal 6, pp. 799-818.
Xu et al., (2008) "Lipid Trafficking between the Endoplasmic Reticulum and the Plastid in *Arabidopsis* Requires the Extraplastidic TGD4 Protein" The Plant Cell, vol. 20: 2190-2204.
Xu et al., (2005) "Mutation of the TGD1 Chloroplast Envelope Protein Affects Phosphatidate Metabolism in *Arabidopsis*" The Plant Cell, vol. 17, 3094-3110.
Xu et al., (2010) "Lipid Transport Mediated by *Arabidopsis* TGD Proteins is Unidirectional from the Endoplasmic Reticulum to the Plastid" Plant Cell Physiol, 51(6): 1019-1028.
Yang et al. (2010) "A distinct type of glycerol-3-phosphate acyltransferase with sn-2 preference and phosphatase activity producing 2-monoacylglycerol" PNAS 107:12040-12045.
Yang & Ohlrogge (2009) "Turnover of Fatty Acids during Natural Senescence of *Arabidopsis, Brachypodium*, and Switchgrass and in *Arabidopsis* b-Oxidation Mutants" Plant Physiology, 150, 1981-1989.
GenBank Accession No. BAC45173.1, Sasaki et al. (2002).
GenBank Accession No. BAC45170.1, Sasaki et al. (2002).
International Search Report issued on Sep. 8, 2009 by the International Searching Authority (ISA/US) in connection with International Application No. PCT/AU2006/000930.
International Preliminary Report issued on Jan. 25, 2011 by the International Searching Authority (ISA/US) in connection with International Application No. PCT/AU2006/000930.
Written Opinion issued on Aug. 18, 2009 by the International Searching Authority (ISA/US) in connection with International Application No. PCT/AU2006/000930.
Dec. 6, 2012 Office Action issued in connection with U.S. Appl. No. 13/011,779.
Jan. 4, 2013 Response filed in connection with U.S. Appl. No. 13/011,779.
Mar. 13, 2013 Office Action issued in connection with U.S. Appl. No. 13/011,779.
Jul. 1, 2011 Office Action issued in connection with U.S. Appl. No. 12/309,276.
Sep. 1, 2011 Response filed in connection with U.S. Appl. No. 12/309,276.
Nov. 4, 2011 Office Communication issued in connection with U.S. Appl. No. 12/309,276.
Dec. 5, 2011 Response filed in connection with U.S. Appl. No. 12/309,276.
Jan. 12, 2012 Office Action issued in connection with U.S. Appl. No. 12/309,276.
Feb. 6, 2012 Petition filed in connection with U.S. Appl. No. 12/309,276.
Mar. 26, 2012 Decision on Petition issued in connection with U.S. Appl. No. 12/309,276.
Aug. 3, 2012 Office Action issued in connection with U.S. Appl. No. 12/309,276.
Dec. 3, 2012 Response filed in connection with U.S. Appl. No. 12/309,276.
Jan. 17, 2013 Office Action issued in connection with U.S. Appl. No. 12/309,276.
Apr. 17, 2013 Response filed in connection with U.S. Appl. No. 12/309,276.
May 6, 2013 Notice of Allowance issued in connection with U.S. Appl. No. 12/309,276.
Abdullah, R., Cocking, E. C., & Thompson, J. A. (1986) "Efficient plant regeneration from rice protoplasts through somatic embryogenesis" Biotechnology, 4, 1087-1090.
Aghoram, K., Wilson, R.F., Burton, J.W., Dewey, R.E. (2006) "A mutation in a 3-keto-acyl-acp synthase ii gene is associated with elevated palmitic acid levels in soybean seeds" Crop Sci. 46:2453-2459.
Akagi et al. (1995) "Nucleotide Sequence of a Stearoyl-Acel carrier Protein Desaturase cDNA from Developing Seeds of Rice" Plant Physiol. 108, 845-846.
Almeida and Allshire, (2005) "RNA silencing and genome regulation." Trends in Cell Biology, 15:251-258.
Anai et al. (2003) "Improvement of rice (*Oryza sativa* L.) seed oil quality through introduction of a soybean microsomal omega-3 fatty acid desaturase gene" Plant Cell Rep. 21,988-992.
Ascherio and Willett (1997) "Health effects of trans fatty acids" Am. J. Clin. Nutr. 66: 1006S-1010S.
Bao and Ohlrogge, (1999) "Supply of Fatty Acid is One Limiting Factor in the Accumulation of Triacylglycerol in Developing Embryos," Plant Physiology, 120:1057-1062.
Bligh and Dyer (1959) "A Rapid Method of Total Lipid Extraction and Purification" Canadian Journal of Biochemistry and Physiology 37:911-917.
Boggs et al. (1964) "Relation of Hexanal in Vapor Above Stored Potato Granules to Subjective Flavor Extimates." J. Food Sci. 29:487-489.
Bonanome and Grundy (1988) "Effect of Dietary Stearic Acid on Plasma Cholesterol and Lipoprotein Levels" N. Engl. Med. 318: 1244-1248.
Brandt et al., (1985) "Primary Structure of a B1 Hordein Gene from Barley" Carlsberg Res. Commun., 50:333-345.
Buhr et al. (2002) "Ribozyme termination of RNA transcripts down-regulate seed fatty acid genes in transgenic soybean" Plant J. 30: 155-163.
Cases et al., (1998) "Identification of a gene encoding an acyl CoA:diacylglycerol acyltransferase, a key enzyme in triacylglycerol synthesis" PNAS 95:13018-13023.
Cases et al., (2001) "Cloning of DGAT2, a second mammalian diacylglycerol acyltransferase, and related family members" J. Biol. Chem. 276(42):38870-38876.
Cao et al., (2003) "Properties of the Mouse Intestinal Acyl-CoA:Monoacylglycerol Acyltransferase, MGAT2" The Journal of Biological Chemistry, 278(28)25657-25669.
Champagne et al. (1995) "Stabilization of Brown Rice Products Using Ethanol Vapors as an Antioxidant Delivery System" Cereal Chem 72:255-258.
Chang et al., (1978) "Chemical Reactions Involved in the Deep-Fat Frying of Foods." Journal of American Oil Chemists' Society, 55:718-727.
Chapman et al. (2001) "Transgenic Cotton Plants with Increased Seed Oleic Acid Content" Journal of American Chemists' Chemistry; vol. 78 No. 9, 941-947.

(56) References Cited

OTHER PUBLICATIONS

Cheng et al., (2003) "Identification of Acyl Coenzyme A:Monoacylglycerol Acyltransferase 3, an Intestinal Specific Enzyme Implicated in Dietary Fat Absorption." The Journal of Biological Chemistry, 278(126):13611-13614.
Choudhury et al. (1980) "Lipids in Developing and Mature Rice Grain" Phytochemistry 19: 1063-1069.
Cicero et al. (2001) "Rice bran oil and [gamma]-oryzanol in the treatment of hyperlipoproteinaemias and other conditions" Phytotherapy Research; vol. 15 No. 4, 277-289.
Clapp et al., (1993) "The 16-Kilodalton N-Terminal Fragment of Human Prolactin is a Potent Inhibitor of Angiogenesis" Endocrinology, 133(3):1292-1299.
Colot et al., (1987) "Localization of sequences in wheat endosperm protein genes which confer tissue-specific expression in tobacco" The EMBO Journal, 6(12):3559-3564.
Comai et al., (2004) "Efficient discovery of DNA polymorphisms in natural populations by Ecotilling" The Plant Journal, 37: 778-786.
Dougherty et al. (1995) "Effects of diets containing high or low amounts of stearic acid on plasma lipoprotein fractions and fecal fatty acid excretion of men" Am. J. Clin. Nutr. 61:1120-1128.
Dubois et al. (2007) "Fatty acid profiles of 80 vegetable oils with regard to their nutritional potential" European Journal of Lipid Science Technology 109(7):710-732.
Dulermo and Nicaud (2011) "Involvement of the G3P shuttle and β-oxidation pathway in the control of TAG synthesis and lipid accumulation in *Yarrowia lipolytica*" Metab. Eng. 13:482-491.
Goffman et al., (2003) "Genetic Diversity for Lipid Content and Fatty Acid Profile in Rice Bran," Journal of the American Oil Chemists' Society 80:485-490.
Ha (2005) "Bioactive components in rice bran oil improve lipid profiles in rats fed on high-cholesterol diet" Nutrition research 25, 597-606.
Haseloff, J. and Gerlach, W.L., (1988) "Simple RNA Enzymes With New and Highly Specific Endoribonuclease Activities," Nature, 334: 585-591.
Henikoff et al., (2004) "TILLING. Traditional Mutagenesis Meets Functional Genomics." Plant Physiology, 2004, 135:630-636.
Hu et al. (1997) "Dietary Fat Intake and the Rist of Coronary Heart Disease in Women." N. Engl. J. Med. 337: 1491-1499.
Jako et al., (2001) "Seed-Specific Over-Expression of an *Arabidopsis* cDNA Encoding a Diacylglycerol Acyltransferase Enhances Seed Oil Content and Seed Weight" Plant Physiology, 126:861-874.
Jennings and Akoh (2000) "Lipase-Catalyzed Modification of Rice Bran Oil to Incorporate Capric Acid." Journal of Agricultural and Food Chemistry, 48:4439-4443.
Jones et al. (1995) "Palmitoyl-Acyl Carrier Protein (ACP) Thioesterase and the Evolutionary Origin of Plant Acyl-ACP Thicesterases." Plant Cell 7: 359-371.
Lemieux B., (2000) "High Throughput Single Nucleotide Polymorphism Genotyping Technology." Current Genomics, 2000, 1:301-311.
Leonard et al. (1997) "*Cuphea wrightii* thioesterases have unexpected broad specificities on saturated fatty acids." Plant Molecular Biology, vol. 34, Issue 4: 669-679.
Li et al., (1997) "Comparison of promoters and selectable marker genes for use in Indica rice transformation." Molecular Breeding, 3:1-14.
Liu et al. (2002) "High-Oleic and High-Stearic Cottonseed Oils: Nutritionally Improved Cooking Oils Developed Using Gene Silencing." J. Am. Coll. Nutr. 21: 205S-211S.
Lu et al. (1993) "High efficiency retroviral mediated gene transduction into single isolated immature and replatable CD343+ hematopoietic stem/progenitor cells from human umbilical cord blood." J. Exp. Med., 178, 2089-2096.
Mensink and Katan (1990) "Effect of Dietary Trans Fatty Acids on High-Density and Low-Density Lipoprotein Cholesterol Levels in Healthy Subjects." N. Engl. J. Med. 323: 439-445.

Mikkilineni and Rocheford (2003) "Sequence variation and genomic organization of fatty acid desaturase-2 (fad2) and fatty acid desaturase-6 (fad6) cDNAs in maize." Theor. Applied Genetics, 106, 1326-1332.
Miller and Waterhouse (2005) "Plant and animal microRNAs: similarities and differences." Funct Integr Genomics, 2005, 5:129-135.
Miquel et al. (1992) "*Arabidopsis* mutants deficient in polyunsaturated fatty acid synthesis: Biochemical and genetic characterization of a plant oleoyl-phosphatidylcholine desaturase" Journal of Biological Chemistry; vol. 267 No. 3, 1502-1509.
Moghadasian and Frohlich (1999) "Effects of Dietary Phytosterols on Cholesterol Metabolism and Atherosclerosis: Clinical and Experimental Evidence." Am. J. Med. 107: 588-94.
Morrison (1988) "Lipids in Cereal Starches: A Review." J Cereal Sci. 8:1-15.
Most et al. (2005) "Rice bran oil, not fiber, lowers cholesterol in humans." Am J Clin Nutr 81:64-8.
Nielsen et al. (2004) Formation of Volatile Compounds in Model Experiments with Crude Leek (*Allium ampeloprasum* Var. Lancelot) Enzyme Extract and Linoleic Acid or Linolenic Acid. Journal of Agricultural and Food Chemistry 52:2315-2321.
Noakes and Clifton (1998) "Oil blends containing partially hydrogenated or interesterified fats: differential effects on plasma lipids." Am. J. Clin. Nutr. 98: 242-247.
Ohlrogge and Jaworski (1997) "Regulation of Fatty Acid Synthesis. Annu Rev Plant Physiol Plant Mol Biol." 48:109-136.
Perriman, R., et al., (1992) "Extended Target-Site Specificity for a Hammerhead Ribozyme," Gene, 113(2): 157-163.
Radcliffe et al. (1997) "Serum Lipids in Rats Fed Diets Containing Rice Bran Oil or High-Linolenic Acid Safflower Oil." Biochemical Archives 13:87-95.
Resurreccion et al. (1979) "Nutrient Content and Distribution in Milling Fractions of Rice Grain." Journal of the Science of Food and Agriculture, 30: 475-481.
Roche and Gibney (2000) "Effect of long-chain n-3 polyunsaturated fatty acids on fasting and postprandial triacylglycerol metabolism." Am. J. Clin. Nutr. 71: 232S-237S.
Rukmini and Raghuram (1991) "Nutritional and Biochemical Aspects of the Hypolipidemic Action of Rice Bran Oil: A Review." Journal of the American College of Nutrition 10(6):593-601.
Senior I.J., (1998) "Uses of Plant Gene Silencing." Biotechnology & Genetic Engineering Reviews, Ed. Tombs, M.P., 15:79-119.
Shin et al. (1986) "Correlation Between Oxidative Deterioration of Unsaturated Lipid and n-Hexanal during Storage of Brown Rice." J. Food Sci. 51:460-463.
Shippy, R., et al., (1999) "The Hairpin Ribozyme—Discovery, Mechanism, and Development for Gene Therapy," Molecular Biotechnology, 12(1): 117-129.
Sivaraman et al. (2004) "Development of high oleic and low linoleic acid transgenics in a zero erucic acid *Brassica juncea* L. (Indian mustard) line by antisense suppression of the fad2 gene" Molecular Breeding, Kluwer Academic Publishers, DO; vol. 13 No. 1, 365-375.
Slade and Knauf, (2005) "TILLING moves beyond functional genomics into crop improvement." Transgenic Research, 14:109-115.
Stalberg et al., (1993) "Deletion Analysis of a 2S Seed Storage Protein Promoter of *Brassica napus* in Transgenic Tobacco," Plant Molecular Biology, 23(4): 671-683.
St Angelo et al. (1980) "Identification of Lipoxygenase-Linoleate Decomposition Products by Direct Gas Chromatography-Mass Spectrometry." J Lipids 1:45-49.
Stoutjesdijk et al. (2002) "hpRNA-mediated targeting of the *Arabidopsis* FAD2 gene gives highly efficient and stable silencing" Plant Physiology, American Society of Plant Physiologists, Rockville, MD, US; vol. 129, 1723-31.
Stoutjesdijk et al., (2000) "High-oleic acid Australian *Brassica napus* and *B. juncea* varieties produced by co-suppression of endogenous Δ2-desaturases." Biochem. Soc. Trans. 28: 938-940.
Suzuki et al. (1999) "Volatile Components in Stored Rice [*Oryza sativa* (L.)] of Varieties with and without Lipoxygenase-3 in Seeds." J. Agric. Food Chem. 47: 1119-1124.

(56) References Cited

OTHER PUBLICATIONS

Taira et al. (1989) "Fatty Acid Composition of Indica-Types and Japonica-Types of Rice Bran and Milled Rice" Journal of the American Oil Chemists' Society; vol. 66 No. 9, 1326-1329.

Taira et al. (1986) "Lipid Content and Fatty-Acid Composition of Indica and Japonica Types of Nonglutinous Brown Rice" Journal of Agriculture and Food Chemistry; vol. 34 No. 3, 542-545.

Thelen and Ohlrogge (2002) "Metabolic Engineering of Fatty Acid Biosynthesis in Plants." Metabolic Engineering 4: 12-21.

Theriault et al. (1999). "Tocotrienol: A Review of its Therapeutic Potential." Clin. Biochem. 32: 309-19.

Tholstrup et al. (1994) "Fat high in stearic acid favorably affects blood lipids and factor VII coagulant activity in comparison with fats high in palmitic acid or high in myristic and lauric acids." Am. J. Clin. Nutr. 59: 371-377.

Toriyama et al., "Haploid and diploid plant regeneration from protoplasts of anther callus in rice." Theor Appl Genet, 1986, 73:16-19.

Tsugita et al (1983) "Cooking Flavor and Texture of Rice Stored under Different Conditions." Agricultural and Biological Chemistry 47: 543-549.

Tsuzuki et al (2004) "Oxidation Rate of Conjugated Linoleic Acid and Conjugated Linolenic Acid is Slowed by Triacylglycerol Esterification and α-Tocopherol." Lipids 39:475-480.

Voelker et al. (1996) "Genetic engineering of a quantitative trait: metabolic and genetic parameters influencing the accumulation of laurate in rapeseed." Plant J. 9: 229-241.

Wagner et al. (1992) "Coupling of adenovirus to transferrin-polylysine/DNA complexes greatly enhances receptor-mediated gene delivery and expression of transfected genes." Proc. Natl. Acad. Sci. USA, 89, 6099-6103.

Wang et al., (1998) "Improved Vectors for *Agrobacterium tumefaciens*-Mediated Transformation of Monocot Plants." Acta Hort, 1998, 461:401-407.

Waterhouse, P.M., et al., (1998) "Virus Resistance and Gene Silencing in Plants Can Be Induced by Simultaneous Expression of Sense and Antisense RNA," Proceedings of the National Academy of Sciences of the United States of America, 95(23): 13959-13964.

Weselake et al. (2009) "Increasing the flow of carbon into seed oil" Biotechnology Advances 27:866-878.

Williams et al. (1999) "Impaired Endothelial Function Following a Meal Rich in Used Cooking Fat." J. Am. Coll. Cardiol. 33:1050-1055.

Whitelaw et al. (1986) "A Rice FATB Insertional Mutant Exhibits Improved Growth and Reduced Photoinhibition at High Temperatures" Proceedings of the 55th Australian Cereal Chemistry Conference, 55th Australian Cereal Chemistry Conference, Jul. 3-7, 2008, Sydney Australia, Jul. 3, 2005, pates 101-104.

Whitelaw et al., (2004) "Investigation of lipid synthesis in the rice grain: modification of fatty acids in rice bran oil." In C.K. Black, J.F. Panozzo, and G.J. Rebetzke (Eds.), Cereals 2004: Proceedings of the 54th Australian Cereal Chemistry Conference and 11th Wheat Breeders Assembly, Sep. 21-24, 2004, Canberra ACT, North Melbourne VIC: Cereal Chemistry Division, Royal Australian Chemical Institute, AU (pp. 418-420).

Yasumatsu et al. (1966) "Studies on Cereals Part V Stale Flavor of Stored Rice." Agric. Biol. Chem. 30:483-486.

Yen et al., Identification of a gene encoding MGAT1, a monoacylglycerol acyltransferase. PNAS, 2002, 99(13):8512-8517.

Zhou et al. (2002) "Ageing of Stored Rice: Changes in Chemical and Physical Attributes." Journal of Cereal Science 35:65-78.

Zock et al. (1994) "Impact of myristic acid versus palmitic acid on serum lipid and piloprotein levels in healthy women and men." Arterioscler Thromb. 14: 567-575.

Connolly et al. (1998) GenBank Accession No. AC004236, NCBI, pp. 1-11.

Sharma et al., (2003) GenBank Accesion No. AC108870, NCBI, pp. 1-27.

Kim et al., (1999) GenBank Accesion No. AF213480, NCBI, p. 1.

Sasaki et al., (2001) GenBank Accession No. AP004047, NCBI, pp. 1-36.

Sasaki et al., (1999) GenBank Accession No. AP000399, NCBI, pp. 1-33.

Sasaki et al., (2001) Genbank Accession No. AP004236, NCBI, pp. 1-37.

Sasaki et al., (2002) GenBank Accession No. AP005168, NCBI, pp. 1-31.

Sasaki et al., (2002) GenBank Accession No. AP005291, NCBI, pp. 1-38.

File History of U.S. Patent Publication No. 2011-0314725, Petrie et al., published Dec. 29, 2011 (U.S. Appl. No. 13/171,032, filed Jun. 28, 2011).

File History of U.S. Patent Publication No. 2011-0223311, Liu et al., published Sep. 15, 2011 (U.S. Appl. No. 13/011,773, filed Jan. 21, 2011).

File History for U.S. Patent Publication No. 2009-0308041, Whitelaw et al., Dec. 17, 2009 (U.S. Appl. No. 12/309,276, filed Jul. 6, 2009).

File History of U.S. Patent Publication No. 2011-0229623, Liu et al., Sep. 22, 2011 (U.S. Appl. No. 13/011,779, filed Jan. 21, 2011)).

File History of U.S. Patent Application Publication No. 2013/0164798, Vanhercke et al., published Jun. 27, 2013 (U.S. Appl. No, 13/725,404, filed Dec. 21, 2013).

U.S. Appl. No. 13/841,641, Vanhercke et al., filed Mar. 15, 2013.

English Language Translation of Jun. 26, 2013 Office Action, issued in connection with Chinese Patent Application No. 200980134226.8.

\* cited by examiner

Oleic
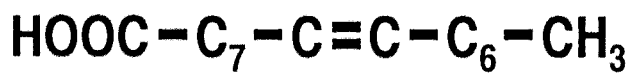
DHS
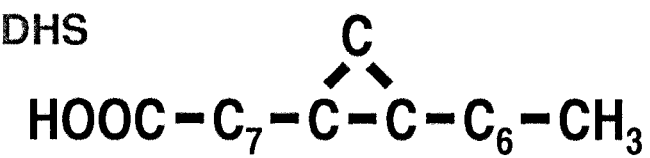
STC
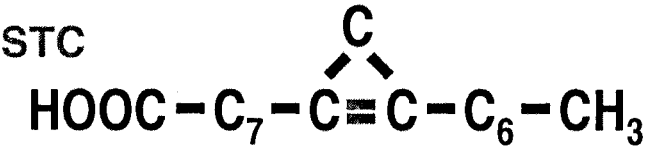
MVL
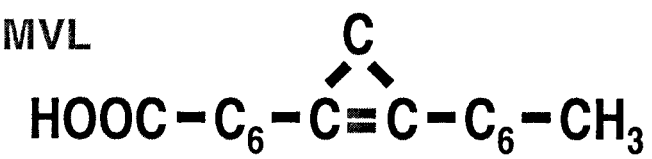
Figure 2

```
                10                         30                         50
CAAAACCAACACGCCTTCTTTGCCTCGTGTTTCATCACCTGGCGTTAAACTGCTTTCTTT
                70                         90                        110
AAAACCAACAAAATGGGTGCCGGGTGGGTAGGATGCCAATTGACGGGTATAAAGGAGGAA
                        M   G   A   G   W   V   G   C   Q   L   T   G   I   K   E   E
               130                        150                        170
AATCGAGGCTCGGTCAATCGAGTTCCGATCGAGAAGCCTCCGTTTACGCTCGGTCAGATC
  N   R   G   S   V   N   R   V   P   I   E   K   P   P   F   T   L   G   Q   I
               190                        210                        230
AAGCAAGCCATTCCGCCCCACTGTTTTCGCCGCTCCCTCCTTCGATCCTTCTCCTACGTG
  K   Q   A   I   P   P   H   C   F   R   R   S   L   L   R   S   F   S   Y   V
               250                        270                        290
GTCCATGACCTATGCTTAGCCTCTCTCTTTTACTACATTGCAACATCATATTTTCACTTT
  V   H   D   L   C   L   A   S   L   F   Y   Y   I   A   T   S   Y   F   H   F
               310                        330                        350
CTCCCACAACCCTTTTCCTACATTGCTTGGCCTGTCTATTGGGTTCTCCAAGGTTGCATC
  L   P   Q   P   F   S   Y   I   A   W   P   V   Y   W   V   L   Q   G   C   I
               370                        390                        410
CTCACCGGTGTTTGGGTCATCGCACACGAATGCGGTCACCACGCTTTCAGTGACTACCAA
  L   T   G   V   W   V   I   A   H   E   C   G   H   H   A   F   S   D   Y   Q
               430                        450                        470
TGGGTTGACGACACCGTCGGGTTGATCCTTCACTCCGCCCTTTTAGTCCCGTACTTCTCG
  W   V   D   D   T   V   G   L   I   L   H   S   A   L   L   V   P   Y   F   S
               490                        510                        530
TGGAAAATCAGTCACCGCCGTCACCACTCGAACACCGGTTCCATGGAGCGTGACGAAGTA
  W   K   I   S   H   R   R   H   H   S   N   T   G   S   M   E   R   D   E   V
               550                        570                        590
TTCGTGCCCAAACCCAAGTCTAAATTATCATGCTTTGCGAAATACTTCAACAATCCACCC
  F   V   P   K   P   K   S   K   L   S   C   F   A   K   Y   F   N   N   P   P
               610                        630                        650
GGTCGAGTTCTCTCTCTTGTAGTCACATTGACTCTTGGTTGGCCTATGTACTTAGCCTTC
  G   R   V   L   S   L   V   V   T   L   T   L   G   W   P   M   Y   L   A   F
               670                        690                        710
AACGTTTCGGGTCGATACTATGATCGATTAGCTTCCCACTATAACCCTTACGGCCCCATT
  N   V   S   G   R   Y   Y   D   R   L   A   S   H   Y   N   P   Y   G   P   I
```

Figure 3

```
       730                750                770
TACTCCGAACGCGAGAGGCTACAAGTTTACATCTCCGATGCTGGTATAGTTGCGGTAATT
 Y  S  E  R  E  R  L  Q  V  Y  I  S  D  A  G  I  V  A  V  I
       790                810                830
TATGTACTTTATAAGATTGCTGCAACAAAAGGGCTGGCTTGGCTTTTATGCACTTATGGG
 Y  V  L  Y  K  I  A  A  T  K  G  L  A  W  L  L  C  T  Y  G
       850                870                890
GTACCTCTACTTATTGTGAATGCCTTCCTTGTGTTGATCACCTACTTGCAACATACTCAC
 V  P  L  L  I  V  N  A  F  L  V  L  I  T  Y  L  Q  H  T  H
       910                930                950
TCGGCATTGCCGCATTACGACTCGTCTGAATGGGATTGGTTTCGAGGAGCATTGTCGACG
 S  A  L  P  H  Y  D  S  S  E  W  D  W  F  R  G  A  L  S  T
       970                990                1010
ATTGATCGAGATTACGGGGTGTTGAACAAAGTGTTCCATAACATCACCGATACGCATGTG
 I  D  R  D  Y  G  V  L  N  K  V  F  H  N  I  T  D  T  H  V
      1030               1050                1070
GCTCATCACCTCTTCTCAACGATGCCACATTATCATGCAATGGAGGCCACTAAAGCAATC
 A  H  H  L  F  S  T  M  P  H  Y  H  A  M  E  A  T  K  A  I
      1090               1110                1130
AAACCGATACTCGGCAAGTATTATCCTTTCGACGGGACACCGATTTATAAGGCAATGTGG
 K  P  I  L  G  K  Y  Y  P  F  D  G  T  P  I  Y  K  A  M  W
      1150               1170                1190
AGGGAGGCAAAAGAGTGCCTTTACGTCGAGGCTGACGTTGGTGGTGGTGGTAGCAAAGGT
 R  E  A  K  E  C  L  Y  V  E  A  D  V  G  G  G  G  S  K  G
      1210               1230                1250
GTTTTTTGGTATCGTAACAAGTTCTAAAGACAGACCAACTGCCTGATAGCTGGCCGGCAA
 V  F  W  Y  R  N  K  F  *
      1270               1290                1310
AATCGACGTAAAACGTACTTATTAGACTAGTGTTAACTAGGGAAGTTAATAATGGTAGGA
      1330               1350
AAATGTGGAATAGCTGCCTAGTAGTTTTATGTATTAAGTGTT
```

Figure 3 continued

```
          10                  30                  50
TTTTGTAGATCGCAAGCCGTAGAAGTAAACAAAGAAGGATTTGCAGATCTTAAATCATGC
          70                  90                 110
TGTAATTTTCTCGAGGAAATTTTTTACCTTCATTGATTCGTTTCTATTTTCGCTTGAGTT
         130                 150                 170
GGAGAATGCTTCAGCTGCCTTTCTAAAAGATTGTTTCCAAAAGAGGGAATTTTAGTGGAT
         190                 210                 230
AATAGAAGTTCTTTTTAATTCTCAAAATCATGGTTGCCACTGCTGCTACATCCTCATTCT
                                  M  V  A  T  A  A  T  S  S  F  F
         250                 270                 290
TTCCCGTAACTTCTTCCCCTGACTCCTcTGACTCAAAAAaCAAGAAGCTTGGAAGTGGAT
   P  V  T  S  S  P  D  S  S  D  S  K  N  K  K  L  G  S  G  S
         310                 330                 350
CTACTAACCTCGGAGGCATCAAGTCGAAACCATCTGCTTCTTCTGGAAGTTTGCAAGTCA
   T  N  L  G  G  I  K  S  K  P  S  A  S  S  G  S  L  Q  V  K
         370                 390                 410
AGGCAAATGCTCAAGCCCCTCCAAAGATAAATGGTACCACTGTTGTAACTTCTCCGGTTG
   A  N  A  Q  A  P  P  K  I  N  G  T  T  V  V  T  S  P  V  E
         430                 450                 470
AAGGTTTCAAGAACGAAGATGGTGCAGGTTCCCCTCATCCTCGGACCTTTATCAATCAAT
   G  F  K  N  E  D  G  A  G  S  P  H  P  R  T  F  I  N  Q  L
         490                 510                 530
TACCTGATTGGAGCATGCTTCTTGCCGCTATCACAACCATTTTCCTGGCTGCTGAGAAGC
   P  D  W  S  M  L  L  A  A  I  T  T  I  F  L  A  A  E  K  Q
         550                 570                 590
AGTGGATGATGCTTGATTGGAAGCCAAGGCGGCCTGACATGCTCATTGATCCTTTTGGTA
   W  M  M  L  D  W  K  P  R  R  P  D  M  L  I  D  P  F  G  I
         610                 630                 650
TAGGGAGGATTGTTCAGGATGGTCTTGTTTTCCGTCAAAACTTCTCGATTAGGTCTTATG
   G  R  I  V  Q  D  G  L  V  F  R  Q  N  F  S  I  R  S  Y  E
         670                 690                 710
AgATAGGTGCTGATCGTACGGCATCCATAGAGACGCTAATGAATCATTTACAGGAAACCG
   I  G  A  D  R  T  A  S  I  E  T  L  M  N  H  L  Q  E  T  A
         730                 750                 770
CGATTAATCATTGTAAAAGTGCTGGACTGcTTGGAgAAgGtTTTGGTGCTACCCCTGAGA
   I  N  H  C  K  S  A  G  L  L  G  E  G  F  G  A  T  P  E  M
```

Figure 4

```
             790                  810                 830
TGTGCAAGAAGAACCTAATTTGGGTGGTCACTCGGATGCAAGTTGTGTTTGATCGGTATC
  C   K   K   N   L   I   W   V   V   T   R   M   Q   V   V   F   D   R   Y   P
             850                  870                 890
CTACTTGGGGTGAtGTTGTTCAAGTAGACACTTGGGTCAGTGCATCAGGAAAGAATGGCA
  T   W   G   D   V   V   Q   V   D   T   W   V   S   A   S   G   K   N   G   M
             910                  930                 950
TGCGAAGAGATTGGCTTGTCAGTGATAGTAAAACTGGTGAAGTTTTAACAAGAGCCTCAA
  R   R   D   W   L   V   S   D   S   K   T   G   E   V   L   T   R   A   S   S
             970                  990                1010
GTGTGTGGGTGATGATGAATAAATTGACTAGAAGGCTATCTAAAATTCCTGAGGAGGTCC
  V   W   V   M   M   N   K   L   T   R   R   L   S   K   I   P   E   E   V   R
            1030                 1050                1070
GAGGAGAAATAGAACCTTATTTTATGAATTCCGATCCTGTTGTGGCAGAAGATAGCCGGA
  G   E   I   E   P   Y   F   M   N   S   D   P   V   V   A   E   D   S   R   K
            1090                 1110                1130
AATTAGTGAAGCTCGATAAAAGCATGGCTGAGCACGTGcGTAAAGGTTTAACTCCTAGAT
  L   V   K   L   D   K   S   M   A   E   H   V   R   K   G   L   T   P   R   W
            1150                 1170                1190
GGAGTGACTTGGATGTCAACCAACATGTCAATAACGTGAAGTACATTGGCTGGATCCTCG
  S   D   L   D   V   N   Q   H   V   N   N   V   K   Y   I   G   W   I   L   E
            1210                 1230                1250
AGAGTGCTCCATTGCCGGTGTTGGAAACTCACGAGCTTTCTTCCATGACACTGGAGTATA
  S   A   P   L   P   V   L   E   T   H   E   L   S   S   M   T   L   E   Y   R
            1270                 1290                1310
GGAGGGAGTGTGGGAGGGAGAGCATACTGCAGTCGCTAACAACCGTGTCCGACTCCAGTG
  R   E   C   G   R   E   S   I   L   Q   S   L   T   T   V   S   D   S   S   V
            1330                 1350                1370
TAGGAGACTTGGTGAATGTGGGTGAAATCGAgTGCCAGCACCTGCTGCAACTCGAGGAAG
  G   D   L   V   N   V   G   E   I   E   C   Q   H   L   L   Q   L   E   E   G
            1390                 1410                1430
GGTCCGAGATTGTGAGAGGGAGAACTCAATGGAGGCCCAAGTATGCCAAAAGTTTTGGTA
  S   E   I   V   R   G   R   T   Q   W   R   P   K   Y   A   K   S.  F   G   N
            1450                 1470                1490
ATGTGGGTCAAATTCCAGCAGAAAGTGCATAGAAGGAAAAAATCCCAAAATTTCTCTTAT
  V   G   Q   I   P   A   E   S   A   *
```

Figure 4 continued

```
       1510                1530                1550
TGTGACCTAAGTGGGGCAATAGTCTGATTGCCGGGTGTCACAATGATTTATGTAGAATCT
       1570                1590                1610
AATCATGTGTTCTATGGATATATATATATATATATTTATGCTTCTTTTTTATATATAAAT
       1630
AATATTATATATTCCTTTTAAAAAAAA
```

Figure 4 continued

```
TAGCGCTAGAAGTTACCGAGAAGAGTTTAGAGATCCCTATTATCGGAAAGAGGGGATTTC
AGCGGATAACAGAAGTTCATTTTAATTTATAAAATCATGGTTGCCACTGCTGCTACATCC
                                        M  V  A  T  A  A  T  S
TCATTCTTTCCAATCACTTCTTCCCCGGACTCCATTGACTCAAAAAACAAGAAGCTTGGA
 S  F  F  P  I  T  S  S  P  D  S  I  D  S  K  N  K  K  L  G
AATGGATCTACTAACCTTGGAGGTATAAAGTTGAAACCATctGCTTCTTCTGGAAGTTTG
 N  G  S  T  N  L  G  G  I  K  L  K  P  S  A  S  S  G  S  L
CAAGTTAAGGCAAATGCACAAGCCCCCCAAAGATAAATGGTACCACAGTTGTGATGACT
 Q  V  K  A  N  A  Q  A  P  P  K  I  N  G  T  T  V  V  M  T
CCAGTAGAAGGTTTCCCGAGCGAAGATGCTGCAAGTTCCCTACCTCCCAGGACGTTTATC
 P  V  E  G  F  P  S  E  D  A  A  S  S  L  P  P  R  T  F  I
AATCAGCTACCTGATTGGAGCATGCTTCTTGCTGCTATGACAACCATTTTCCTGGCTGCT
 N  Q  L  P  D  W  S  M  L  L  A  A  M  T  T  I  F  L  A  A
GAGAAGCAGTGGATGATGCTTGATTGGAAGCCAAAGCGGCCTGACATGCTCATTGACCCA
 E  K  Q  W  M  M  L  D  W  K  P  K  R  P  D  M  L  I  D  P
TTTGGGATAGGGAGGATTGTTCAGGATGGTCTTGTTTTTCGTCAGAACTTCTCAATTAGG
 F  G  I  G  R  I  V  Q  D  G  L  V  F  R  Q  N  F  S  I  R
TCTTATGAGATAGGTGCTGATCGTACAGCATCCATAGAGACGCTAATGAATCATTTACAG
 S  Y  E  I  G  A  D  R  T  A  S  I  E  T  L  M  N  H  L  Q
GAAACAGCGATTAATCATTGTAAAAGTGCTGGACTGCTAGGAGATGGTTTTGGTGCTACC
 E  T  A  I  N  H  C  K  S  A  G  L  L  G  D  G  F  G  A  T
CCTGGGATGTGCAAGAAAAACCTAATATGGGTAGTCACCCGGATGCAAGTTGTGGTTGAT
 P  G  M  C  K  K  N  L  I  W  V  V  T  R  M  Q  V  V  V  D
TGTTATCCAACTTGGGGTGATGTTGTTCAAGTAGACACTTGGGTCAGTGCATCAGGAAAG
 C  Y  P  T  W  G  D  V  V  Q  V  D  T  W  V  S  A  S  G  K
AATGGCATGCGAAGGGATTGGCTTGTCAGCAATAGTAAAACTGGTGAAATTTTAACTAGA
 N  G  M  R  R  D  W  L  V  S  N  S  K  T  G  E  I  L  T  R
GCCTCAAGTGTGTGGGTGATGATGAATAAATTGACCAGAAGGTTATCTAAAATTCCAGAA
 A  S  S  V  W  V  M  M  N  K  L  T  R  R  L  S  K  I  P  E
GAGGTCCGAGGAGAAATAGAACCTCATTTTATGAATTCAGATCCAGTGGTGGCTGAGGAT
 E  V  R  G  E  I  E  P  H  F  M  N  S  D  P  V  V  A  E  D
AACCGGAAATTAGTGAAACTTGACGACAGCACAGCCCAATATGTGCGCAAGGGTTTAACT
 N  R  K  L  V  K  L  D  D  S  T  A  Q  Y  V  R  K  G  L  T
CCTCGATGGAGCGACCTGGATGTGAATCAGCATGTCAACAATGTGAAGTACGTTGGTTGG
 P  R  W  S  D  L  D  V  N  Q  H  V  N  N  V  K  Y  V  G  W
ATCCTTGAGAGTACACCATTGGGAATTGTGGAGAGTCATGAGCTTTGTTCCATGACACTG
 I  L  E  S  T  P  L  G  I  V  E  S  H  E  L  C  S  M  T  L
```

Figure 5

```
GAGTATAGGAGGGAGTGTGGGAgGGACAGCGTGCTGCAGTCACTAACTGCGGTGTCTGGT
 E  Y  R  R  E  C  G  R  D  S  V  L  Q  S  L  T  A  V  S  G
GTGGGCAACCTCGGGAATATGGGGGAAATTGAGTGCCAGCACTTGCTCCAACTTGAAGAG
 V  G  N  L  G  N  M  G  E  I  E  C  Q  H  L  L  Q  L  E  E
GGGTCTGAGATTGTGAGAGGGAGGACACAGTGGAGGCCAAAGAATGCCAAGAGTTTTGGT
 G  S  E  I  V  R  G  R  T  Q  W  R  P  K  N  A  K  S  F  G
AAAATGGATCAAGTTCCCGCACAAAGTGCATAGATCCGAAGTCTCTTTGCTGCGTGTCAA
 K  M  D  Q  V  P  A  Q  S  A  *
AACTAGCAGTCAACGCATTGTGTAGAATCTTTCTTTTGTTCTTTGAATCCATAATATATA
TATATGATATTAGCTTGTAAGCTTTCAAAGCTTGCTGTAATTAGCTCTAAAAAAAAAA
```

Figure 5 continued

```
  1  ATGGTTTACC CACGCGTCCG GTAGAACATG TTGGTGAAGA ATATATTGAG
 51  GAGTTTTACA GATGCTGTGA CCAATTACTG AAAGAAGATG GACTTTTTGT
101  TCTTCAGTTC ATATCTATCC CAGAAGAGCT TTCCAAAGAA ATCCAGCAAA
151  CAGCAGGTTT TCTAAAGGAA TATATATTCC CCGGTGGAAC CCTGCTTTCT
201  TTGGATAGGA ATTTATCAGC CATGGCTGCT GCAACAAGAT TCAGTGTGGA
251  GCATGTGGAA AATATAGGAA TGAGTTATTA CCACACACTG AGATGGTGGA
301  GAAAACTTTT CCTGGAAAAC ACAAGCAAAG TTCTAGCTCT GGGATTCGAC
351  GAGAAGTTCA TGAGGACATG GAATACTAT TTCGATTACT GCGCTGCCGG
401  TTTTAAGACA GGAACCCTTA TAGATTACCA GGTTGTATTT TCGCGGGCCG
451  GAAATTTCGG TACACTCGGA GATCCATACA AAGGTTTCCC TTCTGCATAC
501  TCCTTCATGG ATGATTGAAC AAAGTGTGGT TGAACATTGA TCCAAAGAAG
551  CAAACAAAAT TATCACCACA CTGCCAGTGT TAAGAACAAC CTATCTCCCT
601  AGTCCCTACT TTTCTTTATT ATGGCTATGT TTGCAATGCA AGAATAAGCA
651  AACATTGTAA TGTCAATAAA GTTTGCACTT TTGTAGACTG GATGGGATGT
701  TATCAATGAA GTACCTAGTT TATAAGTAAA AAAAAAAAA AGA
```

Figure 6

```
GCACAAGGTAAAGCAGTGTACCGGCGGCAGTGATGGAAGTGGCCGTGATCGGAGGTGGGA
                                 M  E  V  A  V  I  G  G  G  I
TAAAAGGGTTGCTTTCGGCCTACGTACTGGTCAAAGCCGGCGTGGACGTGGTGGTTTACG
 K  G  L  L  S  A  Y  V  L  V  K  A  G  V  D  V  V  V  Y  E
AGAAAGAAGAACAATTAGGCGGCCATGCAAAGACTGTTAACTTCGACGCCGTTGATTTAG
 K  E  E  Q  L  G  G  H  A  K  T  V  N  F  D  A  V  D  L  D
ACCTTGGCTTCTTGTTTCTCAATCCAGCAAGATATGCAACACTATTGCATATGTTCGACA
 L  G  F  L  F  L  N  P  A  R  Y  A  T  L  L  H  M  F  D  S
GCCTTGGTGTTGATGTAGAAACATCCGATGTTTCATTCTCTATAAGCCATGACAAAGGCA
 L  G  V  D  V  E  T  S  D  V  S  F  S  I  S  H  D  K  G  N
ACAATGGCTATGAATGGTGCAGCCAATATGGATTTTCCAATTACTTTGCTCAAAAGAAGA
 N  G  Y  E  W  C  S  Q  Y  G  F  S  N  Y  F  A  Q  K  K  K
AACTGTTGAACCCTTTCAATTGGCAAAGCCTCAGAGAGATCATCAAATTCGGCAATGATG
 L  L  N  P  F  N  W  Q  S  L  R  E  I  I  K  F  G  N  D  V
TCGAAAGTTACCTTGGATCACTTGAGAACAACCCAGACATTGATCGTACTGAGACCTTGG
 E  S  Y  L  G  S  L  E  N  N  P  D  I  D  R  T  E  T  L  G
GACAGTTTATAAACTCAAAGGGCTACTCTGAAAATTTTCAAAACACTTATCTGGCTCCTA
 Q  F  I  N  S  K  G  Y  S  E  N  F  Q  N  T  Y  L  A  P  I
TATGTGGTTCAATGTGGTCAAGCTCCAAGGAAGATGTTACGAGCTTTTCAGCTTTTTCCA
 C  G  S  M  W  S  S  S  K  E  D  V  T  S  F  S  A  F  S  I
TCCTTTCATTTTGCCGTACTCATCATTTGTACCAGCTATTTGGGCAGTCACAGTGGTTGA
 L  S  F  C  R  T  H  H  L  Y  Q  L  F  G  Q  S  Q  W  L  T
CTATCAAAGGGCACTCACATTTTGTTAAAAGGGTTAGGGAAGTGCTGGAGACTAAAGGTT
 I  K  G  H  S  H  F  V  K  R  V  R  E  V  L  E  T  K  G  C
GTCAATTTAAACTCGGTTGTGAAGTACAATCTGTTTTGCCCGTTGATAATGGTACCGCCA
 Q  F  K  L  G  C  E  V  Q  S  V  L  P  V  D  N  G  T  A  M
TGGTCTGTGGAGATGGTTTCCAAGAAACTTACAATGGATGCATAATGGCTGTTGATGCTC
 V  C  G  D  G  F  Q  E  T  Y  N  G  C  I  M  A  V  D  A  P
CCACTGCCCTAAAATTATTAGGAAACCAAGCAACATTTGAAGAAACAAGAGTACTGGGTG
 T  A  L  K  L  L  G  N  Q  A  T  F  E  E  T  R  V  L  G  A
CTTTCCAATATGCTACCAGTGATATTTTCCTTCACCAGGACAGTACTTTAATGCCACAAA
 F  Q  Y  A  T  S  D  I  F  L  H  Q  D  S  T  L  M  P  Q  N
ACAAATCAGCTTGGAGTGCATTGAATTTTCTAATAGTAGCAAAAATAATGCATTCTTAA
 K  S  A  W  S  A  L  N  F  L  N  S  S  K  N  N  A  F  L  T
CATACTGGCTCAATGCACTACAGAATATTGGGAAAACAAGTGAGCCATTTTTTGTGACTG
 Y  W  L  N  A  L  Q  N  I  G  K  T  S  E  P  F  F  V  T  V
TCAATCCAGACCATACCCCGAAGAATACCTTACTTAAGTGGTCAACCGGCCATGCAATTS
 N  P  D  H  T  P  K  N  T  L  L  K  W  S  T  G  H  A  I  X
CCTCTGTTGCTGCATCAAAAGCTTCACTTGAGCTTGGTCAGATTCAGGGAAAGAGAGGAA
 S  V  A  A  S  K  A  S  L  E  L  G  Q  I  Q  G  K  R  G  I
TCTGGTTCTGTGGCTATGACTTCAATCAGGATGAACTAAAGGCTGGTATGGATGCTGCAC
 W  F  C  G  Y  D  F  N  Q  D  E  L  K  A  G  M  D  A  A  H
ATGGTATCTTGGGAAAGCATTCTTCTGTTCCGCCCAGTCCAAAGAATATGTCACCCTCTT
 G  I  L  G  K  H  S  S  V  P  P  S  P  K  N  M  S  P  S  L
TACCAAAGAATATGTCACCCTCTTTCATGGAAACAACGGCACGCCTCTTTGTTACCAAAT
 P  K  N  M  S  P  S  F  M  E  T  T  A  R  L  F  V  T  K  F
TCTTTCAACAATATATATCTATGGGCTGCGTAATTTTTTTAGAGGAAGGAGGCAGAATTT
 F  Q  Q  Y  I  S  M  G  C  V  I  F  L  E  E  G  G  R  I  F
TCACTTTCAAAGGAAACATGGAAAAGTGTCCTCTTAAAACAGTTCTGAAAGTGCATAATC
 T  F  K  G  N  M  E  K  C  P  L  K  T  V  L  K  V  H  N  P
CTCAGTTTTACTGGAGGATCATGAAAGAAGCTGATATAGGCCTTGCAGACGCATATATCC
 Q  F  Y  W  R  I  M  K  E  A  D  I  G  L  A  D  A  Y  I  H
ATGGAGATTTTTCTTTTCTTGATGAAAATGAAGGCCTTCTTAATCTTTTCCGGATTCTTG
 G  D  F  S  F  L  D  E  N  E  G  L  L  N  L  F  R  I  L  V
TTGCCAATAAAGAGAACTCAGCTGCCTCAGGGTCGACTAAAAGAAGGACTTGGTGGTCGC
 A  N  K  E  N  S  A  A  S  G  S  T  K  R  R  T  W  W  S  P
CTGCTCTGTTAACAGCTAGTATATCATCTGCCAAGTATTTTGTGAAGCATCTCTTAAGAC
 A  L  L  T  A  S  I  S  S  A  K  Y  F  V  K  H  L  L  R  Q
```

Figure 7

```
AAAATACTATTACACAAGCTCGTAGGAACATTTCTCGTCATTATGATCTGAGTAATGAAC
   N  T  I  T  Q  A  R  R  N  I  S  R  H  Y  D  L  S  N  E  L
TTTTCTCTCTATACTTGGGCAAAATGATGCAATACTCTTCTGGAGTCTTTAGGACAGGAG
   F  S  L  Y  L  G  K  M  M  Q  Y  S  S  G  V  F  R  T  G  E
AAGAACATTTGGACGTTGCACAGCGAAGAAAAATCAGTTCTCTAATTGAGAAAACAAGGA
   E  H  L  D  V  A  Q  R  R  K  I  S  S  L  I  E  K  T  R  I
TAGAGAAATGGCATGAAGTTCTAGACATTGGGTGCGGTTGGGGAAGCTTAGCTATTGAAA
   E  K  W  H  E  V  L  D  I  G  C  G  W  G  S  L  A  I  E  T
CTGTGAAAAGAACAGGATGCAAATATACTGGCATCACTCTATCAGAACAGCAACTGAAAT
   V  K  R  T  G  C  K  Y  T  G  I  T  L  S  E  Q  Q  L  K  Y
ATGCTCAAGAAAAAGTGAAGGAAGCTGGACTCGAGGATAACATCAAAATACTTCTCTGTG
   A  Q  E  K  V  K  E  A  G  L  E  D  N  I  K  I  L  L  C  D
ACTATCGCCAGTTACCTAAGGAACACCAATTTGACAGAATCATATCTGTAGAGATGGTAG
   Y  R  Q  L  P  K  E  H  Q  F  D  R  I  I  S  V  E  M  V  E
AACATGTTGGTGAAGAATATATTGAGGAATTTTACAGATGCTGTGATCAATTACTGAAAG
   H  V  G  E  E  Y  I  E  E  F  Y  R  C  C  D  Q  L  L  K  E
AAGATGGACTTTTCGTTCTTCAGTTCATATCTATCCCAGAGGAGCTTTCCAAAGAAATCC
   D  G  L  F  V  L  Q  F  I  S  I  P  E  E  L  S  K  E  I  Q
AGCAAACAGCTGGTTTTCTTAAGGAATATATATTCCCTGGTGGAACCCTGCTTTCTTTGG
   Q  T  A  G  F  L  K  E  Y  I  F  P  G  G  T  L  L  S  L  D
ATAGGAATTTATCAGCCATGGCTGCTGCAACAAGATTCAGTGTGGAGCATGTGGAAAACA
   R  N  L  S  A  M  A  A  A  T  R  F  S  V  E  H  V  E  N  I
TAGGAATGAGTTATTACCACACACTGAGATGGTGGAGAAAACTTTTCCTGAAAAACACAA
   G  M  S  Y  Y  H  T  L  R  W  W  R  K  L  F  L  K  N  T  S
GCAAAGTTCTGGCTTTGGGGTTCGACGAGAAGTTCATGCGGACATGGAATACTATTTCG
   K  V  L  A  L  G  F  D  E  K  F  M  R  T  W  E  Y  Y  F  D
ATTACTGTGCTGCTGGTTTTAAGACAGGAACCCTTATAGATTACCAGGTTGTATTTTCTC
   Y  C  A  A  G  F  K  T  G  T  L  I  D  Y  Q  V  V  F  S  R
GAGCCGGTAATTTCGGTACACTTGGAGATCCATACAAAGGTTTCCCTTCTGCATATTCCT
   A  G  N  F  G  T  L  G  D  P  Y  K  G  F  P  S  A  Y  S  F
TCATGGATGATTGAACAAAGTGTTTGAATATATGATCACCATACAATGATTCAACCAGCT
   M  D  D  *
GGATCAAACTGGTACCAGTGTTTACCTAGTCCCCTGCTTTTGTTTAGTTATGGTTTTCGT
TTCGTTGCGAAAAGAAAAAAGCAAATAATGTATGTTAATAATGAAATGTTTGTATCTGG
TATATCTATACTGGTTGGATTTTATGTATGGAGATCTGTTTCTTTTTAAAAAAAAAAAAA
AAAA
```

Figure 7 continued

```
                    10                    30                    50
         GTCACGGCGGCAGTGATGGAAGTGGCGGTGATCGGAGGTGGGATAAAAGGGTTGGTTTCG
                      M  E  V  A  V  I  G  G  G  I  K  G  L  V  S
                    70                    90                   110
         GCCTACGTACTGGTCAAAGCCGGCGTGGACGTGGTGGTTTACGAGAAAGAAGAGCAATTA
          A  Y  V  L  V  K  A  G  V  D  V  V  V  Y  E  K  E  E  Q  L
                   130                   150                   170
         GGCGGCCATGCGAAGACTGTTAACTTCGACGCCGTTGACTTAGACCTTGGCTTCTTGTTT
          G  G  H  A  K  T  V  N  F  D  A  V  D  L  D  L  G  F  L  F
                   190                   210                   230
         CTTAATCCTGCAAGATATGCAACACTGTTGGATATAATCGACAGCCTTGGTGTTGATGTA
          L  N  P  A  R  Y  A  T  L  L  D  I  I  D  S  L  G  V  D  V
                   250                   270                   290
         GAAACATCCGATGTTTCATTCTCTATAAGCCATGACAAAGGCAACAATGGCTATGAATGG
          E  T  S  D  V  S  F  S  I  S  H  D  K  G  N  N  G  Y  E  W
                   310                   330                   350
         TGCAGTCAATATGGATTTTCCAATTACTTTGCACAAAAGAAGAAACTGTTGAACCCTTTC
          C  S  Q  Y  G  F  S  N  Y  F  A  Q  K  K  K  L  L  N  P  F
                   370                   390                   410
         AATTGGCAAAACCTTAGAGAGATCATCAGATTCAGCAACGATGTCGAAAGTTACCTTGGA
          N  W  Q  N  L  R  E  I  I  R  F  S  N  D  V  E  S  Y  L  G
                   430                   450                   470
         TCACTTGAGAACAACCCAGACATTGATCGTACTGAGACCTTGGGACAGTTTATAAAATCA
          S  L  E  N  N  P  D  I  D  R  T  E  T  L  G  Q  F  I  K  S
                   490                   510                   530
         AAGGGCTACTCTGAAAATTTTCAAAACACTTACCTGGCTCCTATATGTGGTTCAATGTGG
          K  G  Y  S  E  N  F  Q  N  T  Y  L  A  P  I  C  G  S  M  W
                   550                   570                   590
         TCAAGCTCCAAGGAAGATGTTATGAGCTTTTCAGCATTTTCCATCCTTTCATTTTGCCGT
          S  S  S  K  E  D  V  M  S  F  S  A  F  S  I  L  S  F  C  R
                   610                   630                   650
         ACTCATCATTTGTACCAGCAATTTGGGCAGCCACAGTGGTTGACTATCAAAGGGCACTCA
          T  H  H  L  Y  Q  Q  F  G  Q  P  Q  W  L  T  I  K  G  H  S
                   670                   690                   710
         CATTTTGTTAAAAGGGTTAGGGAAGTGCTGGAGACTAAAGGTTGTCAATTTAAACTCGGT
          H  F  V  K  R  V  R  E  V  L  E  T  K  G  C  Q  F  K  L  G
                   730                   750                   770
         TGTGAAGTACAATCTGTTTTGCCTGCTGATAATGGTACCACCATGGTCTGTGGAGATGGT
          C  E  V  Q  S  V  L  P  A  D  N  G  T  T  M  V  C  G  D  G
                   790                   810                   830
         TTCCAAGAAACTTACAATGGATGCATAATGGCTGTTGATGCTCCCACTGCCCTAAAATTA
          F  Q  E  T  Y  N  G  C  I  M  A  V  D  A  P  T  A  L  K  L
                   850                   870                   890
         TTAGGAAACCAAGCAACATTTGAAGAAACAAGAGTACTGGGTGCTTTCCAATATGCTACC
          L  G  N  Q  A  T  F  E  E  T  R  V  L  G  A  F  Q  Y  A  T
                   910                   930                   950
         AGTGATATTTTCCTTCACCGGGACAGTACTTTAATGCCACAAAACAAATCAGCTTGGAGT
          S  D  I  F  L  H  R  D  S  T  L  M  P  Q  N  K  S  A  W  S
                   970                   990                  1010
         GCATTGAATTTTCTCAATAGTAGCAAAAATAATGCATTCTTAACATACTGGCTAAATGCA
          A  L  N  F  L  N  S  S  K  N  N  A  F  L  T  Y  W  L  N  A
                  1030                  1050                  1070
         CTACAGAATATTGGGAAAACAAGTGAGCCATTTTTTGTGACTGTCAATCCAGACCATACC
          L  Q  N  I  G  K  T  S  E  P  F  F  V  T  V  N  P  D  H  T
                  1090                  1110                  1130
         CCGAAGAATACCTTGCTTAAGTGGTCGACTGGCCATGCAATTCCCTCTGTTGCTGCATCA
          P  K  N  T  L  L  K  W  S  T  G  H  A  I  P  S  V  A  A  S
                  1150                  1170                  1190
         AAAGCTTCACTTGAGCTTGGTCAGATTCAGGGGAAGAGAGGAATCTGGTTCTGTGGCTAT
          K  A  S  L  E  L  G  Q  I  Q  G  K  R  G  I  W  F  C  G  Y
```

Figure 8

```
       1210                1230                1250
GACTTCAATCAGGATGAACTAAAGGCTGGTATGGATGCTGCACATGGTATCTTGGGAAAG
 D  F  N  Q  D  E  L  K  A  G  M  D  A  A  H  G  I  L  G  K
       1270                1290                1310
CATTCTTCTGTTCTGCATAGTCCAAAGAGTATGTCACCCTCTTTCATGGAAACAACGGCA
 H  S  S  V  L  H  S  P  K  S  M  S  P  S  F  M  E  T  T  A
       1330                1350                1370
CGCCTCTTTGTTACTAAATTCTTTCAACAATATATATCTATGGGCTGTGTAATTTTCTTA
 R  L  F  V  T  K  F  F  Q  Q  Y  I  S  M  G  C  V  I  F  L
       1390                1410                1430
GAGGAAGGAGGCAGAATTTTCACTTTCAAAGGAAACATGGAAAAGTGTCCTCTTAAAACA
 E  E  G  G  R  I  F  T  F  K  G  N  M  E  K  C  P  L  K  T
       1450                1470                1490
GTTCTGAAAGTACATAATCCTCAGTTTTACTGGAGGATCATGAAAGAAGCTGATATAGGC
 V  L  K  V  H  N  P  Q  F  Y  W  R  I  M  K  E  A  D  I  G
       1510                1530                1550
CTTGCAGATGCATATATCCATGGAGATTTTTCTTTTCTTGATGAAACTGAAGGCCTTCTT
 L  A  D  A  Y  I  H  G  D  F  S  F  L  D  E  T  E  G  L  L
       1570                1590                1610
AATCTTTTCCGGATTCTTGTTGCCAATAAAGAGAACTCAGCTGCCTCAGGGTCGAATAAA
 N  L  F  R  I  L  V  A  N  K  E  N  S  A  A  S  G  S  N  K
       1630                1650                1670
AGAAGGACTTGGTGGTCACCTGCTCTGTTAACAGCTAGTATATCATCTGCAAAGTATTTT
 R  R  T  W  S  P  A  L  L  T  A  S  I  S  S  A  K  Y  F
       1690                1710                1730
GTGAAGCATCTCTTGAGACAAAATACTATTACACAAGCTCGTAGGAACATTTCTCGTCAT
 V  K  H  L  L  R  Q  N  T  I  T  Q  A  R  R  N  I  S  R  H
       1750                1770                1790
TATGATCTGAGTAATGAACTTTTCACTCTATACTTGGGCAAAATGATGCAATACTCTTCT
 Y  D  L  S  N  E  L  F  T  L  Y  L  G  K  M  M  Q  Y  S  S
       1810                1830                1850
GGAGTCTTTAGGACGGGAGAAGAACATTTGGACGTTGCACAGCGTAGAAAAATCAGTTCT
 G  V  F  R  T  G  E  E  H  L  D  V  A  Q  R  R  K  I  S  S
       1870                1890                1910
CTAATTGAGAAAGCAAGGATAGAGAAACGGCACGAAGTTCTCGACATTGGGTGCGGTTGG
 L  I  E  K  A  R  I  E  K  R  H  E  V  L  D  I  G  C  G  W
       1930                1950                1970
GGAAGCTTAGCTATTGAAACTGTGAAAAGAACAGGATGCAAATATACTGGCATCACTCTA
 G  S  L  A  I  E  T  V  K  R  T  G  C  K  Y  T  G  I  T  L
       1990                2010                2030
TCAGAACAGCAACTGAAATATGCTCAAGAAAAAGTGAAGGAAGCTGGACTCCAGGATAAC
 S  E  Q  Q  L  K  Y  A  Q  E  K  V  K  E  A  G  L  Q  D  N
       2050                2070                2090
ATCAAAATACTTCTCTGTGACTATCGCCAGTTACCTAAGGAACACCAATTTGACAGAATC
 I  K  I  L  L  C  D  Y  R  Q  L  P  K  E  H  Q  F  D  R  I
       2110                2130                2150
ATATCTGTAGAGATGGTAGAACATGTTGGTGAAGAATATATTGAGGAGTTTTACAGATGC
 I  S  V  E  M  V  E  H  V  G  E  E  Y  I  E  E  F  Y  R  C
       2170                2190                2210
TGTGACCAATTACTGAAAGAAGATGGGCTTTTTGTTCTTCAGTTCATATCTATCCCAGAA
 C  D  Q  L  L  K  E  D  G  L  F  V  L  Q  F  I  S  I  P  E
       2230                2250                2270
GAGCTTTCCAAAGAAATCCAGCAAACAGCAGGTTTTCTAAAGGAATATATATTCCCTGGA
 E  L  S  K  E  I  Q  Q  T  A  G  F  L  K  E  Y  I  F  P  G
       2290                2310                2330
GGAACCCTGCTTTCTTTGGATAGGAATTTATCAGCCATGGCTGCTGCAACAAGATTCAGT
 G  T  L  L  S  L  D  R  N  L  S  A  M  A  A  A  T  R  F  S
       2350                2370                2390
GTGGAGCATGTGGAAAATATAGGAATGAGTTATTACCACACACTGAGATGGTGGAGAAAA
 V  E  H  V  E  N  I  G  M  S  Y  Y  H  T  L  R  W  W  R  K
```

Figure 8 continued

```
         2410                2430                2450
CTTTTCCTGGAAAACACAAGCAAAGTTCTAGCTCTGGGGTTCGACGAGAAGTTCATGAGG
 L  F  L  E  N  T  S  K  V  L  A  L  G  F  D  E  K  F  M  R
         2470                2490                2510
ACATGGGAATACTATTTCGATTACTGCGCTGCCGGTTTTAAGACAGGAACTCTTATAGAT
 T  W  E  Y  Y  F  D  Y  C  A  A  G  F  K  T  G  T  L  I  D
         2530                2550                2570
TACCAGGTTGTATTTTCAAGGGCCGGAAATTTCGGTACACTCGGAGATCCATACAAAGGT
 Y  Q  V  V  F  S  R  A  G  N  F  G  T  L  G  D  P  Y  K  G
         2590                2610                2630
TTCCCTTCTGCATATTCCTTCATGGATGATTGAACAAAGTGTGGTTGAACATTGATCCAA
 F  P  S  A  Y  S  F  M  D  D  *
         2650                2670                2690
AGAAGCAAACAAAATTATCACCACATGCCAGTGTTAAGAACAACCTATCTCCCTAGTCCC
         2710                2730                2750
TACTTTTGTTTATTATGGCTATGTTTGCAATGCAAGAATAAGCAAACATTGTAATGTTAA
         2770                2790                2810
TAAAGTTTGCACTTTTGTAGACTGGATGGATGTTATCAATGAAGTACCTAGTTTATAAAA

AAAAAAA
```

Figure 8 continued

```
              10                  30                  50
TCCCTATCTCCATTTACTATTTTCTTCTCTCTTCTTCTTCTTTCGAACCATTTTCAGAGT
              70                  90                 110
TCATAAATTCAGGGTTTTGTTTTTTTTTGGGTGTAGTGAAATAAAGGATGAAAATAGCA
                                                      M  K  I  A
             130                 150                 170
GTGATAGGAGGAGGGATAAGTGGGGTGGTATCAGCCTATACTTTAGCCAAAGCCGGTGCA
 V  I  G  G  G  I  S  G  V  V  S  A  Y  T  L  A  K  A  G  A
             190                 210                 230
AATGTAGTGCTTTACGAGAAAGAAGAGTATTTGGGAGGCCATTCCAAGACCGTTCACTTC
 N  V  V  L  Y  E  K  E  E  Y  L  G  G  H  S  K  T  V  H  F
             250                 270                 290
GATGGTGTTGATTTAGACCTTGGTTTCATGGTTTTTAATCGCGTTACATATCCAAATATG
 D  G  V  D  L  D  L  G  F  M  V  F  N  R  V  T  Y  P  N  M
             310                 330                 350
ATGGAGTTGTTTGAGAGCCTTGGGATTGATATGGAACCATTTGATATGTCACTCTCAGTG
 M  E  L  F  E  S  L  G  I  D  M  E  P  F  D  M  S  L  S  V
             370                 390                 410
AGCCTTAATGAAGGCAAAGGCTGTGAATGGGGCAGCCGTAATGGCCTTTCGGCCTTGTTT
 S  L  N  E  G  K  G  C  E  W  G  S  R  N  G  L  S  A  L  F
             430                 450                 470
GCCCAAAAATCCAACCTCTTCAATCCTTACTTTTGGCAAATGCTTAGAGAAATTCTCAAA
 A  Q  K  S  N  L  F  N  P  Y  F  W  Q  M  L  R  E  I  L  K
             490                 510                 530
TTCAAGAATGATGTTATTAGTTATCTTGAATTGCTCGAAAACAACCCGGATATTGACCGT
 F  K  N  D  V  I  S  Y  L  E  L  L  E  N  N  P  D  I  D  R
             550                 570                 590
AATGAAACATTGGGACAGTTCATAAAATCAAAGGGTTACTCTGATTTATTTCAGAAGGCT
 N  E  T  L  G  Q  F  I  K  S  K  G  Y  S  D  L  F  Q  K  A
             610                 630                 650
TATCTGGTGCCTGTATGTGGTTCAATATGGTCATGCCCTACAGAAAGAGTTATGGATTTT
 Y  L  V  P  V  C  G  S  I  W  S  C  P  T  E  R  V  M  D  F
             670                 690                 710
TCAGCTTTCTCTATTCTTTCATTTTGCCGCAATCATCATCTACTTCAGATCTTTGGACGA
 S  A  F  S  I  L  S  F  C  R  N  H  H  L  L  Q  I  F  G  R
             730                 750                 770
CCACAGTGGATGACCGTTCGATGGCGTTCACATCGTTACGTCAATAAGGTTAGAGAAGAG
 P  Q  W  M  T  V  R  W  R  S  H  R  Y  V  N  K  V  R  E  E
             790                 810                 830
CTGGAGAGTACAGGTTGTCAAATAAGAACTGGTTGCGAGGTGCATTCTGTTTTGAGTGAT
 L  E  S  T  G  C  Q  I  R  T  G  C  E  V  H  S  V  L  S  D
             850                 870                 890
GCTGAAGGTTGCACTGTATTATGTGGAGATGACTCTCACGAGTTATATCAAGGGTGCATA
 A  E  G  C  T  V  L  C  G  D  D  S  H  E  L  Y  Q  G  C  I
             910                 930                 950
ATGGCTGTTCATGCACCAtATGCTTTGAGATTGTTAGGGAATCAAGCAACATATGATGAA
 M  A  V  H  A  P  Y  A  L  R  L  L  G  N  Q  A  T  Y  D  E
             970                 990                1010
TCAACAGTGCTTGGCGCTTTCCAATATGTCTATAGTGATATTTATCTTCATCGTGACAAA
 S  T  V  L  G  A  F  Q  Y  V  Y  S  D  I  Y  L  H  R  D  K
            1030                1050                1070
AATTTAATGCCCAAAAACCCAGCAGCATGGAGTGCATGGAATTTTCTTGGAAGTACAGAC
 N  L  M  P  K  N  P  A  A  W  S  A  W  N  F  L  G  S  T  D
            1090                1110                1130
AAGAATGTATCTTTGACATACTGGCTTAATGTGCTTCAGAATCTAGGAGAAACAAGCCTA
 K  N  V  S  L  T  Y  W  L  N  V  L  Q  N  L  G  E  T  S  L
            1150                1170                1190
CCCTTTTTGGTCACTCTCAATCCAGATTATACACCAAAACACACCTTGCTTAAGTGGAGA
 P  F  L  V  T  L  N  P  D  Y  T  P  K  H  T  L  L  K  W  R
```

Figure 9

```
                1210                1230                1250
ACAGGCCATCCAGTACCATCTGTTGCTGCAACAAAAGCTTCTCTTGAGCTTGATCGGATT
 T  G  H  P  V  P  S  V  A  A  T  K  A  S  L  E  L  D  R  I
                1270                1290                1310
CAAGGGAAGAGAGGAATTTGGTTTTGTGGAGCATACCTGGGCTATGGCTTCCATGAAGAT
 Q  G  K  R  G  I  W  F  C  G  A  Y  L  G  Y  G  F  H  E  D
                1330                1350                1370
GGATTAAAGGCTGGGATGATTGCTGCAAACGGTCTGCTGGGAAAAAGTTGTAATATTCTG
 G  L  K  A  G  M  I  A  A  N  G  L  L  G  K  S  C  N  I  L
                1390                1410                1430
AGCAATCCAAAGCATATGGTGCCCTCTCTGATGGAAACAGGGGCACGTCTTTTTGTTACT
 S  N  P  K  H  M  V  P  S  L  M  E  T  G  A  R  L  F  V  T
                1450                1470                1490
AGATTCCTCAGTCATTTTATATCAACCGGCTGTGTGATTTTATTGGAAGAAGGTGGCACT
 R  F  L  S  H  F  I  S  T  G  C  V  I  L  L  E  E  G  G  T
                1510                1530                1550
ATGTTTACCTTTGAAGGAACTAGCAATAAGTGTTCTCTAAAAACTGTAATTAAAGTTCAC
 M  F  T  F  E  G  T  S  N  K  C  S  L  K  T  V  I  K  V  H
                1570                1590                1610
AGTCCACATTTTTATTGGAAGGTTATGACAGAGGCAGATTTAGGCCTTGCAGATTCATAT
 S  P  H  F  Y  W  K  V  M  T  E  A  D  L  G  L  A  D  S  Y
                1630                1650                1670
ATCAATGGGGATTTTTCTTTTGTTGATAAAAAAGACGGTCTGCTGAACCTTGTAATGATT
 I  N  G  D  F  S  F  V  D  K  K  D  G  L  L  N  L  V  M  I
                1690                1710                1730
CTTATTGCCAACAGAGATTTGATTTCTTCCAACTCAAAACTTAGTAAGAAAAGGGGTTGG
 L  I  A  N  R  D  L  I  S  S  N  S  K  L  S  K  K  R  G  W
                1750                1770                1790
TGGACACCATTGTTGTTTACAGCTGGTCTAACATCAGCAAAGTATTTCTTCAAGCATGTC
 W  T  P  L  L  F  T  A  G  L  T  S  A  K  Y  F  F  K  H  V
                1810                1830                1850
TTAAGACAAAATACTCTTACACAAGCTCGTAGGAACATTTCTCGCCATTACGACyTGAGT
 L  R  Q  N  T  L  T  Q  A  R  R  N  I  S  R  H  Y  D  L  S
                1870                1890                1910
AATGACCTTTTTGCACTCTTCTTGGATGAGACAATGACATACTCTTGTGCAGTATTTAAG
 N  D  L  F  A  L  F  L  D  E  T  M  T  Y  S  C  A  V  F  K
                1930                1950                1970
ACAGAAGATGAGGATTTGAAAGATGCACAACACAGAAAGATCTCTCTTTTGATTGAAAAA
 T  E  D  E  D  L  K  D  A  Q  H  R  K  I  S  L  L  I  E  K
                1990                2010                2030
GCAAGAATTGATAGCAAGCATGAAATTCTTGAGATTGGATGTGGTTGGGkAAGCTTAGCT
 A  R  I  D  S  K  H  E  I  L  E  I  G  C  G  W  X  S  L  A
                2050                2070                2090
ATTGAGGTTGTCAAACGAACTGGATGCAAATATACCGGCATTACTTTATCCGAAGAGCAA
 I  E  V  V  K  R  T  G  C  K  Y  T  G  I  T  L  S  E  E  Q
                2110                2130                2150
CTCAAACTTGCAGAAAAAAGAGTGAAGGAAGCTGGACTTCAGGAAAATATAAGATTTCAA
 L  K  L  A  E  K  R  V  K  E  A  G  L  Q  E  N  I  R  F  Q
                2170                2190                2210
CTCTGTGACTATCGACAACTACCTAGCACCTACAAGTATGACAGAATTATATCGTGTGAG
 L  C  D  Y  R  Q  L  P  S  T  Y  K  Y  D  R  I  I  S  C  E
                2230                2250                2270
ATGATAGAAGCTGTTGGCCATGAATACATGGAGGACTTCTTCGGTTGCTGTGAATCAGTG
 M  I  E  A  V  G  H  E  Y  M  E  D  F  F  G  C  C  E  S  V
                2290                2310                2330
TTAGCAGATGATGGACTTCTTGTTTTACAGTTCATATCAATACCAGAGGAACGGTACAAT
 L  A  D  D  G  L  L  V  L  Q  F  I  S  I  P  E  E  R  Y  N
                2350                2370                2390
GAATACAGGCGAAGCTCGGATTTCATCAAGGAATACATCTTCCCTGGTGGATGCTTACCT
 E  Y  R  R  S  S  D  F  I  K  E  Y  I  F  P  G  G  C  L  P
```

Figure 9 continued

```
         2410                2430                2450
TCTCTGGCTAGGATAACAACAGCCATGAATGCTGCGTCCAAACTCTGTGTGGAGCATGTG
 S  L  A  R  I  T  T  A  M  N  A  A  S  K  L  C  V  E  H  V
         2470                2490                2510
GAAAACATCGGACTTCATTACTACCAAACGCTTAGATATTGGAGAAAGAATTTCTTGGAG
 E  N  I  G  L  H  Y  Y  Q  T  L  R  Y  W  R  K  N  F  L  E
         2530                2550                2570
AAACAGAGCAAAATCCATGCCTTGGGATTCAATGACAAGTTCATCCGGACATGGGAATAC
 K  Q  S  K  I  H  A  L  G  F  N  D  K  F  I  R  T  W  E  Y
         2590                2610                2630
TATTTTGATTATTGTGCTGCTGGTTTCAAGTCCAATACTCTTGGTAATTACCAGGTTGTA
 Y  F  D  Y  C  A  A  G  F  K  S  N  T  L  G  N  Y  Q  V  V
         2650                2670                2690
TTTTCTCGGCCTGGAAATGTAGTTGCACTTGGCAACCCATACAAAGACTTCCCCTCAGCT
 F  S  R  P  G  N  V  V  A  L  G  N  P  Y  K  D  F  P  S  A
         2710                2730                2750
TCTTAATTATTTATTTTCTCCTTATTTCAATCGTACCATAGCCATAATTTGAGCTTGTTG
 S  *
         2770                2790                2810
AAAACTGATGCTACACGTTTGGTTTCATTCAAATATGGTATTTGAGTGCATATCTATACA
         2830                2850                2870
TTGATGAATGTAATTCTGGCTTGCCTCGTAGGAACTTGCCAGCAGGATTATCTTTTTACA
         2890                2910
TGGACATTTATTTTAATTCTCTGTTCAAATTT
```

Figure 9 continued

Fragment A, the seed-specific lectin promoter derived from soybean *lec1* gene:

```
   1  GAATTCTCTA GAAAAGTTAA CCCTTCGAAG ATGATACTGA CATTAACACC
  51  ATTTTTTAAT ATTGTTTTTC TATATCGTTA TTGATCTCAG CACATTCTTA
 101  GAAAGATATT TAAATTAGAT AAAAGTAAAT TTATATATAT ATATATATAT
 151  ATATATATAT ATATATATAT ATAAATGTAA CATAAATCTA TGGTCAATTA
 201  CAATATTTAA TTAAATAAAA TAGAAATATA AACACCACTT TAATTTGACT
 251  CGGATACATG CATCCATAAA GACTACAAAA GGCAAAAAGA GAAGGAAATG
 301  AGATACGAAT ATATGTCATA AGTATATATA GGTGACAAGG GCAAATTAAA
 351  TAGGTTGGTA TTTAAATGCA AAATCCTATG TTTGATAAAG AATGGTATGA
 401  AAAACAGGCA AAGTTAATTG CAATTCAAAG GTGAACAAAG CATTTCTTTG
 451  TCTACACTAA TGGCATGTCT AAGTAAATTA TTAGTCTTGT ATCTATATGT
 501  CCACAAGTTA TTAATTAGTC TTATACTATC AAAAACAAGT TAAGTTGCAA
 551  ATCAAACATG AACAAAGCAT TTGTGTTGTA ACCTACGAAA AAATACCCTA
 601  ACATACTGAT ACGAATAATG TGGCCTAAAT TGATCGTTTA CCAAATTACG
 651  GTGCTGGAAA AAAAAATTGC TCCTTTACCA ACAAAATTAA GAACTGATAC
 701  ATCTTGTTTT TTGTCACTGA AGATAAACAC GTGATCTTTG GCAAAACATA
 751  AAGGCCAACA AAACAAACTT GTCTCATCCC TGAATGATTC GAATGCCATC
 801  GTATGCGTGT CACAAAGTGG AATACAGCAA TGAACAAATG CTATCCTCTT
 851  GAGAAAAGTG AATGCAGCAG CAGCAGCAGA CTAGAGTGCT ACAAATGCTT
 901  ATCCTCTTGA GAAAAGTGAA TGCAGCGGCA GCAGACCTGA GTGCTATATA
 951  CAATTAGACA CAGGGTCTAT TAATTGAAAT TGTCTTATTA TTAAATATTT
1001  CGTTTTATAT TAATTTTTTA AATTTTAATT AAATTTATAT ATATTATATT
1051  TAAGACAGAT ATATTTATTT GTGATTATAA ATGTGTCACT TTTTCTTTTA
1101  GTCCATGTAT TCTTCTATTT TTTCAATTTA ACTTTTTATT TTTATTTTTA
1151  AGTCACTCTT GATCAAGAAA ACATTGTTGA CATAAAACTA TTAACATAAA
1201  ATTATGTTAA CATGTGATAA CATCATATTT TACTAATATA ACGTCGCATT
1251  TTAACGTTTT TTTAACAAAT ATCGACTGTA AGAGTAAAAA TGAAATGTTT
1301  GAAAAGGTTA ATTGCATACT AACTATTTTT TTTCCTATAA GTAATCTTTT
1351  TTGGGATCAA TTGTATATCA TTGAGATACG ATATTAAATA TGGGTACCTT
1401  TTCACAAAAC CTAACCCTTG TTAGTCAAAC CACACATAAG AGAGGATGGA
1451  TTTAAACCAG TCAGCACCGT AAGTATATAG TGAAGAAGGC TGATAACACA
1501  CTCTATTATT GTTAGTACGT ACGTATTTCC TTTTTTGTTT AGTTTTTGAA
1551  TTTAATTAAT TAAAATATAT ATGCTAACAA CATTAAATTT TAAATTTACG
1601  TCTAATTATA TATTGTGATG TATAATAAAT TGTCAACCTT TAAAAATTAT
1651  AAAAGAAATA TTAATTTTGA TAAACAACTT TTGAAAAGTA CCCAATAATG
1701  CTAGTATAAA TAGGGGCATG ACTCCCCATG CATCACAGTG CAATTTAACT
1751  GAAGCAAAGC AGCGGCCCCG G
```

Figure 13

Fragment B, chimeric fragment of three target genes:

```
   1  ACCAACACGC CTTCTTTGCC TCGTGTTTCA TCACCTGGCG TTAAACTGCT
  51  TTCTTTAAAA CCAACAAAAT GGGTGCCGGG TGGGTAGGAT GCCAATTGAC
 101  GGGTATAAAG GAGGAAAATC GAGGCTCGGT CAATCGAGTT CCGATCGAGA
 151  AGCCTCCGTT TACGCTCGGT CAGATCAAGC AAGCCATTCC GCCCCACTGT
 201  TTTCGCCGCT CCCTCCTTCG ATCCTTCTCC TACGTGGTCC ATGACCTATG
 251  CTTAGCCTCT CTCTTTTACT ACATTGCAAC ATCATATTTT CACTTTCTCC
 301  CACAACCCTT TTCCTACATT GCTTGGCCTG TCTATTGGGT TCTCCAAGGT
 351  TGGTACCATG GTCTGTGGAG ATGGTTTCCA AGAAACTTAC AATGGATGCA
 401  TAATGGCTGT TGATGCTCCC ACTGCCCTAA AATTATTAGG AAACCAAGCA
 451  ACATTTGAAG AAACAAGAGT ACTGGGTGCT TTCCAATATG CTACCAGTGA
 501  TATTTTCCTT CACCGGGACA GTACTTTAAT GCCACAAAAC AAATCAGCTT
 551  GGAGTGCATT GAATTTTCTC AATAGTAGCA AAAATAATGC ATTCTTAACA
 601  TACTGGCTCA ATGCACTACA GAATATTGGG AAAACAAGTG AGCCATTTTT
 651  TGTGACTGTC AATCCAGACC ATACCCCGAA GAATACCTTG CTTAAGTGGT
 701  CGACTGGCCA TGCAATTCCC TCTGTTGCTG CATCAAAAGC TTCACTTGAG
 751  CTTGGTCAGA TTCAGGGGAA GAGAGGAATC TGGTTCTGTG GCTATGAGAG
 801  CTCCTCGGAC CTTTATCAAT CAATTACCTG ATTGGAGCAT GCTTCTTGCC
 851  GCTATCACAA CCATTTTCCT GGCTGCTGAG AAGCAGTGGA TGATGCTTGA
 901  TTGGAAGCCA AGGCGGCCTG ACATGCTCAT TGATCCTTTT GGTATAGGGA
 951  GGATTGTTCA GGATGGTCTT GTTTTCCGTC AAAACTTCTC GATTAGGTCT
1001  TATGAGATAG GTGCTGATCG TACGGCATCC ATAGAGACGC TAATGAATCA
1051  TTTACAGGAA ACCGCGATTA ATCATTGTAA AAGTGCTGGA CTGCTTGGAG
1101  AAGGTTTTGG TGCTACCCCT GAGATGTGCA AGAAGAACCT AATTTGGGTG
1151  GTCACTCGGA TGCAAGTTGT GTTTGATCGG TATCCTAC
```

Fragment C: Intron from *ghFAD2-1*:

```
   1  GTACATTTCT CTTTAATTTC CTTTTTTTTT CATTTCATGT TTTTCATGTT
  51  AATGTTGCAT TGAAGTGATA AATTTGAGTG AATGATGTTT GGTATATCTT
 101  CTTAGTAACT GACCTTTTGA AAATACTAGC ATTTTTTTTA ATATCAAGTG
 151  AAAGAAGAAG AAGAATTTCG CCATGCAAAA GCTTTTTAAG GCTTTTTCTT
 201  TTCCTTAGAT CAAAATTTAT TTGTTTACTT ATACTGTTCT TTTAAGCCCG
 251  AAGAAAGAAG CCATGGTTTC AATTTTTGAG AGTTTTAAAT CCCAAATACC
 301  AGAGAGCTTC ATCGTTTATT CATATATTTT TAAACATTTT TTAAAGCAAG
 351  AACTTGTGAT TTGTTTTTAA TAAAATATGC AATAAATTTT TATATTTTTC
 401  GTAAATTTAA AATTTAATTT TTCTACTTTT AAAATTTAAA AAAGTAAATT
 451  TTAAAATATA CCTTTCATTA AATTAAATTA TTATAAGTAA TTGAGTATTT
 501  TTAATTTTAA AATTTCACAC ATCAAATTAA AAAAAAGTT AACACTTGCA
 551  CTTGATTTTG AAAAGTAAAA GGATTAAATT TCAAATTTTC AGTAAAAGGA
 601  CTAAATTTCA AATTTTTAAA GAGTATAGAG ACTCCTCTAC ATTTTAGATT
 651  TTAAAATTTA AATCTAACAG TTAACACTTT CTTAATTACT TTACGATAAA
 701  TTTAACTAAA AAATTACAAT ATTAATGGTT AAAATTAAAT TTTGAAAAGT
 751  ATAAAGATTA AATTGTAAAT TTTCAAAAAG CATAGGAAGT TATAGTATAT
 801  TTTAACCTTT ATTTATTTTA TATCTGGTGA GGTTCCTGCA TGCACCGAAG
 851  ATGTCACCTT TTGCCAGTAT TTTCCAGTGG CTTGTTTCTC TCAAAACTAC
 901  CTTGAATCTT GAGACAGAAT TAAATATATT TTTGGCCTTT TCTTCATTTT
 951  CTCTCTCTCT ATTTTCTTTT AAAAATTGCT TTAGAGAATT CAGAAAAAAT
1001  ACTTTCCAAC ACGAAAATTT CTTCAAATTT ATTGTTTATA TCTAATAAAT
1051  GGTTGCTTAA TTTTGGAAAA CAAAAGTTAT TGTAGTTAGT TTTGCTTCTT
1101  GCGTGTCCAG
```

Figure 13 continued

Fragment D, inverted repeat of the chimeric genes:

```
   1  GTAGGATACC GATCAAACAC AACTTGCATC CGAGTGACCA CCCAAATTAG
  51  GTTCTTCTTG CACATCTCAG GGGTAGCACC AAAACCTTCT CCAAGCAGTC
 101  CAGCACTTTT ACAATGATTA ATCGCGGTTT CCTGTAAATG ATTCATTAGC
 151  GTCTCTATGG ATGCCGTACG ATCAGCACCT ATCTCATAAG ACCTAATCGA
 201  GAAGTTTTGA CGGAAAACAA GACCATCCTG AACAATCCTC CCTATACCAA
 251  AAGGATCAAT GAGCATGTCA GGCCGCCTTG GCTTCCAATC AAGCATCATC
 301  CACTGCTTCT CAGCAGCCAG GAAAATGGTT GTGATAGCGG CAAGAAGCAT
 351  GCTCCAATCA GGTAATTGAT TGATAAAGGT CCGAGGAGCT CTCATAGCCA
 401  CAGAACCAGA TTCCTCTCTT CCCCTGAATC TGACCAAGCT CAAGTGAAGC
 451  TTTTGATGCA GCAACAGAGG GAATTGCATG GCCAGTCGAC CACTTAAGCA
 501  AGGTATTCTT CGGGGTATGG TCTGGATTGA CAGTCACAAA AAATGGCTCA
 551  CTTGTTTTCC CAATATTCTG TAGTGCATTG AGCCAGTATG TTAAGAATGC
 601  ATTATTTTTG CTACTATTGA GAAAATTCAA TGCACTCCAA GCTGATTTGT
 651  TTTGTGGCAT TAAAGTACTG TCCCGGTGAA GGAAAATATC ACTGGTAGCA
 701  TATTGGAAAG CACCCAGTAC TCTTGTTTCT TCAAATGTTG CTTGGTTTCC
 751  TAATAATTTT AGGGCAGTGG GAGCATCAAC AGCCATTATG CATCCATTGT
 801  AAGTTTCTTG GAAACCATCT CCACAGACCA TGGTACCAAC CTTGGAGAAC
 851  CCAATAGACA GGCCAAGCAA TGTAGGAAAA GGGTTGTGGG AGAAAGTGAA
 901  AATATGATGT TGCAATGTAG TAAAAGAGAG AGGCTAAGCA TAGGTCATGG
 951  ACCACGTAGG AGAAGGATCG AAGGAGGGAG CGGCGAAAAC AGTGGGCGG
1001  AATGGCTTGC TTGATCTGAC CGAGCGTAAA CGGAGGCTTC TCGATCGGAA
1051  CTCGATTGAC CGAGCCTCGA TTTTCCTCCT TTATACCCGT CAATTGGCAT
1101  CCTACCCACC CGGCACCCAT TTTGTTGGTT TTAAAGAAAG CAGTTTAACG
1151  CCAGGTGATG AAACACGAGG CAAAGAAGGC GTGTTGGT
```

Fragment E, lectin terminator:

```
AGGGGCCGCC ATGTGACAGA TCGAAGGAAG AAAGTGTAAT AAGACGACTC
TCACTACTCG ATCGCTAGTG ATTGTCATTG TTATATATAA TAATGTTATC
TTTCACAACT TATCGTAATG CATGTGAAAC TATAACACAT TAATCCTACT
TGTCATATGA TAACACTCTC CCCATTTAAA ACTCTTGTCA ATTTAAAGAT
ATAAGATTCT TTAAATGATT AAAAAAAATA TATTATAAAT TCAATCACTC
CTACTAATAA ATTATTAATT AATATTTATT GATTAAAAAA ATACTTATAC
TAATTTAGTC TGAATAGAAT AATTAGATTC TAGAGTCGAC CTGCAGGCAT
GCAAGCTT
```

Fragment F, S1 promoter:

```
   1  TCTAGAGGAT CCTATGTTGT AATTTTATAT GGATTAATGA GAATTATTAT
  51  TATTCTGTTC TTCGTCTGTG TTTTTTAAGC TAGCTTCCTC GAAGCAGCGT
 101  ATAACTTTAA TTTGAATTTG GTTTTGGCGC GTTAGTGAAA TTGCGGCTGT
 151  AAACGTGTCA AGTTGTGAGT GGCTGAAATA AGATAATAGA TATATTATTA
 201  TTGTTTTAAT TTAATTCCGC GAAGCGATAT GTTAAGTGAT AAATGAAACG
 251  AAGCGTTTTG ATGACGTCAT ATGTCTCCGT GCCTACGTCA GCACGGGGCT
 301  TAGTATTACC CCCGTGCCGG GATCAGAGAC ATTTGACCAA TAGTTGACTA
 351  GTATAATAGC CCTTGGATTA AATGACACGT GGACGCTCAG GATCTGTGAT
 401  GCTAGTGAAG CGCTTAAGCT GAACGAATCT GACGGAAGAG CGTTCACACT
 451  TAGATCTAGT TAGCGTACTT AGTACGCGTT GTCTTGGGTC TATAAATAGA
 501  GTGCTTCTGA ACAGATTGTT CAGAATTTCA TAGCGCCGAT AACAATGATT
 551  GAACAAGATG GATTGCACGC AGGTTCTCCG GCCGCTTGGG TGGAGAGGCT
 601  ATTCGGCTAT GACTGGGCAC
```

Figure 13 continued

Fragment G, *NPTII* gene:

```
  1  AACAGACAAT CGGCTGCTCT GATGCCGCCG TGTTCCGGCT GTCAGCGCAG
 51  GGGCGCCCGG TTCTTTTTGT CAAGACCGAC CTGTCCGGTG CCCTGAATGA
101  ACTGCAGGTA AATTTCTAGT TTTTCTCCTT CATTTTCTTG GTTAGGACCC
151  TTTTCTCTTT TTATTTTTTT GAGCTTTGAT CTTTCTTTAA ACTGATCTAT
201  TTTTTAATTG ATTGGTTATG GTGTAAATAT TACATAGCTT TAACTGATAA
251  TCTGATTACT TTATTTCGTG TGTCTATGAT GATGATGATA ACTGCAGGAC
301  GAGGCAGCGC GGCTATCGTG GCTGGCCACG ACGGGCGTTC CTTGCGCAGC
351  TGTGCTCGAC GTTGTCACTG AAGCGGGAAG GGACTGGCTG CTATTGGGCG
401  AAGTGCCGGG GCAGGATCTC CTGTCATCTC ACCTTGCTCC TGCCGAGAAA
451  GTATCCATCA TGGCTGATGC AATGCGGCGG CTGCATACGC TTGATCCGGC
501  TACCTGCCCA TTCGACCACC AAGCGAAACA TCGCATCGAG CGAGCACGTA
551  CTCGGATGGA AGCCGGTCTT GTCGATCAGG ATGATCTGGA CGAAGAGCAT
601  CAGGGGCTCG CGCCAGCCGA ACTGTTCGCC AGGCTCAAGG CGCGCATGCC
651  CGACGGCGAG GATCTCGTCG TGACCCATGG CGATGCCTGC TTGCCGAATA
701  TCATGGTGG
```

Fragment H, s3 terminator:

```
  1  AAAATGGCCG CTTTTCTGGA TTCATCGACT GTGGCCGGCT GGGTGTGGCG
 51  GACCGCTATC AGGACATAGC GTTGGCTACC CGTGATATTG CTGAAGAGCT
101  TGGCGGCGAA TGGGCTGACC GCTTCCTCGT GCTTTACGGT ATCGCCGCTC
151  CCGATTCGCA GCGCATCGCC TTCTATCGCC TTCTTGACGA GTTCTTCTGA
201  GCGGGACTCT GGGGTTCGAA ATGACCGACC AAGCGACGCC CAACCTGCCA
251  TCACGAGATT TCGATTCCAC CGCCGCCTTC TATGAAAGGT TGGGCTTCGG
301  AATCGTTTTC CGGGACGCCG GCTGGATGAT CCTCCAGCGC GGGGATCTCA
351  TGCTGGAGTT CTTCGCCCAC CCCGGGTCGA CGGTATTGAG TTTATGTCTA
401  TTGTAATTGA TAGAGGTTCT ATTAAGATAG AATTATGAGA TGTAATTGTG
451  ATTAATGAAT AAAGAGTTGT TATTATTCTT TGAATTACTC CGCGAAGCGG
501  TGTGTTATGT TTTTGTTGGA AGCTTTCTAG ACTCGACTAG AGCGGCCGC
```

Figure 13 continued

SEQUENCE LISTING

```
<160> NUMBER OF SEQ ID NOS: 32

<210> SEQ ID NO 1
<211> LENGTH: 1362
<212> TYPE: DNA
<213> ORGANISM: Gossypium hirsutum

<400> SEQUENCE: 1
caaaaccaac acgccttctt tgcctcgtgt ttcatcacct ggcgttaaac tgctttcttt      60
aaaaccaaca aaatgggtgc cgggtgggta ggatgccaat tgacgggtat aaaggaggaa     120
aatcgaggct cggtcaatcg agttccgatc gagaagcctc cgtttacgct cggtcagatc     180
aagcaagcca ttccgcccca ctgttttcgc cgctccctcc ttcgatcctt ctcctacgtg     240
gtccatgacc tatgcttagc ctctctcttt tactacattg caacatcata ttttcacttt     300
ctcccacaac ccttttccta cattgcttgg cctgtctatt gggttctcca aggttgcatc     360
ctcaccggtg tttgggtcat cgcacacgaa tgcggtcacc acgctttcag tgactaccaa     420
tgggttgacg acaccgtcgg gttgatcctt cactccgccc ttttagtccc gtacttctcg     480
tggaaaatca gtcaccgccg tcaccactcg aacaccggtt ccatggagcg tgacgaagta     540
ttcgtgccca aacccaagtc taaattatca tgctttgcga aatacttcaa caatccaccc     600
ggtcgagttc tctctcttgt agtcacattg actcttggtt ggcctatgta cttagccttc     660
aacgtttcgg gtcgatacta tgatcgatta gcttcccact ataaccctta cggcccatt      720 tactccgaac gcgagaggct acaagtttac atctccgatg ctggtatagt tgcggtaatt     780
tatgtacttt ataagattgc tgcaacaaaa gggctggctt ggcttttatg cacttatggg     840
gtacctctac ttattgtgaa tgccttcctt gtgttgatca cctacttgca acatactcac     900
tcggcattgc cgcattacga ctcgtctgaa tgggattggt ttcgaggagc attgtcgacg     960
attgatcgag attacggggt gttgaacaaa gtgttccata acatcaccga tacgcatgtg    1020
gctcatcacc tcttctcaac gatgccacat tatcatgcaa tggaggccac taaagcaatc    1080
aaaccgatac tcggcaagta ttatccttc gacgggacac cgatttataa ggcaatgtgg    1140
agggaggcaa aagagtgcct ttacgtcgag gctgacgttg tggtggtgg tagcaaaggt    1200 gtttttggt atcgtaacaa gttctaaaga cagaccaact gcctgatagc tggccggcaa    1260
```
aatcgacgta aaacgtactt attagactag tgttaactag ggaagttaat aatggtagga    1320
aaatgtggaa tagctgccta gtagttttat gtattaagtg tt                      1362

<210> SEQ ID NO 2
<211> LENGTH: 384
<212> TYPE: PRT
<213> ORGANISM: Gossypium hirsutum

<400> SEQUENCE: 2

Met Gly Ala Gly Trp Val Gly Cys Gln Leu Thr Gly Ile Lys Glu
1               5                   10                  15

Asn Arg Gly Ser Val Asn Arg Val Pro Ile Glu Lys Pro Pro Phe Thr
                20                  25                  30

Leu Gly Gln Ile Lys Gln Ala Ile Pro Pro His Cys Phe Arg Arg Ser
            35                  40                  45

Leu Leu Arg Ser Phe Ser Tyr Val Val His Asp Leu Cys Leu Ala Ser
        50                  55                  60

Leu Phe Tyr Tyr Ile Ala Thr Ser Tyr Phe His Phe Leu Pro Gln Pro
65                  70                  75                  80

Phe Ser Tyr Ile Ala Trp Pro Val Tyr Trp Val Leu Gln Gly Cys Ile
                85                  90                  95

Leu Thr Gly Val Trp Val Ile Ala His Glu Cys Gly His His Ala Phe
            100                 105                 110

Ser Asp Tyr Gln Trp Val Asp Asp Thr Val Gly Leu Ile Leu His Ser
        115                 120                 125

Ala Leu Leu Val Pro Tyr Phe Ser Trp Lys Ile Ser His Arg Arg His
    130                 135                 140

His Ser Asn Thr Gly Ser Met Glu Arg Asp Glu Val Phe Val Pro Lys
145                 150                 155                 160

Pro Lys Ser Lys Leu Ser Cys Phe Ala Lys Tyr Phe Asn Asn Pro Pro
                165                 170                 175

Gly Arg Val Leu Ser Leu Val Val Thr Leu Thr Leu Gly Trp Pro Met
            180                 185                 190

Tyr Leu Ala Phe Asn Val Ser Gly Arg Tyr Tyr Asp Arg Leu Ala Ser
        195                 200                 205

His Tyr Asn Pro Tyr Gly Pro Ile Tyr Ser Glu Arg Glu Arg Leu Gln
    210                 215                 220

Val Tyr Ile Ser Asp Ala Gly Ile Val Ala Val Ile Tyr Val Leu Tyr
225                 230                 235                 240

Lys Ile Ala Ala Thr Lys Gly Leu Ala Trp Leu Leu Cys Thr Tyr Gly
                245                 250                 255

Val Pro Leu Leu Ile Val Asn Ala Phe Leu Val Leu Ile Thr Tyr Leu
            260                 265                 270

Gln His Thr His Ser Ala Leu Pro His Tyr Asp Ser Ser Glu Trp Asp
        275                 280                 285

Trp Phe Arg Gly Ala Leu Ser Thr Ile Asp Arg Asp Tyr Gly Val Leu
    290                 295                 300

Asn Lys Val Phe His Asn Ile Thr Asp Thr His Val Ala His His Leu
305                 310                 315                 320

Phe Ser Thr Met Pro His Tyr His Ala Met Glu Ala Thr Lys Ala Ile
                325                 330                 335

Lys Pro Ile Leu Gly Lys Tyr Tyr Pro Phe Asp Gly Thr Pro Ile Tyr
            340                 345                 350

Lys Ala Met Trp Arg Glu Ala Lys Glu Cys Leu Tyr Val Glu Ala Asp

```
                     355                 360                 365
Val Gly Gly Gly Gly Ser Lys Gly Val Phe Trp Tyr Arg Asn Lys Phe
         370                 375                 380

<210> SEQ ID NO 3
<211> LENGTH: 5201
<212> TYPE: DNA
<213> ORGANISM: Gossypium hirsutum

<400> SEQUENCE: 3
ctcgagaaaa tttctcatca tttgattcgg ttttttcttc gttaaggtac ggtcgtagtt      60
tttcgtttct cagttttagt ttgatctgag cttttttggt tgaaatgatg ctgatctctt     120
tagttaccga gaaataaat gagaaggatg tattgttata ttgttttttt ttctcgaaag      180
gtttcgagtg attgtggcgg ccataggaga tctaatgttt tctcgcattt tctcggcaat     240
caaaggcagc ttaaatttat aatttatatg aaaaagttca gcttattgtt tattttatcg     300
tatttttttt ctcatgaaac acagaaagac caaagctcca ttctgtattg tttgctattt     360
tctctttcat tttttaagtt tattttccgg ttttcgtct tgtaaacttt ttaagcgtat      420
tactgttttt gttttagcg attctacatc cattttgcaa catatgttct tcaacgccga      480
tttaagattc tttatgcgac gctctttgtt taagtactgt gattttagt acataacaat      540 ttgctttgag ctactggtta atcctatctt ccttttgta aatagatccc tataaatcta      600
gaactttgaa atataaacaa acacgtgtat attatgttct ttagattatg ctgcttatt      660 aaataaagta gaaagaaatt atttacctat tagattggaa cctgcttta aacatataga      720 atatgtaatc ttctatatag tcaaaatctg aagatttatg tgattatatt tattgttagt     780
gcgtcttttg gatatgttct gattctttaa tacatgtgat actgttagct catgcaccag     840
ctgcttgtat aaaaagcttt agattttgca aagaaggga tttcagcacg aaattgaagt      900 tgttttaaa aaccatggtt gctactgctg tgacatcggc gttttccca gtcacttctt      960 cacctgactc ctctgactcg aaaaacaaga agctcggaag catcaagtcg aagccatcgg    1020
tttcttctgg aagtttgcaa gtcaaggcaa atgctcaagc acctccgaaa ataaacggca    1080
ctgtggcgtc gacgactccc gtggaaggtt ccaagaacga tgacggtgca agttcccctc    1140
ctcctaggac gttatcaac cagttacctg attggagcat gcttcttgct gctatcacaa     1200
ccattttctt ggctgctgag aagcagtgga tgatgcttga ttggaagccg aggcggcctg    1260
acatggtcat tgatccgttt ggcatagggga agattgttca ggatggtctt gttttcagtc    1320
agaacttctc gattagatca tatgagatag gcgctgatca aacagcatcc atagagacac    1380
taatgaatca tttacaggta gagttacagt tatttggcta gtatgtttga acaatgaaca    1440
tgggaaaaca ggatttacat ttattggttt cttttgtaga gatatggcat aagcttgagt    1500
tttagttaat acatctcact ttttggcagg aaacagctat aaatcattgt cgaagtgctg    1560
gactgcttgg agaaggtttt ggtgcaacac ctgagatgtg caagaagaac ctaatatggg    1620
ttgtcacacg gatgcaagtt gtggttgatc gctatcctac ttggtaagac atgcttttt     1680 gctcatgatt atagcaacaa ttcatgataa gccacttttg ctctacagta tggctgtggc    1740 atatctttg atactaacta gttcagttct tgaattccag caatattctg tattatacaa     1800
atgatctgta tcacatctgg cggacttgtg tttgtttcat taaaacttgg attgatgtta    1860
ttgtttaagc tttaaaggt taagatatga agtcgaagac aattaaggct agccccagc      1920 aatgaataac ataagaaaga taaacctgat acgcttcttt gtttaatgag attccctgtt    1980
taatactaag aacgggacct taacttgtca ttttttgttaa tgttaatact tcccctctaa    2040
```

```
ttgtgattta ggtacctatg cactatattg ttttaagcac ttggcaagtt attggtgttg    2100
aaaataacat tcacttaact gatattagct tggcattagg gcttgtttca aaaataataa    2160
taaaaacgaa gaagttggcc taaaatagtt acttttagca aggtatgtac ttgttggagc    2220
accgttcttt tttgtatgtc acaaaattag tagttctgga ggtattaaga gtatatagaa    2280
atattattat tattttcgtt aggtgtatgt ctatattgat gaacattgaa cttatttttg    2340
ttgtcttgca ggggtgatgt tgttcaagtc gacacttggg tcagtgcatc ggggaagaat    2400
ggcatgcgaa gagattggct tgtcagcaat agtgaaactg gtgaaatttt aacacgagcc    2460
acaaggtcgg tcattgttta tggaaggatc atgaccatat gttttttttc gtgatgtaac    2520
ctgttgaact ctaaaatatt tcaaaatttg ttttgctagc atttaatatg ttttcaatcg    2580
atacacgaat cgatattttg gtttcccagg ccacatctaa tgacttttc ctgaccttgt     2640 gtttgcactt taatgaacag tgtttcatga gtgactaatc ccagtctcct ctgttttgt     2700 tttgttgatc tgcagtgtat gggtgatgat gaataaactg actagaaggt tatctaaaat    2760
cccagaagag gttcgagggg aaatagaacc ttttttatg aattcagatc ctgttctggc     2820
tgaggatagc cagaaactag tgaaactcga tgacagcaca gctgaacacg tgtgcaaagg    2880
tttaactgta agtccccgct tcccctgttt ctctttcata tacttacagc gtctgtcact    2940
tgtaattgct gttatgttca ttcgttgcaa tttgtaataa agtttatatc taatttgcag    3000
cctaaatgga gcgacttgga tgtcaaccag catgtcaata atgtgaagta cattggctgg    3060
atccttgagg tagactcact ccggttgtat ttcaaggatt ttcttttgaa cattctcacc    3120
attacctctt cgtatccgaa gataacaatt aaatggaaat cataactgat ttttatttcg    3180
tataccttaa ttttttaccta tgatgtcaag ctaatatgaa attggaattt tggtagaagt    3240
ctgcttcaga tcttcacgag ttaagtcatt tatagtctgt tggttacatg cattttaacc    3300
ggatggtagt acttgttgca gagtgctcca ttaccaatct tggagagtca cgagcttttcc    3360 gccttgactc tggaatatag gagggagtgc gggagggaca gcgtgctgca gtcactgacc    3420
actgtgtctg attccaatac ggaaaatgca gtaaatgttg gtgaatttaa ttgccaacat    3480
ttgctccgac tcgacgatgg agctgagatt gtgagaggca ggacccgatg gaggcctaaa    3540
catgccaaaa gttccgctaa catggatcaa attaccgcaa aaagggcata gaaatccaag    3600
taatctcatt gctgtgtgta gtatctatcg tgctctttc ggatttatat acatatattc     3660
cttatgatta ttagtcttcc tttgagaaaa aaaagggggg ttgtaattag gcttgtttag    3720
gagtcgggtt ttcgtacata gccttgtaag gctcagctcg tatgacccga gcctcggaca    3780
cggattttgt gaagttgggc ccgtgcccta accagcatag gctctttcca tggaaaggtg    3840
ggtctgcttt tgaaaaattg aatagccatg tgagatggct ctctccctac attatgggct    3900
tttaaccagt tagagaccgg gtagtttagg ataaaattta tctttaattt gggaggattt    3960
gtatattttt tttgcccttta ttttaaccta aatttgctta taattatttg gttttatatt    4020
taggtattga atcaatgaag ttttaaatt ttaaaatgtt ttgattggct tacattgaca     4080
aagcattgta tcaaccaatt tttttagatc aaatgtaagc ccttgtgtaa ctattgcatg    4140
catgttagga aaaaaaaac aaaaattcac ttaaatttag gtgaggtgtt tatttttta     4200 aggtatatat gcgtttataa attgatttat gtacgtaaat gtatttcatg tgatcggttg    4260
cattcgaaat caaataaagg ggttaaatta atttttaagt tcatcgtttc gaattggtaa    4320 aaaaaatagaa aattgagata aaacagtgat tgaatttgtt tttattattt ttaacatttt    4380
attaatattt taattgtttta tttaatgatt gttggattga tgatcgaact aattaaatta    4440
```

-continued

```
agaattaatg gtttgataag tttgatcatg acgatgaact cataatatct gtatcttgtc    4500
tgaaacacag tcttctgtac atcttgctct ttcactctta attggtatcc agatctcaag    4560
tcaatcttag aaaatacaat ggctcccttt aactaatcaa acaggtcatc aaagacgata    4620
ttactacagg cagactcatt tggtccaact tgaagaacat tcccgtcttt acatttcaac    4680
tcaattatct ttttcccaca gtcgactata acactatgac cagtcaacca atctatccca    4740
aggattatat cgaactcatt aaatgacaat aacatcaagt tagtcgaaaa acaatgacct    4800
ctaattgtca aagggcaatt tctacatact tgatccacta gtgcatgttt gcctaaggga    4860
ttggacactt ttattacaaa ctcagtggac tctgctagca tatccatatg aggtatcaat    4920
tccatacaaa tataagagtg ggtagatctg gggtcaacta aagcaatgac agatatttca    4980
tggatagaaa aggtacccgt gatcacgtca ggagattctg cctcttcccg agcttgaata    5040
gcataagtcc ttgcagttgt tctaccctcg gaccttactg cagcatctct tggtatgcct    5100
ctactgctag ccccacttct ggggttcttt tgtgatctac ccctcaaggg agcactgctt    5160
gctttcacat cttgttttct ctctctctca ttcaactcga g                        5201
```

<210> SEQ ID NO 4
<211> LENGTH: 413
<212> TYPE: PRT
<213> ORGANISM: Gossypium hirsutum

<400> SEQUENCE: 4

```
Met Val Ala Thr Ala Val Thr Ser Ala Phe Phe Pro Val Thr Ser Ser
1               5                   10                  15

Pro Asp Ser Ser Asp Ser Lys Asn Lys Lys Leu Gly Ser Ile Lys Ser
            20                  25                  30

Lys Pro Ser Val Ser Ser Gly Ser Leu Gln Val Lys Ala Asn Ala Gln
        35                  40                  45

Ala Pro Pro Lys Ile Asn Gly Thr Val Ala Ser Thr Thr Pro Val Glu
    50                  55                  60

Gly Ser Lys Asn Asp Asp Gly Ala Ser Ser Pro Pro Arg Thr Phe
65                  70                  75                  80

Ile Asn Gln Leu Pro Asp Trp Ser Met Leu Leu Ala Ala Ile Thr Thr
                85                  90                  95

Ile Phe Leu Ala Ala Glu Lys Gln Trp Met Met Leu Asp Trp Lys Pro
            100                 105                 110

Arg Arg Pro Asp Met Val Ile Asp Pro Phe Gly Ile Gly Lys Ile Val
        115                 120                 125

Gln Asp Gly Leu Val Phe Ser Gln Asn Phe Ser Ile Arg Ser Tyr Glu
    130                 135                 140

Ile Gly Ala Asp Gln Thr Ala Ser Ile Glu Thr Leu Met Asn His Leu
145                 150                 155                 160

Gln Glu Thr Ala Ile Asn His Cys Arg Ser Ala Gly Leu Leu Gly Glu
                165                 170                 175

Gly Phe Gly Ala Thr Pro Glu Met Cys Lys Lys Asn Leu Ile Trp Val
            180                 185                 190

Val Thr Arg Met Gln Val Val Asp Arg Tyr Pro Thr Trp Gly Asp
        195                 200                 205

Val Val Gln Val Asp Thr Trp Val Ser Ala Ser Gly Lys Asn Gly Met
    210                 215                 220

Arg Arg Asp Trp Leu Val Ser Asn Ser Glu Thr Gly Glu Ile Leu Thr
225                 230                 235                 240
```

```
Arg Ala Thr Ser Val Trp Val Met Met Asn Lys Leu Thr Arg Arg Leu
                245                 250                 255

Ser Lys Ile Pro Glu Glu Val Arg Gly Ile Glu Pro Phe Phe Met
            260                 265                 270

Asn Ser Asp Pro Val Leu Ala Glu Asp Ser Gln Lys Leu Val Lys Leu
        275                 280                 285

Asp Asp Ser Thr Ala Glu His Val Cys Lys Gly Leu Thr Pro Lys Trp
    290                 295                 300

Ser Asp Leu Asp Val Asn Gln His Val Asn Asn Val Lys Tyr Ile Gly
305                 310                 315                 320

Trp Ile Leu Glu Ser Ala Pro Leu Pro Ile Leu Glu Ser His Glu Leu
                325                 330                 335

Ser Ala Leu Thr Leu Glu Tyr Arg Arg Glu Cys Gly Arg Asp Ser Val
            340                 345                 350

Leu Gln Ser Leu Thr Thr Val Ser Asp Ser Asn Thr Glu Asn Ala Val
        355                 360                 365

Asn Val Gly Glu Phe Asn Cys Gln His Leu Leu Arg Leu Asp Asp Gly
    370                 375                 380

Ala Glu Ile Val Arg Gly Arg Thr Arg Trp Arg Pro Lys His Ala Lys
385                 390                 395                 400

Ser Ser Ala Asn Met Asp Gln Ile Thr Ala Lys Arg Ala
                405                 410

<210> SEQ ID NO 5
<211> LENGTH: 1647
<212> TYPE: DNA
<213> ORGANISM: Gossypium hirsutum

<400> SEQUENCE: 5
ttttgtagat cgcaagccgt agaagtaaac aaagaaggat ttgcagatct taaatcatgc      60
tgtaattttc tcgaggaaat tttttacctt cattgattcg tttctatttt cgcttgagtt    120
ggagaatgct tcagctgcct ttctaaaaga ttgtttccaa aagagggaat tttagtggat    180
aatagaagtt cttttttaatt ctcaaaatca tggttgccac tgctgctaca tcctcattct    240
ttcccgtaac ttcttcccct gactcctctg actcaaaaaa caagaagctt ggaagtggat    300 ctactaaccct cggaggcatc aagtcgaaac catctgcttc ttctggaagt ttgcaagtca    360
aggcaaatgc tcaagccct caaagataa atggtaccac tgttgtaact tctccggttg    420
aaggtttcaa gaacgaagat ggtgcaggtt cccctcatcc tcggaccttt atcaatcaat    480
tacctgattg gagcatgctt cttgccgcta tcacaaccat tttcctggct gctgagaagc    540
agtggatgat gcttgattgg aagccaaggc ggcctgacat gctcattgat cctttttggta    600 tagggaggat tgttcaggat ggtcttgttt tccgtcaaaa cttctcgatt aggtcttatg    660
agataggtgc tgatcgtacg gcatccatag agacgctaat gaatcattta caggaaaccg    720
cgattaatca ttgtaaaagt gctggactgc ttggagaagg ttttggtgct accccctgaga    780 tgtgcaagaa gaacctaatt tgggtggtca ctcggatgca agttgtgttt gatcggtatc    840
ctacttgggg tgatgttgtt caagtagaca cttgggtcag tgcatcagga agaatggca    900 tgcgaagaga ttggcttgtc agtgatagta aaactggtga agttttaaca agagcctcaa    960
gtgtgtgggt gatgatgaat aaattgacta gaaggctatc taaattcct gaggaggtcc    1020 gaggagaaat agaaccttat tttatgaatt ccgatcctgt tgtggcagaa gatagccgga    1080
aattagtgaa gctcgataaa gcatggctg agcacgtgcg taaggttta actcctagat    1140 ggagtgactt ggatgtcaac caacatgtca ataacgtgaa gtacattggc tggatcctcg    1200
```

```
agagtgctcc attgccggtg ttggaaactc acgagctttc ttccatgaca ctggagtata    1260
ggagggagtg tgggagggag agcatactgc agtcgctaac aaccgtgtcc gactccagtg    1320
taggagactt ggtgaatgtg ggtgaaatcg agtgccagca cctgctgcaa ctcgaggaag    1380
ggtccgagat tgtgagaggg agaactcaat ggaggcccaa gtatgccaaa gttttggta    1440 atgtgggtca aattccagca gaaagtgcat agaaggaaaa aatcccaaaa tttctcttat    1500
tgtgacctaa gtggggcaat agtctgattg ccgggtgtca caatgattta tgtagaatct    1560
aatcatgtgt tctatggata tatatatata tatatttatg cttcttttttt atatataaat    1620 aatattatat attccttttta aaaaaa                                        1647
```

<210> SEQ ID NO 6
<211> LENGTH: 420
<212> TYPE: PRT
<213> ORGANISM: Gossypium hirsutum

<400> SEQUENCE: 6

```
Met Val Ala Thr Ala Ala Thr Ser Ser Phe Phe Pro Val Thr Ser Ser
1               5                   10                  15

Pro Asp Ser Ser Asp Ser Lys Asn Lys Leu Gly Ser Gly Ser Thr
            20                  25                  30

Asn Leu Gly Gly Ile Lys Ser Lys Pro Ser Ala Ser Ser Gly Ser Leu
        35                  40                  45

Gln Val Lys Ala Asn Ala Gln Ala Pro Pro Lys Ile Asn Gly Thr Thr
    50                  55                  60

Val Val Thr Ser Pro Val Glu Gly Phe Lys Asn Glu Asp Gly Ala Gly
65                  70                  75                  80

Ser Pro His Pro Arg Thr Phe Ile Asn Gln Leu Pro Asp Trp Ser Met
                85                  90                  95

Leu Leu Ala Ala Ile Thr Thr Ile Phe Leu Ala Ala Glu Lys Gln Trp
            100                 105                 110

Met Met Leu Asp Trp Lys Pro Arg Arg Pro Asp Met Leu Ile Asp Pro
        115                 120                 125

Phe Gly Ile Gly Arg Ile Val Gln Asp Gly Leu Val Phe Arg Gln Asn
    130                 135                 140

Phe Ser Ile Arg Ser Tyr Glu Ile Gly Ala Asp Arg Thr Ala Ser Ile
145                 150                 155                 160

Glu Thr Leu Met Asn His Leu Gln Glu Thr Ala Ile Asn His Cys Lys
                165                 170                 175

Ser Ala Gly Leu Leu Gly Glu Gly Phe Gly Ala Thr Pro Glu Met Cys
            180                 185                 190

Lys Lys Asn Leu Ile Trp Val Val Thr Arg Met Gln Val Val Phe Asp
        195                 200                 205

Arg Tyr Pro Thr Trp Gly Asp Val Val Gln Val Asp Thr Trp Val Ser
    210                 215                 220

Ala Ser Gly Lys Asn Gly Met Arg Arg Asp Trp Leu Val Ser Asp Ser
225                 230                 235                 240

Lys Thr Gly Glu Val Leu Thr Arg Ala Ser Ser Val Trp Val Met Met
                245                 250                 255

Asn Lys Leu Thr Arg Arg Leu Ser Lys Ile Pro Glu Glu Val Arg Gly
            260                 265                 270

Glu Ile Glu Pro Tyr Phe Met Asn Ser Asp Pro Val Val Ala Glu Asp
        275                 280                 285

Ser Arg Lys Leu Val Lys Leu Asp Lys Ser Met Ala Glu His Val Arg
```

```
                 290                 295                 300
Lys Gly Leu Thr Pro Arg Trp Ser Asp Leu Asp Val Asn Gln His Val
305                 310                 315                 320

Asn Asn Val Lys Tyr Ile Gly Trp Ile Leu Glu Ser Ala Pro Leu Pro
                325                 330                 335

Val Leu Glu Thr His Glu Leu Ser Ser Met Thr Leu Glu Tyr Arg Arg
            340                 345                 350

Glu Cys Gly Arg Glu Ser Ile Leu Gln Ser Leu Thr Thr Val Ser Asp
        355                 360                 365

Ser Ser Val Gly Asp Leu Val Asn Val Gly Glu Ile Glu Cys Gln His
370                 375                 380

Leu Leu Gln Leu Glu Glu Gly Ser Glu Ile Val Arg Gly Arg Thr Gln
385                 390                 395                 400

Trp Arg Pro Lys Tyr Ala Lys Ser Phe Gly Asn Val Gly Gln Ile Pro
                405                 410                 415

Ala Glu Ser Ala
            420

<210> SEQ ID NO 7
<211> LENGTH: 1498
<212> TYPE: DNA
<213> ORGANISM: Gossypium hirsutum

<400> SEQUENCE: 7
tagcgctaga agttaccgag aagagtttag agatccctat tatcggaaag aggggatttc      60
agcggataac agaagttcat tttaatttat aaaatcatgg ttgccactgc tgctacatcc     120
tcattctttc caatcacttc ttccccggac tccattgact caaaaaacaa gaagcttgga     180
aatggatcta ctaaccttgg aggtataaag ttgaaaccat ctgcttcttc tggaagtttg     240
caagttaagg caaatgcaca agcccccca aagataaatg gtaccacagt tgtgatgact     300
ccagtagaag gtttcccgag cgaagatgct gcaagttccc tacctccag gacgtttatc     360 aatcagctac ctgattggag catgcttctt gctgctatga caaccatttt cctggctgct     420
gagaagcagt ggatgatgct tgattggaag ccaaagcggc tgacatgct cattgaccca     480 tttgggatag gaggattgt tcaggatggt cttgttttc gtcagaactt ctcaattagg     540
tcttatgaga taggtgctga tcgtacagca tccatagaa cgctaatgaa tcatttacag     600
gaaacagcga ttaatcattg taaaagtgct ggactgctag agatggtttt ggtgctacc     660 cctgggatgt gcaagaaaaa cctaatatgg gtagtcaccc ggatgcaagt tgtggttgat     720
tgttatccaa cttgggtga tgttgttcaa gtagacactt gggtcagtgc atcaggaaag     780
aatggcatgc gaagggattg gcttgtcagc aatagtaaaa ctggtgaaat tttaactaga     840
gcctcaagtg tgtgggtgat gatgaataaa ttgaccagaa ggttatctaa aattccagaa     900
gaggtccgag gagaaataga acctcatttt atgaattcag atccagtggt ggctgaggat     960
aaccggaaat tagtgaaact tgacgacagc acagcccaat atgtgcgcaa gggtttaact    1020
cctcgatgga gcgacctgga tgtgaatcag catgtcaaca atgtgaagta cgttggttgg    1080
atccttgaga gtacaccatt gggaattgtg agagtcatg agctttgttc catgacactg    1140
gagtatagga gggagtgtgg gagggacagc gtgctgcagt cactaactgc ggtgtctggt    1200
gtgggcaacc tcgggaatat ggggaaatt gagtgccagc acttgctcca acttgaagag    1260
gggtctgaga ttgtgagagg gaggacacag tggaggccaa gaatgccaa gagttttggt    1320 aaaatggatc aagttcccgc acaaagtgca tagatccgaa gtctctttgc tgcgtgtcaa    1380
```

```
aactagcagt caacgcattg tgtagaatct ttctttttgtt ctttgaatcc ataatatata    1440
tatatgatat tagcttgtaa gctttcaaag cttgctgtaa ttagctctaa aaaaaaaa       1498
```

<210> SEQ ID NO 8
<211> LENGTH: 418
<212> TYPE: PRT
<213> ORGANISM: Gossypium hirsutum

<400> SEQUENCE: 8

```
Met Val Ala Thr Ala Ala Thr Ser Ser Phe Phe Pro Ile Thr Ser Ser
1               5                   10                  15

Pro Asp Ser Ile Asp Ser Lys Asn Lys Leu Gly Asn Gly Ser Thr
            20                  25                  30

Asn Leu Gly Gly Ile Lys Leu Lys Pro Ser Ala Ser Ser Gly Ser Leu
            35                  40                  45

Gln Val Lys Ala Asn Ala Gln Ala Pro Pro Lys Ile Asn Gly Thr Thr
        50                  55                  60

Val Val Met Thr Pro Val Glu Gly Phe Pro Ser Glu Asp Ala Ala Ser
65                  70                  75                  80

Ser Leu Pro Pro Arg Thr Phe Ile Asn Gln Leu Pro Asp Trp Ser Met
                85                  90                  95

Leu Leu Ala Ala Met Thr Thr Ile Phe Leu Ala Ala Glu Lys Gln Trp
            100                 105                 110

Met Met Leu Asp Trp Lys Pro Lys Arg Pro Asp Met Leu Ile Asp Pro
        115                 120                 125

Phe Gly Ile Gly Arg Ile Val Gln Asp Gly Leu Val Phe Arg Gln Asn
    130                 135                 140

Phe Ser Ile Arg Ser Tyr Glu Ile Gly Ala Asp Arg Thr Ala Ser Ile
145                 150                 155                 160

Glu Thr Leu Met Asn His Leu Gln Glu Thr Ala Ile Asn His Cys Lys
                165                 170                 175

Ser Ala Gly Leu Leu Gly Asp Gly Phe Gly Ala Thr Pro Gly Met Cys
            180                 185                 190

Lys Lys Asn Leu Ile Trp Val Val Thr Arg Met Gln Val Val Val Asp
        195                 200                 205

Cys Tyr Pro Thr Trp Gly Asp Val Val Gln Val Asp Thr Trp Val Ser
    210                 215                 220

Ala Ser Gly Lys Asn Gly Met Arg Arg Asp Trp Leu Val Ser Asn Ser
225                 230                 235                 240

Lys Thr Gly Glu Ile Leu Thr Arg Ala Ser Ser Val Trp Val Met Met
                245                 250                 255

Asn Lys Leu Thr Arg Arg Leu Ser Lys Ile Pro Glu Glu Val Arg Gly
            260                 265                 270

Glu Ile Glu Pro His Phe Met Asn Ser Asp Pro Val Val Ala Glu Asp
        275                 280                 285

Asn Arg Lys Leu Val Lys Leu Asp Asp Ser Thr Ala Gln Tyr Val Arg
    290                 295                 300

Lys Gly Leu Thr Pro Arg Trp Ser Asp Leu Asp Val Asn Gln His Val
305                 310                 315                 320

Asn Asn Val Lys Tyr Val Gly Trp Ile Leu Glu Ser Thr Pro Leu Gly
                325                 330                 335

Ile Val Glu Ser His Glu Leu Cys Ser Met Thr Leu Glu Tyr Arg Arg
            340                 345                 350

Glu Cys Gly Arg Asp Ser Val Leu Gln Ser Leu Thr Ala Val Ser Gly
        355                 360                 365
```

```
Val Gly Asn Leu Gly Asn Met Gly Glu Ile Glu Cys Gln His Leu Leu
    370                 375                 380

Gln Leu Glu Glu Gly Ser Glu Ile Val Arg Gly Arg Thr Gln Trp Arg
385                 390                 395                 400

Pro Lys Asn Ala Lys Ser Phe Gly Lys Met Asp Gln Val Pro Ala Gln
                405                 410                 415

Ser Ala

<210> SEQ ID NO 9
<211> LENGTH: 743
<212> TYPE: DNA
<213> ORGANISM: Gossypium hirsutum
<220> FEATURE:
<221> NAME/KEY: misc_feature
<222> LOCATION: (571)..(571)
<223> OTHER INFORMATION: n is a, c, g, or t

<400> SEQUENCE: 9
atggtttacc cacgcgtccg gtagaacatg ttggtgaaga atatattgag gagttttaca      60
gatgctgtga ccaattactg aaagaagatg acttttttgt tcttcagttc atatctatcc     120
cagaagagct ttccaaagaa atccagcaaa cagcaggttt tctaaaggaa tatatattcc     180
ccggtggaac cctgctttct ttggatagga atttatcagc catggctgct gcaacaagat     240
tcagtgtgga gcatgtggaa atataggaa tgagttatta ccacacactg agatggtgga      300
gaaaactttt cctggaaaac acaagcaaag ttctagctct gggattcgac agaagttca     360 tgaggacatg ggaatactat ttcgattact gcgctgccgg ttttaagaca ggaaccctta    420
tagattacca ggttgtattt tcgcgggccg gaaatttcgg tacactcgga gatccataca     480
aaggtttccc ttctgcatac tccttcatgg atgattgaac aaagtgtggt tgaacattga    540
tccaaagaag caaacaaaat tatcaccaca ntgccagtgt taagaacaac ctatctccct     600
agtccctact tttctttatt atggctatgt ttgcaatgca agaataagca acattgtaa      660 tgtcaataaa gttttgcactt ttgtagactg gatgggatgt tatcaatgaa gtacctagtt    720
tataagtaaa aaaaaaaaaa aga                                              743

<210> SEQ ID NO 10
<211> LENGTH: 2884
<212> TYPE: DNA
<213> ORGANISM: Gossypium hirsutum

<400> SEQUENCE: 10
gcacaaggta aagcagtgta ccggcggcag tgatggaagt ggccgtgatc ggaggtggga      60 taaagggtt gctttcggcc tacgtactgg tcaaagccgg cgtggacgtg gtggtttacg     120
agaaagaaga acaattaggc ggccatgcaa agactgttaa cttcgacgcc gttgatttag     180
accttggctt cttgtttctc aatccagcaa gatatgcaac actattgcat atgttcgaca     240
gccttggtgt tgatgtagaa acatccgatg tttcattctc tataagccat gacaaaggca     300
acaatggcta tgaatggtgc agccaatatg gattttccaa ttactttgct caaaagaaga     360
aactgttgaa ccctttcaat tggcaaagcc tcagagagat catcaaattc ggcaatgatg     420
tcgaaagtta ccttggatca cttgagaaca acccagacat tgatcgtact gagaccttgg     480
gacagtttat aaaactcaaag ggctactctg aaaattttca aaacacttat ctggctccta     540
tatgtggttc aatgtggtca agctccaagg aagatgttac gagcttttca gcttttcca     600 tcctttcatt ttgccgtact catcatttgt accagctatt tgggcagtca cagtggttga    660
```

```
ctatcaaagg gcactcacat tttgttaaaa gggttaggga agtgctggag actaaaggtt    720
gtcaatttaa actcggttgt gaagtacaat ctgttttgcc cgttgataat ggtaccgcca    780
tggtctgtgg agatggtttc caagaaactt acaatggatg cataatggct gttgatgctc    840
ccactgccct aaaattatta ggaaaccaag caacatttga agaaacaaga gtactgggtg    900
cttttccaata tgctaccagt gatattttcc ttcaccagga cagtacttta atgccacaaa    960
acaaatcagc ttggagtgca ttgaattttc tcaatagtag caaaaataat gcattcttaa   1020
catactggct caatgcacta cagaatattg ggaaaacaag tgagccattt tttgtgactg   1080
tcaatccaga ccatacccg aagaatacct tacttaagtg gtcaaccggc catgcaatts   1140
cctctgttgc tgcatcaaaa gcttcacttg agcttggtca gattcaggga aagagaggaa   1200
tctggttctg tggctatgac ttcaatcagg atgaactaaa ggctggtatg gatgctgcac   1260
atggtatctt gggaaagcat tcttctgttc cgcccagtcc aaagaatatg tcaccctctt   1320
taccaaagaa tatgtcaccc tctttcatgg aaacaacggc acgcctcttt gttaccaaat   1380
tctttcaaca atatatatct atgggctgcg taattttttt agaggaagga ggcagaattt   1440
tcactttcaa aggaaacatg gaaaagtgtc ctcttaaaac agttctgaaa gtgcataatc   1500
ctcagttta ctggaggatc atgaaagaag ctgatatagg ccttgcagac gcatatatcc   1560
atggagattt ttcttttctt gatgaaaatg aaggccttct taatcttttc cggattcttg   1620
ttgccaataa agagaactca gctgcctcag ggtcgactaa aagaaggact tggtggtcgc   1680
ctgctctgtt aacagctagt atatcatctg ccaagtattt tgtgaagcat ctcttaagac   1740
aaaatactat tacacaagct cgtaggaaca tttctcgtca ttatgatctg agtaatgaac   1800
ttttctctct atacttgggc aaaatgatgc aatactcttc tggagtcttt aggacaggag   1860
aagaacattt ggacgttgca cagcgaagaa aaatcagttc tctaattgag aaaacaagga   1920
tagagaaatg gcatgaagtt ctagacattg ggtgcggttg gggaagctta gctattgaaa   1980
ctgtgaaaag aacaggatgc aaatatactg gcatcactct atcagaacag caactgaaat   2040
atgctcaaga aaaagtgaag gaagctggac tcgaggataa catcaaaata cttctctgtg   2100
actatcgcca gttacctaag gaacaccaat ttgacagaat catatctgta gagatggtag   2160
aacatgttgg tgaagaatat attgaggaat tttacagatg ctgtgatcaa ttactgaaag   2220
aagatggact tttcgttctt cagttcatat ctatcccaga ggagctttcc aaagaaatcc   2280
agcaaacagc tggttttctt aaggaatata tattccctgg tggaacctg ctttctttgg   2340
ataggaattt atcagccatg gctgctgcaa caagattcag tgtggagcat gtggaaaaca   2400
taggaatgag ttattaccac acactgagat ggtggagaaa acttttcctg aaaaacacaa   2460
gcaaagttct ggctttgggg ttcgacgaga agttcatgcg gacatgggaa tactatttcg   2520
attactgtgc tgctggtttt aagacaggaa ccccttataga ttaccaggtt gtattttctc   2580
gagccggtaa tttcggtaca cttggagatc catacaaagg tttccccttct gcatattcct   2640
tcatggatga ttgaacaaag tgtttgaata tatgatcacc atacaatgat tcaaccagct   2700
ggatcaaact ggtaccagtg tttacctagt cccctgcttt tgtttagtta tggttttcgt   2760
ttcgttgcga aaagaaaaa agcaaataat gtatgttaat aatgaaatgt ttgtatctgg   2820
tatatctata ctggttggat tttatgtatg gagatctgtt tcttttttaaa aaaaaaaaa   2880
aaaa                                                                2884

<210> SEQ ID NO 11
<211> LENGTH: 873
<212> TYPE: PRT
```

<213> ORGANISM: Gossypium hirsutum
<220> FEATURE:
<221> NAME/KEY: misc_feature
<222> LOCATION: (370)..(370)
<223> OTHER INFORMATION: Xaa can be any naturally occurring amino acid

<400> SEQUENCE: 11

```
Met Glu Val Ala Val Ile Gly Gly Ile Lys Gly Leu Leu Ser Ala
1               5                   10                  15

Tyr Val Leu Val Lys Ala Gly Val Asp Val Val Tyr Glu Lys Glu
                20                  25                  30

Glu Gln Leu Gly Gly His Ala Lys Thr Val Asn Phe Asp Ala Val Asp
                35                  40                  45

Leu Asp Leu Gly Phe Leu Phe Leu Asn Pro Ala Arg Tyr Ala Thr Leu
50                  55                  60

Leu His Met Phe Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Leu Leu
                100                 105                 110

Asn Pro Phe Asn Trp Gln Ser Leu Arg Glu Ile Ile Lys Phe Gly Asn
                115                 120                 125

Asp Val Glu Ser Tyr Leu Gly Ser Leu Glu Asn Asn Pro Asp Ile Asp
130                 135                 140

Arg Thr Glu Thr Leu Gly Gln Phe Ile Asn Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Thr Ser Phe Ser Ala Phe Ser Ile Leu Ser
                180                 185                 190

Phe Cys Arg Thr His His Leu Tyr Gln Leu Phe Gly Gln Ser Gln Trp
                195                 200                 205

Leu Thr Ile Lys Gly His Ser His Phe Val Lys Arg Val Arg Glu Val
210                 215                 220

Leu Glu Thr Lys Gly Cys Gln Phe Lys Leu Gly Cys Glu Val Gln Ser
225                 230                 235                 240

Val Leu Pro Val Asp Asn Gly Thr Ala Met Val Cys Gly Asp Gly Phe
                245                 250                 255

Gln Glu Thr Tyr Asn Gly Cys Ile Met Ala Val Asp Ala Pro Thr Ala
                260                 265                 270

Leu Lys Leu Leu Gly Asn Gln Ala Thr Phe Glu Glu Thr Arg Val Leu
                275                 280                 285

Gly Ala Phe Gln Tyr Ala Thr Ser Asp Ile Phe Leu His Gln Asp Ser
                290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
                340                 345                 350

Asp His Thr Pro Lys Asn Thr Leu Leu Lys Trp Ser Thr Gly His Ala
                355                 360                 365

Ile Xaa Ser Val Ala Ala Ser Lys Ala Ser Leu Glu Leu Gly Gln Ile
    370                 375                 380
```

```
Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
            405                 410                 415

Ser Ser Val Pro Pro Ser Pro Lys Asn Met Ser Pro Ser Leu Pro Lys
        420                 425                 430

Asn Met Ser Pro Ser Phe Met Glu Thr Thr Ala Arg Leu Phe Val Thr
    435                 440                 445

Lys Phe Phe Gln Gln Tyr Ile Ser Met Gly Cys Val Ile Phe Leu Glu
450                 455                 460

Glu Gly Gly Arg Ile Phe Thr Phe Lys Gly Asn Met Glu Lys Cys Pro
465                 470                 475                 480

Leu Lys Thr Val Leu Lys Val His Asn Pro Gln Phe Tyr Trp Arg Ile
                485                 490                 495

Met Lys Glu Ala Asp Ile Gly Leu Ala Asp Ala Tyr Ile His Gly Asp
            500                 505                 510

Phe Ser Phe Leu Asp Glu Asn Glu Gly Leu Leu Asn Leu Phe Arg Ile
        515                 520                 525

Leu Val Ala Asn Lys Glu Asn Ser Ala Ala Ser Gly Ser Thr Lys Arg
530                 535                 540

Arg Thr Trp Trp Ser Pro Ala Leu Leu Thr Ala Ser Ile Ser Ser Ala
545                 550                 555                 560

Lys Tyr Phe Val Lys His Leu Leu Arg Gln Asn Thr Ile Thr Gln Ala
                565                 570                 575

Arg Arg Asn Ile Ser Arg His Tyr Asp Leu Ser Asn Glu Leu Phe Ser
            580                 585                 590

Leu Tyr Leu Gly Lys Met Met Gln Tyr Ser Ser Gly Val Phe Arg Thr
        595                 600                 605

Gly Glu Glu His Leu Asp Val Ala Gln Arg Arg Lys Ile Ser Ser Leu
610                 615                 620

Ile Glu Lys Thr Arg Ile Glu Lys Trp His Glu Val Leu Asp Ile Gly
625                 630                 635                 640

Cys Gly Trp Gly Ser Leu Ala Ile Glu Thr Val Lys Arg Thr Gly Cys
                645                 650                 655

Lys Tyr Thr Gly Ile Thr Leu Ser Glu Gln Gln Leu Lys Tyr Ala Gln
            660                 665                 670

Glu Lys Val Lys Glu Ala Gly Leu Glu Asp Asn Ile Lys Ile Leu Leu
        675                 680                 685

Cys Asp Tyr Arg Gln Leu Pro Lys Glu His Gln Phe Asp Arg Ile Ile
690                 695                 700

Ser Val Glu Met Val Glu His Val Gly Glu Glu Tyr Ile Glu Glu Phe
705                 710                 715                 720

Tyr Arg Cys Cys Asp Gln Leu Leu Lys Glu Asp Gly Leu Phe Val Leu
                725                 730                 735

Gln Phe Ile Ser Ile Pro Glu Glu Leu Ser Lys Glu Ile Gln Gln Thr
            740                 745                 750

Ala Gly Phe Leu Lys Glu Tyr Ile Phe Pro Gly Gly Thr Leu Leu Ser
        755                 760                 765

Leu Asp Arg Asn Leu Ser Ala Met Ala Ala Thr Arg Phe Ser Val
770                 775                 780

Glu His Val Glu Asn Ile Gly Met Ser Tyr Tyr His Thr Leu Arg Trp
785                 790                 795                 800

Trp Arg Lys Leu Phe Leu Lys Asn Thr Ser Lys Val Leu Ala Leu Gly
                805                 810                 815
```

```
Phe Asp Glu Lys Phe Met Arg Thr Trp Glu Tyr Tyr Phe Asp Tyr Cys
            820                 825                 830

Ala Ala Gly Phe Lys Thr Gly Thr Leu Ile Asp Tyr Gln Val Val Phe
            835                 840                 845

Ser Arg Ala Gly Asn Phe Gly Thr Leu Gly Asp Pro Tyr Lys Gly Phe
            850                 855                 860

Pro Ser Ala Tyr Ser Phe Met Asp Asp
865                 870

<210> SEQ ID NO 12
<211> LENGTH: 2827
<212> TYPE: DNA
<213> ORGANISM: Gossypium hirsutum

<400> SEQUENCE: 12
```

| | | | | | |
|---|---|---|---|---|---|
| gtcacggcgg | cagtgatgga | agtggcggtg | atcggaggtg | ggataaaagg | gttggtttcg | 60 |
| gcctacgtac | tggtcaaagc | cggcgtggac | gtggtggttt | acgagaaaga | agagcaatta | 120 |
| ggcggccatg | cgaagactgt | taacttcgac | gccgttgact | tagaccttgg | cttcttgttt | 180 |
| cttaatcctg | caagatatgc | aacactgttg | gatataatcg | acagccttgg | tgttgatgta | 240 |
| gaaacatccg | atgtttcatt | ctctataagc | catgacaaag | gcaacaatgg | ctatgaatgg | 300 |
| tgcagtcaat | atggattttc | caattacttt | gcacaaaaga | gaaactgtt | gaacccttc | 360 |
| aattggcaaa | accttagaga | gatcatcaga | ttcagcaacg | atgtcgaaag | ttaccttgga | 420 |
| tcacttgaga | caacccaga | cattgatcgt | actgagacct | gggacagtt | tataaaatca | 480 |
| aagggctact | ctgaaaattt | tcaaaacact | tacctggctc | ctatatgtgg | ttcaatgtgg | 540 |
| tcaagctcca | aggaagatgt | tatgagcttt | tcagcatttt | ccatcctttc | attttgccgt | 600 |
| actcatcatt | tgtaccagca | atttgggcag | ccacagtggt | tgactatcaa | agggcactca | 660 |
| cattttgtta | aaagggttag | ggaagtgctg | gagactaaag | gttgtcaatt | taaactcggt | 720 |
| tgtgaagtac | aatctgtttt | gcctgctgat | aatggtacca | ccatggtctg | tggagatggt | 780 |
| ttccaagaaa | cttacaatgg | atgcataatg | gctgttgatg | ctcccactgc | cctaaaatta | 840 |
| ttaggaaacc | aagcaacatt | tgaagaaaca | agagtactgg | gtgctttcca | atatgctacc | 900 |
| agtgatattt | tccttcaccg | ggacagtact | ttaatgccac | aaaacaaatc | agcttggagt | 960 |
| gcattgaatt | ttctcaatag | tagcaaaaat | aatgcattct | taacatactg | gctcaatgca | 1020 |
| ctacagaata | ttgggaaaac | aagtgagcca | ttttttgtga | ctgtcaatcc | agaccatacc | 1080 |
| ccgaagaata | ccttgcttaa | gtggtcgact | ggccatgcaa | ttccctctgt | tgctgcatca | 1140 |
| aaagcttcac | ttgagcttgg | tcagattcag | gggaagagag | gaatctggtt | ctgtggctat | 1200 |
| gacttcaatc | aggatgaact | aaaggctggt | atggatgctg | cacatggtat | cttgggaaag | 1260 |
| cattcttctg | ttctgcatag | tccaaagagt | atgtcaccct | ctttcatgga | aacaacggca | 1320 |
| cgcctctttg | ttactaaatt | ctttcaacaa | tatatatcta | tgggctgtgt | aattttctta | 1380 |
| gaggaaggag | gcagaatttt | cactttcaaa | ggaaacatgg | aaaagtgtcc | tcttaaaaca | 1440 |
| gttctgaaag | tacataatcc | tcagttttac | tggaggatca | tgaaagaagc | tgatataggc | 1500 |
| cttgcagatg | catatatcca | tggagatttt | tcttttcttg | atgaaactga | aggccttctt | 1560 |
| aatcttttcc | ggattcttgt | tgccaataaa | gagaactcag | ctgcctcagg | tcgaataaaa | 1620 |
| agaaggactt | ggtggtcacc | tgctctgtta | acagctagta | tatcatctgc | aaagtatttt | 1680 |
| gtgaagcatc | tcttgagaca | aaatactatt | acacaagctc | gtaggaacat | ttctcgtcat | 1740 |
| tatgatctga | gtaatgaact | tttcactcta | tacttgggca | aaatgatgca | atactcttct | 1800 |

```
ggagtctttta ggacgggaga agaacatttg gacgttgcac agcgtagaaa aatcagttct    1860
ctaattgaga aagcaaggat agagaaacgg cacgaagttc tcgacattgg gtgcggttgg    1920
ggaagcttag ctattgaaac tgtgaaaaga acaggatgca aatatactgg catcactcta    1980
tcagaacagc aactgaaata tgctcaagaa aaagtgaagg aagctggact ccaggataac    2040
atcaaaatac ttctctgtga ctatcgccag ttacctaagg aacaccaatt tgacagaatc    2100
atatctgtag agatggtaga acatgttggt gaagaatata ttgaggagtt ttacagatgc    2160
tgtgaccaat tactgaaaga agatgggctt tttgttcttc agttcatatc tatcccagaa    2220
gagctttcca aagaaatcca gcaaacagca ggttttctaa aggaatatat attccctgga    2280
ggaaccctgc tttctttgga taggaattta tcagccatgg ctgctgcaac aagattcagt    2340
gtggagcatg tggaaaatat aggaatgagt tattaccaca cactgagatg gtggagaaaa    2400
cttttcctgg aaaacacaag caaagttcta gctctggggt tcgacgagaa gttcatgagg    2460
acatgggaat actatttcga ttactgcgct gccggtttta agacaggaac tcttatagat    2520
taccaggttg tattttcaag ggccggaaat ttcggtacac tcggagatcc atacaaaggt    2580
ttcccttctg catattcctt catggatgat tgaacaaagt gtggttgaac attgatccaa    2640
agaagcaaac aaaattatca ccacatgcca gtgttaagaa caacctatct ccctagtccc    2700 tactttgtt tattatggct atgtttgcaa tgcaagaata agcaaacatt gtaatgttaa    2760
taaagtttgc acttttgtag actggatgga tgttatcaat gaagtaccta gtttataaaa    2820
aaaaaaa                                                              2827

<210> SEQ ID NO 13
<211> LENGTH: 865
<212> TYPE: PRT
<213> ORGANISM: Gossypium hirsutum

<400> SEQUENCE: 13

Met Glu Val Ala Val Ile Gly Gly Gly Ile Lys Gly Leu Val Ser Ala
1               5                   10                  15

Tyr Val Leu Val Lys Ala Gly Val Asp Val Val Tyr Glu Lys Glu
            20                  25                  30

Glu Gln Leu Gly Gly His Ala Lys Thr Val Asn Phe Asp Ala Val Asp
        35                  40                  45

Leu Asp Leu Gly Phe Leu Phe Leu Asn Pro Ala Arg Tyr Ala Thr Leu
    50                  55                  60

Leu Asp Ile Ile Asp Ser Leu Gly Val Asp Val Glu Thr Ser Asp Val
65                  70                  75                  80

Ser Phe Ser Ile Ser His Asp Lys Gly Asn Asn Gly Tyr Glu Trp Cys
                85                  90                  95

Ser Gln Tyr Gly Phe Ser Asn Tyr Phe Ala Gln Lys Lys Lys Leu Leu
            100                 105                 110

Asn Pro Phe Asn Trp Gln Asn Leu Arg Glu Ile Ile Arg Phe Ser Asn
        115                 120                 125

Asp Val Glu Ser Tyr Leu Gly Ser Leu Glu Asn Asn Pro Asp Ile Asp
    130                 135                 140

Arg Thr Glu Thr Leu Gly Gln Phe Ile Lys Ser Lys Gly Tyr Ser Glu
145                 150                 155                 160

Asn Phe Gln Asn Thr Tyr Leu Ala Pro Ile Cys Gly Ser Met Trp Ser
                165                 170                 175

Ser Ser Lys Glu Asp Val Met Ser Phe Ser Ala Phe Ser Ile Leu Ser
            180                 185                 190
```

```
Phe Cys Arg Thr His His Leu Tyr Gln Gln Phe Gly Gln Pro Gln Trp
            195                 200                 205

Leu Thr Ile Lys Gly His Ser His Phe Val Lys Arg Val Arg Glu Val
            210                 215                 220

Leu Glu Thr Lys Gly Cys Gln Phe Lys Leu Gly Cys Glu Val Gln Ser
225                 230                 235                 240

Val Leu Pro Ala Asp Asn Gly Thr Thr Met Val Cys Gly Asp Gly Phe
                245                 250                 255

Gln Glu Thr Tyr Asn Gly Cys Ile Met Ala Val Asp Ala Pro Thr Ala
                260                 265                 270

Leu Lys Leu Leu Gly Asn Gln Ala Thr Phe Glu Glu Thr Arg Val Leu
            275                 280                 285

Gly Ala Phe Gln Tyr Ala Thr Ser Asp Ile Phe Leu His Arg Asp Ser
            290                 295                 300

Thr Leu Met Pro Gln Asn Lys Ser Ala Trp Ser Ala Leu Asn Phe Leu
305                 310                 315                 320

Asn Ser Ser Lys Asn Asn Ala Phe Leu Thr Tyr Trp Leu Asn Ala Leu
                325                 330                 335

Gln Asn Ile Gly Lys Thr Ser Glu Pro Phe Phe Val Thr Val Asn Pro
            340                 345                 350

Asp His Thr Pro Lys Asn Thr Leu Leu Lys Trp Ser Thr Gly His Ala
            355                 360                 365

Ile Pro Ser Val Ala Ala Ser Lys Ala Ser Leu Glu Leu Gly Gln Ile
            370                 375                 380

Gln Gly Lys Arg Gly Ile Trp Phe Cys Gly Tyr Asp Phe Asn Gln Asp
385                 390                 395                 400

Glu Leu Lys Ala Gly Met Asp Ala Ala His Gly Ile Leu Gly Lys His
                405                 410                 415

Ser Ser Val Leu His Ser Pro Lys Ser Met Ser Pro Ser Phe Met Glu
            420                 425                 430

Thr Thr Ala Arg Leu Phe Val Thr Lys Phe Phe Gln Gln Tyr Ile Ser
            435                 440                 445

Met Gly Cys Val Ile Phe Leu Glu Glu Gly Gly Arg Ile Phe Thr Phe
            450                 455                 460

Lys Gly Asn Met Glu Lys Cys Pro Leu Lys Thr Val Leu Lys Val His
465                 470                 475                 480

Asn Pro Gln Phe Tyr Trp Arg Ile Met Lys Glu Ala Asp Ile Gly Leu
                485                 490                 495

Ala Asp Ala Tyr Ile His Gly Asp Phe Ser Phe Leu Asp Glu Thr Glu
                500                 505                 510

Gly Leu Leu Asn Leu Phe Arg Ile Leu Val Ala Asn Lys Glu Asn Ser
            515                 520                 525

Ala Ala Ser Gly Ser Asn Lys Arg Arg Thr Trp Trp Ser Pro Ala Leu
530                 535                 540

Leu Thr Ala Ser Ile Ser Ser Ala Lys Tyr Phe Val Lys His Leu Leu
545                 550                 555                 560

Arg Gln Asn Thr Ile Thr Gln Ala Arg Arg Asn Ile Ser Arg His Tyr
            565                 570                 575

Asp Leu Ser Asn Glu Leu Phe Thr Leu Tyr Leu Gly Lys Met Met Gln
            580                 585                 590

Tyr Ser Ser Gly Val Phe Arg Thr Gly Glu Glu His Leu Asp Val Ala
            595                 600                 605

Gln Arg Arg Lys Ile Ser Ser Leu Ile Glu Lys Ala Arg Ile Glu Lys
```

```
                610                 615                 620
Arg His Glu Val Leu Asp Ile Gly Cys Gly Trp Gly Ser Leu Ala Ile
625                 630                 635                 640

Glu Thr Val Lys Arg Thr Gly Cys Lys Tyr Thr Gly Ile Thr Leu Ser
                645                 650                 655

Glu Gln Gln Leu Lys Tyr Ala Gln Glu Lys Val Lys Glu Ala Gly Leu
                660                 665                 670

Gln Asp Asn Ile Lys Ile Leu Leu Cys Asp Tyr Arg Gln Leu Pro Lys
                675                 680                 685

Glu His Gln Phe Asp Arg Ile Ile Ser Val Glu Met Val Glu His Val
                690                 695                 700

Gly Glu Glu Tyr Ile Glu Glu Phe Tyr Arg Cys Cys Asp Gln Leu Leu
705                 710                 715                 720

Lys Glu Asp Gly Leu Phe Val Leu Gln Phe Ile Ser Ile Pro Glu Glu
                725                 730                 735

Leu Ser Lys Glu Ile Gln Gln Thr Ala Gly Phe Leu Lys Glu Tyr Ile
                740                 745                 750

Phe Pro Gly Gly Thr Leu Leu Ser Leu Asp Arg Asn Leu Ser Ala Met
                755                 760                 765

Ala Ala Ala Thr Arg Phe Ser Val Glu His Val Glu Asn Ile Gly Met
770                 775                 780

Ser Tyr Tyr His Thr Leu Arg Trp Trp Arg Lys Leu Phe Leu Glu Asn
785                 790                 795                 800

Thr Ser Lys Val Leu Ala Leu Gly Phe Asp Glu Lys Phe Met Arg Thr
                805                 810                 815

Trp Glu Tyr Tyr Phe Asp Tyr Cys Ala Ala Gly Phe Lys Thr Gly Thr
                820                 825                 830

Leu Ile Asp Tyr Gln Val Val Phe Ser Arg Ala Gly Asn Phe Gly Thr
                835                 840                 845

Leu Gly Asp Pro Tyr Lys Gly Phe Pro Ser Ala Tyr Ser Phe Met Asp
                850                 855                 860

Asp
865

<210> SEQ ID NO 14
<211> LENGTH: 2912
<212> TYPE: DNA
<213> ORGANISM: Gossypium hirsutum

<400> SEQUENCE: 14
tccctatctc catttactat tttcttctct cttcttcttc tttcgaacca ttttcagagt      60
tcataaattc agggttttgt ttttttttg ggtgtagtga aataaggat gaaatagca        120 gtgataggag gagggataag tggggtggta tcagcctata ctttagccaa agccggtgca    180
aatgtagtgc tttacgagaa agaagagtat tgggaggcc attccaagac cgttcacttc     240
gatggtgttg atttagacct tggtttcatg gttttaatc gcgttacata tccaaatatg      300
atggagttgt ttgagagcct tgggattgat atggaaccat tgatatgtc actctcagtg     360 agccttaatg aaggcaaagg ctgtgaatgg ggcagccgta atggcctttc ggccttgttt    420
gcccaaaaat ccaacctctt caatccttac ttttggcaaa tgcttagaga aattctcaaa   480
ttcaagaatg atgttattag ttatcttgaa ttgctcgaaa caacccggga tattgaccgt   540
aatgaaacat tgggacagtt cataaaatca aagggttact ctgatttatt tcagaaggct   600
tatctggtgc ctgtatgtgg ttcaatatgg tcatgcccta cagaaagagt tatggatttt   660
```

```
tcagctttct ctattctttc attttgccgc aatcatcatc tacttcagat ctttggacga   720
ccacagtgga tgaccgttcg atggcgttca catcgttacg tcataaggt tagagaagag    780
ctggagagta caggttgtca aataagaact ggttgcgagg tgcattctgt tttgagtgat   840
gctgaaggtt gcactgtatt atgtggagat gactctcacg agttatatca agggtgcata   900
atggctgttc atgcaccata tgctttgaga ttgttaggga atcaagcaac atatgatgaa   960
tcaacagtgc ttggcgcttt ccaatatgtc tatagtgata tttatcttca tcgtgacaaa  1020
aatttaatgc ccaaaaaccc agcagcatgg agtgcatgga attttcttgg aagtacagac  1080
aagaatgtat ctttgacata ctggcttaat gtgcttcaga atctaggaga acaagcctta  1140
cccttttttgg tcactctcaa tccagattat acaccaaaac acaccttgct taagtggaga  1200
acaggccatc cagtaccatc tgttgctgca acaaaagctt ctcttgagct tgatcggatt  1260
caagggaaga gaggaatttg gttttgtgga gcatacctgg gctatggctt ccatgaagat  1320
ggattaaagg ctgggatgat tgctgcaaac ggtctgctgg gaaaaagttg taatattctg  1380
agcaatccaa agcatatggt gccctctctg atggaaacag gggcacgtct ttttgttact  1440
agattcctca gtcattttat atcaaccggc tgtgtgattt tattggaaga aggtggcact  1500
atgtttacct ttgaaggaac tagcaataag tgttctctaa aaactgtaat taaagttcac  1560
agtccacatt tttattggaa ggttatgaca gaggcagatt taggccttgc agattcatat  1620
atcaatgggg attttctttt tgttgataaa aaagacggtc tgctgaacct tgtaatgatt  1680
cttattgcca acagagattt gatttcttcc aactcaaaac ttagtaagaa aaggggttgg  1740
tggacaccat tgttgtttac agctggtcta acatcagcaa agtatttctt caagcatgtc  1800
ttaagacaaa atactcttac acaagctcgt aggaacattt ctcgccatta cgacytgagt  1860
aatgaccttt ttgcactctt cttggatgag acaatgacat actcttgtgc agtatttaag  1920
acagaagatg aggatttgaa agatgcacaa cacagaaaga tctctctttt gattgaaaaa  1980
gcaagaattg atagcaagca tgaaattctt gagattggat gtggttgggk aagcttagct  2040
attgaggttg tcaaacgaac tggatgcaaa tataccggca ttactttatc cgaagagcaa  2100
ctcaaacttg cagaaaaaag agtgaaggaa gctggacttc aggaaaatat aagatttcaa  2160
ctctgtgact atcgacaact acctagcacc tacaagtatg acagaattat atcgtgtgag  2220
atgatagaag ctgttggcca tgaatacatg gaggacttct tcggttgctg tgaatcagtg  2280
ttagcagatg atggacttct tgttttacag ttcatatcaa taccagagga acggtacaat  2340
gaatacaggc gaagctcgga tttcatcaag gaatacatct tccctggtgg atgcttacct  2400
tctctggcta ggataacaac agccatgaat gctgcgtcca aactctgtgt ggagcatgtg  2460
gaaaacatcg gacttcatta ctaccaaacg cttagatatt ggagaaagaa tttcttggag  2520
aaacagagca aaatccatgc cttgggattc aatgacaagt tcatccggac atgggaatac  2580
tattttgatt attgtgctgc tggtttcaag tccaatactc ttggtaatta ccaggttgta  2640
ttttctcggc ctggaaatgt agttgcactt ggcaacccat acaaagactt cccctcagct  2700
tcttaattat ttattttctc cttatttcaa tcgtaccata gccataattt gagcttgttg  2760
aaaactgatg ctacacgttt ggtttcattc aaatatggta tttgagtgca tatctataca  2820
ttgatgaatg taattctggc ttgcctcgta ggaacttgcc agcaggatta tcttttttaca  2880
tggacatttta ttttaattct ctgttcaaat tt                                 2912
```

<210> SEQ ID NO 15
<211> LENGTH: 865
<212> TYPE: PRT

<213> ORGANISM: Gossypium hirsutum
<220> FEATURE:
<221> NAME/KEY: misc_feature
<222> LOCATION: (641)..(641)
<223> OTHER INFORMATION: Xaa can be any naturally occurring amino acid

<400> SEQUENCE: 15

```
Met Lys Ile Ala Val Ile Gly Gly Ile Ser Gly Val Val Ser Ala
1               5                   10                  15

Tyr Thr Leu Ala Lys Ala Gly Ala Asn Val Val Leu Tyr Glu Lys Glu
            20                  25                  30

Glu Tyr Leu Gly Gly His Ser Lys Thr Val His Phe Asp Gly Val Asp
            35                  40                  45

Leu Asp Leu Gly Phe Met Val Phe Asn Arg Val Thr Tyr Pro Asn Met
50              55                  60

Met Glu Leu Phe Glu Ser Leu Gly Ile Asp Met Glu Pro Phe Asp Met
65              70                  75                  80

Ser Leu Ser Val Ser Leu Asn Glu Gly Lys Gly Cys Glu Trp Gly Ser
            85                  90                  95

Arg Asn Gly Leu Ser Ala Leu Phe Ala Gln Lys Ser Asn Leu Phe Asn
            100                 105                 110

Pro Tyr Phe Trp Gln Met Leu Arg Glu Ile Leu Lys Phe Lys Asn Asp
            115                 120                 125

Val Ile Ser Tyr Leu Glu Leu Glu Asn Asn Pro Asp Ile Asp Arg
130                 135                 140

Asn Glu Thr Leu Gly Gln Phe Ile Lys Ser Lys Gly Tyr Ser Asp Leu
145                 150                 155                 160

Phe Gln Lys Ala Tyr Leu Val Pro Val Cys Gly Ser Ile Trp Ser Cys
                165                 170                 175

Pro Thr Glu Arg Val Met Asp Phe Ser Ala Phe Ser Ile Leu Ser Phe
                180                 185                 190

Cys Arg Asn His His Leu Leu Gln Ile Phe Gly Arg Pro Gln Trp Met
                195                 200                 205

Thr Val Arg Trp Arg Ser His Arg Tyr Val Asn Lys Val Arg Glu Glu
            210                 215                 220

Leu Glu Ser Thr Gly Cys Gln Ile Arg Thr Gly Cys Glu Val His Ser
225                 230                 235                 240

Val Leu Ser Asp Ala Glu Gly Cys Thr Val Leu Cys Gly Asp Asp Ser
                245                 250                 255

His Glu Leu Tyr Gln Gly Cys Ile Met Ala Val His Ala Pro Tyr Ala
                260                 265                 270

Leu Arg Leu Leu Gly Asn Gln Ala Thr Tyr Asp Glu Ser Thr Val Leu
            275                 280                 285

Gly Ala Phe Gln Tyr Val Tyr Ser Asp Ile Tyr Leu His Arg Asp Lys
290                 295                 300

Asn Leu Met Pro Lys Asn Pro Ala Ala Trp Ser Ala Trp Asn Phe Leu
305                 310                 315                 320

Gly Ser Thr Asp Lys Asn Val Ser Leu Thr Tyr Trp Leu Asn Val Leu
                325                 330                 335

Gln Asn Leu Gly Glu Thr Ser Leu Pro Phe Leu Val Thr Leu Asn Pro
            340                 345                 350

Asp Tyr Thr Pro Lys His Thr Leu Leu Lys Trp Arg Thr Gly His Pro
            355                 360                 365

Val Pro Ser Val Ala Ala Thr Lys Ala Ser Leu Glu Leu Asp Arg Ile
370                 375                 380
```

```
Gln Gly Lys Arg Gly Ile Trp Phe Cys Gly Ala Tyr Leu Gly Tyr Gly
385                 390                 395                 400

Phe His Glu Asp Gly Leu Lys Ala Gly Met Ile Ala Ala Asn Gly Leu
            405                 410                 415

Leu Gly Lys Ser Cys Asn Ile Leu Ser Asn Pro Lys His Met Val Pro
        420                 425                 430

Ser Leu Met Glu Thr Gly Ala Arg Leu Phe Val Thr Arg Phe Leu Ser
    435                 440                 445

His Phe Ile Ser Thr Gly Cys Val Ile Leu Glu Glu Gly Gly Thr
450                 455                 460

Met Phe Thr Phe Glu Gly Thr Ser Asn Lys Cys Ser Leu Lys Thr Val
465                 470                 475                 480

Ile Lys Val His Ser Pro His Phe Tyr Trp Lys Val Met Thr Glu Ala
                485                 490                 495

Asp Leu Gly Leu Ala Asp Ser Tyr Ile Asn Gly Asp Phe Ser Phe Val
            500                 505                 510

Asp Lys Lys Asp Gly Leu Leu Asn Leu Val Met Ile Leu Ile Ala Asn
        515                 520                 525

Arg Asp Leu Ile Ser Ser Asn Ser Lys Leu Ser Lys Lys Arg Gly Trp
530                 535                 540

Trp Thr Pro Leu Leu Phe Thr Ala Gly Leu Thr Ser Ala Lys Tyr Phe
545                 550                 555                 560

Phe Lys His Val Leu Arg Gln Asn Thr Leu Thr Gln Ala Arg Arg Asn
            565                 570                 575

Ile Ser Arg His Tyr Asp Leu Ser Asn Asp Leu Phe Ala Leu Phe Leu
        580                 585                 590

Asp Glu Thr Met Thr Tyr Ser Cys Ala Val Phe Lys Thr Glu Asp Glu
            595                 600                 605

Asp Leu Lys Asp Ala Gln His Arg Lys Ile Ser Leu Leu Ile Glu Lys
    610                 615                 620

Ala Arg Ile Asp Ser Lys His Glu Ile Leu Glu Ile Gly Cys Gly Trp
625                 630                 635                 640

Xaa Ser Leu Ala Ile Glu Val Val Lys Arg Thr Gly Cys Lys Tyr Thr
                645                 650                 655

Gly Ile Thr Leu Ser Glu Glu Gln Leu Lys Leu Ala Glu Lys Arg Val
            660                 665                 670

Lys Glu Ala Gly Leu Gln Glu Asn Ile Arg Phe Gln Leu Cys Asp Tyr
        675                 680                 685

Arg Gln Leu Pro Ser Thr Tyr Lys Tyr Asp Arg Ile Ile Ser Cys Glu
    690                 695                 700

Met Ile Glu Ala Val Gly His Glu Tyr Met Glu Asp Phe Phe Gly Cys
705                 710                 715                 720

Cys Glu Ser Val Leu Ala Asp Asp Gly Leu Leu Val Leu Gln Phe Ile
                725                 730                 735

Ser Ile Pro Glu Glu Arg Tyr Asn Glu Tyr Arg Arg Ser Ser Asp Phe
            740                 745                 750

Ile Lys Glu Tyr Ile Phe Pro Gly Gly Cys Leu Pro Ser Leu Ala Arg
        755                 760                 765

Ile Thr Thr Ala Met Asn Ala Ala Ser Lys Leu Cys Val Glu His Val
    770                 775                 780

Glu Asn Ile Gly Leu His Tyr Tyr Gln Thr Leu Arg Tyr Trp Arg Lys
785                 790                 795                 800

Asn Phe Leu Glu Lys Gln Ser Lys Ile His Ala Leu Gly Phe Asn Asp
                805                 810                 815
```

Lys Phe Ile Arg Thr Trp Glu Tyr Tyr Phe Asp Tyr Cys Ala Ala Gly
            820                 825                 830

Phe Lys Ser Asn Thr Leu Gly Asn Tyr Gln Val Val Phe Ser Arg Pro
        835                 840                 845

Gly Asn Val Val Ala Leu Gly Asn Pro Tyr Lys Asp Phe Pro Ser Ala
    850                 855                 860

Ser
865

<210> SEQ ID NO 16
<211> LENGTH: 1771
<212> TYPE: DNA
<213> ORGANISM: Artificial
<220> FEATURE:
<223> OTHER INFORMATION: Artificial

<400> SEQUENCE: 16

```
gaattctcta gaaaagttaa cccttcgaag atgatactga cattaacacc atttttaat       60 attgttttc tatatcgtta ttgatctcag cacattctta gaaagatatt taaattagat      120
aaaagtaaat ttatatatat atatatatat atatatatat atatatatat ataaatgtaa    180
cataaatcta tggtcaatta caatatttaa ttaaataaaa tagaaatata aacaccactt    240
taatttgact cggatacatg catccataaa gactacaaaa ggcaaaaaga gaaggaaatg    300
agatacgaat atatgtcata agtatatata ggtgacaagg gcaaattaaa taggttggta    360
tttaaatgca aaatcctatg tttgataaag aatggtatga aaaacaggca aagttaattg    420
caattcaaag gtgaacaaag catttctttg tctacactaa tggcatgtct aagtaaatta    480
ttagtcttgt atctatatgt ccacaagtta ttaattagtc ttatactatc aaaaacaagt    540
taagttgcaa atcaaacatg aacaaagcat tgtgttgta acctacgaaa aaatacccta    600
acatactgat acgaataatg tggcctaaat tgatcgtta ccaaattacg gtgctggaaa    660
aaaaaattgc tcctttacca acaaaattaa gaactgatac atcttgtttt ttgtcactga    720
agataaacac gtgatctttg gcaaaacata aaggccaaca aaacaaactt gtctcatccc    780
tgaatgattc gaatgccatc gtatgcgtgt cacaaagtgg aatacagcaa tgaacaaatg    840
ctatcctctt gagaaaagtg aatgcagcag cagcagcaga ctagagtgct acaaatgctt    900
atcctcttga gaaagtgaa tgcagcggca gcagacctga gtgctataca aattagaca    960 cagggtctat taattgaaat tgtcttatta ttaaatatt cgttttatat taattttta    1020 aattttaatt aaatttatat atattatatt taagacagat atttatttt gtgattataa    1080 atgtgtcact ttttctttta gtccatgtat tcttctattt tttcaattta acttttatt    1140 ttatttta agtcactctt gatcaagaaa acattgttga cataaaacta ttaacataaa    1200
attatgttaa catgtgataa catcatattt tactaatata acgtcgcatt taacgttttt    1260
tttaacaaat atcgactgta agagtaaaaa tgaaatgttt gaaaaggtta attgcatact    1320
aactattttt tttcctataa gtaatctttt ttgggatcaa ttgtatatca ttgagatacg    1380
atattaaata tgggtacctt tcacaaaac ctaacccttg ttagtcaaac cacacataag    1440
agaggatgga tttaaaccag tcagcaccgt aagtatatag tgaagaaggc tgataacaca    1500
ctctattatt gttagtacgt acgtatttcc ttttttgtt agttttgaa tttaattaat    1560 taaatatat atgctaacaa cattaaattt taaatttacg tctaattata tattgtgatg    1620
tataataaat tgtcaacctt taaaaattat aaaagaaata ttaatttga taaacaactt    1680 ttgaaaagta cccaataatg ctagtataaa tagggggcatg actccccatg catcacagtg    1740
```

```
caatttaact gaagcaaagc agcggccccg g                                  1771
```

<210> SEQ ID NO 17
<211> LENGTH: 1188
<212> TYPE: DNA
<213> ORGANISM: Artificial
<220> FEATURE:
<223> OTHER INFORMATION: Artificial

<400> SEQUENCE: 17

```
accaacacgc cttctttgcc tcgtgtttca tcacctggcg ttaaactgct ttctttaaaa    60
ccaacaaaat gggtgccggg tgggtaggat gccaattgac gggtataaag gaggaaaatc   120
gaggctcggt caatcgagtt ccgatcgaga agcctccgtt tacgctcggt cagatcaagc   180
aagccattcc gccccactgt tttcgccgct ccctccttcg atccttctcc tacgtggtcc   240
atgacctatg cttagcctct ctcttttact acattgcaac atcatatttt cactttctcc   300
cacacccctt ttcctacatt gcttggcctg tctattgggt ctccaaggt tggtaccatg    360
gtctgtggag atggtttcca agaaacttac aatggatgca taatggctgt tgatgctccc   420
actgccctaa aattattagg aaaccaagca acatttgaag aaacaagagt actgggtgct   480
ttccaatatg ctaccagtga tattttcctt caccgggaca gtactttaat gccacaaaac   540
aaatcagctt ggagtgcatt gaattttctc aatagtagca aaaataatgc attcttaaca   600
tactggctca atgcactaca gaatattggg aaaacaagtg agccattttt tgtgactgtc   660
aatccagacc ataccccgaa gaatacccttg cttaagtggt cgactggcca tgcaattccc   720
tctgttgctg catcaaaagc ttcacttgag cttggtcaga ttcagggga gagaggaatc    780
tggttctgtg gctatgagag ctcctcggac ctttatcaat caattacctg attggagcat   840
gcttcttgcc gctatcacaa ccattttcct ggctgctgag aagcagtgga tgatgcttga   900
ttggaagcca aggcggcctg acatgctcat tgatcctttt ggtataggga ggattgttca   960
ggatggtctt gttttccgtc aaaacttctc gattaggtct tatgagatag gtgctgatcg  1020
tacggcatcc atagagacgc taatgaatca tttacaggaa accgcgatta atcattgtaa  1080
aagtgctgga ctgcttggag aaggttttgg tgctaccccct gagatgtgca agaagaacct  1140
aatttgggtg gtcactcgga tgcaagttgt gtttgatcgg tatcctac               1188
```

<210> SEQ ID NO 18
<211> LENGTH: 1110
<212> TYPE: DNA
<213> ORGANISM: Artificial
<220> FEATURE:
<223> OTHER INFORMATION: Artificial

<400> SEQUENCE: 18

```
gtacatttct ctttaatttc cttttttttt catttcatgt ttttcatgtt aatgttgcat    60
tgaagtgata aatttgagtg aatgatgttt ggtatatctt cttagtaact gacctttga    120
aaatactagc attttttta atatcaagtg aagaagaag aagaatttcg ccatgcaaaa     180
gcttttaag gcttttctt tccttagat caaaattat tgtttactt atactgttct       240
tttaagcccg aagaagaag ccatggtttc aatttttgag agttttaaat cccaaatacc   300
agagagcttc atcgtttatt catatatttt taaacatttt ttaaagcaag aacttgtgat  360
ttgttttaa taaatatgc aataaatttt tatattttc gtaaatttaa aatttaatttt    420
ttctactttt aaaatttaaa aaagtaaatt ttaaaatata cctttcatta aattaaatta   480
ttataagtaa ttgagtattt ttaattttaa aatttcacac atcaaattaa aaaaaaagtt  540
```

```
aacacttgca cttgattttg aaaagtaaaa ggattaaatt tcaaattttc agtaaaagga      600
ctaaatttca aattttaaaa gagtatagag actcctctac attttagatt ttaaaattta      660
aatctaacag ttaacacttt cttaattact ttacgataaa tttaactaaa aaattacaat      720
attaatggtt aaaattaaat tttgaaaagt ataaagatta aattgtaaat tttcaaaaag      780
cataggaagt tatagtatat tttaaccttt atttattta tatctggtga ggttcctgca       840
tgcaccgaag atgtcacctt tgccagtat tttccagtgg cttgtttctc tcaaaactac       900
cttgaatctt gagacagaat taaatatatt tttggccttt tcttcatttt ctctctctct      960
attttctttt aaaaattgct ttagagaatt cagaaaaat actttccaac acgaaaattt       1020
cttcaaattt attgtttata tctaataaat ggttgcttaa ttttggaaaa caaaagttat      1080
tgtagttagt tttgcttctt gcgtgtccag                                        1110

<210> SEQ ID NO 19
<211> LENGTH: 1188
<212> TYPE: DNA
<213> ORGANISM: Artificial
<220> FEATURE:
<223> OTHER INFORMATION: Artificial

<400> SEQUENCE: 19
gtaggatacc gatcaaacac aacttgcatc cgagtgacca cccaaattag gttcttcttg       60
cacatctcag gggtagcacc aaaaccttct ccaagcagtc cagcacttt acaatgatta       120 atcgcggttt cctgtaaatg attcattagc gtctctatgg atgccgtacg atcagcacct     180
atctcataag acctaatcga gaagttttga cggaaaacaa gaccatcctg aacaatcctc     240
cctataccaa aaggatcaat gagcatgtca ggccgccttg gcttccaatc aagcatcatc    300
cactgcttct cagcagccag gaaaatggtt gtgatagcgg caagaagcat gctccaatca    360
ggtaattgat tgataaaggt ccgaggagct ctcatagcca cagaaccaga ttcctctctt     420
cccctgaatc tgaccaagct caagtgaagc ttttgatgca gcaacagagg gaattgcatg    480
gccagtcgac cacttaagca aggtattctt cggggtatgg tctggattga cagtcacaaa    540
aaatggctca cttgttttcc caatattctg tagtgcattg agccagtatg ttaagaatgc    600 attattttg ctactattga gaaaattcaa tgcactccaa gctgatttgt tttgtggcat     660
taaagtactg tcccggtgaa ggaaaatatc actggtagca tattggaaag cacccagtac    720
tcttgtttct tcaaatgttg cttggtttcc taataatttt agggcagtgg gagcatcaac    780
agccattatg catccattgt aagtttcttg gaaaccatct ccacagacca tggtaccaac    840
cttggagaac ccaatagaca ggccaagcaa tgtaggaaaa gggttgtggg agaaagtgaa    900
aatatgatgt tgcaatgtag taaaagagag aggctaagca taggtcatgg accacgtagg   960
agaaggatcg aaggagggag cggcgaaaac agtggggcgg aatggcttgc ttgatctgac   1020
cgagcgtaaa cggaggcttc tcgatcggaa ctcgattgac cgagcctcga ttttcctcct   1080
ttatacccgt caattggcat cctacccacc cggcacccat tttgttggtt taaagaaag    1140 cagtttaacg ccaggtgatg aaacacgagg caaagaaggc gtgttggt                1188

<210> SEQ ID NO 20
<211> LENGTH: 358
<212> TYPE: DNA
<213> ORGANISM: Artificial
<220> FEATURE:
<223> OTHER INFORMATION: Artificial

<400> SEQUENCE: 20
```

```
aggggccgcc atgtgacaga tcgaaggaag aaagtgtaat aagacgactc tcactactcg      60
atcgctagtg attgtcattg ttatatataa taatgttatc tttcacaact tatcgtaatg     120
catgtgaaac tataacacat taatcctact tgtcatatga taacactctc cccatttaaa     180
actcttgtca atttaaagat ataagattct ttaaatgatt aaaaaaaata tattataaat     240
tcaatcactc ctactaataa attattaatt aatatttatt gattaaaaaa atacttatac     300
taatttagtc tgaatagaat aattagattc tagagtcgac ctgcaggcat gcaagctt      358
```

<210> SEQ ID NO 21
<211> LENGTH: 620
<212> TYPE: DNA
<213> ORGANISM: Artificial
<220> FEATURE:
<223> OTHER INFORMATION: Artificial

<400> SEQUENCE: 21

```
tctagaggat cctatgttgt aatttatat ggattaatga gaattattat tattctgttc      60
ttcgtctgtg ttttttaagc tagcttcctc gaagcagcgt ataactttaa tttgaatttg     120
gttttggcgc gttagtgaaa ttgcggctgt aaacgtgtca agttgtgagt ggctgaaata     180
agataataga tatattatta ttgttttaat ttaattccgc gaagcgatat gttaagtgat     240
aaatgaaacg aagcgttttg atgacgtcat atgtctccgt gcctacgtca gcacgggct      300 tagtattacc cccgtgccgg gatcagagac atttgaccaa tagttgacta gtataatagc     360
ccttggatta aatgacacgt ggacgctcag gatctgtgat gctagtgaag cgcttaagct     420
gaacgaatct gacggaagag cgttcacact tagatctagt tagcgtactt agtacgcgtt     480
gtcttgggtc tataaataga gtgcttctga acagattgtt cagaatttca tagcgccgat     540
aacaatgatt gaacaagatg gattgcacgc aggttctccg gccgcttggg tggagaggct     600
attcggctat gactgggcac                                                 620
```

<210> SEQ ID NO 22
<211> LENGTH: 709
<212> TYPE: DNA
<213> ORGANISM: Artificial
<220> FEATURE:
<223> OTHER INFORMATION: Artificial

<400> SEQUENCE: 22

```
aacagacaat cggctgctct gatgccgccg tgttccggct gtcagcgcag ggcgcccgg       60 ttcttttgt caagaccgac ctgtccggtg ccctgaatga actgcaggta aatttctagt      120
ttttctcctt catttcttg gttaggaccc ttttctcttt ttattttttt gagctttgat      180
ctttctttaa actgatctat ttttaattg attggttatg gtgtaaatat tacatagctt     240
taactgataa tctgattact ttatttcgtg tgtctatgat gatgatgata actgcaggac     300
gaggcagcgc ggctatcgtg gctggccacg acgggcgttc cttgcgcagc tgtgctcgac     360
gttgtcactg aagcgggaag ggactggctg ctattgggcg aagtgccggg gcaggatctc     420
ctgtcatctc accttgctcc tgccgagaaa gtatccatca tggctgatgc aatgcggcg      480 ctgcatacgc ttgatccggc tacctgccca ttcgaccacc aagcgaaaca tcgcatcgag     540
cgagcacgta ctcggatgga agccggtctt gtcgatcagg atgatctgga cgaagagcat     600
caggggctcg cgccagccga actgttcgcc aggctcaagg cgcgcatgcc cgacggcgag     660
gatctcgtcg tgacccatgg cgatgcctgc ttgccgaata tcatggtgg                 709
```

<210> SEQ ID NO 23
<211> LENGTH: 549
<212> TYPE: DNA
<213> ORGANISM: Artificial
<220> FEATURE:
<223> OTHER INFORMATION: Artificial

<400> SEQUENCE: 23

```
aaaatggccg cttttctgga ttcatcgact gtggccggct gggtgtggcg gaccgctatc    60
aggacatagc gttggctacc cgtgatattg ctgaagagct tggcggcgaa tgggctgacc   120
gcttcctcgt gctttacggt atcgccgctc ccgattcgca gcgcatcgcc ttctatcgcc   180
ttcttgacga gttcttctga gcgggactct ggggttcgaa atgaccgacc aagcgacgcc   240
caacctgcca tcacgagatt tcgattccac cgccgccttc tatgaaaggt tgggcttcgg   300
aatcgttttc cgggacgccg gctggatgat cctccagcgc ggggatctca tgctggagtt   360
cttcgcccac cccgggtcga cggtattgag tttatgtcta ttgtaattga tagaggttct   420
attaagatag aattatgaga tgtaattgtg attaatgaat aaagagttgt tattattctt   480
tgaattactc cgcgaagcgg tgtgttatgt ttttgttgga agctttctag actcgactag   540
agcggccgc                                                           549
```

<210> SEQ ID NO 24
<211> LENGTH: 1386
<212> TYPE: DNA
<213> ORGANISM: Gossypium hirsutum

<400> SEQUENCE: 24

```
tgcttcgtgt ttcatcaacc tggcgttaaa ctgctttctt taaagccagc aaaatgggtg    60
ccggtggtag gatgccaatt gacggtataa aggaggaaaa tcgaggctcg gtcaatcgag   120
ttccgatcga gaagcctccg tttacgctcg gtcagatcaa gcaagccatt ccgccccact   180
gttttcgccg ctccctcctt cgatccttct cctacgtggt ccatgaccta tgcttagcct   240
cttttctttta ctacattgca acatcatatt ttcactttct cccacaaccc ttttcctaca   300
ttgcttggcc tgtctattgg ttctccaag gttgcatcct caccggtgtt tgggtcatcg   360
cacacgagtg gggtcaccac gctttcagag actaccaatg ggttgacgac accgtcgggt   420
tgatccttca ttccgccctt ttagtcccgt acttctcgtg gaaaatcagt caccgccgtc   480
accactcgaa caccggttcc atggagcgtg acgaagtatt cgtgcccaaa cccaagtcta   540
aattatcatg ctttgcgaaa tacttaaaca atccacccgg tcgagttcta tctcttgtag   600
tcacattgac tcttggttgg cctatgtact tagccttcaa cgtttcgggt cgatactatg   660
atcgattagc ttcccactat aacccttatg gccccattta ctccgatcgc gagaggctac   720
aagtttacat ctccgatact ggtatatttg cggtaattta tgtactttat aagattgctg   780
caacaaaagg gctggcttgg ctttatgca cttatggggt gcctctactt attgtgaatg   840
ccttccttgt gttgatcacc tacttgcaac atactcactc ggcattgccg cattatgact   900
cgtccgaatg ggattggttg cgaggagcat tgtcgacgat ggatcgagat tcggggtgt   960
tgaacaaagt gttccataac atcaccgata cgcatgttgc tcatcacctc ttctcaacga  1020
tgccacatta tcatgcaatg gaggccacta agcaatcaa accaatactc ggcaagtatt  1080
atcctttcga cgggacaccg atttacaagg caatgtggag ggaggcaaaa gagtgccttt  1140
acgttgagcc tgacgttggt ggtggtggtg gtggtagcaa aggtgttttt tggtatcgta  1200
acaagttcta aagaccgacc aactgcctga tagctggccg gcgaaatcaa cgtaaaacgt  1260
acttattaga ctagtgttaa ctagggaagt taataattaa tggtaggaaa atgtggaata  1320
```
gttgcctagt agttttatgt attaagtgtt gtattaataa actatatggt agaaaaaaaa    1380
aaaaaa    1386

<210> SEQ ID NO 25
<211> LENGTH: 385
<212> TYPE: PRT
<213> ORGANISM: Gossypium hirsutum

<400> SEQUENCE: 25

Met Gly Ala Gly Gly Arg Met Pro Ile Asp Gly Ile Lys Glu Glu Asn
1               5                   10                  15

Arg Gly Ser Val Asn Arg Val Pro Ile Glu Lys Pro Pro Phe Thr Leu
            20                  25                  30

Gly Gln Ile Lys Gln Ala Ile Pro Pro His Cys Phe Arg Arg Ser Leu
        35                  40                  45

Leu Arg Ser Phe Ser Tyr Val Val His Asp Leu Cys Leu Ala Ser Phe
    50                  55                  60

Phe Tyr Tyr Ile Ala Thr Ser Tyr Phe His Phe Leu Pro Gln Pro Phe
65                  70                  75                  80

Ser Tyr Ile Ala Trp Pro Val Tyr Trp Val Leu Gln Gly Cys Ile Leu
                85                  90                  95

Thr Gly Val Trp Val Ile Ala His Glu Trp Gly His His Ala Phe Arg
            100                 105                 110

Asp Tyr Gln Trp Val Asp Asp Thr Val Gly Leu Ile Leu His Ser Ala
        115                 120                 125

Leu Leu Val Pro Tyr Phe Ser Trp Lys Ile Ser His Arg Arg His His
    130                 135                 140

Ser Asn Thr Gly Ser Met Glu Arg Asp Glu Val Phe Val Pro Lys Pro
145                 150                 155                 160

Lys Ser Lys Leu Ser Cys Phe Ala Lys Tyr Leu Asn Asn Pro Pro Gly
                165                 170                 175

Arg Val Leu Ser Leu Val Val Thr Leu Thr Leu Gly Trp Pro Met Tyr
            180                 185                 190

Leu Ala Phe Asn Val Ser Gly Arg Tyr Tyr Asp Arg Leu Ala Ser His
        195                 200                 205

Tyr Asn Pro Tyr Gly Pro Ile Tyr Ser Asp Arg Glu Arg Leu Gln Val
    210                 215                 220

Tyr Ile Ser Asp Thr Gly Ile Phe Ala Val Ile Tyr Val Leu Tyr Lys
225                 230                 235                 240

Ile Ala Ala Thr Lys Gly Leu Ala Trp Leu Leu Cys Thr Tyr Gly Val
                245                 250                 255

Pro Leu Leu Ile Val Asn Ala Phe Leu Val Leu Ile Thr Tyr Leu Gln
            260                 265                 270

His Thr His Ser Ala Leu Pro His Tyr Asp Ser Ser Glu Trp Asp Trp
        275                 280                 285

Leu Arg Gly Ala Leu Ser Thr Met Asp Arg Asp Phe Gly Val Leu Asn
    290                 295                 300

Lys Val Phe His Asn Ile Thr Asp Thr His Val Ala His His Leu Phe
305                 310                 315                 320

Ser Thr Met Pro His Tyr His Ala Met Glu Ala Thr Lys Ala Ile Lys
                325                 330                 335

Pro Ile Leu Gly Lys Tyr Tyr Pro Phe Asp Gly Thr Pro Ile Tyr Lys
            340                 345                 350

Ala Met Trp Arg Glu Ala Lys Glu Cys Leu Tyr Val Glu Pro Asp Val

```
              355                 360                 365
        Gly Gly Gly Gly Gly Ser Lys Gly Val Phe Trp Tyr Arg Asn Lys
        370                 375                 380

Phe
        385

<210> SEQ ID NO 26
<211> LENGTH: 1422
<212> TYPE: DNA
<213> ORGANISM: Gossypium hirsutum

<400> SEQUENCE: 26
taaaaaaaaa aggcatttct ttcatcttaa agagacagcg aggaagccac gaagataata      60
gagtgatttt caatctccat tttaagggtg tggaacaatg ggtgctggag cagaatgtc     120 ggttccaacg agtccaaaaa aacccgaatt caactcactg aagcgagttc atactcaaa     180 gccacccttc actctgagtg aaatcaagaa agccatccca ccacactgtt ccagcgctc     240 cgttttacgc tcattctcat atctccttta cgactttata ttggcctctc tttttacca     300 tgtggccacc aattacttcc ctaaccttcc tcaggctctc tccaacgtgg cttgccctct     360
ttattgggcc atgcaaggtt gcattttgac cggcgtttgg gtcatagccc atgaatgtgg     420
ccaccatgct ttcagtgatt atcaatggct tgacgcacac cgtgggcctta tcctccactc     480 ttctctctta gttccatatt tctcttggaa atatagccac cggcgtcacc attctaacac     540
cggttccctc gaaagggatg aagtgttcgt tcccaagaaa aaatctggtt taagatggtg     600
ggccaaacac ttcaacaatc caccgggtcg gtttctgtca atcaccattc aacttaccct     660
tggttggccg ctttacttag ctttcaacgt tgccggccgg ccttacgaca ggttcgcttg     720
ccactatgac ccttacggcc ccatattttc cgaccgggaa cgactccaaa tctatatctc     780
tgacgccggc gtcctcgctg tcgcctatgc gctctaccgt ctcgtgttgg ccaaaggggt     840
aggttgggtt attagcgttt atggggtgcc attattggtg gttaacgcct tcttagtaat     900
gatcacgtat ttgcaacaca ctcacccatc tttgccgcac tatgattcct cggagtggga     960
ctggatgaga ggagctttat caactgtgga cagagattat gggattttaa caaggtttt    1020 ccataacata accgacactc atgtggctca tcatttgttt tcgacaatgc ctcactatca    1080
tgccatggtg gccaccaagg cgataaagcc catattgggg gaatactatc agttcgatgg    1140
gatgcctgtc tataaggcga tatggaggga ggcgaaggag tgtctctacg ttgaaccaga    1200
tgagggcgac aaggataaag gtgtgttttg gtttagaaac aagctttaaa tatttgcatt    1260
ttaccttagg catgttctag tcgttgatgt tttaaggata ttttagccga catacttggt    1320
tttccttttt gggacttttt agctttgtat ttgcagacaa taatcttgtt cactattaaa    1380
taatggtaga aataaataca cagcatggat tggcaataaa aa                       1422

<210> SEQ ID NO 27
<211> LENGTH: 383
<212> TYPE: PRT
<213> ORGANISM: Gossypium hirsutum

<400> SEQUENCE: 27

Met Gly Ala Gly Gly Arg Met Ser Val Pro Thr Ser Pro Lys Lys Pro
1               5                   10                  15

Glu Phe Asn Ser Leu Lys Arg Val Pro Tyr Ser Lys Pro Pro Phe Thr
            20                  25                  30

Leu Ser Glu Ile Lys Lys Ala Ile Pro Pro His Cys Phe Gln Arg Ser
        35                  40                  45
```

```
Val Leu Arg Ser Phe Ser Tyr Leu Leu Tyr Asp Phe Ile Leu Ala Ser
     50                  55                  60

Leu Phe Tyr His Val Ala Thr Asn Tyr Phe Pro Asn Leu Pro Gln Ala
 65                  70                  75                  80

Leu Ser Asn Val Ala Trp Pro Leu Tyr Trp Ala Met Gln Gly Cys Ile
                 85                  90                  95

Leu Thr Gly Val Trp Val Ile Ala His Glu Cys Gly His His Ala Phe
                100                 105                 110

Ser Asp Tyr Gln Trp Leu Asp Asp Thr Val Gly Leu Ile Leu His Ser
            115                 120                 125

Ser Leu Leu Val Pro Tyr Phe Ser Trp Lys Tyr Ser His Arg Arg His
 130                 135                 140

His Ser Asn Thr Gly Ser Leu Glu Arg Asp Glu Val Phe Val Pro Lys
145                 150                 155                 160

Lys Lys Ser Gly Leu Arg Trp Trp Ala Lys His Phe Asn Asn Pro Pro
                165                 170                 175

Gly Arg Phe Leu Ser Ile Thr Ile Gln Leu Thr Leu Gly Trp Pro Leu
            180                 185                 190

Tyr Leu Ala Phe Asn Val Ala Gly Arg Pro Tyr Asp Arg Phe Ala Cys
            195                 200                 205

His Tyr Asp Pro Tyr Gly Pro Ile Phe Ser Arg Glu Arg Leu Gln
210                 215                 220

Ile Tyr Ile Ser Asp Ala Gly Val Leu Ala Val Ala Tyr Ala Leu Tyr
225                 230                 235                 240

Arg Leu Val Leu Ala Lys Gly Val Gly Trp Val Ile Ser Val Tyr Gly
                245                 250                 255

Val Pro Leu Leu Val Val Asn Ala Phe Leu Val Met Ile Thr Tyr Leu
            260                 265                 270

Gln His Thr His Pro Ser Leu Pro His Tyr Asp Ser Ser Glu Trp Asp
        275                 280                 285

Trp Met Arg Gly Ala Leu Ser Thr Val Asp Arg Asp Tyr Gly Ile Leu
290                 295                 300

Asn Lys Val Phe His Asn Ile Thr Asp Thr His Val Ala His His Leu
305                 310                 315                 320

Phe Ser Thr Met Pro His Tyr His Ala Met Val Ala Thr Lys Ala Ile
                325                 330                 335

Lys Pro Ile Leu Gly Glu Tyr Tyr Gln Phe Asp Gly Met Pro Val Tyr
            340                 345                 350

Lys Ala Ile Trp Arg Glu Ala Lys Glu Cys Leu Tyr Val Glu Pro Asp
        355                 360                 365

Glu Gly Asp Lys Asp Lys Gly Val Phe Trp Phe Arg Asn Lys Leu
370                 375                 380

<210> SEQ ID NO 28
<211> LENGTH: 1933
<212> TYPE: DNA
<213> ORGANISM: Gossypium arboreum

<400> SEQUENCE: 28
ccacttcgca gcaatattat tgcagttcct ggttggctac ctctgagttt tcaacttaaa      60
atttcttggt tttcctcaag aaggaagaag atgttgcaaa tagctttcag ctcgtattca     120
tggctgttga ctgctagcaa ccagaaagat ggaatgttgt tcccagtagc tttgtcattt     180
ttggtagcca tattgggaat tcactgtggg cacgtatgga ccataaggaa gccaagaaa     240
```

```
gacatcgccc cattaccgcc gggtccccgt gggttgccaa tagtgggata tcttccatat    300
cttggaactg ataatcttca cttggtgttt acagatttgg ctgcagctta cggtcccatc    360
tacaagcttt ggctaggaaa caaattatgc gtagtcatta gctcggcacc actggcgaaa    420
gaagtggttc gtgacaacga catcacattt tctgaaaggg atcctcccgt ttgtgcaaag    480
attattacct ttggcctcaa tgatattgta tttgattctt acagtagtcc agattggaga    540
atgaagagaa aagtgctggt acgtgaaatg cttagccata gtagcattaa agcttgttat    600
ggtctaagga gggaacaagt gcttaaaggc gtacaaaatg ttgctcaaag tgctggcaag    660
ccaattgatt ttggtgaaac ggcattttta acatcaatca atgcgatgat gagcatgctg    720
tggggtggca acagggagg agagcggaaa ggggccgacg tttggggcca atttcgagat    780
ctcataaccg aactaatggt gatacttgga aaaccaaacg tttctgatat tttcccggtg    840
cttgcaaggt ttgacataca gggattggag aaggaaatga ctaaaatcgt taattctttc    900
gataagcttt tcaactccat gattgaagaa agagagaact ttagcaacaa attgagcaaa    960
gaagatggaa acactgaaac aaaagacttc ttgcagcttc tgttggacct caagcagaag   1020
aacgatagcg aatatcgat aacaatgaat caagtcaagg ccttgctcat ggacattgtg   1080
gtcggtggaa ctgatacaac atcaaccatg atggaatgga caatggctga actaattgca   1140
aatcctgaag caatgaaaaa ggtgaagcaa gaaatagacg atgttgtcgg ttcggatggc   1200
gccgtcgatg agactcactt gcctaagttg cgctatctag atgctgcagt aaaggagacc   1260
ttccgattgc acccaccgat gccactcctt gtaccccgtt gcccgggcga ctcaagcaac   1320
gttggtggct atagcgtacc aaagggcacc agggtcttct taaacatttg gtgtattcag   1380
agggatccac agctttggga aaatccttta gaattcaagc ctgagaggtt cttgactgat   1440
catgagaagc tcgattattt aggaaacgat tcccggtaca tgccgtttgg ttctggaagg   1500
agaatgtgtg ccggagtatc tctcggtgaa aagatgttgt attcctcctt ggcagcaatg   1560
atccatgctt atgattggaa cttggccgac ggtgaagaaa atgacttgat tggcttattt   1620
ggaattatta tgaagaaaaa gaagccttta attcttgttc ctacaccaag accatcaaat   1680
ctccagcact atatgaagta actttactat tgtatttctt ttataccact ttattgcctc   1740
tttgtcatgt ttaggcaaca attctaagta ataagtttgg ctatatggtg aacaataatg   1800
tgtttattat acatcataag caatgagctc ttcccgaccc tagggcaata caatgatact   1860
gtgtattaag tgaaatcaac aaatctttta ttctaaaaaa aaaaaaaaaa aaaaaaaaa   1920 aaaaaaaaaa aaa                                                      1933

<210> SEQ ID NO 29
<211> LENGTH: 20
<212> TYPE: DNA
<213> ORGANISM: Artificial
<220> FEATURE:
<223> OTHER INFORMATION: Artificial

<400> SEQUENCE: 29
atggttgcta ctgctgtgac                                                 20

<210> SEQ ID NO 30
<211> LENGTH: 21
<212> TYPE: DNA
<213> ORGANISM: Artificial
<220> FEATURE:
<223> OTHER INFORMATION: Artificial

<400> SEQUENCE: 30
```

-continued

```
ctgtaaatga ttcattagtg t                                         21

<210> SEQ ID NO 31
<211> LENGTH: 25
<212> TYPE: DNA
<213> ORGANISM: Artificial
<220> FEATURE:
<223> OTHER INFORMATION: Artificial

<400> SEQUENCE: 31
cctgagaggt tcttgactga tcatg                                     25

<210> SEQ ID NO 32
<211> LENGTH: 27
<212> TYPE: DNA
<213> ORGANISM: Artificial
<220> FEATURE:
<223> OTHER INFORMATION: Artificial

<400> SEQUENCE: 32
gcttatgatg tataataaac acattat                                   27
```

COTTONSEED OIL AND USES

This application is a continuation-in-part of PCT International Application No. PCT/AU2009/000929, filed Jul. 21, 2009, and claims the benefit of U.S. Provisional Application No. 61/135,554, filed Jul. 21, 2008, the contents of all of which are hereby incorporated by reference into this application.

This application incorporates-by-reference nucleotide and/or amino acid sequences which are present in the file named "110121_0687_79598_B_SequenceListing_DES.txt," which is 86 kilobytes in size, and which was created Jan. 20, 2011 in the IBM-PC machine format, having an operating system compatibility with MS-Windows, which is contained in the text file filed Jan. 21, 2011 as part of this application.

FIELD

The present specification relates to the production of cotton plants and seeds and oil prepared therefrom having elevated levels of oleic and reduced levels of palmitic and linoleic acids. Furthermore, cottonseeds having low levels of cyclopropane and/or cyclopropene fatty acids and/or reduced levels of gossypol are described herein. The specification also describe FatB and CPA-FAS nucleotide and amino acid sequences derived from cotton facilitating, inter alia the direct modification of plant oil content and/or composition.

BACKGROUND

Cotton is a dual purpose crop, producing both fiber and seed as valuable primary agricultural products. Normally, cottonseed products, including hulls (26%), linters (9%), oil (16%) and cottonseed meal (45%) represent approximately 15% of the farm value of the cotton crop (Cherry and Leffler, Seed. In "Cotton, agronomy monograph No. 24" (eds R J Kohel, C F Lewis) pp. 511-569. Crop Science Society of America, Madison, Wis., USA, 1984), while lint provides most of the remaining 85% of the value. Cottonseed oil is the most valuable product derived from cottonseed.

Cottonseed oil has a long tradition of use in food processing. Since cottonseed oil has a bland, neutral flavor that does not mask the inherent flavor of food, it is a popular and widely used oil for deep frying in the snack food and food service sector (Jones and King, Cottonseed Oil. National Cottonseed Products Associations, Inc. and the Cotton Foundation, Memphis, Tenn., USA, 1993). Cottonseed oil is also commonly used as an ingredient in marinades, dressings, pastries, margarines, and shortenings.

The nutritional and industrial value of cottonseed oil, like other vegetable oils, is affected by the composition of fatty acids in the oil, ie. the relative level of each the fatty acids in the oil, and the properties conferred by the carbon chain length and level of unsaturation of each fatty acid.

Isolated and purified cottonseed oil is composed mostly (>95%) of triacylglycerols (TAGs) that are synthesized and deposited during seed development. TAG molecules consist of three fatty acids esterified to a glycerol backbone, designated the sn-1, sn-2 and sn-3 positions. Briefly, the de novo biosynthesis of fatty acids in cotton seed, as in other oilseeds, occurs in the stroma of plastids during development and growth of the seeds, ie. before maturation. Fatty acids are then exported from the plastids in the form of acyl-CoA thioesters to the cytoplasmic endomembrane systems (endoplasmic reticulum, ER) where modification of fatty acids occurs after transfer of the acyl groups from the CoA thioesters to phospholipids by acyltransferases. This is followed by TAG assembly and storage in the oleosomes.

The biotin-containing enzyme acetyl-CoA carboxylase (ACCase) catalyses the first committed step in the pathway by activating acetyl-CoA to the three carbon intermediate, malonyl-CoA, by addition of a carboxyl group. The malonyl group is then transferred from CoA to an acyl-carrier protein (ACP), which serves as the carrier for the growing fatty acid chain. Malonyl-ACP is reacted with a second acetyl-CoA condensing enzyme, ketoacyl-ACP synthase III (KASIII), resulting in a four carbon chain. The repeated process of adding two-carbon units on the elongated fatty acid chain is catalyzed by KASI leading to the formation of palmitoyl-ACP. KASII catalyzes the elongation of palmitoyl-ACP to stearoyl-ACP. A soluble stearoyl-ACP Δ9-desaturase introduces the first double bond into stearoyl-ACP to convert it to oleoyl-ACP in the plastid. The extended, saturated fatty acyl chain and the monounsaturated oleate are cleaved off the ACP by a specific thioesterase enzyme, FatB or FatA, respectively, enabling them to exit the plastid and enter the cytoplasm. Saturated fatty acids released into the cytoplasm are not further modified. However, oleic acid can be further modified on the endoplasmic reticulum (ER) membranes by the action of membrane-bound desaturases. Phosphatidylcholine (PC)-bound acyl chains serve as a substrate for ER localized, lipid modifying enzymes, such as fatty acid desaturase 2 (FAD2) which introduces a double bond into oleic acid on the sn-2 position of PC to produce linoleic acid. All the modified and unmodified fatty acyl groups then form a pool while attached to CoA. In cotton, but not in other temperate zone oilseeds, oleic acid may be used as substrate for cyclopropanation catalysed by cyclopropane fatty acid synthase to produce dihydrosterculic acid. This fatty acid is subsequently desaturated to produce sterculic acid and then α-oxidased to produce malvalic acids. Finally fatty acyl groups are incorporated into storage lipids via the Kennedy pathway by the sequential esterification of glycerol-3-phosphate by the action of a series of TAG assembly enzymes.

The enzyme acyl-ACP thioesterase (FatB) (EC 3.1.2.14) catalyses the hydrolysis of the thioester bond between the acyl moiety and ACP in acyl-ACP and the release of free fatty acid in the plastid. The free fatty acid is then re-esterified to CoA in the plastid envelope as it is transported out of the plastid. FatB belongs to a class of nuclear encoded, soluble, fatty acid thioesterase (FAT) enzymes which are first translated as a precursor proteins. The substrate specificity of the FAT enzymes in the plastid is therefore involved in determining the spectrum of chain length and degree of saturation of the fatty acids exported from the plastid. FAT enzymes can be classified into two classes based on their substrate specificity and nucleotide sequences, FatA and FatB (Jones et al., *Plant Cell* 7: 359-371, 1995). FatA prefers oleoyl-ACP as substrate, while FatB shows higher activity towards saturated acyl-ACPs of different chain lengths. Genes encoding FatB enzyme were first isolated from plant species accumulating medium chain-length saturated fatty acids such as lauric acid (C12:0) from California bay tree (*Umbellularia californica*). Overexpression of the *U. californica* FatB1 gene in transgenic canola led to production of high-laurate oil with laurate comprising 50% of the total fatty acids in the oil (Voelker et al., *Plant Journal* 9: 229-241, 1996). Subsequent studies demonstrated that several FatB orthologues are present in tissues of plants, including in seeds, with substrate specificity ranging from C8:0-ACP to C18:0-ACP.

Cottonseed oil produced by conventional (wild-type) upland cotton (*G. hirsutum*) typically contains approximately 26% palmitic acid (range 22-28%), 2% stearic acid, 15% oleic acid (range 13-18%) and 58% linoleic acid (range 52-60%) (Cherry, *J. Am. Oil Chem. Soc.* 60: 360-367, 1983; O'Brien, Cottonseed Oil. In: F. D. Gunstone (Ed.) Vegetable Oils in Food Technology: Composition, Properties and Uses. Blackwell Publishing, Oxford, pp. 203-230, 2002). In addition to these fatty acids which are also present in most other temperate zone oilseed crops, unhydrogenated cottonseed oil also contains low levels (0.5-1%) of cyclopropane or cyclopropene fatty acids, mainly malvalic, sterculic and dihydrosterculic acids (Shenstone and Vickery, *Nature* 190: 68-169, 1961; Cherry, 1983 (supra)). Cyclopropane (CPA) and cyclopropene (CPE) fatty acids are found in the seed oils of plants in the order of Malvales and some gymnosperms, including in cotton. Two Sapindaceae species, Lychee (*Litchi chinensis*) and Longan (*Euphoria longan*) contain up to 40% CPA fatty acids in their seedoils, mostly as dihydrosterculic acid (DHS). The seed oil of *Sterculia foetida* contains up to 78% CPE fatty acids, mainly sterculic (STC) and malvalic acids (MVL). Unhydrogenated cottonseed oil contains relatively small amounts (0.5-1.0%) of CPE and CPA fatty acids, mostly in embryo axes. Cotton roots and hypocotyls are also found to accumulate low levels of STC and MVL. CPA and CPE are not found at detectable levels in major oilseed crops other than cotton, including in palm oil, soybean, corn, canola, mustard, sunflower, safflower, peanut, linseed, other Brassicas etc.

The first committed step to produce these uncommon fatty acids is catalysed by a cyclopropane fatty acid synthase (CPA-FAS) which adds a methylene group across the double bond of oleic acid to produce DM (FIG. 2). In cotton, most of the DHS is desaturated by the enzyme CPA desaturase to produce STC, most of which is further modified by α-oxidation to form MVL (FIG. 2). MVL is the predominant cyclopropenoid fatty acid in wild-type cottonseed oil.

The relatively high level of saturated fatty acids, mainly palmitic acid, in cottonseed oil compared to oils from most other temperate zone oilseed crops contributes to the oxidative stability of cottonseed oil by offsetting the greater instability of the other, unsaturated fatty acid components. It also imparts the high melting point required for making such products as margarine and shortening. On the other hand, higher levels of palmitic acid are nutritionally less desirable because of its property of raising LDL-cholesterol in humans, associated with increased risk of cardiovascular heart disease (CHD) (Lindsey et al., *Exp. Biol. Med.* 195: 261-269, 1990). Except for palm oil, cottonseed contains the highest palmitic acid level (26%) among the major commodity vegetable oils. Palmitic acid and other shorter chain saturated fatty acids are widely reported to raise total plasma cholesterol and low density lipoprotein cholesterol levels (Kris-Etherton et al., *Nutrition-today* (*USA*). 28: 30-38, 1993). Cottonseed oil also contains a high level of linoleic acid which is oxidatively unstable and therefore limits the shelf life of the oil and makes it unsuitable for some food applications.

Conventional cottonseed oil is therefore often processed by partial hydrogenation during which the polyunsaturated linoleic acid is transformed into more stable monounsaturated (oleic) and saturated (stearic) fatty acids. Partial hydrogenation results in a number of structural changes to a fraction of the fatty acids, including the shifting of a double bond. This may lead to the production of trans fatty acids (TFA) which are isomers of the naturally occurring unsaturated fatty acids. In most naturally occurring unsaturated fatty acids such as oleic acid, the two hydrogen atoms joined to the double-bonded carbon atoms are on the same side of the double bonds of the carbon chain, and this is termed a cis double bond. However, partial hydrogenation re-configures some of the double bonds so that the two hydrogen atoms are on opposite sides of the carbon-carbon double bond, as it is the lower energy form, and this is termed the trans configuration. Thus partial hydrogenation produces trans fatty acids, such as elaidic acid from oleic acid. Oleic and elaidic acids contain the same number of atoms (C18:1), with a double bond in the same location, but it is the conformation of the double bond that sets them apart. TAG containing elaidic acid, with the trans double bond configuration, has a much higher melting point than oleic acid. In recent years TFA have been increasingly recognized to have significant LDL-cholesterol raising and HDL-cholesterol lowering properties and therefore increases the risk of cardiovascular disease based on evidence derived from epidemiologic and clinical studies (Oomen et al., *Lancet* 357: 746-751, 2001; Mozaffarian et al., *N. Engl. J. Med.* 354: 1601-1613, 2006). Partial hydrogenation also converts cyclopropanoic or cyclopropenoic fatty acids to branched chain fatty acids by opening up the cyclopropane ring, producing a branched fatty acid with a additional methyl group attached to C9 or C10 of the fatty acid carbon chain.

Compared with polyunsaturated fatty acids, oleic acid is more stable towards oxidation both at ambient storage temperatures and at the high temperatures used in cooking and frying of food. Studies with a number of vegetable oils such as safflower and soybean oils indicate that high-oleic vegetable oils are slower to develop rancidity during storage, or to oxidatively decompose during frying or other use, compared to oils that contain high amounts of polyunsaturated fatty acids (Fuller et al., *J. Food Sci.* 31: 477-480, 1966; Mounts et al., *J. Am. Oil Chem. Soc.* 65: 624-628, 1998).

As mentioned above, cottonseed oil is also characterized by the presence of small amounts of malvalic, sterculic and dihydrosterculic acids, a group of cyclic propane fatty acids derived from oleic acid. It is known that malvalic and sterculic acids are potent inhibitors of animal Δ9-stearoyl-CoA desaturase. Although the CPA and CPE fatty acids are not stable and are mostly eliminated during oil processing, particularly by hydrogenation, the residual oil in the meal and the whole cottonseed used in the feed industry could exert negative effects on animal health. Feeding farmed animals with excess amounts of cottonseed is thought to possibly cause a number of health problems for animals and may affect the quality of animal products, such as the hardening of fats in egg yolk and milk (Johnson et al., *Nature* 214: 1244-1245, 1967; Roehm et al., *Lipids* 5: 80-84, 1970). Methods have been developed to inactivate cyclopropenoid fatty acids through specialised partial hydrogenation processes. Merker and Mattil, 1965 reported a hydrogenation process in which malvalic and sterculic acids were selectively reduced to their dihydro or tetrahydro derivatives, by means of a nickel catalyst, without significant reduction of the linoleic acid or trans acid formation. Hutchins et al., *Journal of American Oil Chemists Society* 45: 397-399, 1968 showed selective hydrogenation of the cyclopropenoid groups in cottonseed oil by means of a packed-bed reactor and nickel catalysts under milder conditions. However, these hydrogenation processes add additional costs for processing of the oil and are not desirable.

In the 1970's, the cotton breeding program of the Acala SJ series in California (Cherry, 1983 (supra)) reduced palmitic acid from 23.3 to 22.7%, increased oleic acid from 16.6% to 17.3% and reduced total cyclic fatty acids from 0.9% to 0.8% in cottonseed oil. However, compared to achievements in other oilseed crops, these changes were only minor, reflecting the narrow genetic base of elite cotton varieties as a result of persistent selection on traits other than oil quality.

Four different cDNAs encoding FAD2 were isolated from cotton (Liu et al., *Australian Journal of Plant Physiology* 26: 101-106, 1999a; Liu et al., *Plant Physiol.* 120: 339, 1999b; Pirtle et al., *Biochim. Biophys. Acta* 1522: 122-129, 2001, all herein incorporated by reference), among which ghFAD2-1 was determined to play a major role in the production of linoleic acid in cottonseed oil. Analysis of gene expression suggested that the ghFAD2-1 gene was specifically expressed in developing seeds, with maximal expression during the middle maturity stage of seed development (Liu et al., 1999a (supra)).

U.S. Pat. No. 6,974,898 (herein incorporated by reference) describes the generation of cottonseed oil containing up to 77% oleic acid by downregulation of microsomal Δ12 desaturase (FAD2) by RNAi methods.

Chapman et al., *J. Am. Oil Chem. Soc.* 78: 941-947, 2001, herein incorporated by reference, transformed cotton plants with a construct encoding a non-functional, mutant allele of fad2, obtained from rapeseed, and expressed from a seed-specific phaseolin promoter in sense orientation. About half of the 43 transgenic lines that were generated showed slightly increased oleic acid content in seedoil, ranging from 24-30%. In subsequent generations, seeds with higher levels of oleic acid up to 40% were identified.

*Arabidopsis* fatB mutants which had seedoil with reduced palmitic acid levels showed reduced vegetative growth under normal temperatures (Bonaventure et al., *Plant Cell* 15: 1020-1033, 2003). However, in previous studies with antisense constructs to down-regulate AtFatB in *Arabidopsis*, using the CaMV35S promoter to express the antisense RNA, a substantial reduction of palmitic acid levels was observed only in flowers and seeds, not in leaves and roots, and there was no obvious visual phenotype (Dormann et al., *Plant Physiol.* 123: 637-644, 2000, herein incorporated by reference).

In cotton, as in many temperate plants, FatB enzymes appear to be encoded by a multigene family. Yoder et al., *Biochimica et Biophysica Acta* 1446: 403-413, 1999, herein incorporated by reference, isolated a genomic DNA sequence which was thought to encode a acyl-ACP thioesterase in cotton.

Wilson et al., *J. Am. Oil Chem. Soc.* 78: 335-340, 2001 and Buhr et al., *Plant J.* 30: 155-163, 2002, both herein incorporated by reference, used antisense and ribozyme approaches, respectively, to reduce palmitic acid in soybean seeds.

A CPA-FAS gene was recently isolated from *Sterculia foetida* using an EST based approach (Bao et al., *Proc. Natl. Acad. Sci. U.S.A.* 99: 7172-7177, 2002), Two EST sequences from *G. hirsutum* were identified as being differentially expressed by infection of cotton roots/hypocotyls following inoculation of *Fusarium* (Dowd et al., *Molecular Plant-Microbe Interactions.* 17: 654-667, 2004, herein incorporated by reference).

There is therefore a need for improved cottonseed oil.

SUMMARY

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers. Each embodiment is to be applied mutatis mutandis to every other embodiment unless expressly stated otherwise.

As used herein the singular forms "a", "an" and "the" include plural aspects unless the context clearly dictates otherwise. Thus, for example, reference to "a mutation" includes a single mutation, as well as two or more mutations; reference to "an agent" includes one agent, as well as two or more agents; and so forth.

Bibliographic details of the publications referred to by author in this specification are collected at the end of the description.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The term "derived from" indicates that the specified integer is obtained from a specific source although not necessarily directly from that source.

The designation of exemplary amino acid sequences is set out in Table 5.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of sequence identifiers is provided in Table 4. A sequence listing is provided after the claims.

Genes and other genetic material (eg mRNA, nucleic acid constructs etc) are represented herein in italics while their proteinaceous expression products are represented in non-italicised form.

In one embodiment, the present specification describes a method of producing modified cottonseed oil, comprising the steps of (i) obtaining cottonseed, (ii) extracting the oil from the cottonseed, and (iii) recovering the cottonseed oil, wherein the cottonseed oil has a modified fatty acid composition such that 72% to 88% of the total fatty acid content in the cottonseed oil is oleic acid, 4% to 16% is palmitic acid and 4% to 15% is linoleic acid. In some embodiments, 74% to 86% of the total fatty acid content of the cottonseed oil is oleic acid. In other embodiments, 4% to 10% is palmitic acid. In other embodiments, 4% to 12% is linoleic acid. In relation to trans fatty acids, in some embodiments, the cottonseed oil has less than 0.5%, preferably less than 0.1%, of the total fatty acid content is a trans fatty acid. In some embodiments, the trans fatty acid is elaidic acid. In some embodiments, 0.1% to 0.5% of the total fatty acid content in the cottonseed oil is cyclopropane fatty acid (CPA) or cyclopropene fatty acid (CPE). In particular embodiments, the cyclopropane or cyclopropene fatty acid is malvalic acid, sterculic acid, dihydrosterculic acid or any combination of two of these or all three of these. In other embodiments, less than 0.5%, preferably less than 0.1%, of the total fatty acid content is a branched fatty acid at C9 or C10. In preferred embodiments, the total fatty acid content of the seedoil has the composition of 74% to 86% oleic acid, 4% to 10% palmitic acid, 4% to 12% linoleic acid, and optionally 0.1% to 0.5% in total of cyclopropane fatty acid (CPA) and cyclopropene fatty acid (CPE), and optionally less than 1.0%, preferably less than 0.5%, more preferably less than 0.1%, of the total fatty acid content is a trans fatty acid.

In some embodiments, the production method further comprises harvesting lint comprising the cottonseed from a cotton plant and/or ginning the cottonseed from lint comprising the cottonseed. Alternatively or in addition, step (ii) comprises crushing the cottonseed and/or solvent extraction of the crushed cottonseed. In a further embodiment, step (iii) comprises purifying the cottonseed oil. Purifying the seedoil may comprise degumming the oil, decolorizing the oil, deodorizing the oil, altering the pH of the oil, hydrolyzing the oil, or any combination thereof.

Advantageously, in some embodiments, the method does not comprise a step of hydrogenation or partial hydrogenation of the cottonseed oil. Without limitation to any particular mode of action, the low level of linoleic acid and relatively high level of oleic acid obviates the need to stabilise the fatty acids, and thus avoids the de nova production of trans fatty acids induced by some forms of hydrogenation.

Accordingly, in another aspect, the specification provides cottonseed oil having a modified fatty acid composition, wherein 72% to 88% of the total fatty acid content in the cottonseed oil is oleic acid, 4% to 16% is palmitic acid and 4% to 15% is linoleic acid. In some embodiments, 74% to 86% of the total fatty acid content of the cottonseed oil is oleic acid. In other embodiments, 4% to 10% is palmitic acid. In other embodiments, 4% to 12% is linoleic acid. In some embodiments, 0.1% to 0.5% of the total fatty acid content in the cottonseed oil is cyclopropane fatty acid (CPA) or cyclopropene fatty acid (CPE). In particular embodiments, the cyclopropane or cyclopropene fatty acid is malvalic acid, sterculic acid, dihydrosterculic acid or any combination of two of these or all three of these. In preferred embodiments, the total fatty acid content of the seedoil has the composition of 74% to 86% oleic acid, 4% to 10% palmitic acid, 4% to 12% linoleic acid, and optionally 0.1% to 0.5% in total of cyclopropane fatty acid (CPA) and cyclopropene fatty acid (CPE), and optionally less than 1.0%, preferably less than 0.5%, more preferably less than 0.1%, of the total fatty acid content is a trans fatty acid.

In another aspect, the specent specification provides cottonseed having a modified fatty acid composition in its oil, wherein 72% to 88% of the total fatty acid content in the oil of the cotton seed is oleic acid, 4% to 16% is palmitic acid and 4% to 15% is linoleic acid. In other embodiments, 74% to 86% of the total fatty acid content in the oil of the cotton seed is oleic acid. In other embodiments, 4% to 10% is palmitic acid. In other embodiments, 4% to 12% is linoleic acid. In still further embodiments, 0.1% to 0.5% of the total fatty acid content in the oil is a cyclopropane fatty acid (CPA). In still yet further embodiments, the cottonseed has a reduced level of gossypol, wherein the level of gossypol in the cottonseed is reduced by at least 10% relative to the level of gossypol in a cottonseed of cotton variety Coker. In preferred embodiments, the total fatty acid content of the seedoil has the composition of 74% to 86% oleic acid, 4% to 10% palmitic acid, 4% to 12% linoleic acid, and optionally 0.1% to 0.5% in total of cyclopropane fatty acid (CPA) and cyclopropene fatty acid (CPE), and optionally less than 1.0%, preferably less than 0.5%, more preferably less than 0.1%, of the total fatty acid content is a trans fatty acid.

In some embodiments the specification provides cottonseed or cottonseed oil recovered therefrom wherein the cottonseed is transgenic for a genetic construct which encodes an RNA molecule which inhibits expression of two or more genes which are selected from the group consisting of FAD2, FatB-2 and CPA-FAS-2. In some embodiments the genes are ghFAD2-1, ghFatB-2 and ghCPA-FAS-2. In an illustrative embodiment, the genetic construct comprises the MonoCott construct described schematically in FIG. 12. In another embodiment, the cottonseed is transgenic for a genetic construct which encodes an RNA molecule which inhibits expression of two genes which are ghFAD2-1 and ghFatB-2. In another illustrative embodiment, the cottonseed is of the species *Gossypium hirsutum* or *Gossypium barbadense*.

In another aspect the specification described a method of producing the herein described cottonseed comprising harvesting lint from a cotton plant and ginning the lint, thereby producing the cottonseed. In another embodiment, the method comprises sowing the herein described cottonseed and allowing the seed to grow into the cotton plant.

The present invention provides a cotton plant which is capable of producing the herein described cottonseed and cotton lint obtained from said cotton plant.

Pursuant to the present invention, the specification provides a method of identifying cottonseed which has a modified fatty acid composition in its oil, comprising (i) obtaining transgenic cottonseed, (ii) determining the fatty acid composition of the oil of the cottonseed, and (iii) if 72% to 88% of the total fatty acid content in the oil of the cotton seed is oleic acid, 4% to 16% is palmitic acid and 4% to 15% is linoleic acid, selecting the cottonseed. In some embodiments, the method further comprises transformation of a cotton cell with a genetic construct and regeneration of a transgenic cotton plant prior to step (i). In some embodiments, the cottonseed of step (i) is transgenic for a genetic construct which encodes an RNA molecule which inhibits expression of two or three genes which are ghFAD2-1 and ghFatB-2 or ghFAD2-1 and ghFatB-2 and ghCPA-FAS-2. In some embodiments, the method comprises the step of selecting a cottonseed having a modified fatty acid composition in its oil, wherein 72% to 88% of the total fatty acid content in the oil of the cotton seed is oleic acid, 4% to 16% is palmitic acid and 4% to 15% is linoleic acid. In some embodiments, the method further comprises the steps of producing a cotton plant from the seed and crossing said cotton plant with a second cotton plant, preferably of a different genetic background.

Accordingly, the specification contemplates the use of the herein described cottonseed to produce isolated oil or cottonseed meal and the use of the cotton seed as animal feed or in the production of a food product or as fuel. It is contemplated that the oil is used to increase the oleic acid content or to reduce the palmitic acid content of the food product. Alternatively or in addition the oil is used to reduce the level of, or the intake of, saturated fatty acids or trans fatty acids in the food product or by the animal. It would be understood that this is relative to the use of an equal amount of an unmodified cottonseed, oil or cottonseed meal.

In a particular embodiment, the specification provide a food product comprising a food ingredient which is the cottonseed oil as described herein.

In another aspect the invention provides a method of preparing a fried food product, comprising frying a food product in the cottonseed oil as described according herein.

The subject product may be used therapeutically and the present invention contemplates a method for treating or preventing a disease in a subject, comprising administering orally to the subject, the cottonseed oil, the cottonseed or the food product as described herein. In some embodiments, the disease is obesity, heart disease, high serum TAG content, high serum cholesterol, high serum LDL, low serum HDL, hypertension, cancer, diabetes, or any combination thereof. Any subject who could benefit from the present methods or compositions is encompassed. The term "subject" includes, without limitation, humans and non-human primates, livestock animals, companion animals, laboratory test animals, captive wild animals, reptiles and amphibians, fish, birds and any other organism. A subject, regardless of whether it is a human or non-human organism may be referred to as a patient, individual, subject, animal, host or recipient. In a particular embodiment the subject is a human.

In a particular aspect, the specification describes a nucleic acid molecule encoding a chimeric gene silencing nucleic acid which reduces gene expression of two or more genes selected from cotton FatB, cotton FAD2 and cotton CPA-FAS in a cotton plant. In some embodiments, the gene-silencing nucleic acid reduces gene expression of cotton FAD2-1 and cotton FatB-2, or cotton FAD2-1 and cotton FatB-2 and CPA-FAS-2. In some embodiments, the nucleic acid molecule comprises: (i) a contiguous sequence of nucleotides set forth in SEQ ID NO: 17 or a complementary form thereof, or a sequence having 90% identity thereto or a sequence that hybridizes to a complement thereof under high stringency hybridization conditions, or (ii) a variant of the nucleic acid molecule of (i) lacking sequences encoding to CPA-FAS-2 polypeptide or their complementary forms. In an illustrative embodiment the gene-silencing nucleic acid molecule is a hairpin RNA. In some embodiments the nucleic acid molecule is provided within a genetic construct.

In some embodiments, the gene construct comprises the nucleic acid and further comprises the structure set out in FIG. 12 or the sequences of Fragments A, E, F, G, and H set out in FIG. 13, or a functional variant thereof. In other embodiments, the nucleic acid molecule is provided in a host cell. In other embodiments, a plant or tissue or cell therefrom is provided comprising a subject nucleic acid. In some embodiments, the nucleic acid molecules are used to reduce expression of cotton FAD2-1, cotton FatB-2 and/or cotton CPA-FAS-2 genes in a cotton plant. The specification provides therefore a modified cotton plant or seed therefrom comprising a reduced level of one or more endogenous genes selected from cotton FAD2, cotton FatB and CPA-FAS, preferably two or more of said genes or all three genes wherein the cottonseed oil therein or therefrom exhibits elevated levels of oleic acid or reduced levels of palmitic acid and linoleic acid.

In a further embodiment, the cottonseed oil exhibits reduced levels of cyclopropene and/or cyclopropane fatty acids, or gossypol.

In another aspect, the specification provides an isolated nucleic acid molecule comprising a nucleotide sequence encoding a polypeptide having cotton FatB activity or a functional fragment or variant thereof, or a complementary form thereof, said nucleotide sequence selected from the group consisting of: (i) a nucleotide sequence having at least 90% identity to the nucleotide sequence of the protein encoding region of the nucleotide sequence set forth in SEQ ID NO: 5 or 7; (ii) a nucleotide sequence encoding a polypeptide having at least 80% sequence identity to the amino acid sequence set forth in SEQ ID NO: 6 or 7; (iii) a nucleotide sequence that hybridizes under at least moderate stringency hybridization conditions to at least 30 contiguous nucleotides derived from SEQ ID NO: 5 or 7; (iv) a nucleotide sequence that is complementary to (i), (ii) or (iii); and (v) a nucleotide sequence comprising nucleotides 548-843 of SEQ ID NO: 5. In some embodiment, the nucleic acid, particularly RNA, or a functional variant or fragment thereof is provided as a sense, antisense, ribozyme, co-suppression, or double-stranded RNA or other gene-silencing agent. Thus the specification provides an antisense or co-suppression molecule which comprises a fragment of any one of (i)-(v) above which is expressed and reduces expression of a cotton FatB gene.

In another embodiment, an isolated probe or primer is provided comprising at least 15 contiguous nucleotides derived from SEQ ID NO: 5 or SEQ ID NO: 7 or a complementary form thereof.

In another aspect, the specification provides an isolated nucleic acid molecule comprising a nucleotide sequence encoding a polypeptide having cotton CPA-FAS activity or a functional fragment or variant thereof, or a complementary form thereof, said nucleotide sequence selected from the group consisting of: (i) a nucleotide sequence having at least 90% identity to the nucleotide sequence of the protein encoding region of the nucleotide sequence set forth in SEQ ID NO: 10, 12 or 14; (ii) a nucleotide sequence encoding a polypeptide having at least 80% sequence identity to the amino acid sequence set forth in SEQ ID NO: 11, 13 or 15; (iii) a nucleotide sequence that hybridizes under at least moderate stringency hybridization conditions to at least 30 contiguous nucleotides derived from SEQ ID NO: 10, 12 or 14; (iv) a nucleotide sequence that is complementary to (i), (ii) or (iii); and (v) a nucleotide sequence comprising 442 nucleotides of CPA-FAS-2 encoding sequences set forth in Fragment B of FIG. 13. In some embodiment, the nucleic acid, particularly RNA, or a functional variant or fragment thereof is provided as a sense, antisense, ribozyme, co-suppression, or double-stranded RNA or other gene-silencing agent. Thus the specification provides an antisense or co-suppression molecule which comprises a fragment of any one of (i)-(v) above which is expressed and reduces expression of a cotton CPA-FAS-2 gene.

In another embodiment, an isolated probe or primer is provided comprising at least 15 contiguous nucleotides derived from SEQ ID NO: 10, SEQ ID NO: 12 or SEQ ID NO: 14 or a complementary form thereof.

The above summary is not and should not be seen in any way as an exhaustive recitation of all embodiments of the present invention.

BRIEF DESCRIPTION OF THE DRAWINGS

FIG. 2 is a schematic representation of biosynthesis of cyclopropane (CPA) and cyclopropene (CPE) fatty acids in developing cottonseed. Oleic acid is the fatty acid substrate for cyclopropane fatty acid synthase (CPA-FAS). S-adenosyl-L-methionine is the methylene donor and the cyclopropanation of oleic acid is catalysed by CPA-FAS, producing dihydrosterculic acid (DHS). DHS can be further modified by desaturation by the enzyme CPA desaturase to produce sterculic acid (STC). Subsequently, malvalic acid (MVL) is produced by α-oxidation of SIC catalysed by an oxidase.

FIG. 3 is a representation of the nucleotide sequence of cDNA corresponding to the ghFAD2-1 gene, and the predicted amino acid sequence of the encoded precursor ghFAD2-1 polypeptide. The protein encoding region is from nucleotides 73 to 1227 (TAA stop codon).

FIG. 4 is a representation of the nucleotide sequence of cotton acyl-ACP thioesterase (ghFatB-2) cDNA and the predicted amino acid sequence of the precursor polypeptide ghFatB-2 encoded by cDNA. The protein encoding region is from nucleotides 210 to 1472 (TAG stop codon).

FIG. 5 is a representation of the nucleotide sequence of cotton acyl-ACP thioesterase (ghFatB-3) cDNA and the predicted amino acid sequence of the precursor polypeptide ghFatB-3 encoded by cDNA. The protein encoding region is from nucleotides 97 to (TAG stop codon).

FIG. 6 is a representation of the DNA sequence of the EST sequence CD486555 referred to in Example 4.

FIG. 7 is a representation of the DNA sequence of ghCPA-FAS-1 and the putative polypeptides it encodes FIG. 8 is a representation of the DNA sequence of ghCPA-FAS-2 and the putative polypeptides it encodes FIG. 9 is a representation of the DNA sequence of ghCPA-FAS-3 and the putative polypeptides it encodes

FIG. 13 is a representation of the DNA sequences used to make the RNAi construct illustrated in FIG. 12. Fragment A is the seed-specific Lec1 promoter; Fragment B is the chimeric fragment of the three target genes, including ghFAD2-1 (underlined), ghCPA-FAS-2 (italic font), and ghFatB-2 (bold font); Fragment C is the ghFAD2-1 intron used to separate the inverted repeats. Fragment D is the inverted repeat of fragment B; Fragment E is the lectin gene transcription terminator/polyadenylation sequence; Fragment F is the s1 promoter controlling the expression of the selectable marker gene (F+G+H); Fragment G is the NPTII protein coding region conferring kanamycin resistance and used as the selectable marker; Fragment H, the s3 transcription terminator/polyadenylation sequence.

DETAILED DESCRIPTION

Figure 1:
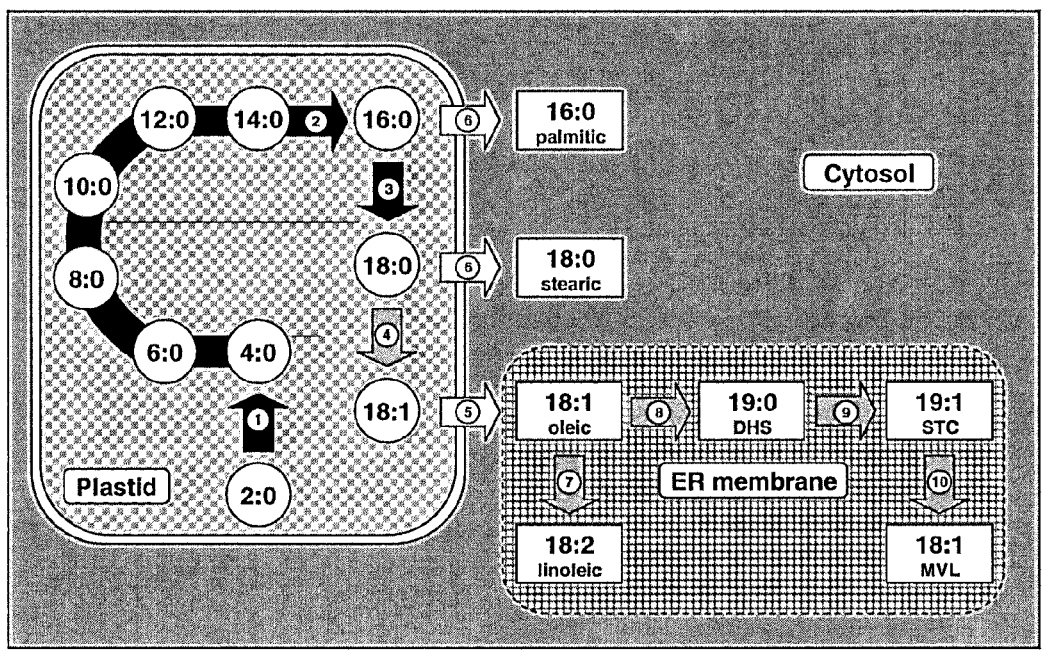
FIG. 1 is a simplified schematic diagram of fatty acid biosynthesis in developing cottonseed showing important enzymatic steps: 1. keto-acyl synthase III (KASIII), 2. keto-acyl synthase I (KASI), 3. keto-acyl synthase II (KASII), 4. Δ9-stearoyl-ACP desaturase (SAD), 5, oleoyl-ACP thioesterase, 6. acyl-ACP thioesterase, 7. Δ12-oleoyl-lipid desaturase (FAD2), 8. cyclopropane fatty acid synthase (CPA-FAS), 9. cyclopropane fatty acid desaturase (CPA-FAD), 10. α-oxidase. DHS: dihydrosterculic acid; STC, sterculic acid; MVL, malvalic acid.

The present specification is based upon the production of modified cotton plants wherein the plants are modified using chimeric hairpin RNA gene-silencing constructs. Stable progeny are characterised by comprising oil having the highly desirable properties including significantly lower levels of palmitic acid and linoleic acid, and significantly higher levels of oleic acid than controls and than the levels that are typically found in cottonseed oil extracted from commercially useful cultivars of cotton. Reduced gene expression of CPA-FAS-2 facilitated a reduction in the level of cyclopropenoid fatty acids and the presence of CPA and/or CPE in cottonseed oil. Although the present invention is illustrated using hairpin RNA gene-silencing constructs, it is not so limited and other methods known to those of skill in the art such as those described herein are also contemplated for use in producing plants and products derived therefrom with the herein disclosed advantages.

Reference herein to cottonseed oil refers to endogenous cottonseed oil and cottonseed oil extracted from cottonseeds derived from the modified cotton plants described herein. Thus the present invention does not relate to post-extraction modification of cottonseed oil in a way that substantially alters the fatty acid composition.

The present invention involves modification of gene activity and the construction and use of chimeric genes. As used herein, the term "gene" includes any deoxyribonucleotide sequence which includes a protein coding region or which is transcribed in a cell but not translated, as well as associated non-coding and regulatory regions. Such associated regions are typically located adjacent to the coding region or the transcribed region on both the 5' and 3' ends for a distance of about 2 kb on either side. In this regard, the gene may include control signals such as promoters, enhancers, termination and/or polyadenylation signals that are naturally associated with a given gene, or heterologous control signals in which case the gene is referred to as a "chimeric gene". The sequences which are located 5' of the coding region and which are present on the mRNA are referred to as 5' non-translated sequences. The sequences which are located 3' or downstream of the coding region and which are present on the mRNA are referred to as 3' non-translated sequences. The term "gene" encompasses both cDNA and genomic forms of a gene.

A "cotton FAD2-1 gene", "ghFAD2-1 gene" or the like as used herein refers to a nucleotide sequence encoding oleoyl-Δ12-desaturase in cotton, which is expressed in developing cottonseed. A ghFAD2-1 gene can readily be distinguished from genes encoding other oleoyl-Δ12-desaturases or other proteins by those skilled in the art, in particular from a ghFAD2-2 gene, for example SEQ ID NO: 26. Cotton FAD2-1 genes include the naturally occurring alleles or variants existing in cotton, including those encoded by the A and D genomes of tetraploid cotton, as well as non-naturally occurring variants which may be produced by those skilled in the art of gene modification. An example of a naturally occurring variant of cotton ghFAD2-1 is the sequence shown herein as SEQ ID NO: 24, which has about 96% identity along its full length to SEQ ID NO: 1. In a preferred embodiment, a ghFAD2-1 gene refers to a nucleic acid molecule, which may be present in or isolated from cotton or derived therefrom, comprising nucleotides having a sequence having at least 90% identity to the protein coding region of the cDNA sequence shown in SEQ ID NO: 1.

A "cotton FatB-2 gene", "ghFatB-2 gene" or the like as used herein refers to a nucleotide sequence encoding acyl-ACP thioesterase in cotton, which is expressed in developing cottonseed. A ghFatB-2 gene can readily be distinguished from genes encoding other acyl-ACP thioesterase or other proteins by those skilled in the art, in particular from a ghFatB-1, for example SEQ ID NO: 3, or from a ghFatB-3 gene, for example SEQ ID NO: 7. Cotton FatB-2 genes include the naturally occurring alleles or variants existing in cotton, including those encoded by the A and D genomes of tetraploid cotton, as well as non-naturally occurring variants which may be produced by those skilled in the art of gene modification. In a preferred embodiment, a ghFatB-2 gene refers to a nucleic acid molecule, which may be present in or isolated from cotton or derived therefrom, comprising nucleotides having a sequence having at least 90% identity to the protein coding region of the cDNA sequence shown in SEQ ID NO: 5.

A "cotton CPA-FAS-2 gene", "ghCPA-FAS-2 gene" or the like as used herein refers to a nucleotide sequence encoding CPA fatty acid synthase in cotton, which is expressed in developing cottonseed. A ghCPA-FAS-2 gene can readily be distinguished from genes encoding other CPA fatty acid synthases or other proteins by those skilled in the art, in particular from a ghCPA-FAS-1, for example SEQ ID NO: 10, or from a ghCPA-FAS-3 gene, for example SEQ ID NO: 14. Cotton CPA-FAS-2 genes include the naturally occurring alleles or variants existing in cotton, including those encoded by the A and D genomes of tetraploid cotton, as well as non-naturally occurring variants which may be produced by those skilled in the art of gene modification. In a preferred embodiment, a ghCPA-FAS-2 gene refers to a nucleic acid molecule, which may be present in or isolated from cotton or derived therefrom, comprising nucleotides having a sequence having at least 90% identity to the protein coding region of the cDNA sequence shown in SEQ ID NO: 12.

A genomic form or clone of a gene containing the transcribed region may be interrupted with non-coding sequences termed "introns" or "intervening regions" or "intervening sequences." An "intron" as used herein is a segment of a gene which is transcribed as part of a primary RNA transcript but is not present in the mature mRNA molecule. Introns are removed or "spliced out" from the nuclear or primary transcript; introns therefore are absent in the messenger RNA (mRNA). Introns may contain regulatory elements such as enhancers. "Exons" as used herein refer to the DNA regions corresponding to the RNA sequences which are present in the mature mRNA or the mature RNA molecule in cases where the RNA molecule is not translated. An mRNA functions during translation to specify the sequence or order of amino acids in a nascent polypeptide. The term "gene" includes a synthetic or fusion molecule encoding all or part of the proteins of the invention described herein and a complementary nucleotide sequence to any one of the above. A gene may be introduced into an appropriate vector for extrachromosomal maintenance in a cell or for integration into the host genome.

As used herein, a "chimeric gene" refers to any gene that is not a native gene in its native location. Typically a chimeric gene comprises regulatory and transcribed or protein coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. The term "endogenous" is used herein to refer to a substance that is normally present or produced in an unmodified plant at the same developmental stage as the plant under investigation. An "endogenous gene" refers to a native gene in its natural location in the genome of an organism. As used herein, "recombinant nucleic acid molecule" refers to a nucleic acid molecule which has been constructed or modified by recombinant DNA technology. The terms "foreign polynucleotide" or "exogenous polynucleotide" or "heterologous polynucleotide" and the like refer to any nucleic acid which is introduced into the genome of a cell by experimental manipulations. These include gene sequences found in that cell so long as the introduced gene contains some modification (e.g. a mutation, the presence of a selectable marker gene, etc.) relative to the naturally-occurring gene. Foreign or exogenous genes may be genes that are inserted into a non-native organism, native genes introduced into a new location within the native host, or chimeric genes. A "transgene" is a gene that has been introduced into the genome by a transformation procedure. The term "genetically modified" includes introducing genes into cells by transformation or transduction, mutating genes in cells and altering or modulating the regulation of a gene in a cell or organisms to which these acts have been done or their progeny.

Polynucleotides

The present invention refers to various polynucleotides. As used herein, a "polynucleotide" or "nucleic acid" or "nucleic acid molecule" means a polymer of nucleotides, which may be DNA or RNA or a combination thereof, and includes mRNA, cRNA, cDNA, tRNA, siRNA, shRNA and hpRNA. It may be DNA or RNA of cellular, genomic or synthetic origin, for example made on an automated synthesizer, and may be combined with carbohydrate, lipids, protein or other materials, labelled with fluorescent or other groups, or attached to a solid support to perform a particular activity defined herein, or comprise one or more modified nucleotides not found in nature, well known to those skilled in the art. The polymer may be single-stranded, essentially double-stranded or partly double-stranded. An example of a partly-double stranded RNA molecule is a hairpin RNA (hpRNA), short hairpin RNA (shRNA) or self-complementary RNA which include a double stranded stem formed by basepairing between a nucleotide sequence and its complement and a loop sequence which covalently joins the nucleotide sequence and its complement. Basepairing as used herein refers to standard basepairing between nucleotides, including G:U basepairs. "Complementary" means two polynucleotides are capable of basepairing (hybridizing) along part of their lengths, or along the full length of one or both. A "hybridized polynucleotide" means the polynucleotide is actually basepaired to its complement. The term "polynucleotide" is used interchangeably herein with the term "nucleic acid".

By "isolated" is meant material that is substantially or essentially free from components that normally accompany it in its native state. As used herein, an "isolated polynucleotide" or "isolated nucleic acid molecule" means a polynucleotide which is at least partially separated from, preferably substantially or essentially free of, the polynucleotide sequences of the same type with which it is associated or linked in its native state. For example, an "isolated polynucleotide" includes a polynucleotide which has been purified or separated from the sequences which flank it in a naturally occurring state, e.g., a DNA fragment which has been removed from the sequences which are normally adjacent to the fragment. Preferably, the isolated polynucleotide is also at least 90% free from other components such as proteins, carbohydrates, lipids etc. The term "recombinant polynucleotide" as used herein refers to a polynucleotide formed in vitro by the manipulation of nucleic acid into a form not normally found in nature. For example, the recombinant polynucleotide may be in the form of an expression vector. Generally, such expression vectors include transcriptional and translational regulatory nucleic acid operably connected to the nucleotide sequence.

The present invention refers to use of oligonucleotides. As used herein, "oligonucleotides" are polynucleotides up to 50 nucleotides in length. They can be RNA, DNA, or combinations or derivatives of either. Oligonucleotides are typically relatively short single stranded molecules of 10 to 30 nucleotides, commonly 15-25 nucleotides in length. When used as a probe or as a primer in an amplification reaction, the minimum size of such an oligonucleotide is the size required for the formation of a stable hybrid between the oligonucleotide and a complementary sequence on a target nucleic acid molecule. Preferably, the oligonucleotides are at least 15 nucleotides, more preferably at least 18 nucleotides, more preferably at least 19 nucleotides, more preferably at least 20 nucleotides, even more preferably at least 25 nucleotides in length.

Polynucleotides used as a probe are typically conjugated with a detectable label such as a radioisotope, an enzyme, biotin, a fluorescent molecule or a chemiluminescent molecule. Oligonucleotides of the invention are useful in methods of detecting an allele of an ghFAD2-1, ghFatB-2 and ghCPA-FAS-2 or other gene linked to a trait of interest, for example modified oil composition. Such methods, for example, employ nucleic acid hybridization and in many instances include oligonucleotide primer extension by a suitable polymerase (as used in PCR).

A variant of an oligonucleotide of the invention includes molecules of varying sizes of, and/or are capable of hybridising, for example, to the cotton genome close to that of, the specific oligonucleotide molecules defined herein. For example, variants may comprise additional nucleotides (such as 1, 2, 3, 4, or more), or less nucleotides as long as they still hybridise to the target region. Furthermore, a few nucleotides may be substituted without influencing the ability of the oligonucleotide to hybridise to the target region. In addition, variants may readily be designed which hybridise close to, for example to within 50 nucleotides, the region of the plant genome where the specific oligonucleotides defined herein hybridise.

The terms "polynucleotide variant" and "variant" and the like refer to polynucleotides or their complementary forms displaying substantial sequence identity with a reference polynucleotide sequence. These terms also encompass polynucleotides that are distinguished from a reference polynucleotide by the addition, deletion or substitution of at least one nucleotide. Accordingly, the terms "polynucleotide variant" and "variant" include polynucleotides in which one or more nucleotides have been added or deleted, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide. Accordingly, these terms encompass polynucleotides that encode polypeptides that exhibit enzymatic or other regulatory activity, or polynucleotides capable of serving as selective probes or other hybridising agents. In particular, this includes polynucleotides which encode the same polypeptide or amino acid sequence but which vary in nucleotide sequence by redundancy of the genetic code. The terms "polynucleotide variant" and "variant" also include naturally occurring allelic variants.

By "corresponds to" or "corresponding to" is meant a polynucleotide (a) having a nucleotide sequence that is substantially identical or complementary to all or most of a reference polynucleotide sequence or (b) encoding an amino acid sequence identical to an amino acid sequence in a peptide or protein. This phrase also includes within its scope a peptide or polypeptide having an amino acid sequence that is substantially identical to a sequence of amino acids in a reference peptide or protein. Terms used to describe sequence relationships between two or more polynucleotides or polypeptides include "reference sequence", "comparison window", "sequence identity", "percentage of sequence identity", "substantial identity" and "identical", and are defined with respect to a minimum number of nucleotides or amino acid residues or over the full length. The terms "sequence identity" and "identity" are used interchangeably herein to refer to the extent that sequences are identical on a nucleotide-by-nucleotide basis or an amino acid-by-amino acid basis over a window of comparison. Thus, a "percentage of sequence identity" is calculated by comparing two optimally aligned sequences over the window of comparison, determining the number of positions at which the identical nucleic acid base (e.g., A, T, C, G, U) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The % identity of a polynucleotide can be determined by GAP (Needleman and Wunsch, *J. Mol. Biol.* 48: 443-453, 1970) analysis (GCG program) with a gap creation penalty=5, and a gap extension penalty=0.3. Unless stated otherwise, the query sequence is at least 45 nucleotides in length, and the GAP analysis aligns the two sequences over a region of at least 45 nucleotides. Preferably, the query sequence is at least 150 nucleotides in length, and the GAP analysis aligns the two sequences over a region of at least 150 nucleotides. More preferably, the query sequence is at least 300 nucleotides in length and the GAP analysis aligns the two sequences over a region of at least 300 nucleotides, or at least 400, at least 500 or at least 600 nucleotides in each case. Reference also may be made to the BLAST family of programs as for example disclosed by Altschul et al., *Nucleic Acids Res.* 25: 3389, 1997. A detailed discussion of sequence analysis can be found in Unit 19.3 of Ausubel et al., *Current Protocols in Molecular Biology*, John Wiley & Sons Inc, 1994-1998, Chapter 15.

Nucleotide or amino acid sequences are indicated as "essentially similar" when such sequences have a sequence identity of at least 90%, especially at least 95%, more especially are identical. It is clear that when RNA sequences are described as essentially similar to, correspond to, or have a certain degree of sequence identity with, DNA sequences, thymine (T) in the DNA sequence is considered equal to uracil (U) in the RNA sequence.

With regard to the defined polynucleotides, it will be appreciated that % identity figures higher than those provided above will encompass preferred embodiments. Thus, where applicable, in light of the minimum % identity figures, it is preferred that the polynucleotide comprises a polynucleotide sequence which is at least 70%, preferably at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Preferably, a polynucleotide of the invention which encodes a polypeptide with ghFAD2-1, ghFatB-2 or ghCPA- FAS-2 activity is greater than 800, preferably greater than 900, and even more preferably greater than 1,000 nucleotides in length.

Polynucleotides of the present invention may possess, when compared to naturally occurring molecules, one or more mutations which are deletions, insertions, or substitutions of nucleotide residues. Mutants can be either naturally occurring (that is to say, isolated from a natural source) or synthetic (for example, by performing site-directed mutagenesis on the nucleic acid).

The present invention refers to the stringency of hybridization conditions to define the extent of complementarity of two polynucleotides. "Stringency" as used herein, refers to the temperature and ionic strength conditions, and presence or absence of certain organic solvents, during hybridization and washing. The higher the stringency, the higher will be the degree of complementarity between a target nucleotide sequence and the labelled polynucleotide sequence (probe). "Stringent conditions" refers to temperature and ionic conditions under which only nucleotide sequences having a high frequency of complementary bases will hybridize. As used herein, the term "hybridizes under low stringency, medium stringency, high stringency, or very high stringency conditions" describes conditions for hybridization and washing. Guidance for performing hybridization reactions can be found in Ausubel et al., (eds.), *Current Protocols in Molecular Biology*, John Wiley & Sons, NY, 6.3.1-6.3.6., 1989. Aqueous and nonaqueous methods are described in that reference and either can be used. Specific hybridization conditions referred to herein are as follows: 1) low stringency hybridization conditions are for hybridization in 6× sodium chloride/sodium citrate (SSC) at 45° C., followed by two washes in 0.2×SSC, 0.1% SDS at 50-55° C.; 2) medium stringency hybridization conditions are for hybridization in 6×SSC at about 45° C., followed by one or more washes in 0.2×SSC, 0.1% SDS at 60° C.; 3) high stringency hybridization conditions are for hybridization in 6×SSC at 45° C., followed by one or more washes in 0.2×SSC, 0.1% SDS at 65° C.; and 4) very high stringency hybridization conditions are for hybridization in 0.5 M sodium phosphate buffer, 7% SDS at 65° C., followed by one or more washes at 0.2×SSC, 1% SDS at 65° C.

Polypeptides

The terms "polypeptide" and "protein" are generally used interchangeably. The terms "proteins" and "polypeptides" as used herein also include variants, mutants, modifications, analogs and/or derivatives of the polypeptides of the invention as described herein. As used herein, "substantially purified polypeptide" refers to a polypeptide that has been separated from the lipids, nucleic acids, other peptides and other molecules with which it is associated in its native state. Preferably, the substantially purified polypeptide is at least 90% free from other components with which it is naturally associated. By "recombinant polypeptide" is meant a polypeptide made using recombinant techniques, i.e., through the expression of a recombinant polynucleotide in a cell, preferably a plant cell and more preferably a cereal plant cell.

The % identity of a polypeptide relative to another polypeptide can be determined by GAP (Needleman and Wunsch, 1970 (supra)) analysis (GCG program) with a gap creation penalty=5, and a gap extension penalty=0.3. The query sequence is at least 15 amino acids in length, and the GAP analysis aligns the two sequences over a region of at least 15 amino acids. More preferably, the query sequence is at least 50 amino acids in length, and the GAP analysis aligns the two sequences over a region of at least 50 amino acids. More preferably, the query sequence is at least 100 amino acids in length and the GAP analysis aligns the two sequences over a region of at least 100 amino acids. Even more preferably, the query sequence is at least 250 amino acids in length and the GAP analysis aligns the two sequences over a region of at least 250 amino acids.

As used herein a "biologically active" fragment of a polypeptide is a portion of a polypeptide of the invention, less than full length, which maintains a defined activity of the full-length polypeptide. Biologically active fragments can be any size as long as they maintain the defined activity, but are preferably at least 200 or at least 250 amino acid residues long.

With regard to a defined polypeptide, it will be appreciated that % identity figures higher than those provided above will encompass preferred embodiments. Thus, where applicable, in light of the minimum % identity figures, it is preferred that the polypeptide comprises an amino acid sequence which is at least 80%, more preferably at least 85%, more preferably at least 90%, more preferably at least 91%, more preferably at least 92%, more preferably at least 93%, more preferably at least 94%, more preferably at least 95%, more preferably at least 96%, more preferably at least 97%, more preferably at least 98%, more preferably at least 99%, more preferably at least 99.1%, more preferably at least 99.2%, more preferably at least 99.3%, more preferably at least 99.4%, more preferably at least 99.5%, more preferably at least 99.6%, more preferably at least 99.7%, more preferably at least 99.8%, and even more preferably at least 99.9% identical to the relevant nominated SEQ ID NO.

Amino acid sequence mutants of the polypeptides of the present invention can be prepared by introducing appropriate nucleotide changes into a nucleic acid of the present invention, or by in vitro synthesis of the desired polypeptide. Such mutants include, for example, deletions, insertions or substitutions of residues within the amino acid sequence. A combination of deletion, insertion and substitution can be made to arrive at the final construct, provided that the final peptide product possesses the desired characteristics.

Mutant (altered) peptides can be prepared using any technique known in the art. For example, a polynucleotide of the invention can be subjected to in vitro mutagenesis. Such in vitro mutagenesis techniques include sub-cloning the polynucleotide into a suitable vector, transforming the vector into a "mutator" strain such as the *E. coli* XL-1 red (Stratagene) and propagating the transformed bacteria for a suitable number of generations. In another example, the polynucleotides of the invention are subjected to DNA shuffling techniques as broadly described by Harayama, *Trends Biotechnol.* 16: 76-82, 1998. These DNA shuffling techniques may include genes related to those of the present invention, such as genes from plant species other than cotton, and/or include different genes from the same plant encoding similar proteins. Products derived from mutated/altered DNA can readily be screened using techniques described herein to determine if they possess, for example, FAD2 activity.

In designing amino acid sequence mutants, the location of the mutation site and the nature of the mutation will depend on characteristic(s) to be modified. The sites for mutation can be modified individually or in series, e.g., by (1) substituting first with conservative amino acid choices and then with more radical selections depending upon the results achieved, (2) deleting the target residue, or (3) inserting other residues adjacent to the located site.

Amino acid sequence deletions generally range from about 1 to 15 residues, more preferably about 1 to 10 residues and typically about 1 to 5 contiguous residues.

Substitution mutants have at least one amino acid residue in the polypeptide molecule removed and a different residue inserted in its place. The sites of greatest interest for substitutional mutagenesis include sites identified as the active site(s). Other sites of interest are those in which particular residues obtained from various strains or species are identical. These positions may be important for biological activity. These sites, especially those falling within a sequence of at least three other identically conserved sites, are preferably substituted in a relatively conservative manner. Such conservative substitutions are shown in Table 5 under the heading of "exemplary substitutions".

Polypeptides of the present invention can be produced in a variety of ways, including production and recovery of natural polypeptides, and production and recovery of recombinant polypeptides. In one embodiment, an isolated polypeptide of the present invention is produced by culturing a cell capable of expressing the polypeptide under conditions effective to produce the polypeptide, and recovering the polypeptide. A preferred cell to culture is a recombinant cell of the present invention.

The present invention refers to elements which are operably connected or linked. "Operably connected" or "operably linked" and the like refer to a linkage of polynucleotide elements in a functional relationship. Typically, operably connected nucleic acid sequences are contiguously linked and, where necessary to join two protein coding regions, contiguous and in reading frame. A coding sequence is "operably connected to" another coding sequence when RNA polymerase will transcribe the two coding sequences into a single RNA, which if translated is then translated into a single polypeptide having amino acids derived from both coding sequences. The coding sequences need not be contiguous to one another so long as the expressed sequences are ultimately processed to produce the desired protein.

As used herein, the term "cis-acting sequence", "cis-acting element" or "cis-regulatory region" or "regulatory region" or similar term shall be taken to mean any sequence of nucleotides, which when positioned appropriately and connected relative to an expressible genetic sequence, is capable of regulating, at least in part, the expression of the genetic sequence. Those skilled in the art will be aware that a cis-regulatory region may be capable of activating, silencing, enhancing, repressing or otherwise altering the level of expression and/or cell-type-specificity and/or developmental specificity of a gene sequence at the transcriptional or post-transcriptional level. In certain embodiments of the present invention, the cis-acting sequence is an activator sequence that enhances or stimulates the expression of an expressible genetic sequence.

"Operably connecting" a promoter or enhancer element to a transcribable polynucleotide means placing the transcribable polynucleotide (e.g., protein-encoding polynucleotide or other transcript) under the regulatory control of a promoter, which then controls the transcription of that polynucleotide. In the construction of heterologous promoter/structural gene combinations, it is generally preferred to position a promoter or variant thereof at a distance from the transcription start site of the transcribable polynucleotide which is approximately the same as the distance between that promoter and the protein coding region it controls in its natural setting; i.e., the gene from which the promoter is derived. As is known in the art, some variation in this distance can be accommodated without loss of function. Similarly, the preferred positioning of a regulatory sequence element (e.g., an operator, enhancer etc) with respect to a transcribable polynucleotide to be placed under its control is defined by the positioning of the element in its natural setting; i.e., the genes from which it is derived.

"Promoter" or "promoter sequence" as used herein refers to a region of a gene, generally upstream (5') of the RNA encoding region, which controls the initiation and level of transcription in the cell of interest. A "promoter" includes the transcriptional regulatory sequences of a classical genomic gene, including a TATA box and CCAAT box sequences, as well as additional regulatory elements (i.e., upstream activating sequences, enhancers and silencers) that alter gene expression in response to developmental and/or environmental stimuli, or in a tissue-specific or cell-type-specific manner. A promoter is usually, but not necessarily (for example, some PolIII promoters), positioned upstream of a structural gene, the expression of which it regulates. Furthermore, the regulatory elements comprising a promoter are usually positioned within 2 kb of the start site of transcription of the gene. Promoters may contain additional specific regulatory elements, located more distal to the start site to further enhance expression in a cell, and/or to alter the timing or inducibility of expression of a structural gene to which it is operably connected.

"Constitutive promoter" refers to a promoter that directs expression of an operably linked transcribed sequence in many or all tissues of a plant. The term constitutive as used herein does not necessarily indicate that a gene is expressed at the same level in all cell types, but that the gene is expressed in a wide range of cell types, although some variation in level is often detectable. "Selective expression" as used herein refers to expression almost exclusively in specific organs of the plant, such as, for example, endosperm, embryo, leaves, fruit, tubers or root. In a preferred embodiment, a promoter is expressed selectively or preferentially in developing seed of a plant, preferably a cotton plant. The term may also refer to expression at specific developmental stages in an organ, such as in early, mid or late embryogenesis or different stages of maturity, or to expression that is inducible by certain environmental conditions or treatments. Selective expression may therefore be contrasted with constitutive expression, which refers to expression in many or all tissues of a plant under most or all of the conditions experienced by the plant.

Selective expression may also result in compartmentation of the products of gene expression in specific plant tissues, organs or developmental stages. Compartmentation in specific subcellular locations such as the plastid, cytosol, vacuole, or apoplastic space may be achieved by the inclusion in the structure of the gene product of appropriate signals, eg. a signal peptide, for transport to the required cellular compartment, or in the case of the semi-autonomous organelles (plastids and mitochondria) by integration of the transgene with appropriate regulatory sequences directly into the organelle genome.

A "tissue-specific promoter" or "organ-specific promoter" is a promoter that is preferentially expressed in one tissue or organ relative to many other tissues or organs, preferably most if not all other tissues or organs in a plant. Typically, the promoter is expressed at a level 10-fold higher in the specific tissue or organ than in other tissues or organs. An illustrative tissue specific promoter is the promoter from a lectin gene (SEQ ID NO: 16) which is expressed preferentially in the developing seed of dicot plants such as cotton. Other seed specific promoters are well known in the art.

The promoters contemplated by the present invention may be native to the host plant to be transformed or may be derived from an alternative source, where the region is functional in the host plant. Other sources include the *Agrobacterium*

T-DNA genes, such as the promoters of genes for the biosynthesis of nopaline, octapine, mannopine, or other opine promoters, tissue specific promoters (see, e.g., U.S. Pat. No. 5,459,252 to Conkling et al.; WO 91/13992 to Advanced Technologies); promoters from viruses (including host specific viruses), or partially or wholly synthetic promoters. Numerous promoters that are functional in mono- and dicotyledonous plants are well known in the art (see, for example, Greve, *J. Mol. Appl. Genet.*, 1: 499-511, 1983; Salomon et al., *EMBO J.*, 3: 141-146, 1984; Garfinkel et al., *Cell*, 27: 143-153, 1983: Barker et al., *Plant Mol. Biol.*, 2: 235-350, 1983; including various promoters isolated from plants and viruses such as the cauliflower mosaic virus promoter (CaMV 35S, 19S). Many tissue specific promoter regions are known. Other transcriptional initiation regions which preferentially provide for transcription in certain tissues or under certain growth conditions, include those from genes encoding napin, seed ACP, zein, or other seed storage proteins. Non-limiting methods for assessing promoter activity are disclosed by Medberry et al., *Plant Cell*, 4: 185-192, 1992, Medberry et al., *Plant J.* 3: 619-626, 1993, Sambrook et al., *Molecular Cloning: A Laboratory Manual* (2nd Ed). Cold Spring Harbour Laboratory, Cold Spring Harbour, N.Y. 1989 and McPherson et al., (U.S. Pat. No. 5,164,316).

Alternatively or additionally, the promoter may be an inducible promoter or a developmentally regulated promoter which is capable of driving expression of the introduced polynucleotide at an appropriate developmental stage of the plant. Other cis-acting sequences which may be employed include transcriptional and/or translational enhancers. Enhancer regions are well known to persons skilled in the art, and can include an ATG translational initiation codon and adjacent sequences. When included, the initiation codon should be in phase with the reading frame of the coding sequence relating to the foreign or exogenous polynucleotide to ensure translation of the entire sequence if it is to be translated. Translational initiation regions may be provided from the source of the transcriptional initiation region, or from a foreign or exogenous polynucleotide. The sequence can also be derived from the source of the promoter selected to drive transcription, and can be specifically modified so as to increase translation of the mRNA.

The nucleic acid construct of the present invention may comprise a 3' non-translated sequence from about 50 to 1,000 nucleotide base pairs which may include a transcription termination sequence. A 3' non-translated sequence may contain a transcription termination signal which may or may not include a polyadenylation signal and any other regulatory signals capable of effecting mRNA processing. A polyadenylation signal functions for addition of polyadenylic acid tracts to the 3' end of a mRNA precursor. Polyadenylation signals are commonly recognized by the presence of homology to the canonical form 5' AATAAA-3' although variations are not uncommon. Transcription termination sequences which do not include a polyadenylation signal include terminators for PolI or PolIII RNA polymerase which comprise a run of four or more thymidines. Examples of suitable 3' non-translated sequences are the 3' transcribed non-translated regions containing a polyadenylation signal from a lectin gene (SEQ ID NO: 20), the S3 gene of Subclover Stunt Virus (SEQ ID NO: 23), or nopaline synthase (nos) gene of *Agrobacterium tumefaciens* (Bevan et al., *Nucl. Acid Res.*, 11: 369, 1983). Suitable 3' non-translated sequences may also be derived from plant genes such as the 3' end of the protease inhibitor I or II genes from potato or tomato, the soybean storage protein genes and the small subunit of the ribulose-1,5-bisphosphate carboxylase (ssRUBISCO) gene, although other 3' elements known to those of skill in the art can also be employed.

As the DNA sequence inserted between the transcription initiation site and the start of the coding sequence, i.e., the untranslated 5' leader sequence (5'UTR), can influence gene expression if it is translated as well as transcribed, one can also employ a particular leader sequence. Suitable leader sequences include those that comprise sequences selected to direct optimum expression of the foreign or endogenous DNA sequence. For example, such leader sequences include a preferred consensus sequence which can increase or maintain mRNA stability and prevent inappropriate initiation of translation as for example described by Joshi, *Nucl. Acid Res.* 15: 6643, 1987.

Additionally, targeting sequences may be employed to target the enzyme encoded by the foreign or exogenous polynucleotide to an intracellular compartment, for example to the chloroplast, within plant cells or to the extracellular environment. For example, a nucleic acid sequence encoding a transit or signal peptide sequence may be operably linked to a sequence that encodes a chosen enzyme of the subject invention such that, when translated, the transit or signal peptide can transport the enzyme to a particular intracellular or extracellular destination, and can then be optionally post-translationally removed. Transit or signal peptides act by facilitating the transport of proteins through intracellular membranes, e.g., endoplasmic reticulum, vacuole, vesicle, plastid, mitochondrial and plasmalemma membranes. For example, the targeting sequence can direct a desired protein to a particular organelle such as a vacuole or a plastid (e.g., a chloroplast), rather than to the cytosol. Thus, the nucleic acid construct of the invention can further comprise a plastid transit peptide-encoding nucleic acid sequence operably linked between a promoter region and the foreign or exogenous polynucleotide. Sequences encoding such signal peptides are often found in naturally occurring genes and may be employed, such as, for example, in the ghFatB genes described herein.

Vectors

The present invention includes use of vectors for manipulation or transfer of genetic constructs. By "vector" is meant a nucleic acid molecule, preferably a DNA molecule derived, for example, from a plasmid, bacteriophage, or plant virus, into which a nucleic acid sequence may be inserted or cloned. A vector preferably is double-stranded DNA and contains one or more unique restriction sites and may be capable of autonomous replication in a defined host cell including a target cell or tissue or a progenitor cell or tissue thereof, or capable of integration into the genome of the defined host such that the cloned sequence is reproducible. Accordingly, the vector may be an autonomously replicating vector, i.e., a vector that exists as an extrachromosomal entity, the replication of which is independent of chromosomal replication, e.g., a linear or closed circular plasmid, an extrachromosomal element, a minichromosome, or an artificial chromosome. The vector may contain any means for assuring self-replication. Alternatively, the vector may be one which, when introduced into a cell, is integrated into the genome of the recipient cell and replicated together with the chromosome(s) into which it has been integrated. A vector system may comprise a single vector or plasmid, two or more vectors or plasmids, which together contain the total DNA to be introduced into the genome of the host cell, or a transposon. The choice of the vector will typically depend on the compatibility of the vector with the cell into which the vector is to be introduced. The vector may also include a selection marker such as an antibiotic resistance gene, a herbicide resistance gene or other gene that can be used for selection of suitable transformants. Examples of such genes are well known to those of skill in the art.

The nucleic acid construct of the invention can be introduced into a vector, such as a plasmid. Plasmid vectors typically include additional nucleic acid sequences that provide for easy selection, amplification, and transformation of the expression cassette in prokaryotic and eukaryotic cells, e.g., pUC-derived vectors, pSK-derived vectors, pGEM-derived vectors, pSP-derived vectors, pBS-derived vectors, or binary vectors containing one or more T-DNA regions. Additional nucleic acid sequences include origins of replication to provide for autonomous replication of the vector, selectable marker genes, preferably encoding antibiotic or herbicide resistance, unique multiple cloning sites providing for multiple sites to insert nucleic acid sequences or genes encoded in the nucleic acid construct, and sequences that enhance transformation of prokaryotic and eukaryotic (especially plant) cells.

Figure 12:
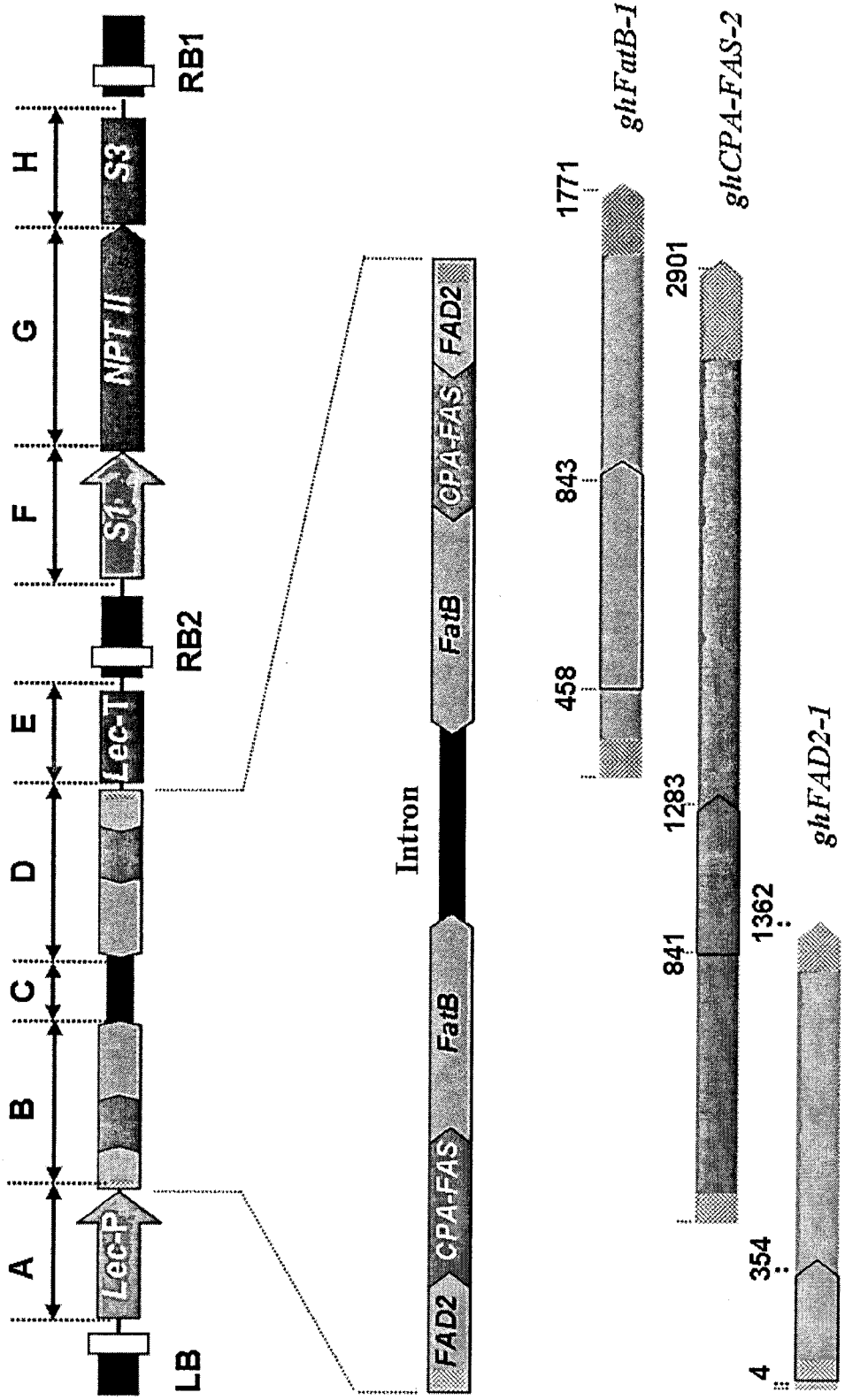
FIG. 12 is a schematic diagram of the chimeric transgene used to generate triple-gene silencing in cotton (MonoCott construct). DNA sequences of the fragments labelled on the top of the construct are detailed in FIG. 11. (Abbreviations: LB: T-DNA left border; LecP: soybean lectin promoter; ghFAD2-1: cotton microsomal oleoyl Δ12 desaturase cDNA; ghCPA-FAS-2: cotton cyclopropane fatty acid synthase; ghFatB-1: cotton palmitoyl-ACP thioesterase; lee-T: soybean lectin terminator; RB2: T-DNA right border 2; S1: subterranean clover stunt virus segment I promoter; S3: subterranean clover stunt virus segment 3 terminator; NPTII: neomycin phosphotransferase gene. The sizes of the full length cDNA and the selected fragments of each target gene in making the RNAi construct were also indicated).

By "marker gene" is meant a gene that imparts a distinct phenotype to cells expressing the marker gene and thus allows such transformed cells to be distinguished from cells that do not have the marker. A selectable marker gene confers a trait for which one can "select" based on resistance to a selective agent (e.g., a herbicide, antibiotic, radiation, heat, or other treatment damaging to untransformed cells). A screenable marker gene (or reporter gene) confers a trait that one can identify through observation or testing, i.e., by "screening" (e.g., β-glucuronidase, luciferase, GFP or other enzyme activity not present in untransformed cells). The marker gene and the nucleotide sequence of interest do not have to be linked. An example of a selectable marker gene is the S1-NptII-S3 terminator gene shown schematically in FIG. 12, comprising SEQ ID NOs: 21-23.

To facilitate identification of transformants, the nucleic acid construct desirably comprises a selectable or screenable marker gene as, or in addition to, the foreign or exogenous polynucleotide. The actual choice of a marker is not crucial as long as it is functional (i.e., selective) in combination with the plant cells of choice. The marker gene and the foreign or exogenous polynucleotide of interest do not have to be linked, since co-transformation of unlinked genes as, for example, described in U.S. Pat. No. 4,399,216 is also an efficient process in plant transformation.

Examples of bacterial selectable markers are markers that confer antibiotic resistance such as ampicillin, erythromycin, chloramphenicol or tetracycline resistance, preferably kanamycin resistance. Exemplary selectable markers for selection of plant transformants include, but are not limited to, a hyg gene which encodes hygromycin B resistance; a neomycin phosphotransferase (nptII) gene conferring resistance to kanamycin, paromomycin, G418; a glutathione-S-transferase gene from rat liver conferring resistance to glutathione derived herbicides as, for example, described in EP-A 256223; a glutamine synthetase gene conferring, upon overexpression, resistance to glutamine synthetase inhibitors such as phosphinothricin as, for example, described in WO87/05327, an acetyltransferase gene from *Streptomyces viridochromogenes* conferring resistance to the selective agent phosphinothricin as, for example, described in EP-A 275957, a gene encoding a 5-enolshikimate-3-phosphate synthase (EPSPS) conferring tolerance to N-phosphonomethylglycine as, for example, described by Hinchee et al., *Biotech.* 6: 915, 1988, a bar gene conferring resistance against bialaphos as, for example, described in WO91/02071; a nitrilase gene such as bxn from *Klebsiella ozaenae* which confers resistance to bromoxynil (Stalker et al., *Science,* 242: 419, 1988); a dihydrofolate reductase (DHFR) gene conferring resistance to methotrexate (Millet et al., *J. Biol. Chem.* 263: 12500, 1988); a mutant acetolactate synthase gene (ALS), which confers resistance to imidazolinone, sulfonylurea or other ALS-inhibiting chemicals (EP-A-154 204); a mutated anthranilate synthase gene that confers resistance to 5-methyl tryptophan; or a dalapon dehalogenase gene that confers resistance to the herbicide.

Preferred screenable markers include, but are not limited to, a uidA gene encoding a β-glucuronidase (GUS) enzyme for which various chromogenic substrates are known, a β-galactosidase gene encoding an enzyme for which chromogenic substrates are known, an aequorin gene (Prasher et al., *Biochem. Biophys. Res. Comm.* 126: 1259-68, 1985), which may be employed in calcium-sensitive bioluminescence detection; a green fluorescent protein gene (Niedz et al., *Plant Cell Reports,* 14: 403, 1995.) or derivatives thereof; a luciferase (luc) gene (Ow et al., *Science,* 234: 856, 1986), which allows for bioluminescence detection, and others known in the art. By "reporter molecule" as used in the present specification is meant a molecule that, by its chemical nature, provides an analytically identifiable signal that facilitates determination of promoter activity by reference to protein product.

Methods of Modifying Gene Expression

The level of a protein, for example an enzyme involved in oil biosynthesis in developing seeds of a plant, may be modulated by increasing the level of expression of a nucleotide sequence that codes for the protein in a plant cell, or decreasing the level of expression of a gene encoding the protein in the plant, leading to modified oil composition in the mature seed. The level of expression of a gene may be modulated by altering the copy number per cell, for example by introducing a synthetic genetic construct comprising the coding sequence and a transcriptional control element that is operably connected thereto and that is functional in the cell. A plurality of transformants may be selected and screened for those with a favourable level and/or specificity of transgene expression arising from influences of endogenous sequences in the vicinity of the transgene integration site. A favourable level and pattern of transgene expression is one which results in a substantial modification of oil composition. This may be detected by simple testing of seedoil from the transformants. Alternatively, a population of mutagenized grain or a population of plants from a breeding program may be screened for individual lines with altered oil content or composition.

Reducing gene expression may be achieved through introduction and transcription of a "gene-silencing chimeric gene" introduced into the plant cell. The gene-silencing chimeric gene may be introduced stably into the plant cell's genome, preferably nuclear genome, or it may be introduced transiently, for example on a viral vector. As used herein "gene-silencing effect" refers to the reduction of expression of a target nucleic acid in a plant cell, which can be achieved by introduction of a silencing RNA. Such reduction may be the result of reduction of transcription, including via methylation of chromatin remodeling, or post-transcriptional modification of the RNA molecules, including via RNA degradation, or both. Gene-silencing includes an abolishing of the expression of the target nucleic acid or gene and a partial effect in either extent or duration. It is sufficient that the level of expression of the target nucleic acid in the presence of the silencing RNA is lower that in the absence thereof. The level of expression may be reduced by at least about 40%, or at least about 50%, or at least about 60%, or at least about 70%, or at least about 80%, or at least about 90%, or at least about 95%, or at least about 99%. In preferred embodiments, the expression of the cotton ghCPA-FAS-2 gene is reduced in seed by at least 60%, more preferably by at least 80% relative to a corresponding seed lacking the gene-silencing chimeric DNA. The target nucleic acid may be a gene involved in oil biosynthesis, oil accumulation such as genes involved in TAG assembly, including but not limited to acyltransferases or other enzymes of the Kennedey pathway, or oil metabolism, or may be any other endogenous genes, transgenes or exogenous genes such as viral genes which may not be present in the plant cell at the time of introduction of the transgene. In some embodiment the specification provides a method of modifying the endogenous oil of a cotton plant comprising producing a transgenic cotton plant having a gene construct which comprises a nucleotide sequence of a fatty acid biosynthesis gene or a gene fragment thereof, wherein said gene or gene fragment is placed operably in connection with a promoter sequence capable of conferring expression of said gene or gene fragment in the seed of a cotton plant, and wherein said fatty acid biosynthesis gene is two or more of FAD2 desaturase, FatB thioesterase, and CPA-FAS-2 fatty acid synthase. As described herein, reduction in gene expression improves the fatty acid content of endogenous and extracted oil.

Antisense RNA Molecules

Antisense techniques may be used to reduce gene expression according to the invention. The term "antisense RNA" shall be taken to mean an RNA molecule that is complementary to at least a portion of a specific mRNA molecule and capable of reducing expression of the gene encoding the mRNA. Such reduction typically occurs in a sequence-dependent manner and is thought to occur by interfering with a post-transcriptional event such as mRNA transport from nucleus to cytoplasm, mRNA stability or inhibition of translation. The use of antisense methods is well known in the art (see for example, Hartmann and Endres, *Manual of Antisense Methodology*, Kluwer, 1999). The use of antisense techniques in plants has been reviewed by Bourque, *Plant Science*, 105: 125-149, 1995 and Senior, *Biotech. Genet. Engin. Revs.* 15: 79-119, 1998. Bourque, 1995 (supra) lists a large number of examples of how antisense sequences have been utilized in plant systems as a method of gene inactivation. She also states that attaining 100% inhibition of any enzyme activity may not be necessary as partial inhibition will more than likely result in measurable change in the system. Senior, 1998 (supra) states that antisense methods are now a very well established technique for manipulating gene expression.

As used herein, the term "an antisense polynucleotide which hybridises under physiological conditions" means that the polynucleotide (which is fully or partially single stranded) is at least capable of forming a double stranded polynucleotide with an RNA product of the gene to be inhibited, typically the mRNA encoding a protein such as those provided herein, under normal conditions in a cell. Antisense molecules may include sequences that correspond to the structural genes or for sequences that effect control over the gene expression or splicing event. For example, the antisense sequence may correspond to the coding region of the targeted gene, or the 5'-untranslated region (UTR) or the 3'-UTR or combination of these. It may be complementary in part to intron sequences, which may be spliced out during or after transcription, but is preferably complementary only to exon sequences of the target gene. In view of the generally greater divergence of the UTRs, targeting these regions provides greater specificity of gene inhibition.

The length of the antisense sequence should be at least 19 contiguous nucleotides, preferably at least 25 or 30 or 50 nucleotides, and more preferably at least 100, 200, 500 or 1000 nucleotides, to a maximum of the full length of the gene to be inhibited. The full-length sequence complementary to the entire gene transcript may be used. The length is most preferably 100-2000 nucleotides. The degree of identity of the antisense sequence to the targeted transcript should be at least 90% and more preferably 95-100%. Preferred antisense sequences comprise at least 30 contiguous nucleotides which are the complement of any sequence of at least 30 contiguous nucleotides from SEQ ID NOs: 1, 5, or 12. The antisense RNA molecule may of course comprise unrelated sequences which may function to stabilize the molecule.

Genetic constructs to express an antisense RNA may be readily made by joining a promoter sequence to a region of the target gene in an "antisense" orientation, which as used herein refers to the reverse orientation relative to the orientation of transcription and translation (if it occurs) of the sequence in the target gene in the plant cell. Accordingly, also provided by this invention is a nucleic acid molecule such as a chimeric DNA coding for an antisense RNA of the invention, including cells, tissues, organs, plants, seeds, particularly cotton plants or cottonseed and the like comprising the nucleic acid molecule.

Ribozymes

The term "ribozyme" as used herein refers to an RNA molecule which specifically recognizes a distinct substrate RNA and catalyzes its cleavage. Typically, the ribozyme contains a region of nucleotides which are complementary to a region of the target RNA, enabling the ribozyme to specifically hybridize to the target RNA under physiological conditions, for example in the cell in which the ribozyme acts, and an enzymatic region referred to herein as the "catalytic domain". The types of ribozymes that are particularly useful in this invention are the hammerhead ribozyme (Haseloff and Gerlach, *Nature* 334: 585-591, 1988, Perriman et al., *Gene*, 113: 157-163, 1992) and the hairpin ribozyme (Shippy et al., *Mol. Biotech.* 12: 117-129, 1999). DNA encoding the ribozymes can be synthesized using methods well known in the art and may be incorporated into a genetic construct or expression vector for expression in the cell of interest. Accordingly, also provided by this invention is a nucleic acid molecule such as a chimeric DNA coding for a ribozyme of the invention, including cells, tissues, organs, plants, grain and the like comprising the nucleic acid molecule. Typically, the DNA encoding the ribozyme is inserted into an expression cassette under control of a promoter and a transcription termination signal that function in the cell. Specific ribozyme cleavage sites within any potential RNA target may be identified by scanning the target molecule for ribozyme cleavage sites which include the trinucleotide sequences GUA, GUU and GUC. Once identified, short RNA sequences of between about 5 and 20 ribonucleotides corresponding to the region of the target gene 5' and 3' of the cleavage site may be evaluated for predicted structural features such as secondary structure that may render the oligonucleotide sequence less suitable. When employed, ribozymes may be selected from the group consisting of hammerhead ribozymes, hairpin ribozymes, axehead ribozymes, newt satellite ribozymes, Tetrahymena ribozymes and RNAse P ribozymes, and are designed according to methods known in the art based on the sequence of the target gene (for instance, see U.S. Pat. No. 5,741,679). The suitability of candidate targets may also be evaluated by testing their accessibility to hybridization with complementary oligonucleotides, using ribonuclease protection assays.

As with antisense polynucleotides described herein, ribozymes of the invention should be capable of hybridizing to a target nucleic acid molecule (for example SEQ ID NOs: 1, 5 or 12) under "physiological conditions", namely those conditions within a cell, especially conditions in a plant cell such as a wheat or barley cell.

RNA Interference/Duplex RNA

As used herein, "artificially introduced dsRNA molecule" refers to the introduction of dsRNA molecule, which may be produced in the cell by transcription from a chimeric gene encoding such dsRNA molecule, however does not refer to the conversion of a single stranded RNA molecule into a dsRNA inside the eukaryotic cell or plant cell. RNA interference (RNAi) is particularly useful for specifically reducing the expression of a gene or inhibiting the production of a particular protein. Although not wishing to be limited by theory, Waterhouse et al., *Proc. Natl. Acad. Sci. U.S.A.* 95: 13959-13964, 1998 have provided a model for the mechanism by which dsRNA can be used to reduce gene expression or protein production. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are transcribed to produce a hairpin RNA in which the sense and anti-sense sequences hybridize to form the dsRNA region with an intervening sequence or spacer region forming a loop structure, so the hairpin RNA comprises a stem-loop structure. The design and production of suitable dsRNA molecules for the present invention is well within the capacity of a person skilled in the art, particularly considering Waterhouse et al., 1998 (supra), Smith et al., *Nature*, 407: 319-320, 2000, WO 99/53050, WO 99/49029, and WO 01/34815. Accordingly, also provided by this invention is a nucleic acid molecule such as a chimeric DNA coding for a duplex RNA such as a hairpin RNA of the invention, including cells, tissues, organs, plants, seeds, particularly cotton plants or cottonseed, and the like comprising the nucleic acid molecule. In a preferred embodiment, the chimeric DNA has the structure shown schematically in FIG. 12, comprising the sequence shown in FIG. 13, referred to herein as the MonoCott construct.

In one example, a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. A preferred intron is an intron from the ghFAD2-1 gene, for example SEQ ID NO: 18. This arrangement has been shown to result in a higher efficiency of gene silencing (Smith et al., 2000 (supra)). The double-stranded region may comprise one or two RNA molecules, transcribed from either one DNA region or two. The dsRNA may be classified as long hpRNA, having long, sense and antisense regions which can be largely complementary, but need not be entirely complementary (typically forming a basepaired region larger than about 100 bp, preferably ranging between 200-1000 bp). hpRNA can also be smaller with the double-stranded portion ranging in size from about 30 to about 50 bp, or from 30 to about 100 bp (see WO04/073390, herein incorporated by reference). The presence of the double stranded RNA region is thought to trigger a response from an endogenous plant system that processes the double stranded RNA to oligonucleotides of 21-24 nucleotides long, and also uses these oligonucleotides for sequence-specific cleavage of the homologous RNA transcript from the target plant gene, efficiently reducing or eliminating the activity of the target gene.

The length of the sense and antisense sequences that hybridise should each be at least 19 contiguous nucleotides, preferably at least 27 or 30 or 50 nucleotides, and more preferably at least 100, 200, or 500 nucleotides, up to the full-length sequence corresponding to the entire gene transcript. The lengths are most preferably 100-2000 nucleotides. The degree of identity of the sense and antisense sequences to the targeted transcript should be at least 85%, preferably at least 90% and more preferably 95-100%. The longer the sequence, the less stringent the requirement is for overall sequence identity. The RNA molecule may of course comprise unrelated sequences which may function to stabilize the molecule. The RNA molecule may be a hybrid between different sequences targeting different target RNAs, allowing reduction in expression of more than one target gene, or it may be one sequence which corresponds to a family of related target genes such as a multigene family. In a preferred embodiment, the RNA molecule targets at least three different target genes, more preferably the ghFAD2-1, ghFatB-2 and ghCPA-FAS-2 genes in cotton. The sequences used in the dsRNA preferably correspond to exon sequences of the target gene and may correspond to 5' and/or 3' untranslated sequences or protein coding sequences or any combination thereof. The promoter used to express the dsRNA-forming construct may be any type of promoter if the resulting dsRNA is specific for a gene product in the cell lineage targeted for destruction. Alternatively, the promoter may be lineage specific in that it is only expressed in cells of a particular development lineage. This might be advantageous where some overlap in homology is observed with a gene that is expressed in a non-targeted cell lineage. The promoter may also be inducible by externally controlled factors, or by intracellular environmental factors. Typically, the RNA molecule is expressed under the control of a RNA polymerase II or RNA polymerase III promoter. Examples of the latter include tRNA or snRNA promoters.

Examples of genetic constructs that encode dsRNA molecules that may be used to down-regulate the production of polypeptides for modification of oil composition in cottonseed are provided in Example 5.

Other silencing RNA may be "unpolyadenylated RNA" comprising at least 20 consecutive nucleotides having at least 95% sequence identity to the complement of a nucleotide sequence of an RNA transcript of the target gene, such as described in WO01/12824 or U.S. Pat. No. 6,423,885 (both documents herein incorporated by reference). Yet another type of silencing RNA is an RNA molecule as described in WO03/076619 (herein incorporated by reference) comprising at least 20 consecutive nucleotides having at least 95% sequence identity to the sequence of the target nucleic acid or the complement thereof, and further comprising a largely-double stranded region as described in WO03/076619.

MicroRNA regulation is a specialized branch of the RNA silencing pathway that evolved towards gene regulation, diverging from conventional RNAi/PTGS. MicroRNAs are a specific class of small RNAs that are encoded in gene-like elements organized in a characteristic partial inverted repeat. When transcribed, microRNA genes give rise to partially basepaired stem-looped precursor RNAs from which the microRNAs are subsequently processed. Processed microRNAs are typically 21 contiguous nucleotides in length or 21-23 nucleotides in length which are at least 95% identical in sequence to 21 contiguous nucleotides of the complement of the RNA transcript of the target gene. The released miRNAs are incorporated into RISC-like complexes containing a particular subset of Argonaute proteins that exert sequence-specific gene repression (see, for example, Millar and Waterhouse, *Funct Integr Genomics*, 5: 129-135, 2005; Pasquinelli et al., *Curr Opin Genet Develop* 15: 200-205, 2005; Almeida and Allshire, *Trends Cell Biol.* 15: 251-258, 2005, herein incorporated by reference).

Cosuppression

Another molecular biological approach that may be used for specifically reducing gene expression is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the "sense orientation" with respect to a promoter for its expression, which as used herein refers to the same orientation as transcription and translation (if it occurs) of the sequence relative to the sequence in the target gene. The size of the sense fragment, its correspondence to target gene regions, and its degree of homology to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches. The antisense, co-suppression or double stranded RNA molecules may also comprise a largely double-stranded RNA region, preferably comprising a nuclear localization signal, as described in WO 03/076619.

Any of these technologies for reducing gene expression can be used to coordinately reduce the activity of multiple genes. For example, one RNA molecule can be targeted against a family of related genes by targeting a region of the genes which is in common. Alternatively, unrelated genes may be targeted by including multiple regions in one RNA molecule, each region targeting a different gene. This can readily be done by fusing the multiple regions under the control of a single promoter, such as in Example 5.

Methods of Introducing Nucleic Acids into Plant Cells/Transformation

A number of techniques are available for the introduction of nucleic acid molecules into a plant host cell, well known to workers in the art. The term "transformation" means alteration of the genotype of an organism, for example a bacterium or a plant, by the introduction of a foreign or exogenous nucleic acid. By "transformant" is meant an organism so altered. As used herein the term "transgenic" refers to a genetically modified plant in which the endogenous genome is supplemented or modified by the integration, or stable maintenance in a replicable non-integrated form, of an introduced foreign or exogenous gene or sequence. By "transgene" is meant a foreign or exogenous gene or sequence that is introduced into the genome of a plant. The nucleic acid molecule may be stably integrated into the genome of the plant, or it may be replicated as an extrachromosomal element. By "genome" is meant the total inherited genetic complement of the cell, plant or plant part, and includes chromosomal DNA, plastid DNA, mitochondrial DNA and extrachromosomal DNA molecules. The term "regeneration" as used herein in relation to plant materials means growing a whole, differentiated plant from a plant cell, a group of plant cells, a plant part such as, for example, from an embryo, scutellum, protoplast, callus, or other tissue, but not including growth of a plant from a seed.

The particular choice of a transformation technology will be determined by its efficiency to transform certain plant species as well as the experience and preference of the person practicing the invention with a particular methodology of choice. It will be apparent to the skilled person that the particular choice of a transformation system to introduce a nucleic acid construct into plant cells is not essential to or a limitation of the invention, provided it achieves an acceptable level of nucleic acid transfer. Guidance in the practical implementation of transformation systems for plant improvement is provided by Birch, *Ann Rev Plant Physiol Plant Mol Biol.* 48: 297-326, 1997.

In principle, both dicotyledonous and monocotyledonous plants that are amenable to transformation can be modified by introducing a nucleic acid construct according to the invention into a recipient cell and growing a new plant that harbors and expresses a polynucleotide according to the invention.

Introduction and expression of foreign or exogenous polynucleotides in dicotyledonous plants such as cotton, tobacco, potato and legumes or monocotyledonous plants such as cereals, including wheat, barley, rice, corn, oats, rye and sorghum has been shown to be possible using the T-DNA of the tumor-inducing (Ti) plasmid of *Agrobacterium tumefaciens* (See, for example, Umbeck, U.S. Pat. No. 5,004,863, and International application PCT/US93/02480). A construct of the invention may be introduced into a plant cell utilizing *A. tumefaciens* containing the Ti plasmid. In using an *A. tumefaciens* culture as a transformation vehicle, it is most advantageous to use a non-oncogenic strain of the *Agrobacterium* as the vector carrier so that normal non-oncogenic differentiation of the transformed tissues is possible. It is preferred that the *Agrobacterium* harbors a binary Ti plasmid system. Such a binary system comprises (1) a first Ti plasmid having a virulence region essential for the introduction of transfer DNA (T-DNA) into plants, and (2) a chimeric plasmid. The chimeric plasmid contains at least one border region of the T-DNA region of a wild-type Ti plasmid flanking the nucleic acid to be transferred. Binary Ti plasmid systems have been shown effective to transform plant cells as, for example, described by De Framond, *Biotechnology*, 1: 262, 1983 and Hoekema et al., *Nature*, 303: 179, 1983. Such a binary system is preferred inter alia because it does not require integration into the Ti plasmid in *Agrobacterium*.

Methods involving the use of *Agrobacterium* include, but are not limited to transformation of plant cells or tissues with *Agrobacterium* such as transformation of seeds, apices or meristems with *Agrobacterium*, or inoculation in planta such as the floral-dip method as described by Bechtold et al., *C.R. Acad. Sci. Paris*, 316: 1194, 1993. This approach is based on the infiltration of a suspension of *Agrobacterium* cells. Alternatively, the chimeric construct may be introduced using root-inducing (Ri) plasmids of *Agrobacterium* as vectors.

Methods for transformation of cotton plants by introduction of an exogenous nucleic acid and for regeneration of plants from cells by somatic embryogenesis are well known in the art, Other methods for introducing the nucleic acid construct into a plant cell are by electroporation, or high velocity ballistic penetration by small particles (also known as particle bombardment or microprojectile bombardment) with the nucleic acid to be introduced contained either within the matrix of small beads or particles, or on the surface thereof as, for example described by Klein et al., *Nature*, 327: 70, 1987.

As used herein, an "induced mutation" is an artificially induced genetic variation which may be the result of chemical, radiation or biologically-based mutagenesis, for example transposon or T-DNA insertion. Preferred mutations are null mutations such as nonsense mutations, frameshift mutations, insertional mutations or splice-site variants which completely inactivate the gene of interest. Nucleotide insertional derivatives include 5' and 3' terminal fusions as well as intra-sequence insertions of single or multiple nucleotides. Insertional nucleotide sequence variants are those in which one or more nucleotides are introduced into the nucleotide sequence, which may be obtained by random insertion with suitable screening of the resulting products. Deletional variants are characterised by the removal of one or more nucleotides from the sequence. Preferably, a mutant gene has only a single insertion or deletion of a sequence of nucleotides relative to the wild-type gene. Substitutional nucleotide variants are those in which at least one nucleotide in the sequence has been removed and a different nucleotide inserted in its place. The preferred number of nucleotides affected by substitutions in a mutant gene relative to the wild-type gene is a maximum of ten nucleotides, more preferably a maximum of 9, 8, 7, 6, 5, 4, 3, or 2, or only one nucleotide. Such a substitution may be "silent" in that the substitution does not change the amino acid defined by the codon. Alternatively, conservative substituents are designed to alter one amino acid for another similar acting amino acid.

The term "mutation" as used herein does not include silent nucleotide substitutions which do not affect the activity of the gene, and therefore includes only alterations in the gene sequence which affect the gene activity. The term "polymorphism" refers to any change in the nucleotide sequence including such silent nucleotide substitutions.

Mutagenesis can be achieved by chemical or radiation means, for example EMS or sodium azide (Zwar and Chandler, *Planta* 197: 39-48, 1995) treatment of seed, or gamma irradiation, well know in the art. Isolation of mutants may be achieved by screening mutagenised plants or seed. In a polyploid plant such as cotton, screening is preferably done in a genotype that is already lacks one of the enzyme activities, so that a mutant entirely lacking the functional activity is sought. Alternatively, the mutation may be identified using techniques such as "tilling" in a population mutagenised with an agent such as EMS (Slade and Knauf, *Transgenic Res.* 14: 109-115, 2005). Such mutations may then be introduced into desirable genetic backgrounds by crossing the mutant with a plant of the desired genetic background and performing a suitable number of backcrosses to cross out the originally undesired parent background. The invention clearly extends to methods of producing or identifying such plants or the seed produced by such plants.

The process of producing plants of the invention may include mutagenesis and/or screening steps such as TILLING (Targeting Induced Local Lesions IN Genomes). In a first step, introduced mutations such as novel single base pair changes are induced in a population of plants by treating cells, seeds, pollen or other plant parts with a chemical mutagen or radiation, and then advancing plants to a generation where mutations will be stably inherited. DNA is extracted, and seeds are stored from all members of the population to create a resource that can be accessed repeatedly over time. For a TILLING assay, PCR primers are designed to specifically amplify a single gene target of interest. Specificity is especially important if a target is a member of a gene family or part of a polyploid genome. Next, dye-labeled primers can be used to amplify PCR products from pooled DNA of multiple individuals. These PCR products are denatured and reannealed to allow the formation of mismatched base pairs. Mismatches, or heteroduplexes, represent both naturally occurring single nucleotide polymorphisms (SNPs) (i.e., several plants from the population are likely to carry the same polymorphism) and induced SNPs (i.e., only rare individual plants are likely to display the mutation). After heteroduplex formation, the use of an endonuclease, such as CelI, that recognizes and cleaves mismatched DNA is the key to discovering novel SNPs within a TILLING population.

Using this approach, many thousands of plants can be screened to identify any individual with a single base change as well as small insertions or deletions (1-30 bp) in any gene or specific region of the genome. Genomic fragments being assayed can range in size anywhere from 0.3 to 1.6 kb. At 8-fold pooling, 1.4 kb fragments (discounting the ends of fragments where SNP detection is problematic due to noise) and 96 lanes per assay, this combination allows up to a million base pairs of genomic DNA to be screened per single assay, making TILLING a high-throughput technique TILLING is further described in Slade and Knauf, 2005 (supra), and Henikoff et al., *Plant Physiol.* 135: 630-636, 2004, herein incorporated by reference.

In addition to allowing efficient detection of mutations, high-throughput TILLING technology is ideal for the detection of natural polymorphisms. Therefore, interrogating an unknown homologous DNA by heteroduplexing to a known sequence reveals the number and position of polymorphic sites. Both nucleotide changes and small insertions and deletions are identified, including at least some repeat number polymorphisms. This has been called Ecotilling (Comai et al., *Plant J.* 37: 778-786, 2004).

As used herein, the term "genetically linked" refers to a marker locus and a second locus being sufficiently close on a chromosome that they will be inherited together in more than 50% of meioses, e.g., not randomly. This definition includes the situation where the marker locus and second locus form part of the same gene. Furthermore, this definition includes the situation where the marker locus comprises a polymorphism that is responsible for the trait of interest (in other words the marker locus is directly "linked" to the phenotype). Thus, the percent of recombination observed between the loci per generation (centimorgans (cM)), will be less than 50. In particular embodiments of the invention, genetically linked loci may be 45, 35, 25, 15, 10, 5, 4, 3, 2, or 1 or less cM apart on a chromosome. Preferably, the markers are less than 5 cM or 2 cM apart and most preferably about 0 cM apart.

As used herein, the "other genetic markers" may be any molecules which are linked to a desired trait of a cotton plant. Such markers are well known to those skilled in the art and include molecular markers linked to genes determining traits such disease resistance, yield, plant morphology, lint quality. Any molecular biological technique known in the art which is capable of detecting alleles of genes of interest can be used in the methods of the present invention. Such methods include, but are not limited to, the use of nucleic acid amplification, nucleic acid sequencing, nucleic acid hybridization with suitably labelled probes, single-strand conformational analysis (SSCA), denaturing gradient gel electrophoresis (DGGE), heteroduplex analysis (HET), chemical cleavage analysis (CCM), catalytic nucleic acid cleavage or a combination thereof. The invention also includes the use of molecular marker techniques to detect polymorphisms linked to alleles of. Such methods include the detection or analysis of restriction fragment length polymorphisms (RFLP), RAPD, amplified fragment length polymorphisms (AFLP) and microsatellite (simple sequence repeat, SSR) polymorphisms. The closely linked markers can be obtained readily by methods well known in the art, such as Bulked Segregant Analysis.

The "polymerase chain reaction" ("PCR") is a reaction in which replicate copies are made of a target polynucleotide using a "pair of primers" or "set of primers" consisting of "upstream" and a "downstream" primer, and a catalyst of polymerization, such as a DNA polymerase, and typically a thermally-stable polymerase enzyme. Methods for PCR are known in the art, and are taught, for example, in "PCR" (McPherson and Moller (Ed), BIOS Scientific Publishers Ltd, Oxford, 2000). PCR can be performed on cDNA obtained from reverse transcribing mRNA isolated from plant cells expressing an SSII gene or on genomic DNA isolated from a plant. A primer in this context is an oligonucleotide sequence that is capable of hybridising in a sequence specific fashion to the target sequence and being extended during the PCR. Amplicons or PCR products or PCR fragments or amplification products are extension products that comprise the primer and the newly synthesized copies of the target sequences. Primers may be perfectly matched to the target sequence or they may contain internal mismatched bases that can result in the introduction of restriction enzyme or catalytic nucleic acid recognition/cleavage sites in specific target sequences. Primers may also contain additional sequences and/or contain modified or labelled nucleotides to facilitate capture or detection of amplicons. Repeated cycles of heat denaturation of the DNA, annealing of primers to their complementary sequences and extension of the annealed primers with polymerase result in exponential amplification of the target sequence. The terms target or target sequence or template refer to nucleic acid sequences which are amplified.

Methods for direct sequencing of nucleotide sequences are well known to those skilled in the art and can be found for example in Ausubel et al. (supra) and Sambrook et al., 1989 (supra). Sequencing can be carried out by any suitable method, for example, dideoxy sequencing, chemical sequencing or variations thereof. Direct sequencing has the advantage of determining variation in any base pair of a particular sequence.

Plants

The term "plant" as used herein as a noun refers to whole plants and refers to any member of the Kingdom Plantae, but as used as an adjective refers to any substance which is present in, obtained from, derived from, or related to a plant, such as for example, plant organs (e.g. leaves, stems, roots, flowers), single cells (e.g. pollen), seeds, plant cells and the like. Plantlets and germinated seeds from which roots and shoots have emerged are also included within the meaning of "plant". The term "plant parts" as used herein refers to one or more plant tissues or organs which are obtained from a plant and which comprises genomic DNA of the plant. Plant parts include vegetative structures (for example, leaves, stems), roots, floral organs/structures, seed (including embryo, cotyledons, and seed coat), plant tissue (for example, vascular tissue, ground tissue, and the like), cells and progeny of the same. The term "plant cell" as used herein refers to a cell obtained from a plant or in a plant and includes protoplasts or other cells derived from plants, gamete-producing cells, and cells which regenerate into whole plants. Plant cells may be cells in culture. By "plant tissue" is meant differentiated tissue in a plant or obtained from a plant ("explant") or undifferentiated tissue derived from immature or mature embryos, seeds, roots, shoots, fruits, tubers, pollen, tumor tissue, such as crown galls, and various forms of aggregations of plant cells in culture, such as calli. Exemplary plant tissues in or from seeds are cotyledon, embryo and embryo axis. The invention accordingly includes plants and plant parts and products comprising these, particularly seed comprising modified oil composition.

As used herein, the term "seed" refers to "mature seed" of a plant, which is either ready for harvesting or has been harvested from the plant, such as is typically harvested commercially in the field, or as "developing seed" which occurs in a plant after fertilisation and prior to seed dormancy being established and before harvest.

A "transgenic plant" as used herein refers to a plant that contains a gene construct not found in a wild-type plant of the same species, variety or cultivar. That is, transgenic plants (transformed plants) contain genetic material (a transgene) that they did not contain prior to the transformation. The transgene may include genetic sequences obtained from or derived from a plant cell, or another plant cell, or a non-plant source, or a synthetic sequence. Typically, the transgene has been introduced into the plant by human manipulation such as, for example, by transformation but any method can be used as one of skill in the art recognizes. The genetic material is preferably stably integrated into the genome of the plant. The introduced genetic material may comprise sequences that naturally occur in the same species but in a rearranged order or in a different arrangement of elements, for example an antisense sequence. Plants containing such sequences are included herein in "transgenic plants". A "non-transgenic plant" is one which has not been genetically modified by the introduction of genetic material by recombinant DNA techniques. In a preferred embodiment, the transgenic plants are homozygous for each and every gene that has been introduced (transgene) so that their progeny do not segregate for the desired phenotype.

As used herein, the term "corresponding non-transgenic plant" refers to a plant which is isogenic relative to the transgenic plant but without the transgene of interest. Preferably, the corresponding non-transgenic plant is of the same cultivar or variety as the progenitor of the transgenic plant of interest, or a sibling plant line which lacks the construct, often termed a "segregant", or a plant of the same cultivar or variety transformed with an "empty vector" construct, and may be a non-transgenic plant. "Wild type", as used herein, refers to a cell, tissue or plant that has not been modified according to the invention. Wild-type cells, tissue or plants may be used as controls to compare levels of expression of an exogenous nucleic acid or the extent and nature of trait modification with cells, tissue or plants modified as described herein. A typical wild-type plant with respect to cotton is of the variety "Coker".

Transgenic plants, as defined in the context of the present invention include progeny of the plants which have been genetically modified using recombinant techniques, wherein the progeny comprise the transgene of interest. Such progeny may be obtained by self-fertilisation of the primary transgenic plant or by crossing such plants with another plant of the same species. This would generally be to modulate the production of at least one protein/enzyme defined herein in the desired plant or plant organ. Transgenic plant parts include all parts and cells of said plants comprising the transgene such as, for example, cultured tissues, callus and protoplasts.

Any of several methods may be employed to determine the presence of a transgene in a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers to amplify a specific DNA, the presence of which will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed may also be identified i.e. distinguished from non-transformed or wild-type plants by their phenotype, for example conferred by the presence of a selectable marker gene, or conferred by the phenotype of modified oil composition of seed of the plant, or related phenotype such as altered enzyme activity.

As used herein, "germination" refers to the emergence of the root tip from the seed coat after imbibition. "Germination rate" refers to the percentage of seeds in a population which have germinated over a period of time, for example 14 or 21 days, after imbibition. A population of seeds can be assessed daily over several days to determine the germination percentage over time. With regard to seeds of the present invention, as used herein the term "germination rate which is substantially the same" means that the germination rate of the transgenic seeds is at least 80% that of isogenic wild-type seeds.

Plants provided by or contemplated for use in the practice of the present invention include angiosperms, including both monocotyledons and dicotyledons. In preferred embodiments, the plants of the present invention are crop plants (for example, cereals and pulses, maize, wheat, potatoes, tapioca, rice, sorghum, millet, cassava, barley, or pea), or other legumes. The plants may be grown for production of edible roots, tubers, leaves, stems, flowers or fruit. Preferably, the plant is a cotton plant. Examples of cereal plants include, but are not limited to, wheat, barley, rice, maize (corn), sorghum, oats, and rye. In an embodiment, the cotton plant is a progeny plant of the line DCS9 (Example 7) and contains the same transgene located in the same position in the genome.

Reference to a "cotton plant" refers to any plant belonging to the genus *Gossypium* and to any wild relatives, progenitor species, germplasm, cultivar or variety thereof. For example, cotton plants include species such as: *G. anapoides, G. anomalum, G. arboreum, G. areysianum, G. aridum, G. armourianum, G. australe, G. barbadense, G. barbosanum, G. benadirense, G. bickii, G. briccetti, G. capitis-viridis, G. costulatum, G. cunningharnii, G. darwinii, G. davidsonii, G. enthyle, G. exiguum, G. gossypioides, G. harknessii, G. herbaceum, G. hirsutum, G. incanum, G. klotzschianum, G. laxum, G. lobatum, G. londonderriense, G. longicalyx, G. marchantii, G. mustelinum, G. nandewarense, G. nelsonii, G. nobile, G. pilosum, G. populifoliurn, G. pulchellum, G. raimondii, G. robinsonii, G. rotundifoliurn, G. schwendimantii, G. somalense, G. soudanense, G. stocksii, G. sturtianum, G. thurberi, G. timorense, G. tomentosum, G. trilobum, G. triphyllum,* and *G. vindis*. Particular species are *Gossypium hirsutum* (gh) and *Gossypium barbadense* (gb). As will be appreciated by those of skill in the art, one convenient variety, cultivar or mutant maybe genetically modified and the phenotype bred into related varieties or species by standard breeding techniques. Reference to "progenitor" refers to any of the species, varieties, cultivars, or germplasm, from which a plant is derived. As will be known to those skilled in the art, most commercially useful cotton is a naturally-occurring allotetraploid derived by sexual hybridisation between ancient diploid progenitor parents. Based upon the teaching provided herein, those skilled in the art can readily perform the inventive method on one or more diploid or allotetraploid cottons and produce sexual hybrids between the transgenic plants produced therefrom.

As used herein, the term "derivative species, germplasm or variety" shall be taken to mean any plant species, germplasm or variety that is produced using a stated cotton species, variety, cultivar, or germplasm, using standard procedures of sexual hybridisation, recombinant DNA technology, tissue culture, mutagenesis, or a combination of any one or more said procedures. In particular, interspecific hybrids have been produced between various important cotton species such as *G. barbadense,* and *G. hirsutum,* and between certain diploid species, and the production of such interspecific hybrids is routine to those skilled in the art.

As used herein, the term "cotton" refers to any species of the Genus *Gossypium*, preferably of the species *Gossypium hirsutum* or *Gossypium barbadense*. In some embodiments, a suitable control or reference plant is a non-transformed substantially isogenic cotton plant treated in the same way as the "test" plant. Cottonseed oil may be distinguished by the presence therein of CPE and/or CPA fatty acids.

Food Production

In another aspect, the invention provides cotton plants and cottonseed, and products obtained therefrom comprising oil from the seed, particularly cottonseed oil, that is useful for food or feed production, the seed having modified seedoil composition compared to corresponding wild-type seed. Preferably the plant from which the seed is obtained has a reduced level of ghFAD2-1, ghFatB-2 and ghCPA-FAS-2 activities in the seed during development. The cottonseed oil of the present invention is useful for food production and in particular for commercial food production. Such food production might include mixing the cottonseed oil as one ingredient with other ingredients in commercial food production. In preferred embodiments which is desirable for use in food production, the cottonseed oil has a modified composition as specified herein.

Oil is readily isolated from cleaned, de-linted and hulled seeds of the invention using standard methods, for example cooking at high temperatures, pressing, milling using screw press (high pressure) and/or procedures for extraction of oil using solvents, steam and/or high pressure. The oil content of cottonseed, or the content of any fatty acid in the oil of cottonseed is conveniently determined as described herein or as well understood in the art. Alternatively or in addition the procedures of Folch et al., *J. Biol. Chem.* 226: 497, 1957 or variations thereof as described elsewhere (see for example Liu et al., 2002 (supra)) may be employed. The fatty acid content and/or composition of cotton seed oil may be conveniently determined using gas liquid chromatography against known standard fatty acids, by comparing the fatty acid methyl ester peaks and retention times of reference standards with the sample being tested, and by standard integration of the peaks obtained. However, the present invention is not to be limited by the method of determining the content and/or composition of cottonseed oil, in particular the means for determining fatty acid or other lipid components. Oil is composed almost entirely of triacylglycerols (TAGs) that comprise three fatty acids esterified to a glycerol backbone. To assess the TAG content of oil, oil may be purified such as by solid phase extraction (SPE) on silica gel cartridges. The TAG composition may be qualitatively assessed by reverse phase high resolution liquid chromatography (HPLC) using a refractive index detector and propionitrile as mobile phase. From purified oil, fatty acid methyl esters (FAMEs) are prepared such as by methylation with cold solution of KOH in methanol and the esters analysed by capillary gas chromatography (GC) using high polar columns. From the fatty acid composition, the theoretical TAG composition may be calculated by a computer program employing a typical distribution of fatty acids in the triacylglycerol for cottonseed oil. Mathematical algorithms may be calculated from theoretical and experimental (HPLC) triacylglycerol compositions, and the resulting values compared with those contained in a data base comprising data sets determined by conducting the analysis on different standards of oils.

Food Products

The invention also encompasses foods, beverages or pharmaceutical preparations produced with products comprising the cottonseed oil. The plant of the invention or products derived therefrom containing oil or lint may be used in a variety of applications for human use or consumption. As used herein, "humans" refers to Homo sapiens. The cottonseed oil can be used readily in food processing procedures, in particular frying of food products. The oil may be incorporated into products such as margarine, shortening, salad dressing, mayonnaise, dairy products such as icecream, yogurt or cheese, or added as an ingredient to other foods or food materials, such as bread, cake, biscuits, pastries, breakfast cereals, pasta, noodles or sauces.

Other parts of the plants of the invention that are edible may be used as foods for human consumption or as feed for animal use. For example, leaves, stems, roots, tubers, fruit, pods or extracts or parts of these comprising cells of the invention from any of these may be used for human or animal consumption. Modified oil content and composition of the plants of the invention and parts thereof may provide advantages for use of these materials as animal feed such as, for example, as feed for pigs, cattle, horses, poultry such as chickens and other animals.

The food or beverage or pharmaceutical preparation may be packaged ready for sale or in bulk form. The invention also provides methods of preparing the food, beverage or pharmaceutical preparation of the invention, and recipes or instructions for preparing such foods or beverages. The methods may comprise the steps of crushing, extracting, milling, cooking, frying, canning, packaging or other processing steps known in the art. The methods or recipes or instructions may include the steps of processing the oil of the invention and/or admixing it with other food ingredients, such as heating or baking the mixture or the product to, for example, at least 100° C. The method may include the step of packaging the product so that it is ready for sale.

Methods

The products of the present invention can be formulated in pharmaceutic compositions which are prepared according to conventional pharmaceutical compounding techniques. See, for example, Remington's Pharmaceutical Sciences, 18$^{th}$ Ed. (1990, Mack Publishing, Company, Easton, Pa., U.S.A.). The composition may contain the active agent or pharmaceutically acceptable derivative active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration.

For oral administration, the compounds can be formulated into liquid preparations such as capsules. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders.

The active agent is preferably administered in a therapeutically effective amount. The actual amount administered and the rate and time-course of administration will depend on the nature and severity of the condition being treated. Prescription of treatment, e.g. decisions on dosage, timing, etc. is within the responsibility of general practitioners or specialists and typically takes account of the disorder to be treated, the condition of the individual patient, the site of delivery, the method of administration and other factors known to practitioners. Examples of techniques and protocols can be found in Remington's Pharmaceutical Sciences, (supra).

Industrial Use

The plant products, preferably oil, may be used in production of industrial products such as, for example, ethanol.

The present invention is further described by the following non-limiting Examples.

Example 1

Illustrative Methods and Materials

Isolation of RNA

Two grams of cotton embryos or leaf tissue frozen with liquid nitrogen were ground to a fine powder using a mortar and pestle and transferred to a beaker containing 22 mls cold extraction buffer and stirred constantly. The extraction buffer contained 200 mM Tris-HCl pH8.5, 1.5% Lithium dodecylsulfate, 300 mM LiCl, 10 mM $Na_2EDTA$, 1% sodium deoxycholate, 1% Nonidet P-40. This was followed by adding 5% insoluble PVP, 90 mM mercaptoethanol, 10 mM DTT (dithiothreitol), 0.1% DEPC and stirred for 10 min prior to being transferred to a Corex tube. Then 18.4 ml of 3M ammonium acetate was added and mixed well. It was centrifuged at 6,000× rpm for 20 min at 4° C. The supernatant was transferred to a new tube and precipitated by adding 1/10 volume of 3 M NaAc, pH5.2 and ½ final volume of cold isopropanol and stored at −20° C. for 1 hour prior to centrifugation at 6,000× rpm for 30 min using a swing rotor. The pellet was resuspended in 1 ml $dH_2O$ and transferred to two Eppendorf tubes (500 µl in each tube). The suspension was extracted with an equal volume of phenol/chloroform/isoamyl alcohol solution (25:24:1) and the phases were separated by centrifugation for 5 min at 4° C. The aqueous top layer was carefully transferred into a new Eppendorf tube and it was extracted again with chloroform as above. Half volume of 5M LiCl was added to the aqueous sample, mixed well and left on ice for 3 hours prior to centrifugation at 12,000× rpm for 15 min at 4° C. The pellet was resuspended in 50 µl $dH_2O$. Finally, the RNA sample was precipitated by adding 5 µl NaAc and 138 µl cold ethanol and incubated on dry ice for 30 minute prior to centrifugation for 15 min at 4° C. The RNA pellet was dried under vacuum and then dissolved in 30 µl RNase-free $H_2O$.

Construction of a Cottonseed cDNA Library

Cotton poly(A)$^+$ RNA was isolated from total RNA prepared as described above, using a mRNA purification kit (Pharmacia), essentially as described by the manufacturer. To prepare cDNA, a cDNA synthesis kit (Pharmacia) was used, essentially as described by the manufacturer, using 1-5 µg poly(A)$^+$ RNA as starting material. The double-stranded cDNA product was blunt-ended, and ligated to EcoRI/NotI adaptors, using standard procedures. Following the removal of excess unligated adaptors, the cDNA was cloned into the bacteriophage vector Lambda ZAPII (Stratagene, USA), and packaged using a commercially-available packaging system (Stratagene, USA), according to the manufacturer's instructions.

The cDNA libraries described herein generally contained about 92% recombinant bacteriophage particles, in a total of about 1.5×10$^7$ plaque forming units (pfu) per ml of unamplified library.

Following plaque-purification of positively hybridizing plaques, the ExAssist/SOLR system (Stratagene, USA) was used to excise the pBluescript SK(−) phagemid from the Lambda ZAPII vector, as described by the manufacturer.

All other methods such as gel electrophoresis, transfer of nucleic acids to membranes for hybridisation, preparation of labelled DNA probes, and screening of cDNA libraries were by standard methods (Ausubel et al., (supra)). Unless otherwise stated hybridization conditions were as described by Khandjian, *Bio/Technology*, 5: 165-167, 1987, herein incorporated by reference) using 50 mM Tris-HO pH7.5, 1M NaCl, 50% formamide, 10×Denhardt's solution, 10% dextran sulfate, 1% SDS, 0.1% sodium pyrophosphate, 0.1 mg/ml herring sperm DNA at 42° C. Membranes were then briefly washed in 2×SSC, 0.1% SDS at 65° C., followed by two further washes in 0.2×SSC, 0.1% SDS at 65° C. for 15 min each (high stringency).

Example 2

Isolation of FAD2 Genes from Cotton

Four different FAD2 genes have been isolated from cotton, each encoding possible microsomal oleoyl-Δ12 desaturases which could desaturate oleic acid to linoleic acid (Liu et al., 1999a (supra), Liu et al., 1999b (supra); Kargiotidou et al., *Journal of Experimental Botany* 2008 59(8): 2043-2056, 2008, both herein incorporated by reference). A first gene, designated ghFAD2-1, was specifically expressed in developing seeds at about the same time as active oil biosynthesis (Liu et al., 1999a (supra)). Two nucleotide sequences for ghFAD2-1 are presented herein (SEQ ID Nos: 1 and 24) which are 96% identical along their full lengths and therefore probably represent cDNAs corresponding to either different alleles or more likely the homoeologous FAD2-1 genes in the tetraploid cotton. A second gene, ghFAD2-2, (Accession No. Y10112) had a low level constitutive expression and was expressed at a low level throughout seed development (Pirtle et al., 2001 (supra)). The nucleotide sequence of ghFAD2-2 (SEQ ID NO: 26) is about 72% identical to the central half of ghFAD2-1 (SEQ ID NO: 1). The third and fourth members ghFAD2-3 (Accession No. AF331163) and ghFAD2-4 (Accession No. AY279314) appeared to be expressed more highly in leaves and other cotton tissues rather than seeds (Kargiotidou et al., 2008 (supra)). ghFAD2-3 and ghFAD2-4 have nucleotide sequences which are about 72% identical to ghFAD2-1 (SEQ ID NO: 1).

Based on these observations and the previous production of high-oleic cottonseed oil by RNAi down-regulation of ghFAD2-1 (Liu et al., *Plant Physiol.* 129: 1732-1743, 2002; U.S. Pat. No. 6,974,898), this gene was thought to encode the major FAD2 activity in cotton seeds. Therefore, a region of the ghFAD2-1 gene having the sequence of nucleotides 5-354 of SEQ ID NO: 1) was selected to make an RNAi construct for down-regulation of the gene. This was the same region as described by Liu et al., 2002 (supra) and was expected to be specific for ghFAD2-1. Other regions of the gene could equally have been selected. For example, U.S. Pat. No. 6,974,898 used a 92 bp region from the 5'-UTR of ghFAD2-1, and Liu et al., 2002 (supra)), used a 540 bp region from the 5' end of the transcribed part of the gene. The nucleotide and amino acid sequence of FAD-2-1 is shown in FIG. 3.

Example 3

Isolation of FATB Genes from Cotton

Two cDNA clones encoding proteins with homology to FatB in cotton were identified and isolated from a developing cottonseed cDNA library (Example 1) as follows. A PCR fragment corresponding to approximately 480 bp of the first exon of the ghFatB-1 gene (Yoder et al., 1999 (supra); accession number: AF076535) corresponding in sequence to nucleotides 210 to 713 of SEQ ID NO: 3 was amplified using forward (sense) and reverse (antisense) primers: 5'-atggttgctactgctgtgac-3' (SEQ ID NO: 29 and 5'-ctgtaaatgattcattagtgt-3' (SEQ ID NO: 30) and template RNA obtained from developing cotton embryos (Example 1). The PCR fragment was used to probe the cDNA library under high stringency and two different FatB-like cDNAs were isolated. These were designated ghFatB-2 and ghFatB-3. Both sequences appeared to be full length cDNAs as they had untranslated regions at both 5' and 3' ends. The ghFatB-2 cDNA was 1647 bp long (SEQ ID NO: 5) and encoded a predicted protein of 421 amino acids (SEQ ID NO: 6), which included the signal sequence used for translocation of the protein into the plastid. The ghFatB-3 cDNA was 1498 bp long (SEQ ID NO: 7) and encoded a predicted protein of 419 amino acids (SEQ ID NO: 8).

The predicted amino acid sequences of ghFatB-2, and -3 each had 60-75% identity along their full length with several reported FatB thioesterases, such as those from *Arabidopsis* and soybean (Accession No. DQ418764) and *Brassica juncea* (DQ856315), whereas only 30-40% homology with FatA thioesterase from dicot plants, such as *Arabidopsis* (AK176105). The putative polypeptides encoded by the coding region of ghFatB-2 and -3 showed 89% identity to each other. Because their 3'UTR sequences were quite different, it was thought that they were derived from two different genes belonging to a FatB gene family in cotton. A cDNA encoding FatB and its corresponding structural gene were isolated by Pirtle et al., *Plant Cell Physiology*, 40: 155-163, 1999, herein incorporated by reference (cDNA: Accession No. AF034266; structural gene: AF076535). Compared to the previously isolated ghFatB-1 (Yoder et al., 1999 (supra); accession number: AF076535), ghFatB-2 has about 87% identity and ghFatB-3 has about 84% identity. As do all the acyl-ACP thioesterases characterised to date, the cotton FatB thioesterases have transit peptide sequences in the N-terminus to direct the proteins into plastids. The exact transit peptide cleavage site is not known, but has been suggested to be somewhere at the beginning of a highly conserved hydrophobic region unique to the plant FatB sequences (Jones et al., 1995 (supra)). FIGS. 4 and 5 show the nucleotide sequences and putative polypeptides of ghFatB-2 and -3, respectively.

It has previously been suggested that plant FatB genes are constitutively expressed (Dormann et al., *Arch. Biochem. Biophys.* 316: 612-618, 1995). Consistent with this, expression analysis showed that the ghFatB-1 gene was expressed in embryos, seedlings and leaves of mature cotton plants (Pirtle et al., 1999 (supra)). Both ghFatB-2 and -3 were thought to be expressed in developing seeds as they were isolated from the cottonseed cDNA library as described above, and possibly other tissues. The expression level of ghFatB-2 in seeds was higher than ghFatB-3, and therefore the former was suggested to encode the major FatB activity in cotton seed. However, to establish that this gene rather than the other two encoded the major FatB activity in cottonseed, it was necessary to show that its inactivation would result in reduced thioesterase activity and reduced release of palmitic acid from the plastid. It was also possible that two or three of the genes in combination would need to be silenced to reduce palmitic acid levels. Therefore, a gene silencing construct was made using a region from ghFatB-2, having the sequence of nucleotides 458-843 of SEQ ID NO: 5.

Example 4

Cloning of Genes Encoding Cyclopropane Fatty Acid Synthase (CPA-FAS) in Cotton

CPA-FAS catalyses the first committed step in production of cyclopropane fatty acids, the conversion of oleic acid to DHS. Two EST sequences from *G. hirsutum* were identified as being differentially expressed after infection of cotton roots and hypocotyls with *Fusarium oxysporeum* (Dowd et al., 2004 (supra)). One of the EST sequences, CD486555, was used as a DNA probe to screen the cDNA library made from developing cottonseed (Example 1) and a second cDNA library made from RNA obtained from cotton roots. The DNA sequence of the probe DNA is shown in FIG. 6 (SEQ ID NO: 9).

After high stringency hybridization with the probe, two different full length cDNAs with unique 5 and 3' UTR sequences were isolated from the cDNA library made from cotton root RNA. A third cDNA clone was isolated from the cottonseed cDNA library. They were designated as ghCPA-FAS-1, 2 and -3 respectively. The DNA sequences and the predicted amino acid sequences of the encoded polypeptides are shown in FIGS. 7-9 (SEQ ID NO: 10-15).

The deduced ghCPA-FAS polypeptides each comprised 865-873 amino acids and had calculated molecular masses of approximately 99 kDa. This probably represented the mature protein since CPA-FAS enzyme, being active in the ER, was not expected to have a 5' signal peptide. Similarly to CPA-FAS from *Sterculia foetida* and the homologous proteins from *Arabidopsis* (Accession No. AT23510) and rice (AK069115) predicted from genomic sequences, the encoded ghCPA-FAS proteins had an N-terminal FAD-binding domain fused to a C-terminal domain which had homology to various methyltransferases. This was consistent with predicted CPA-FAS activity of the proteins. At the N-terminus, the first 20 amino acids of the ghCPA-FAS proteins appeared to be hydrophobic and were thought to be involved in membrane anchoring.

When the deduced amino acid sequences of the three different ghCPA-FAS cDNAs were compared with homolgous DNA sequences from *Sterculia foetida, Arabidopsis* and rice, it was observed that ghCPA-FAS-1 (AY574036) and ghCPA-FAS-2 (AY574037) shared 97% amino acid identity, but only 64-65% identity to ghCPA-FAS-3 (AY574038). In contrast, ghCPA-FAS-3 showed higher sequence homology with each of the *Arabidopsis* genes—74% amino acid identity with At23510, and 75% amino acid identity with At23530. This suggested that ghCPA-FAS-3 evolved separately before cotton speciation. *Arabidopsis* and rice are not known to accumulate CPA or CPE fatty acids and therefore the functionality of the CPA-FAS genes in these plants is determined.

Figure 10:
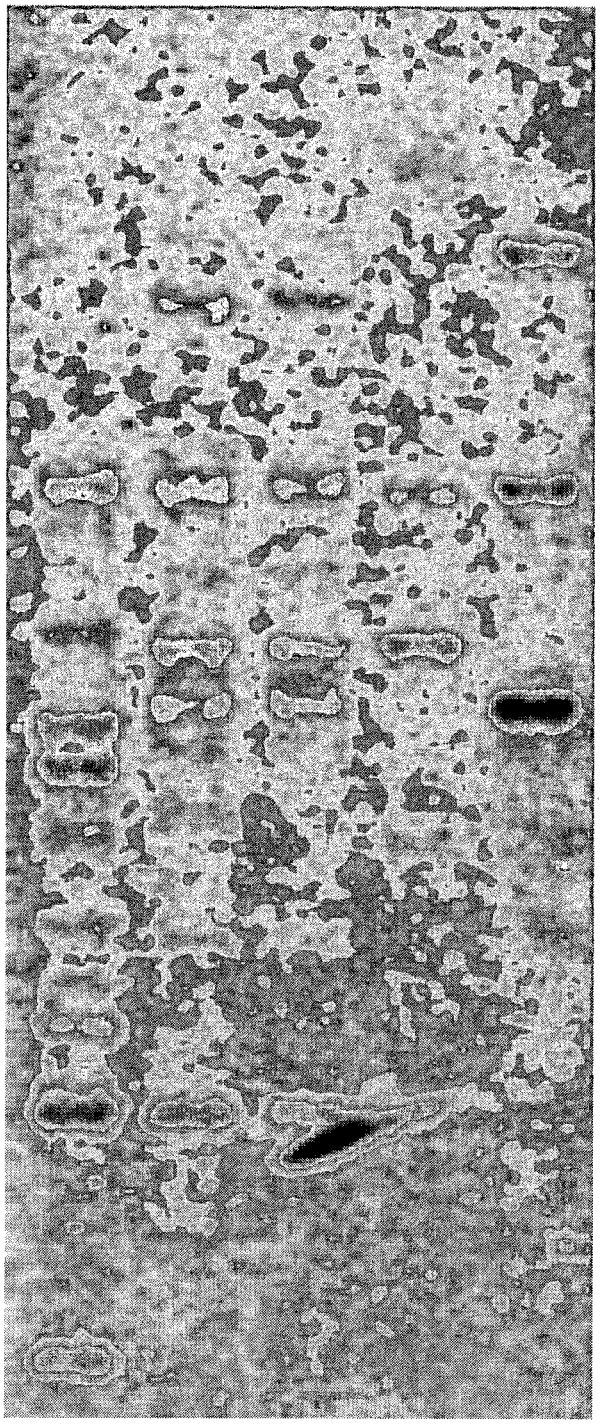
FIG. 10 is a representation of the Southern blot analysis of CPA-FAS genes in cotton. Total genomic DNAs from various diploid or tetraploid *Gossypium* species were digested with HindIII. Lane I, *G. barbadense* (A+D genomes); lane 2, *G. hirsutum* cv. Deltapine-16 (A+D genomes); lane 3, *G. hirsutum* cv Sicala-V4 (A+D genomes); lane 4, *G. herbaceum* (A genome); lane 5, *G. raimondii* (D geneome).

The genomic organization of CPA-FAS genes in cotton was investigated by Southern blot hybridization analysis using the protein coding region of ghCPA-FAS-1 as a probe. At least three hybridizing bands were detected in HindIII digested DNA from diploid cottons, while there were twice as many hybridizing bands in tetraploid cottons (FIG. 10). It was concluded that each of the three ghCPA-FAS genes were represented by a single locus in diploid *Gossypium* and two homoeologous loci in tetraploid cottons. This demonstrated that allotetraploid cotton contained two copies of each of the three genes present in the A- and D-genome diploid progenitors.

Figure 11:
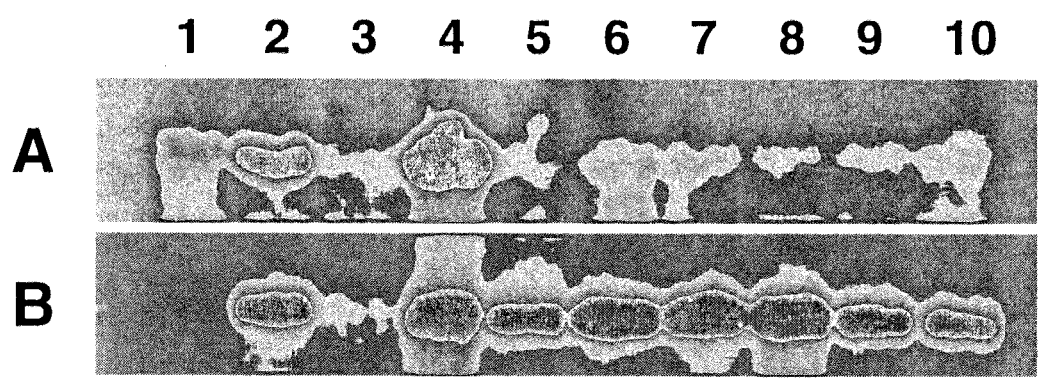
FIG. 11 is a representation of the RNA Northern blot analysis of expression of ghCPA-FAS-1 (A) ghCPA-FAS-2 (B) genes in cotton. RNA samples blotted onto the membrane were derived from: lane 1, cotyledon; 2, hypocotyl; 3, leaf; 4, root; 5-9, developing cotton embryos at 25, 30, 35, 40, 45 days after anthesis, respectively; 10, embryo axis.

Expression of the cotton CPA-FAS genes were analysed, looking for differentially expression in cotton tissues. As shown in FIG. 11, the analysis of total RNA extracted from various cotton tissues including roots, hypocotyls, leaves and developing embryos at various times after anthesis revealed that the ghCPA-FAS-1 transcript level was high in roots and hypocotyls, but not detected in leaves and developing embryos, while ghCPA-FAS-2 expression was detected in all tissues examined except the leaves. In the developing embryos, maximal transcript levels of ghCPA-FAS-2 were found in embryos during the middle part of seed development, from approximately 20-40 days after anthesis. This was the main time period for oil production in developing cotton embryos. It was therefore predicted that ghCPA-FAS-2 played a key role in determining the biosynthesis of cyclopropenoid fatty acids in cottonseed and therefore was a candidate target gene for down-regulation to reduce CPA and CPE fatty acids in cottonseed oil.

Example 5

Genetic Construct to Simultaneously Down-Regulate GHFAD2-1, GHCPA-FAS-2 and GHFATB-2 in Cottonseed A genetic construct to express a chimeric hairpin RNA molecule for RNAi mediated reduction of gene expression was made as follows. The RNAi gene silencing construct was designed to simultaneously target three different genes with the goal of achieving significant reductions in palmitic acid and cyclopropane fatty acids in combination with significantly increased oleic acid in cottonseed oil. The construct is shown schematically in FIG. 12 and contained an inverted repeat of a chimeric sequence made from 350 bp of ghFAD2-1, 442 bp of ghCPA-FAS-2 and 358 bp of ghFatB-1 fused together. The inverted repeat units of this chimeric sequence were separated by Intron 1 from the ghFad2-1 gene, which was 1120 bp long, with intact 5' and 3' exon/intron boundaries (FIG. 13, fragment C). The intron acted as a spacer to stabilize the inverted repeat and thereby facilitate the cloning of the inverted repeat in the plasmid vector in *E. coli*. To achieve seed specific expression, the inverted repeat sequence was placed under the control of a soybean lectin promoter (Lec-P) and a transcription terminator/polyadenylation sequence (Lec-T) (Cho et al., *Plant Molecular Biology Reporter* 13: 255-269, 1995). The hairpin RNA-expressing gene was positioned adjacent to the 3' end of a selectable marker gene comprised of an NPTII protein coding region driven by the sub-clover stunt virus promoter (Sc1-P) and terminator (Sc3-T). The specific sequences used are shown in FIG. 13 (SEQ ID NOs: 16-23). This genetic construct was named the MonoCott construct.

A second genetic construct, designated LY-2, was also made. This was the same as the MonoCott construct except that the 442 bp segments of the ghCPA-FAS-2 gene were replaced with a region of a cotton gene encoding cadinene hydroxylase, an enzyme required for synthesis of gossypol in developing seeds. To make LY-2, a 401 bp DNA fragment derived from the gene ghCAD-H encoding (+)-delta-cadinene-8-hydroxylase (accession number: AF332974), corresponding to nucleotides having the sequence 1420 to 1821 of SEQ ID NO: 28 were amplified in PCR reactions using the primers: S1: 5'-cctgagaggttcttgactgatcatg-3' (SEQ ID NO: 31) and A1: 5'-gcttatgatgtataataaacacattat-3' (SEQ ID NO: 32). This fragment was substituted for the ghCPA-FAS-2 portions in the MonoCott construct to make LY-2.

Example 6

Transformation of Cotton with the Monocott Construct

The MonoCott and LY-2 genetic constructs were each inserted into a binary vector and introduced into *Agrobacte-*

*rium tumefaciens* strain AGL1. The transformed bacteria were used to transform cotton variety Coker315 as described by Liu et al., 2002 (supra). Briefly, cotyledons excised from 10-days old aseptically-grown cotton seedlings were used as explants and were infected and co-cultivated with the *A. tumefaciens* transformants for a period of two days. This was followed by a six-week period of selection on MS medium (Murashige and Skoog, *Physiologia Plantarum*. 15: 473-497, 1962) containing 0.1 mg/l 2,4-D, 0.1 mg/l kinetin. 50 mg/l kanamycin sulphate, and 25 mg/l cefotaxime. Healthy calli derived from the cotyledon explants were then transferred to MS medium containing 5 mg/l 6-(γ,γ-dimethylallylamino)-purine (2ip), 0.1 mg/l naphthalene acetic acid (NAA), 25 mg/l kanamycin, and 250 mg/l cefotaxime for a second period of six weeks at 28° C. Somatic embryos started to form after about six to ten weeks of incubation and were transferred to fresh plates, but without added phytohormone or antibiotics, until they germinated. Plantlets that developed from the somatic embryos were subsequently transferred to soil and maintained in a glasshouse once leaves and roots were developed, with 28/20° C. (day/night) growth temperature.

Six independent cotton lines transformed with the Mono-Cott RNAi construct were regenerated from calli and allowed to grow to maturity in the greenhouse, flowering and producing seed as normal. No obvious phenotypic differences were observed between the transgenic plants and the non-transgenic (wild-type) parental plants of the variety Coker315. Ten independent cotton lines transformed with the LY-2 RNAi construct were also regenerated from calli and treated similarly.

Example 7

Phenotypic Analysis of Cotton Transformants

A portion consisting of about ⅛ of the cotyledons of the mature seeds was excised from the $T_2$ seeds obtained from the primary $T_1$ transgenic plants and each portion subjected to of fatty acid composition analysis by FAME and GC-MS. Total lipids were isolated using the method of Bligh et al., *Canadian Journal of Biochemistry and Physiology* 37: 911-917, 1959 and fatty acid methylesters (FAMEs) were prepared using standard methods as described by Liu et al., 2002 (supra). FAMEs were subsequently separated by gas chromatography (GC), using an Agilent 6890 GC fitted with a forte GC capillary column (30 m×0.25 mm). Fatty acids were identified by reference to FAME standards.

Seeds of transgenic line DCS9-34 had a fatty acid composition having a markedly increased level of oleic acid, in combination with reduced palmitic acid and reduced cyclopropane fatty acid levels. This transgenic line was selected and bred to homozygosity. Data showing the inheritance of fatty acid composition in seed oil of progeny is given in Table 1. As shown in Table 1, the oleic acid content in the seedoil of line DCS9-34 was increased to about 75%-80% and the palmitic acid content was reduced down to below 10%. In the high-oleic lines previously developed (Liu et al., 2002 (supra)), palmitic acid levels were reduced to 16% of the total fatty acids in the seedoil as a pleiotropic effect of RNAi-mediated down-regulation of ghFAD2-1 (Liu et al., 2002 (supra)). The further reduction of palmitic acid down to 7% obtained with the MonoCott construct was presumed to be due to the combined effect of down-regulation of both ghFAD2-1 and ghFatB-2. Similar phenotypes were seen in the other plants transformed with the MonoCott construct, but to a lesser extent.

Figure 14:
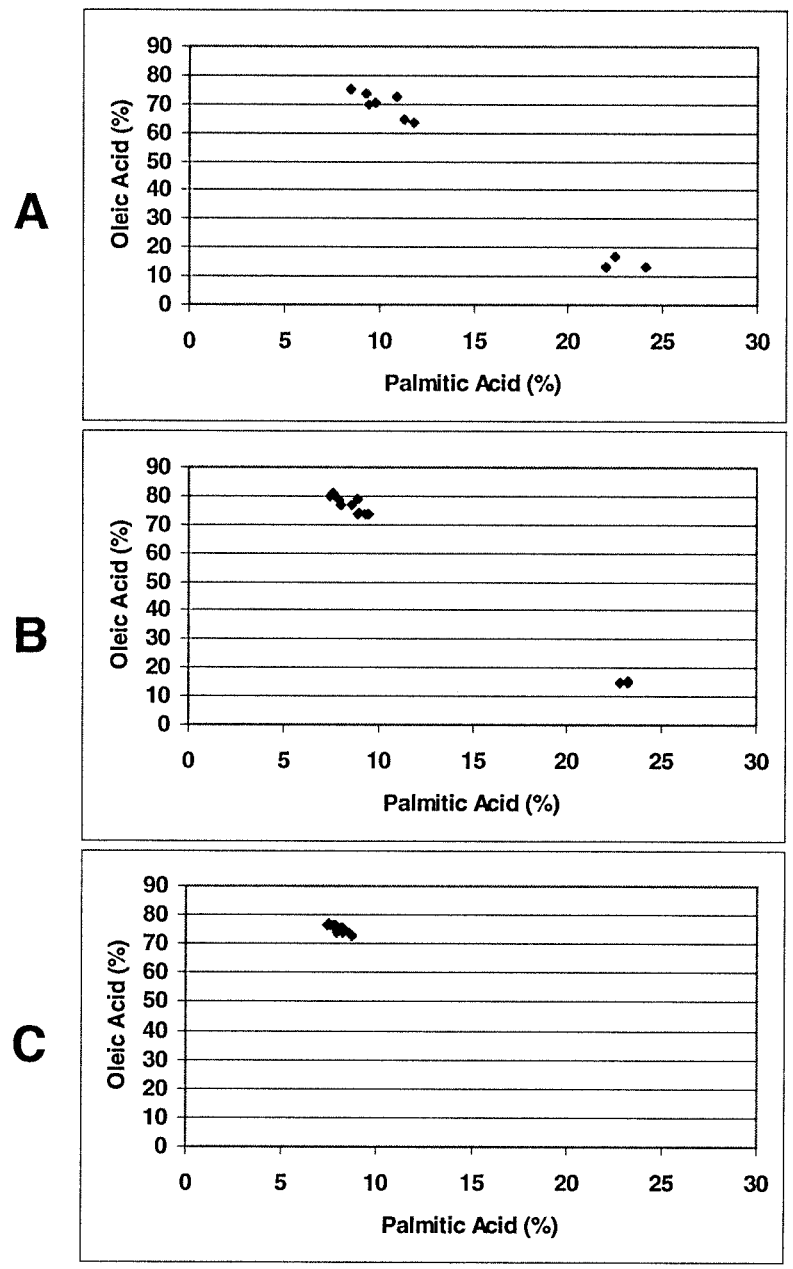
FIG. 14 is a graphical representation of the accumulation of palmitic and oleic acids in individual seeds of three generations of DCS9-34: $T_2$ seeds borne on the primary transgenic line (A); $T_3$ seeds borne on the selected $T_2$ plant (B) and $T_4$ seeds borne on a selected $T_3$ plant (C).

In the $T_2$ seeds obtained from the primary, transgenic DCS9-34 plants, three out of ten seeds were null segregants. Therefore it appeared that the transgene segregated as a single dominant gene with Mendelian inheritance pattern. In the subsequent $T_3$ seeds, three out of 15 seeds were nulls/segregants lacking the transgene. No null seeds were found in thirty $T_4$ seeds analysed; therefore these represented a homozygous population. Since only an approximately ⅛ portion of the cotyledons of the $T_2$ and $T_3$ seeds were used in the fatty acid analysis, cyclic fatty acids were not detected due to their predominant presence in seed radicals. As also shown in FIG. 14, the fatty acid composition across each of the three generations was characterized by increased oleic acid and reduced palmitic acid levels. These levels remained constant and were stably inherited in plants that were either heterozygous or homozygous for the transgene as shown in Table 2. This correlation clearly demonstrated that stable inheritance of the genetic alteration of fatty acid composition was achieved by transgenic expression of the MonoCott RNAi construct simultaneously targeting the three genes ghFAD2-1, ghCPA-FAS-2 and ghFatB-2.

In the LY-2 transgenic seed, oleic acid levels were also elevated, to above 80% and in some seed greater than 85%. The palmitic acid level in many seeds was about 7%, and the linoleic acid level about 6-10% (Table 2). These altered levels were stably inherited as a Mendelian locus together with the transgene (Table 2).

Figure 15:
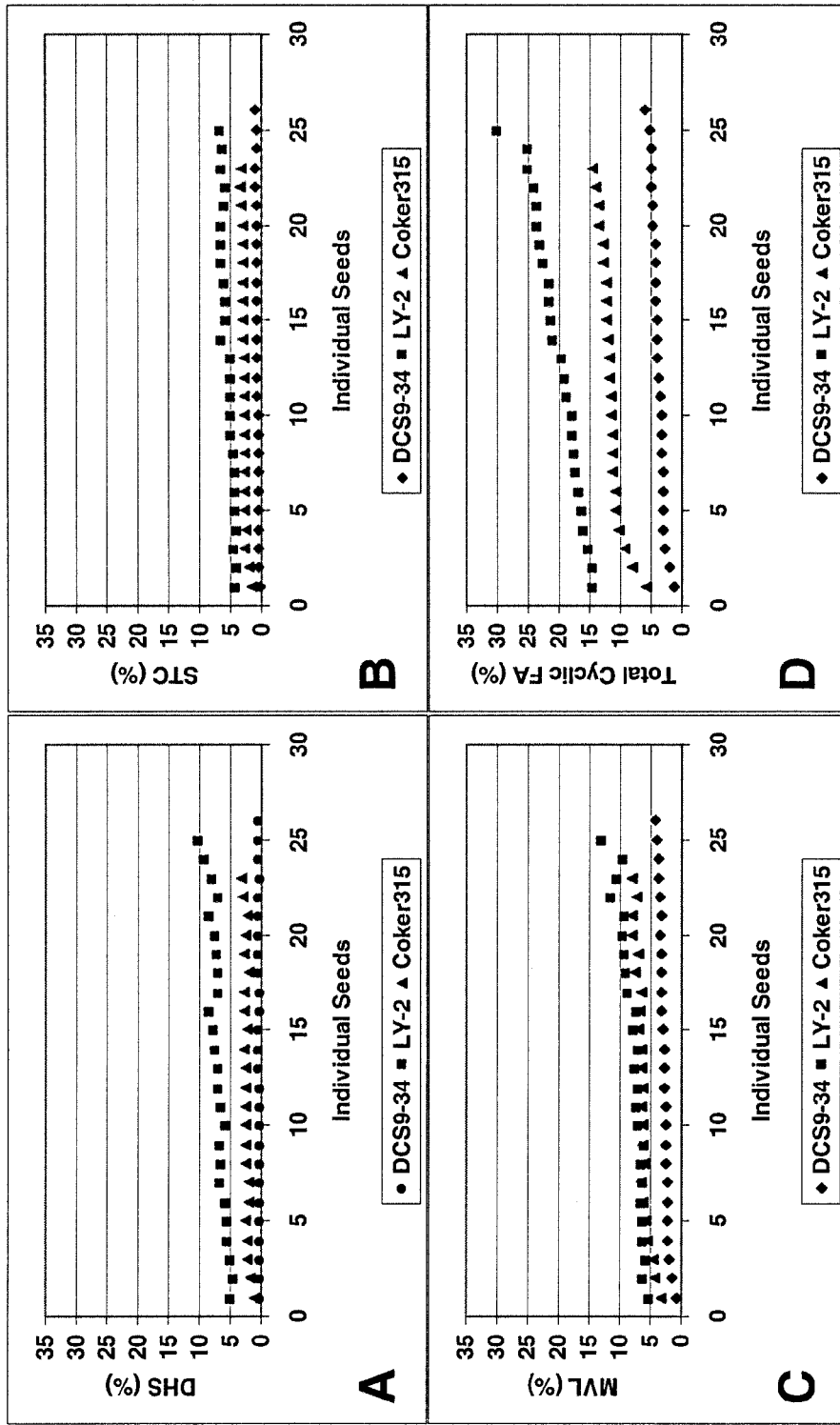
FIG. 15 is a graphical representation of the accumulation of total cyclic fatty acids in the excised embryo axes of individual cotton seeds. DCS9-34 is the MonoCott line with HO, LP and low-cyclic fatty acids traits; LY-2 is the line with HO and LP traits; and increased cyclic fatty acids; Coker315 is the conventional or control cotton.

The cyclopropane fatty acids, including DHS, STC and MVL are not present at significant levels in cotton cotyledons in mature cottonseed, but rather are concentrated in the embryo axes of the mature seeds. In order to analyse cyclopropane fatty acid levels in the transgenic lines, embryo axis were excised and subjected to fatty acid composition analysis. Full fatty acid profile of the DCS9-34 embryo axes, together with the untransformed control, Coker315 and a transgenic line transformed with the LY-2 construct is tabulated in Table 3 and graphed in FIG. 15. LY-2 transformed seed were also analysed. As shown above. LY-2 transformed seed showed similarly modified, low-palmitic and high-oleic levels as DCS9-34-transformed seed. As shown in Table 3, the non-transformed cotton embryo axes, as represented by the untransformed Coker315, contained total cyclopropane fatty acids at a level of 11.5% of total fatty acids (average of 23 randomly sampled seeds). In LY-2 seed, as a result of the substantial increase of oleic acid which is the substrate for CPA-FAS enzyme, each of the three cyclopropane fatty acids DHS, STC and MVL, as well as the total percentage of cyclopropane fatty acids, were increased substantially compared to the untransformed control. This was in sharp contrast to the MonoCott line, DCS9-34, which showed a substantial reduction in all three cyclopropane fatty acids with total cyclic fatty acid level averaging only 3.8% in 26 randomly selected seeds. This represented a reduction of total cyclopropane fatty acids more than 60% compared to wild-type and more than 80% compared to the LY-2 transgenic seed.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 1

Seedoil fatty acid composition in the cotton seed of transgenic line DCS9-34, in three generations. Seeds with greater than 20% palmitic acid content were null segregants, and were essentially the same as the wild-type level.

| Generation | Seed No. | % Palmitic (16:0) | % Stearic (18:0) | % Oleic (18:1) | % Linoleic (18:2) | Total % CPFAs |
|---|---|---|---|---|---|---|
| $T_2$ | 1 | 24.1 | 1.8 | 13.3 | 58.5 | ND |
|  | 2 | 22.0 | 1.8 | 13.4 | 60.4 | ND |
|  | 3 | 11.8 | 1.6 | 63.7 | 21.6 | ND |
|  | 4 | 9.3 | 1.6 | 73.4 | 14.6 | ND |
|  | 5 | 9.8 | 1.7 | 70.6 | 16.7 | ND |
|  | 6 | 22.5 | 1.8 | 17.0 | 56.6 | ND |
|  | 7 | 11.3 | 1.6 | 64.8 | 20.9 | ND |
|  | 8 | 9.5 | 1.8 | 70.0 | 17.6 | ND |
|  | 9 | 8.5 | 1.6 | 75.4 | 13.3 | ND |
|  | 10 | 10.9 | 1.6 | 72.3 | 14.1 | ND |
| $T_3$ | 1 | 8.6 | 2.2 | 76.6 | 12.0 | ND |
|  | 2 | 9.5 | 2.2 | 73.4 | 14.5 | ND |
|  | 3 | 8.9 | 2.6 | 73.6 | 14.5 | ND |
|  | 4 | 7.4 | 2.4 | 80.0 | 9.8 | ND |
|  | 5 | 22.8 | 2.4 | 15.0 | 58.8 | ND |
|  | 6 | 7.6 | 2.3 | 81.0 | 8.7 | ND |
|  | 7 | 9.3 | 2.4 | 73.4 | 14.4 | ND |
|  | 8 | 8.0 | 2.5 | 76.7 | 12.3 | ND |
|  | 9 | 8.9 | 2.6 | 78.7 | 9.2 | ND |
|  | 10 | 9.0 | 2.6 | 74.3 | 13.7 | ND |
|  | 11 | 7.9 | 2.9 | 78.6 | 10.2 | ND |
|  | 12 | 23.2 | 2.8 | 15.6 | 57.4 | ND |
|  | 13 | 9.0 | 2.6 | 74.2 | 13.7 | ND |
|  | 14 | 7.8 | 2.2 | 79.5 | 10.1 | ND |
|  | 15 | 23.2 | 2.7 | 14.9 | 58.4 | ND |
| $T_4$ | 1 | 8.3 | 2.3 | 74.2 | 12.6 | 0.2 |
|  | 2 | 8.2 | 2.5 | 75.6 | 11.2 | 0.4 |
|  | 3 | 8.1 | 2.5 | 74.9 | 11.9 | 0.2 |
|  | 4 | 8.7 | 2.3 | 72.9 | 13.6 | 0.2 |
|  | 5 | 8.0 | 2.5 | 75.3 | 11.6 | 0.3 |
|  | 6 | 8.2 | 2.3 | 75.2 | 11.8 | 0.2 |
|  | 7 | 7.8 | 2.6 | 76.3 | 10.7 | 0.3 |
|  | 8 | 7.6 | 2.4 | 76.6 | 11.0 | 0.2 |
|  | 9 | 8.2 | 2.7 | 75.1 | 11.4 | 0.3 |
|  | 10 | 8.3 | 2.5 | 74.4 | 12.4 | 0.2 |
|  | 11 | 8.0 | 2.5 | 75.6 | 11.5 | 0.2 |
|  | 12 | 8.2 | 2.4 | 75.5 | 11.2 | 0.2 |
|  | 13 | 7.4 | 2.5 | 76.5 | 11.3 | 0.2 |
|  | 14 | 7.8 | 2.4 | 76.3 | 11.3 | 0.0 |
|  | 15 | 7.8 | 2.6 | 75.2 | 12.1 | 0.3 |
|  | 16 | 8.3 | 2.2 | 74.5 | 12.4 | 0.3 |
|  | 17 | 8.2 | 2.3 | 74.6 | 12.3 | 0.3 |
|  | 18 | 8.3 | 2.3 | 74.1 | 12.8 | 0.2 |
|  | 19 | 8.5 | 2.3 | 73.9 | 12.6 | 0.3 |
|  | 20 | 7.8 | 2.6 | 75.5 | 11.7 | 0.2 |
|  | 21 | 7.7 | 2.5 | 76.3 | 11.1 | 0.2 |
|  | 22 | 8.3 | 2.6 | 74.4 | 12.2 | 0.3 |
|  | 23 | 7.9 | 2.6 | 73.8 | 13.2 | 0.2 |
|  | 24 | 7.5 | 2.5 | 76.7 | 11.0 | 0.1 |
|  | 25 | 8.0 | 2.5 | 75.5 | 11.5 | 0.2 |
|  | 26 | 8.2 | 2.3 | 74.7 | 12.0 | 0.3 |
|  | 27 | 7.9 | 2.4 | 75.6 | 11.6 | 0.2 |
|  | 28 | 7.9 | 2.6 | 74.9 | 12.0 | 0.3 |
|  | 29 | 8.1 | 2.4 | 75.3 | 11.8 | 0.2 |
|  | 30 | 8.2 | 2.4 | 73.8 | 12.9 | 0.4 |

ND: not determined

TABLE 2

Fatty acid composition of three generations of transgenic cotton expressing the LY-2 RNAi construct targeting three genes, namely ghFad2-1, ghCAD-H and ghFatB-2. LY2-1, LY2-8 and LY2-9 appear to show wild-type fatty acid composition and may be non-transformed "escapes".

| Sample | Myristic | Palmitic | Stearic | Oleic | Linoleic | Linolenic | Arachidic |
|---|---|---|---|---|---|---|---|
| T2 seeds |  |  |  |  |  |  |  |
| LY2-1 | 0.88 | 21.26 | 1.47 | 11.34 | 65.50 | 0.00 | 0.00 |
| LY2-2 | 0.13 | 8.22 | 0.87 | 78.27 | 12.37 | 0.21 | 0.00 |
| LY2-3 | 0.20 | 9.65 | 0.66 | 74.23 | 15.21 | 0.15 | 0.00 |
| LY2-4 | 0.00 | 9.42 | 1.46 | 76.76 | 12.20 | 0.16 | 0.00 |
| LY2-5 | 0.00 | 8.88 | 0.60 | 76.82 | 13.70 | 0.00 | 0.00 |
| LY2-6 | 0.16 | 8.10 | 1.52 | 80.67 | 9.36 | 0.18 | 0.00 |
| LY2-7 | 0.22 | 8.41 | 1.68 | 79.97 | 9.36 | 0.23 | 0.14 |
| LY2-8 | 0.85 | 21.37 | 1.73 | 12.22 | 63.58 | 0.24 | 0.00 |
| LY2-9 | 0.67 | 21.45 | 1.65 | 11.50 | 64.45 | 0.28 | 0.00 |
| LY2-10 | 0.21 | 8.02 | 1.46 | 80.51 | 9.67 | 0.13 | 0.00 |
| T3 seeds |  |  |  |  |  |  |  |
| LY2.2-1 | 0.35 | 6.97 | 2.07 | 83.35 | 6.94 | 0.13 | 0.19 |
| LY2.2-2 | 0.43 | 6.88 | 2.03 | 83.10 | 7.25 | 0.14 | 0.17 |
| LY2.2-3 | 0.34 | 7.16 | 1.71 | 83.37 | 7.15 | 0.12 | 0.16 |
| LY2.2-4 | 0.12 | 7.13 | 2.10 | 82.05 | 8.28 | 0.18 | 0.14 |
| LY2.2-5 | 0.14 | 7.13 | 1.91 | 83.54 | 7.00 | 0.12 | 0.17 |
| LY2.2-6 | 0.11 | 6.82 | 2.07 | 83.79 | 6.87 | 0.14 | 0.19 |
| LY2.2-7 | 0.12 | 6.85 | 1.69 | 85.53 | 7.48 | 0.13 | 0.20 |
| LY2.2-8 | 0.15 | 7.18 | 2.03 | 83.11 | 7.22 | 0.16 | 0.16 |
| LY2.2-9 | 0.12 | 6.69 | 1.93 | 84.04 | 6.87 | 0.13 | 0.23 |
| LY2.2-10 | 0.32 | 6.45 | 1.91 | 85.02 | 5.94 | 0.17 | 0.19 |
| LY2.2-11 | 0.24 | 7.85 | 1.74 | 83.46 | 6.39 | 0.11 | 0.18 |
| LY2.2-12 | 0.22 | 7.38 | 1.24 | 85.48 | 5.39 | 0.13 | 0.17 |
| LY2.2-13 | 0.35 | 8.57 | 1.27 | 83.34 | 6.15 | 0.20 | 0.12 |
| LY2.2-14 | 0.19 | 6.83 | 1.68 | 85.62 | 5.37 | 0.13 | 0.19 |
| LY2.2-15 | 0.23 | 7.47 | 1.94 | 83.22 | 6.79 | 0.14 | 0.21 |
| T4 seeds |  |  |  |  |  |  |  |
| LY2.2.1-1 | 0.20 | 8.96 | 1.93 | 77.80 | 10.41 | 0.17 | 0.29 |
| LY2.2.1-2 | 0.16 | 7.88 | 2.15 | 81.14 | 8.06 | 0.18 | 0.26 |
| LY2.2.1-3 | 0.17 | 8.08 | 2.00 | 81.33 | 7.87 | 0.16 | 0.26 |
| LY2.2.1-4 | 0.17 | 8.96 | 2.17 | 78.29 | 9.61 | 0.25 | 0.26 |
| LY2.2.1-5 | 0.16 | 8.34 | 2.39 | 79.31 | 8.94 | 0.21 | 0.30 |
| LY2.2.1-6 | 0.17 | 7.81 | 2.09 | 81.32 | 7.96 | 0.16 | 0.30 |
| LY2.2.1-7 | 0.15 | 7.77 | 2.01 | 81.42 | 8.00 | 0.17 | 0.27 |
| LY2.2.1-8 | 0.19 | 8.66 | 2.03 | 79.96 | 8.61 | 0.15 | 0.26 |
| LY2.2.1-9 | 0.18 | 8.31 | 2.08 | 80.60 | 8.21 | 0.17 | 0.27 |
| LY2.2.1-10 | 0.19 | 8.77 | 1.76 | 80.39 | 8.28 | 0.16 | 0.24 |
| LY2.2.1-11 | 0.16 | 8.26 | 2.03 | 80.52 | 8.41 | 0.18 | 0.25 |
| LY2.2.1-12 | 0.26 | 10.60 | 2.45 | 74.43 | 11.41 | 0.47 | 0.30 |
| LY2.2.1-13 | 0.17 | 8.02 | 2.14 | 81.09 | 8.01 | 0.18 | 0.25 |
| LY2.2.1-14 | 0.13 | 7.28 | 2.24 | 82.01 | 7.72 | 0.18 | 0.28 |
| LY2.2.1-15 | 0.17 | 8.16 | 1.83 | 81.27 | 8.03 | 0.15 | 0.26 |
| LY2.2.1-16 | 0.17 | 8.04 | 1.95 | 81.25 | 8.03 | 0.16 | 0.25 |
| LY2.2.1-17 | 0.15 | 7.19 | 1.83 | 83.02 | 7.31 | 0.14 | 0.25 |
| LY2.2.1-18 | 0.20 | 8.88 | 2.01 | 79.40 | 8.89 | 0.17 | 0.27 |
| LY2.2.1-19 | 0.15 | 7.70 | 2.16 | 81.75 | 7.69 | 0.15 | 0.27 |
| LY2.2.1-20 | 0.19 | 8.64 | 1.89 | 79.62 | 9.04 | 0.16 | 0.26 |
| LY2.2.1-21 | 0.18 | 8.19 | 2.01 | 81.25 | 7.84 | 0.15 | 0.25 |
| LY2.2.1-22 | 0.19 | 8.56 | 2.06 | 80.19 | 8.35 | 0.16 | 0.27 |
| LY2.2.1-23 | 0.18 | 8.67 | 2.03 | 80.45 | 8.00 | 0.20 | 0.25 |
| LY2.2.1-24 | 0.16 | 7.95 | 1.95 | 81.53 | 7.89 | 0.15 | 0.26 |
| LY2.2.1-25 | 0.16 | 7.92 | 2.33 | 81.02 | 8.02 | 0.17 | 0.27 |
| LY2.2.1-26 | 0.18 | 8.49 | 2.08 | 80.43 | 8.15 | 0.17 | 0.27 |
| LY2.2.1-27 | 0.18 | 8.58 | 2.05 | 80.19 | 8.32 | 0.18 | 0.27 |
| LY2.2.1-28 | 0.17 | 8.26 | 2.04 | 80.08 | 8.88 | 0.18 | 0.26 |
| LY2.2.1-29 | 0.16 | 7.77 | 2.04 | 81.44 | 7.99 | 0.17 | 0.27 |
| LY2.2.1-30 | 0.18 | 8.14 | 1.76 | 81.16 | 8.16 | 0.19 | 0.24 |
| T4 seeds |  |  |  |  |  |  |  |
| LY2.2.4-1 | 0.17 | 9.14 | 2.76 | 79.72 | 7.65 | 0.13 | 0.31 |
| LY2.2.4-2 | 0.18 | 9.57 | 2.82 | 78.68 | 8.08 | 0.17 | 0.31 |
| LY2.2.4-3 | 0.15 | 9.16 | 3.18 | 78.75 | 8.05 | 0.17 | 0.31 |
| LY2.2.4-4 | 0.17 | 9.28 | 2.97 | 79.31 | 7.62 | 0.15 | 0.32 |
| LY2.2.4-5 | 0.17 | 9.33 | 2.56 | 79.58 | 7.79 | 0.15 | 0.28 |
| LY2.2.4-6 | 0.17 | 9.29 | 2.79 | 79.09 | 8.03 | 0.16 | 0.29 |
| LY2.2.4-7 | 0.16 | 9.42 | 2.66 | 78.09 | 9.00 | 0.17 | 0.29 |
| LY2.2.4-8 | 0.21 | 9.82 | 2.59 | 77.69 | 9.03 | 0.18 | 0.30 |

TABLE 2-continued

Fatty acid composition of three generations of transgenic cotton expressing the LY-2 RNAi construct targeting three genes, namely ghFad2-1, ghCAD-H and ghFatB-2. LY2-1, LY2-8 and LY2-9 appear to show wild-type fatty acid composition and may be non-transformed "escapes".

| Sample | My-ristic | Pal-mitic | Stea-ric | Oleic | Lin-oleic | Lin-olenic | Ara-chidic |
|---|---|---|---|---|---|---|---|
| LY2.2.4-9 | 0.19 | 9.15 | 2.43 | 80.02 | 7.66 | 0.14 | 0.28 |
| LY2.2.4-10 | 0.18 | 9.00 | 2.72 | 79.48 | 8.10 | 0.13 | 0.31 |
| LY2.2.4-11 | 0.18 | 9.63 | 2.99 | 78.71 | 7.84 | 0.17 | 0.30 |
| LY2.2.4-12 | 0.22 | 9.88 | 2.42 | 78.79 | 8.05 | 0.15 | 0.31 |
| LY2.2.4-13 | 0.21 | 9.62 | 2.37 | 79.01 | 8.22 | 0.13 | 0.30 |
| LY2.2.4-14 | 0.16 | 9.01 | 2.92 | 79.82 | 7.53 | 0.15 | 0.30 |
| LY2.2.4-15 | 0.18 | 9.52 | 2.76 | 79.06 | 7.85 | 0.16 | 0.29 |
| LY2.2.4-16 | 0.19 | 9.75 | 2.76 | 78.63 | 8.05 | 0.16 | 0.29 |
| LY2.2.4-17 | 0.18 | 9.24 | 2.38 | 80.03 | 7.62 | 0.14 | 0.27 |
| LY2.2.4-18 | 0.20 | 9.82 | 2.73 | 77.41 | 9.15 | 0.18 | 0.31 |
| LY2.2.4-19 | 0.23 | 10.18 | 2.16 | 78.61 | 8.36 | 0.13 | 0.25 |
| LY2.2.4-20 | 0.16 | 9.06 | 2.74 | 80.11 | 7.43 | 0.14 | 0.27 |
| LY2.2.4-21 | 0.17 | 9.31 | 2.77 | 79.66 | 7.47 | 0.15 | 0.31 |
| LY2.2.4-22 | 0.18 | 9.26 | 2.73 | 79.77 | 7.44 | 0.18 | 0.28 |
| LY2.2.4-23 | 0.19 | 8.94 | 2.38 | 79.98 | 7.99 | 0.13 | 0.27 |
| LY2.2.4-24 | 0.19 | 9.41 | 2.38 | 79.71 | 7.70 | 0.17 | 0.27 |
| LY2.2.4-25 | 0.19 | 9.47 | 2.43 | 79.60 | 7.74 | 0.14 | 0.28 |
| LY2.2.4-26 | 0.20 | 10.08 | 2.84 | 76.62 | 9.54 | 0.17 | 0.31 |
| LY2.2.4-27 | 0.21 | 9.90 | 2.49 | 77.69 | 9.06 | 0.17 | 0.29 |
| LY2.2.4-28 | 0.20 | 9.84 | 2.65 | 78.72 | 7.91 | 0.19 | 0.30 |
| LY2.2.4-29 | 0.18 | 9.08 | 2.90 | 79.08 | 8.19 | 0.14 | 0.32 |
| LY2.2.4-30 | 0.16 | 8.89 | 2.65 | 79.82 | 7.91 | 0.15 | 0.27 |

Reduction of cyclopropane fatty acids in cotton embryo axes of $T_4$ homozygous DCS9-34 seed

TABLE 3

Fatty acid composition of embryo axes in three types of cottons, including DCS9-34 (MonoCott) with combined traits of HO, LP and low-cyclic fatty acids, LY-2 with HO and LP traits, but increased cyclic fatty acids and Coker315 as the conventional cotton control.

| Seed No | 14:0 | 16:0 | 16:1 | 18:0 | 18:1 n-9 | 18:1 n-7 | 18:2 | 18:3 | CPFAs DHS | MVA | STC | Total CPFA |
|---|---|---|---|---|---|---|---|---|---|---|---|---|
| DCS9 embryo axes | | | | | | | | | | | | |
| 1 | 0.5 | 16.6 | 0.8 | 2.5 | 48.5 | 1.0 | 25.8 | 0.8 | 0.3 | 2.1 | 0.5 | 3.0 |
| 2 | 0.5 | 15.1 | 0.8 | 2.2 | 47.4 | 1.0 | 27.7 | 0.9 | 0.4 | 2.8 | 0.7 | 4.0 |
| 3 | 0.6 | 16.0 | 0.8 | 1.5 | 43.8 | 1.1 | 29.3 | 1.2 | 0.4 | 4.1 | 0.8 | 5.3 |
| 4 | 0.5 | 14.7 | 0.8 | 2.1 | 49.0 | 1.0 | 26.7 | 0.8 | 0.4 | 2.9 | 0.7 | 4.0 |
| 5 | 0.4 | 13.0 | 0.8 | 2.2 | 54.5 | 1.0 | 25.0 | 0.7 | 0.2 | 1.4 | 0.4 | 2.1 |
| 6 | 0.6 | 16.3 | 0.8 | 1.5 | 42.0 | 1.1 | 31.5 | 1.1 | 0.4 | 3.4 | 0.8 | 4.6 |
| 7 | 0.6 | 17.3 | 0.9 | 1.4 | 39.5 | 1.1 | 32.6 | 1.1 | 0.5 | 3.8 | 0.9 | 5.1 |
| 8 | 0.5 | 14.6 | 0.8 | 1.7 | 47.9 | 1.0 | 28.8 | 0.8 | 0.2 | 2.5 | 0.6 | 3.4 |
| 9 | 0.5 | 14.0 | 0.8 | 2.3 | 51.3 | 1.0 | 25.5 | 0.9 | 0.3 | 2.4 | 0.5 | 3.3 |
| 10 | 0.6 | 16.0 | 0.8 | 1.5 | 43.7 | 1.1 | 30.4 | 1.0 | 0.4 | 3.2 | 0.7 | 4.4 |
| 11 | 0.4 | 14.1 | 0.7 | 2.2 | 49.4 | 1.0 | 27.0 | 0.8 | 0.3 | 2.8 | 0.7 | 3.8 |
| 12 | 0.4 | 14.5 | 0.8 | 1.7 | 48.9 | 1.0 | 28.3 | 0.9 | 0.2 | 2.2 | 0.6 | 3.0 |
| 13 | 0.4 | 14.8 | 0.8 | 2.0 | 48.5 | 1.1 | 27.6 | 0.7 | 0.3 | 2.5 | 0.7 | 3.6 |
| 14 | 0.6 | 16.8 | 0.9 | 1.3 | 40.6 | 1.1 | 32.7 | 1.2 | 0.3 | 3.2 | 0.7 | 4.2 |
| 15 | 0.6 | 16.9 | 0.8 | 1.5 | 40.3 | 1.0 | 31.2 | 1.2 | 0.6 | 4.3 | 1.1 | 5.9 |
| 16 | 0.4 | 12.4 | 0.8 | 2.1 | 57.5 | 1.0 | 23.4 | 0.6 | 0.2 | 0.8 | 0.3 | 1.3 |
| 17 | 0.5 | 15.8 | 0.8 | 2.1 | 43.9 | 1.0 | 29.7 | 0.9 | 0.5 | 3.3 | 0.9 | 4.7 |
| 18 | 0.6 | 16.1 | 0.9 | 1.4 | 43.5 | 1.1 | 30.7 | 1.1 | 0.3 | 3.1 | 0.7 | 4.2 |
| 19 | 0.4 | 13.1 | 0.7 | 2.4 | 54.6 | 0.9 | 23.9 | 0.8 | 0.2 | 2.0 | 0.5 | 2.7 |
| 20 | 0.5 | 15.2 | 0.9 | 1.3 | 45.4 | 1.2 | 30.9 | 1.1 | 0.2 | 2.3 | 0.5 | 2.9 |
| 21 | 0.6 | 16.0 | 0.9 | 1.4 | 43.1 | 1.1 | 31.1 | 1.1 | 0.4 | 3.2 | 0.8 | 4.3 |
| 22 | 0.5 | 15.2 | 0.7 | 1.7 | 46.8 | 1.0 | 28.6 | 0.9 | 0.4 | 2.9 | 0.7 | 4.0 |
| 23 | 0.5 | 14.7 | 0.9 | 1.4 | 46.5 | 1.2 | 29.8 | 1.2 | 0.2 | 2.6 | 0.5 | 3.3 |
| 24 | 0.5 | 16.6 | 0.8 | 1.7 | 43.9 | 1.0 | 29.1 | 0.9 | 0.6 | 3.5 | 0.9 | 5.0 |
| 25 | 0.6 | 16.8 | 0.9 | 1.5 | 41.0 | 1.1 | 31.4 | 1.2 | 0.4 | 3.8 | 0.9 | 5.1 |
| 26 | 0.5 | 15.2 | 0.8 | 1.8 | 47.9 | 1.1 | 28.0 | 1.0 | 0.2 | 2.3 | 0.5 | 3.0 |
| Average | | | | | | | | | 0.3 | 2.8 | 0.7 | 3.8 |
| LY2 embryo axes | | | | | | | | | | | | |
| 1 | 0.4 | 18.1 | 0.6 | 5.0 | 27.5 | 0.6 | 20.9 | 0.8 | 9.2 | 9.5 | 6.3 | 25.0 |
| 2 | 0.4 | 18.6 | 0.5 | 5.1 | 22.2 | 0.5 | 20.5 | 1.1 | 10.3 | 12.9 | 6.8 | 30.0 |
| 3 | 0.4 | 17.1 | 0.7 | 3.6 | 41.3 | 0.7 | 20.0 | 0.9 | 4.4 | 6.2 | 4.0 | 14.6 |
| 4 | 0.4 | 16.8 | 0.7 | 4.3 | 34.2 | 0.7 | 19.3 | 1.1 | 6.9 | 8.7 | 6.0 | 21.6 |
| 5 | 0.3 | 14.7 | 0.6 | 4.5 | 42.4 | 0.6 | 15.6 | 0.8 | 7.1 | 7.4 | 5.1 | 19.6 |
| 6 | 0.3 | 15.5 | 0.6 | 4.3 | 37.4 | 0.6 | 18.4 | 0.6 | 7.8 | 7.8 | 5.7 | 21.3 |
| 7 | 0.3 | 14.3 | 0.6 | 4.1 | 46.1 | 0.6 | 17.2 | 0.7 | 4.9 | 5.8 | 4.5 | 15.2 |
| 8 | 0.5 | 18.5 | 0.6 | 4.1 | 29.2 | 0.7 | 21.9 | 1.0 | 7.0 | 9.0 | 6.6 | 22.6 |
| 9 | 0.3 | 16.4 | 0.6 | 4.5 | 33.3 | 0.6 | 18.6 | 1.2 | 7.5 | 9.5 | 6.5 | 23.5 |
| 10 | 0.3 | 13.4 | 0.6 | 4.5 | 44.9 | 0.6 | 15.2 | 0.7 | 6.9 | 7.1 | 5.0 | 19.0 |
| 11 | 0.4 | 15.5 | 0.6 | 4.6 | 42.0 | 0.6 | 17.0 | 0.7 | 6.9 | 5.9 | 5.0 | 17.7 |
| 12 | 0.4 | 16.5 | 0.6 | 4.9 | 32.6 | 0.6 | 18.7 | 1.1 | 8.4 | 9.2 | 5.9 | 23.5 |
| 13 | 0.4 | 16.1 | 0.7 | 3.9 | 33.0 | 0.7 | 20.3 | 1.0 | 7.3 | 9.3 | 6.4 | 23.1 |

TABLE 3-continued

Fatty acid composition of embryo axes in three types of cottons, including DCS9-34 (MonoCott) with combined traits of HO, LP and low-cyclic fatty acids, LY-2 with HO and LP traits, but increased cyclic fatty acids and Coker315 as the conventional cotton control.

| Seed No | 14:0 | 16:0 | 16:1 | 18:0 | 18:1 n-9 | 18:1 n-7 | 18:2 | 18:3 | CPFAs DHS | MVA | STC | Total CPFA |
|---|---|---|---|---|---|---|---|---|---|---|---|---|
| 14 | 0.4 | 16.1 | 0.6 | 4.5 | 43.0 | 0.6 | 17.2 | 0.7 | 5.6 | 6.2 | 4.1 | 15.9 |
| 15 | 0.4 | 16.7 | 0.6 | 4.2 | 38.9 | 0.6 | 19.0 | 0.8 | 5.7 | 7.1 | 5.0 | 17.8 |
| 16 | 0.4 | 18.1 | 0.5 | 4.7 | 37.4 | 0.6 | 18.7 | 0.8 | 6.5 | 6.6 | 4.6 | 17.6 |
| 17 | 0.3 | 14.3 | 0.6 | 4.4 | 46.0 | 0.6 | 15.2 | 0.6 | 6.7 | 6.3 | 4.2 | 17.1 |
| 18 | 0.3 | 16.2 | 0.6 | 5.1 | 35.7 | 0.6 | 18.0 | 0.8 | 8.6 | 7.2 | 5.8 | 21.6 |
| 19 | 0.3 | 14.0 | 0.6 | 4.2 | 44.6 | 0.6 | 15.5 | 0.7 | 6.4 | 7.2 | 5.1 | 18.7 |
| 20 | 0.7 | 21.7 | 0.6 | 4.2 | 19.9 | 0.6 | 26.1 | 1.2 | 7.0 | 11.4 | 5.6 | 24.1 |
| 21 | 0.3 | 13.7 | 0.6 | 4.3 | 47.3 | 0.6 | 15.4 | 0.7 | 5.5 | 6.3 | 4.4 | 16.1 |
| 22 | 0.3 | 13.5 | 0.6 | 3.8 | 49.0 | 0.6 | 16.3 | 0.6 | 5.1 | 5.2 | 4.2 | 14.4 |
| 23 | 0.3 | 14.2 | 0.6 | 4.1 | 45.5 | 0.6 | 16.4 | 0.7 | 5.8 | 6.5 | 4.4 | 16.7 |
| 24 | 0.3 | 15.8 | 0.7 | 4.3 | 37.1 | 0.6 | 18.5 | 0.8 | 7.4 | 7.0 | 6.6 | 20.9 |
| 25 | 0.5 | 19.5 | 0.6 | 4.5 | 25.5 | 0.6 | 21.8 | 1.2 | 7.9 | 10.6 | 6.4 | 24.9 |
| Average | | | | | | | | | 6.9 | 7.8 | 5.4 | 20.1 |
| Coker embryo axes | | | | | | | | | | | | |
| B.1 | 0.6 | 25.1 | 0.5 | 3.4 | 12.0 | 0.6 | 44.5 | 0.7 | 2.2 | 7.0 | 3.0 | 12.2 |
| B.2 | 0.6 | 26.3 | 0.5 | 3.5 | 11.2 | 0.6 | 44.3 | 0.6 | 2.4 | 6.5 | 2.7 | 11.6 |
| B.3 | 0.7 | 26.1 | 0.4 | 4.0 | 10.6 | 0.6 | 41.6 | 0.7 | 3.1 | 8.1 | 3.2 | 14.4 |
| B.4 | 0.7 | 26.7 | 0.4 | 3.9 | 11.5 | 0.6 | 42.0 | 0.6 | 2.8 | 7.1 | 3.0 | 12.9 |
| B.5 | 0.6 | 27.2 | 0.5 | 3.7 | 12.0 | 0.6 | 45.0 | 0.4 | 2.2 | 4.4 | 2.7 | 9.3 |
| B.6 | 0.6 | 27.3 | 0.5 | 3.6 | 11.4 | 0.6 | 42.4 | 0.6 | 2.7 | 6.7 | 2.9 | 12.3 |
| B.7 | 0.7 | 27.2 | 0.5 | 3.5 | 11.6 | 0.6 | 43.9 | 0.6 | 2.4 | 5.7 | 2.7 | 10.8 |
| B.8 | 0.6 | 26.6 | 0.4 | 4.1 | 11.5 | 0.6 | 42.8 | 0.5 | 2.7 | 6.4 | 2.9 | 12.0 |
| B.9 | 0.7 | 26.2 | 0.4 | 3.8 | 11.3 | 0.6 | 44.6 | 0.5 | 2.4 | 6.0 | 2.7 | 11.2 |
| B.10 | 0.7 | 26.8 | 0.5 | 3.8 | 11.6 | 0.6 | 42.4 | 0.6 | 2.7 | 6.6 | 3.0 | 12.3 |
| B.11 | 0.7 | 26.4 | 0.5 | 3.3 | 10.8 | 0.7 | 42.8 | 0.8 | 2.4 | 7.9 | 3.1 | 13.4 |
| B.12 | 0.7 | 27.0 | 0.4 | 3.9 | 11.5 | 0.6 | 43.1 | 0.6 | 2.4 | 6.3 | 2.7 | 11.4 |
| B.13 | 0.7 | 26.5 | 0.5 | 3.9 | 12.0 | 0.6 | 42.9 | 0.6 | 2.6 | 6.3 | 2.8 | 11.6 |
| B.14 | 0.7 | 26.5 | 0.5 | 3.7 | 11.7 | 0.6 | 43.7 | 0.6 | 2.5 | 6.1 | 2.7 | 11.3 |
| B.15 | 0.6 | 26.9 | 0.5 | 3.5 | 12.2 | 0.6 | 44.1 | 0.5 | 2.3 | 5.5 | 2.6 | 10.3 |
| B.16 | 0.6 | 26.4 | 0.5 | 3.3 | 12.2 | 0.6 | 48.0 | 0.4 | 1.8 | 4.2 | 1.9 | 8.0 |
| B.17 | 0.6 | 26.6 | 0.5 | 3.7 | 11.5 | 0.6 | 43.4 | 0.6 | 2.6 | 6.4 | 2.7 | 11.8 |
| B.18 | 0.6 | 28.8 | 0.5 | 4.1 | 11.2 | 0.7 | 39.2 | 0.7 | 2.3 | 7.9 | 3.2 | 13.5 |
| B.19 | 0.7 | 26.0 | 0.5 | 3.2 | 11.2 | 0.7 | 45.3 | 0.7 | 2.0 | 6.5 | 2.7 | 11.1 |
| B.20 | 0.6 | 26.8 | 0.5 | 3.8 | 10.7 | 0.6 | 43.0 | 0.7 | 2.1 | 7.6 | 3.0 | 12.7 |
| B.21 | 0.7 | 27.2 | 0.5 | 3.6 | 11.3 | 0.6 | 40.7 | 0.7 | 3.0 | 7.3 | 3.6 | 13.9 |
| B.22 | 0.7 | 26.4 | 0.5 | 3.2 | 11.8 | 0.7 | 44.5 | 0.6 | 2.0 | 6.2 | 2.6 | 10.9 |
| B.23 | 0.5 | 24.6 | 0.5 | 2.9 | 12.7 | 0.6 | 51.4 | 0.4 | 1.0 | 3.3 | 1.5 | 5.8 |
| Average | | | | | | | | | 2.4 | 6.3 | 2.8 | 11.5 |

TABLE 4

Summary of sequence identifiers

| SEQUENCE ID NO: | DESCRIPTION |
|---|---|
| 1 | cDNA sequence encoding cotton FAD2 from ghFAD2-1 gene. 1362 nucleotides, protein coding region: nucleotides 73-1227 |
| 2 | amino acid sequence encoded by SEQ ID NO: 1: 384 amino acids |
| 3 | Nucleotide sequence of ghFatB-1 genomic DNA encoding acyl-acyl carrier protein thioesterase (FatB-1) from *Gossypium hirsutum* (Yoder et al., 1999 (supra)), Accession No. AF076535, 5201 bp. The complete cDNA sequence corresponds to nucleotides 915-1397, 1530-1663, 2352-2465, 2716-2887, 3001-3069, and 3322-3591 all joined together |
| 4 | amino acid sequence encoded by SEQ ID NO: 3: 413 amino acids |
| 5 | cDNA sequence from ghFatB-2 gene, 1647 nucleotides, The protein encoding region is from nucleotides 210 to 1472 (TAG stop codon) |
| 6 | amino acid sequence encoded by SEQ ID NO: 5: 420 amino acids |
| 7 | cDNA sequence from ghFatB-3 gene, 1498 nt |

TABLE 4-continued

Summary of sequence identifiers

| SEQUENCE ID NO: | DESCRIPTION |
|---|---|
| 8 | amino acid sequence encoded by SEQ ID NO: 7: 418 amino acids |
| 9 | EST sequence from *G. hirsutum* (Dowd et al., 2004 (supra)). Accession No. CD486555 |
| 10 | Nucleotide sequence of ghCPA-FAS-1 encoding *Gossypium hirsutum* cyclopropane fatty acid synthase (CPA-FAS-1), Accession No. AY574036, complete cDNA sequence, 2884 bp, protein coding region: nucleotides 33-2654 |
| 11 | amino acid sequence encoded by SEQ ID NO: 10: 873 amino acids |
| 12 | Nucleotide sequence of ghCPA-FAS-2 encoding *Gossypium hirsutum* cyclopropane fatty acid synthase (CPA-FAS-2), Accession No. AY574037, complete cDNA sequence, 2827 bp, protein coding region: nucleotides 16-2613 |
| 13 | amino acid sequence encoded by SEQ ID NO: 12: 865 amino acids |
| 14 | Nucleotide sequence of ghCPA-FAS-3 encoding *Gossypium hirsutum* cyclopropane fatty acid synthase (CPA-FAS-3), Accession No. AY574038, complete |

TABLE 4-continued

Summary of sequence identifiers

| SEQUENCE ID NO: | DESCRIPTION |
|---|---|
| | cDNA sequence, 2912 bp, protein coding region: nucleotides 109-2706 |
| 15 | amino acid sequence encoded by SEQ ID NO: 4: 865 amino acids |
| 16 | Fragment A of MonoCott, comprising the seed-specific lectin promoter derived from soybean lec1 gene: 1771 nucleotides |
| 17 | Fragment B of MonoCott, chimeric DNA of three target gene fragments |
| 18 | Fragment C of MonoCott: Intron from ghFAD2-1 |
| 19 | Fragment D of MonoCott, complement of the chimeric DNA |
| 20 | Fragment E of MonoCott, lectin gene transcription terminator/polyadenylation region |
| 21 | Fragment F of MonoCott, S1 promoter |
| 22 | Fragment G of MonoCott, NPTII gene |
| 23 | Fragment H of MonoCott, S3 gene transcription terminator/polyadenylation region |
| 24 | *Gossypium hirsutum* mRNA for omega-6 desaturase (FAD2-1) also known as oleoyl-delta12 desaturase. Accession No. X97016 1386 bp protein coding region: nucleotides 54-1211. Homology with SEQ ID NO: 1 was 96% along the full length of the cDNAs |
| 25 | amino acid sequence encoded by SEQ ID NO: 24: 385 amino acids |
| 26 | cDNA sequence from ghFAD2-2 gene, Accession No. Y10112 (Liu et al., 1999), 1422 nucleotides, protein coding region: nucleotides 98-1249 |
| 27 | amino acid sequence encoded by SEQ ID NO: 26: 383 amino acids |
| 28 | Complete cDNA sequence of *Gossypium arboreum* P450 monooxygenase gene, Accession No. AF332974, 1933 nt, protein coding region nucleotides 91-1701 |
| 29 | sense primer for amplification of nucleotides 210 to 713 of SEQ ID NO: 3 |
| 30 | antisense primer for amplification of nucleotides 210 to 713 of SEQ ID NO: 3 |
| 31 | sense primer for amplification of nucleotides 1420 to 1821 of SEQ ID NO: 28 |
| 32 | antisense primer for amplification of nucleotides 1420 to 1821 of SEQ ID NO: 28 |

TABLE 5

Exemplary and Preferred Amino Acid Substitutions

| Original Residue | EXEMPLARY SUBSTITUTIONS | PREFERRED SUBSTITUTIONS |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn, His, Lys, | Asn |
| Glu | Asp, Lys | Asp |
| Gly | Pro | Pro |
| His | Asn, Gln, Lys, Arg | Arg |
| Ile | Leu, Val, Met, Ala, Phe, Norleu | Leu |
| Leu | Norleu, Ile, Val, Met, Ala, Phe | Ile |
| Lys | Arg, Gln, Asn | Arg |
| Met | Leu, Ile, Phe | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala, Norleu | Leu |

BIBLIOGRAPHY

Almeida and Allshire, *Trends Cell Biol.* 15: 251-258, 2005.
Altschul et al., *Nucleic Acids Res.* 25: 3389, 1997.
Ausubel et al., (eds.), *Current Protocols in Molecular Biology*, John Wiley & Sons, NY, 6.3.1-6.3.6., 1989.
Ausubel et al., *Current Protocols in Molecular Biology*, John Wiley & Sons Inc, 1994-1998, Chapter 15.
Bao et al., *Proc. Natl. Acad. Sci. U.S.A.* 99: 7172-7177, 2002,
Barker et al., *Plant Mol. Biol.*, 2: 235-350, 1983.
Bechtold et al., *C.R. Acad. Sci. Paris*, 316:1194, 1993.
Bevan et al., *Nucl. Acid Res.*, 11: 369, 1983.
Birch, *Ann Rev Plant Physiol Plant Mol Biol.* 48: 297-326, 1997.
Bligh et al., *Canadian Journal of Biochemistry and Physiology* 37: 911-917, 1959.
Bonaventure et al., *Plant Cell* 15: 1020-1033, 2003.
Bourque, *Plant Science,* 105: 125-149, 1995.
Buhr et al., *Plant J.* 30: 155-163, 2002.
Chapman et al., *J. Am. Oil Chem. Soc.* 78: 941-947, 2001.
Cherry and Leffler, Seed. In "Cotton, agronomy monograph No. 24" (eds R J Kohel, C F Lewis) pp. 511-569. Crop Science Society of America, Madison, Wis., USA, 1984.
Cherry, *J. Am. Oil Chem. Soc.* 60: 360-367, 1983.
Cho et al., *Plant Molecular Biology Reporter* 13: 255-269, 1995.
Comai et al., *Plant J.* 37: 778-786, 2004.
De Framond, *Biotechnology,* 1: 262, 1983.
Dormann et al., *Plant Physiol.* 123: 637-644, 2000.
Dormann et al., *Arch. Biochem. Biophys.* 316: 612-618, 1995.
Dowd et al., *Molecular Plant-Microbe Interactions.* 17: 654-667, 2004.
Folch et al., *J. Biol. Chem.*, 226: 497, 1957.
Fuller et al., *J. Food Sci.* 31: 477-480, 1966.
Garfinkel et al., *Cell,* 27: 143-153, 1983.
Greve, *J. Mol. Appl. Genet.,* 1:499-511, 1983.
Harayama, *Trends Biotechnol.* 16: 76-82, 1998.
Hartmann and Endres, *Manual of Antisense Methodology*, Kluwer, 1999.
Haseloff and Gerlach, *Nature* 334: 585-591, 1988.
Henikoff et al., *Plant Physiol.* 135: 630-636, 2004.
Hinchee et al., *Biotech,* 6: 915, 1988.
Hoekema et al., *Nature,* 303: 179, 1983.
Hutchins et al., *Journal of American Oil Chemists Society* 45:397-399, 1968.
Johnson et al., *Nature* 214: 1244-1245, 1967.
Jones and King, Cottonseed Oil. National Cottonseed Products Associations, Inc. and the Cotton Foundation, Memphis, Tenn., USA, 1993.
Jones et al., *Plant Cell* 7: 359-371, 1995.
Joshi, *Nucl. Acid Res.* 15: 6643, 1987.
Kargiotidou et al., *Journal of Experimental Botany* 2008 59(8): 2043-2056, 2008.
Khandjian, *Bio/Technology,* 5: 165-167, 1987.
Klein et al., *Nature,* 327: 70, 1987.
Kris-Etherton et al., *Nutrition-today (USA).* 28: 30-38, 1993.
Lindsey et al., *Exp. Biol. Med.* 195: 261-269, 1990.
Liu et al., *Plant Physiol.* 120: 339, 1999b.
Liu et al., *Plant Physiol.* 129: 1732-1743, 2002.
Liu et al., *Australian Journal of Plant Physiology* 26: 101-106, 1999a.
McPherson and Moller (Ed), BIOS Scientific Publishers Ltd, Oxford, 2000.
Medberry et al., *Plant Cell,* 4: 185-192, 1992.
Medberry et al., *Plant J.* 3: 619-626, 1993.
Merker and Mattil, 1965. U.S. Pat. No. 3,201,431.

Millar and Waterhouse, *Funct Integr Genomics,* 5: 129-135, 2005.
Mounts et al., *J. Am. Oil Chem. Soc.* 65: 624-628, 1998.
Mozaffarian et al., *N. Engl. J. Med.* 354: 1601-1613, 2006.
Murashige and Skoog, *Physiologia Plantarum.* 15: 473-497, 1962.
Needleman and Wunsch, *J. Mol. Biol.* 48: 443-453, 1970.
Niedz et al., *Plant Cell Reports,* 14: 403, 1995.
O'Brien, Cottonseed Oil. In: F. D. Gunstone (Ed.) Vegetable Oils in Food Technology: Composition, Properties and Uses. Blackwell Publishing, Oxford, pp. 203-230, 2002.
OGTR DM-039/2003 Field evaluation of genetically modified high-oleic (HO) cotton
Oomen et al., *Lancet* 357: 746-751, 2001.
Ow et al., *Science,* 234: 856, 1986.
Pasquinelli et al., *Curr Opin Genet Develop* 15: 200-205, 2005.
Perriman et al., *Gene,* 113: 157-163, 1992.
Pirtle et al., *Plant Cell Physiology,* 40: 155-163, 1999.
Pirtle et al., *Biochim. Biophys. Acta* 1522: 122-129, 2001.
Prasher et al., *Biochem. Biophys. Res. Comm.* 126: 1259-68, 1985.
Roehm et al. *Lipids* 5: 80-84, 1970.
Salomon et al., *EMBO J.,* 3: 141-146, 1984.
Sambrook et al., *Molecular Cloning: A Laboratory Manual* (2nd Ed). Cold Spring Harbour Laboratory, Cold Spring Harbour, N.Y. 1989.
Senior, *Biotech. Genet. Engin. Revs,* 15: 79-119, 1998.
Shenstone and Vickery, *Nature* 190: 68-169, 1961.
Shippy et al., *Mol. Biotech.* 12: 117-129, 1999.
Slade and Knauf, *Transgenic Res.* 14: 109-115, 2005.
Smith et al., *Nature,* 407: 319-320, 2000.
Stalker et al., *Science,* 242: 419, 1988.
Thillet et al., *J. Biol. Chem.* 263: 12500, 1988.
Voelker et al., *Plant Journal* 9: 229-241, 1996.
Waterhouse et al., *Proc. Natl. Acad. Sci. U.S.A.* 95: 13959-13964, 1998.
Wilson et al., *J. Am. Oil Chem. Soc.* 78: 335-340, 2001.
Yoder et al., *Biochimica et Biophysica Acta* 1446: 403-413, 1999.
Zwar and Chandler, *Planta* 197: 39-48, 1995.

The invention claimed is:

1. A process for producing cottonseed oil comprising the steps of
   (i) obtaining cottonseed of the species *Gossypium hirsutum*, wherein in the oil of the cottonseed 72% to 88% by weight of the total fatty acid content is oleic acid, 4% to 16% by weight of the total fatty acid content is palmitic acid and 4% to 15% by weight of the total fatty acid content is linoleic acid, and wherein the cottonseed has a reduced level of each of cotton FAD2-1 protein, cotton FatB-2 protein, and cotton CPA-FAS-2 protein relative to the level of cotton FAD2-1 protein, cotton FatB-2 protein, and cotton CPA-FAS-2 protein, respectively, in cottonseed of cotton variety Coker when grown under the same conditions;
   (ii) extracting the oil from the cottonseed; and
   (iii) recovering the cottonseed oil.

2. The process of claim 1, wherein 0.1% to 0.5% by weight of the total fatty acid content in the cottonseed oil is cyclopropane fatty acid (CPA), cyclopropene fatty acid (CPE) or a combination of CPA and CPE.

3. The process of claim 2, wherein the fatty acid of the CPA or the CPE is malvalic acid, sterculic acid, dihydrosterculic acid or any combination of two or all three of these fatty acids.

4. The process of claim 1, wherein the level of gossypol in the cottonseed is reduced by at least 10% relative to the level of gossypol in cottonseed of cotton variety Coker.

5. The process of claim 2, wherein the level of gossypol in the cottonseed is reduced by at least 10% relative to the level of gossypol in cottonseed of cotton variety Coker.

6. The process of claim 1, wherein step (ii) comprises crushing the cottonseed.

7. The process of claim 1, wherein step (iii) comprises purifying the cottonseed oil.

8. The process of claim 1, wherein the cottonseed oil is not hydrogenated.

9. A cottonseed of the species *Gossypium hirsutum* comprising oil, wherein in the oil of the cottonseed 72% to 88% by weight of the total fatty acid content is oleic acid, 4% to 16% by weight of the total fatty acid content is palmitic acid and 4% to 15% by weight of the total fatty acid content is linoleic acid, and wherein the cottonseed has a reduced level of each of cotton FAD2-1 protein, cotton FatB-2 protein and cotton CPA-FAS-2 protein relative to the levels of cotton FAD2-1 protein, cotton FatB-2 protein and cotton CPA-FAS-2 protein respectively, in cottonseed of cotton variety Coker when grown under the same conditions.

10. The cottonseed of claim 9, wherein 0.1% to 0.5% by weight of the total fatty acid content in the cottonseed oil is cyclopropane fatty acid (CPA), cyclopropene fatty acid (CPE) or a combination of CPA and CPE.

11. The cottonseed of claim 9, wherein the level of gossypol in the cottonseed is reduced by at least 10% relative to the level of gossypol in cottonseed of cotton variety Coker.

12. The process of claim 1, wherein 4% to 10% by weight of the total fatty acid content in the cottonseed oil is palmitic acid.

13. The cottonseed of claim 9, wherein 4% to 10% by weight of the total fatty acid content in the cottonseed oil is palmitic acid.

14. The process of claim 1, wherein the cottonseed has a germination rate which is substantially the same as cottonseed of the cotton variety Coker.

15. The cottonseed of claim 9, wherein the cottonseed has a germination rate which is substantially the same as cottonseed of the cotton variety Coker.

16. The cottonseed of claim 9, wherein
   i) 0.1% to 0.5% by weight of the total fatty acid content in the cottonseed oil is cyclopropane fatty acid (CPA), cyclopropene fatty acid (CPE) or a combination of CPA and CPE, and
   ii) the level of gossypol in the cottonseed is reduced by at least 10% relative to the level of gossypol in cottonseed of cotton variety Coker.

* * * * *